United States Patent [19]

Taylorson et al.

[11] Patent Number: 5,985,281
[45] Date of Patent: Nov. 16, 1999

[54] CHEMICAL COMPOUNDS

[75] Inventors: Christopher John Taylorson, London; Hendrikus Johannes Eggelte, Harrow; Antonio Tarragona-Fiol; Brian Robert Rabin, both of London; Francis Thomas Boyle, Macclesfield; John Frederick Hennam, Macclesfield; David Charles Blakey, Macclesfield; Peter Robert Marsham, Macclesfield; David William Heaton, Macclesfield; David Huw Davies, Macclesfield; Anthony Michael Slater, Macclesfield, all of United Kingdom; Laurent Francois Andre Hennequin, Cergy Cedex, France

[73] Assignee: Zeneca Limited, London, United Kingdom

[21] Appl. No.: 08/860,882

[22] PCT Filed: Dec. 21, 1995

[86] PCT No.: PCT/GB95/02991

§ 371 Date: Jun. 23, 1997

§ 102(e) Date: Jun. 23, 1997

[87] PCT Pub. No.: WO96/20011

PCT Pub. Date: Jul. 4, 1996

[30] Foreign Application Priority Data

Dec. 23, 1994 [GB] United Kingdom .................. 9426192
Aug. 16, 1995 [GB] United Kingdom .................. 9516810

[51] Int. Cl.$^6$ .................................................. A61K 39/395
[52] U.S. Cl. ..................... 424/178.1; 424/182.1; 424/1.17; 424/1.1; 514/12; 530/391.1; 530/391.7; 536/23.1; 536/23.4; 562/11; 435/320.1
[58] Field of Search ..................... 424/1.1, 1.17, 424/178.1, 182.1; 514/12; 530/391.1, 391.7; 536/23.1, 23.4; 435/975, 243, 320.1; 562/11

[56] References Cited

U.S. PATENT DOCUMENTS

| 4,975,278 | 12/1990 | Senter et al. . |
| 5,389,537 | 2/1995 | Raines et al. ........................... 435/199 |
| 5,433,955 | 7/1995 | Bredehorst et al. . |
| 5,632,990 | 5/1997 | Bagshawe et al. .................. 424/178.1 |

FOREIGN PATENT DOCUMENTS

| WO 88/07378 | 10/1988 | WIPO . |
| WO 89/10140 | 11/1989 | WIPO . |
| WO 90/07929 | 7/1990 | WIPO . |
| WO 93/15208 | 8/1993 | WIPO . |
| 95 13095 | 5/1995 | WIPO . |

OTHER PUBLICATIONS

Wallace et al: "Invitro and in vivo activitis of monoclonal antibody–alkaline phosphatase conjugates in combination with phenol mustard phosphate", Bioconjugate Chemistry, vol. 2, No. 5, Sep. 1, 1991, pp. 349–352, XP000226372.

Davies et al: "A novel bisiodo–phenol mustard prodrug. ZD2767P,for antibody–directed enzyme prodrug therapy", Data Biosis Biosciences Information Service,AN=95:187056,XPOO2OOO815 see abstract, & 86th Annual Meeting of the Americ.Assoc. for Cancer Res. & Proceedings of the Americ.Assoc. for Cancer Res. Annual Meeting, vol. 36, No. 0, Mar. 18–22, 1995.p. 482.

Bosslet et al: "Tumor–selective prodrug activation by fusion protein–mediated catalysis", Cancer Research, vol. 54, Apr. 15, 1994, pp. 2151–2159, XP002000814 cited in the application, See p. 2151, col. 1, para 1, See p. 2151, col. 2, para 2.

Graf et al., Selective Alteration of Substrate Specificity by Replacement of Aspartic Acid–189 with Lysine in the Binding Pocket of Trypsin, Biochemistry, 1987, 2616–2623.

Soman et al., Electrical Potentials in Trypsin Isozymes, Biochemistry, 1989, 9918–9926.

McGrath et al., Structure of an Engineered, Metal–Actuated Switch in Trypsin, Biochemistry, 1993, 1914–1919.

Tsu et al., Structural Basis for the Broad Substrate Specificity of Fiddler Crab Collagenolytic Serine Protease 1, Biochemistry, 1997, 5393–5401.

Sprang et al., Studies of Specificity and Catalysis in Trypsin by Structural Analysis of Site–Directed Mutants, CRC Critical Reviews in Biotechnology, 1988, Issue 3, 225–236.

Bone et al., Mutational Remodeling of Enzyme Specificity, Methods in Enzymology, 1991, vol. 202, 643–671.

Craik et al., Redesigning Trypsin Via Genetic Engineering, Journal of Cellular Biochemistry, 1987, 199–211.

Wilke et al., Crystal Structure of Rat Trypsin–S195C at −150°—Analysis of Low Activity of Recombinant and Semisynthetic Thiol Proteases, Journal of Molecular Biology, 1991, 511–523.

Wilke et al., Crystallographic Analysis of Trypsin–G226A—A Specificity Pocket Mutant of Rat Trypsin with Altered Binding and Catalysis, Journal of Molecular Biology, 1991, 525–532.

(List continued on next page.)

Primary Examiner—Sheela Huff
Attorney, Agent, or Firm—Cushman Darby & Cushman Intellectual Property Group of Pillsbury Madison & Sutro, LLP

[57] ABSTRACT

A two component system for therapeutic treatment of a host, having a first component comprising a targeting moiety capable of binding with a tumour associated antigen, linked to a mutated enzyme capable of converting a prodrug into an antineoplastic drug, and a second component comprising a prodrug convertible under the influence of the mutated enzyme to the antineoplastic drug. The mutated enzyme is a mutated form of a natural host enzyme which recognizes its natural substrate by an ion pair interaction with the substrate, wherein the mutated enzyme and prodrug have structures such that the polarity of the mutated enzyme/prodrug ion pair interaction is reversed relative to the natural host enzyme/natural substrate ion pair interaction. The first component is substantially non-immunogenic in the host and the prodrug second component is not significantly convertible into antineoplastic drug in the host by natural unmutated host enzyme.

39 Claims, 28 Drawing Sheets

OTHER PUBLICATIONS

Perona et al., Relocating a Negative Charge in the Binding Pocket of Trypsin, Journal of Molecular Biology, 1993, 934–949.

Craik et al., Redesigning Trypsin: Alteration of Substrate Specificity, Science, Apr. 1985, 291–297.

Sprang et al., The Three–Dimensional Structure of $Asn^{102}$ Mutant of Trypsin: Role of $Asp^{102}$ in Serine Protease Catalysis, Aug. 1997, 905–909.

Phillips et al., Transition–State Characterization: A New Approach Combining Inhibitor Analogues and Variation in Enzyme Structure, Biochemistry, 1992, 959–963.

Kuefner et al., Carboxypeptidase–Mediated Release of Methotrexate from Methotrexate α–Peptides, Biochemistry, 1989, 2288–2297.

Rectenwald et al., Protein engineering and design—Method and industrial relevance, Journal of Biotechnology, 1993, 1–23.

Hwang et al., Why ion pair reversal by protein engineering is unlikely to succeed, Nature, Jul. 1988, 270–272.

Wells et al., Designing substrate specificity by protein engineering of electrostatic interactions, Proc. Natl. Acad. Sci. USA, Mar. 1987, 1219–1223.

Olesen et al., Altering substrate preference of carboxypeptidase Y by a novel strategy of mutagenesis eliminating wild type background, Protein Engineering, 1993, 409–415.

Tarragona–Fiol, et al., Indentification by site–directed mutagenesis of amino acids in the B2 subsite of bovine pancreatic ribonuclease A, Protein Engineering, 1993, 901–906.

Lesk et al., Antibody Structure and Stuctural Predictions Useful in Guiding Antibody Engineering, Antibody Engineering, 1992, 1–38.

Fig. 8.

*Primers used in RCPCR for the introduction of the mutation K66E in RNase.*

Primer A: 5'-GGT CTG CCC ATT CTC GCA GGC AAC ATT TTT-3'
Primer B: 5'-TGC TAC CAG AGC TAC TCC ACC ATG AGC ATC-3'

Primer C: 5'-AAT GTT GCC TGC GAG AAT GGG CAG ACC AAT-3'
Primer D: 5'-CTG GGA GCA CAC GGC CTG GAC ATC AGC CA-3' nucleotides in bold indicate position to be mutated.

*Primers for the isolation of the HP-RNase gene and for the construction of a chimeric gene expressable in E.coli.*

Primer 1: 5'-CGC GCG AAT TCG GGT CCA GCC TTC CCT GGG C-3'
Primer 2: 5'-GGC CGG AAT TCC ATC AAA GTG GAC TGG CAC A-3'
Primer 3: 5'-CGC TGT TGG TCC TGG TGC TGC TGG TGC GGG TCC AGC CTT CCC-3'
Primer 4: 5'-TGATGG CTC TGA AGT CCC TGG TCC TGT TGT CGC TGT TGG TCC TGG-3'
Primer 5: 5'-GCG CGA ATT CAT GTT CTT GGA GGA TGA TTG ATG GCT CTG AAG TCC C-3'
Primer 6: 5'-CGC GGA ATT CCT AGG TAG AGT CTT CAA CAG AAG CAT CAA CAG AGT GGA CTG-3'

*Primers used in RCPCR for the introduction of the mutations R4A:K6A in HP-RNase.*

Primer E: 5'-AAG GAA TCC GCT GCC GCT AAA TTC CAG CGG CAG-3'
Primer F: 5'-GGA AGG CTG GAC CCG CAC CAG CAG CAG CAG CAC-3'

Primer G: 5'-CTG GAA TTT AGC GGC AGC GGA TTC CTT GCC CAG-3'
Primer H: 5'-CAT ATG GAC TCA GAC AGT TCC CCC AGC AGC-3' nucleotides in bold indicate position to be mutated.

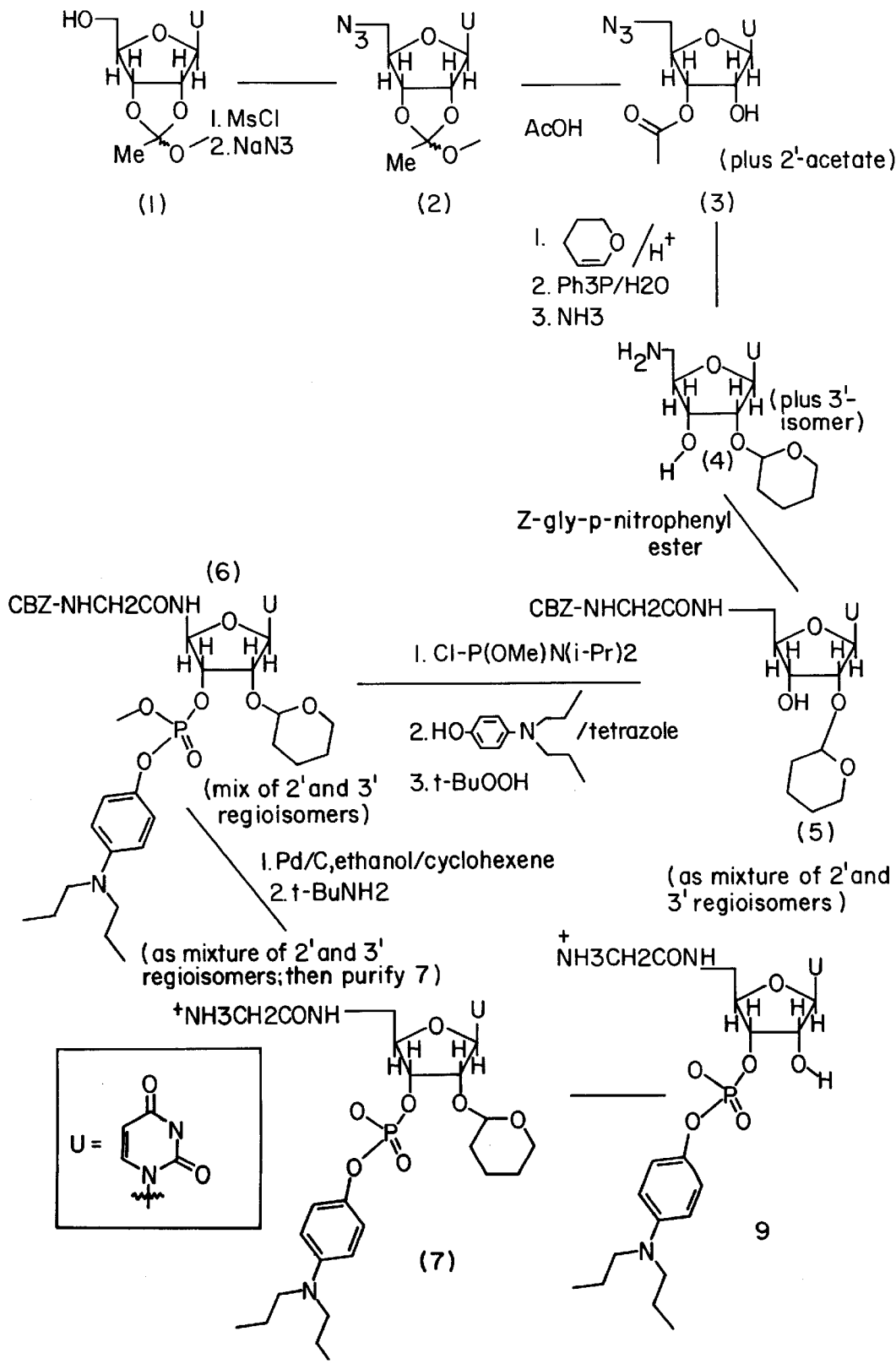
Fig.9. Synthesis of uridine based prodrug analogue

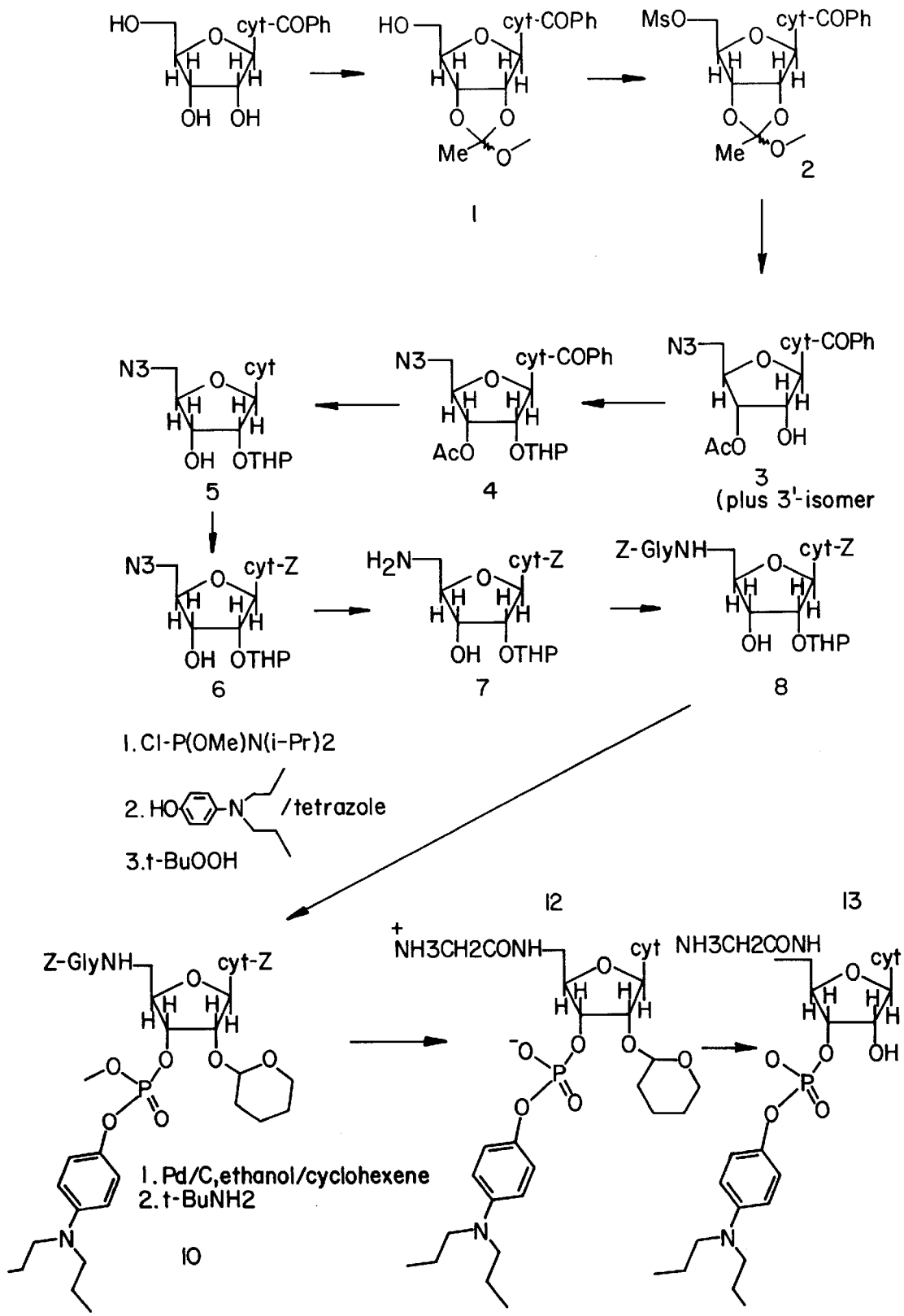
Synthesis of cytidine based prodrug analogue Fig.10.

Fig.11.
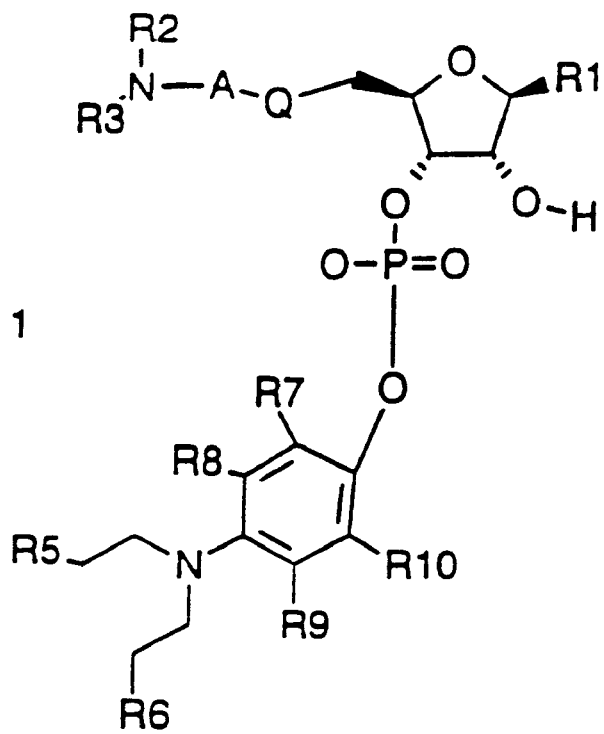
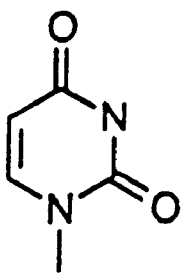
Uracil
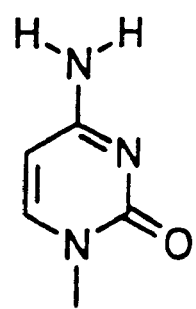
Cytosine
R1

Example of Prodrug for use with a mutant RNase K66E.

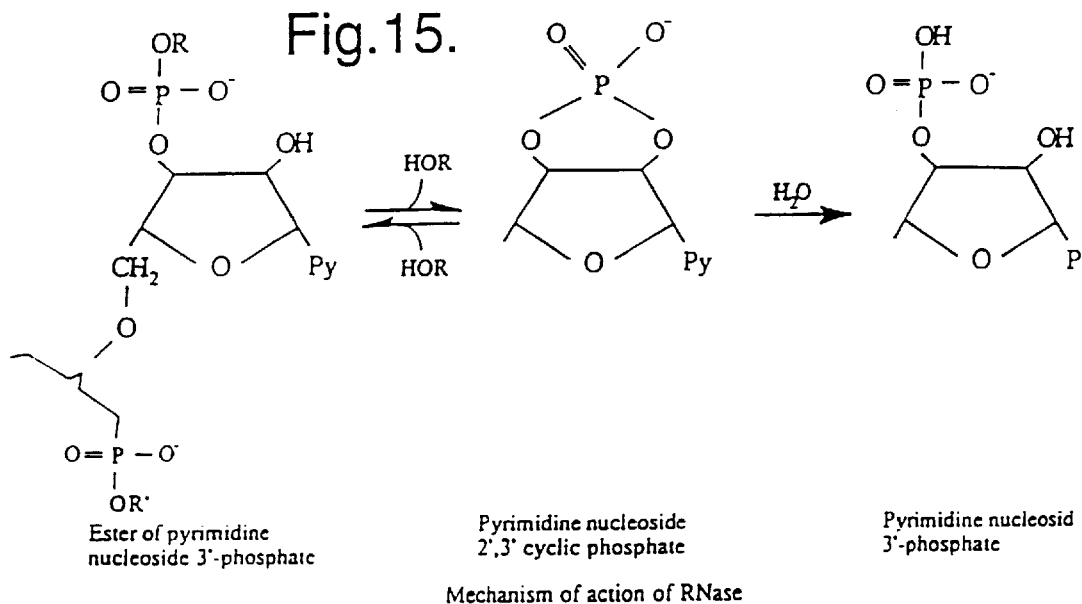
Fig.15.
Ester of pyrimidine nucleoside 3'-phosphate
Pyrimidine nucleoside 2',3' cyclic phosphate
Pyrimidine nucleosid 3'-phosphate
Mechanism of action of RNase
Fig.16.
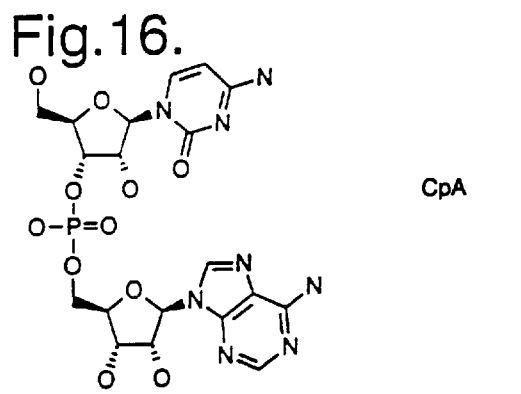
CpA
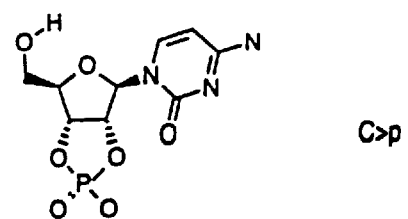
C>p Fig. 17. Christensen, L.F. and Broom, A.D. J.Org.Chem. (1972) 37 3398-401

Human Pancreatic Carboxypeptidase B

Cloning

Human Pancreatic Carboxypeptidase B

Sequencing

All 6 clones have identical sequence, and all have :-

∅ Aspartate in the enzyme recognition site. ie Carboxypeptidase B.

When compared with published sequence :-

⊗ TGC codon insert, changing polypeptide ...GSSIG... to ...GSSCIG... .

Fig.21.

pICI266 expression vector - gene cloning

```
TCACACTTTGCAAAGCATTAGCATTTTTGTCCATAAGATAAGCGGATCCTGCCTGACGGTTTTTGCCGGACTCTCTACTGTTTCTCCAT   1170

NcoI
                                  PelB →                                            .....
ACCTGTTTTTCTGGATGGAGTAAGACC|ATGAAATACCTATTGCCTACGGACAGCCGCTGGATTGTTATTACTCGCTGCCAACCAGCCATG   1260
                            Met Lys Tyr Leu Leu Pro Thr Ala Ala Gly Leu Leu Leu Leu Ala Ala Gln Pro Ala Met

XbaI      XhoI    AsuII EcoRI
                         .....     .....   ..... .....
GCC|GGTACCAATAGCAGATCTAATGTCTCTAGATGTTACCTCGAGTTCGAAGAATTCCTAGAGTCGACATTATTACTAATTAATTGGGG    1350
Ala Val Pro Ile Ala Asp Leu Met Ser Leu Asp Val Thr Ser Ser Ser Lys Asn Ser •
← Insert gene
KpnI  BglII                                    SphI
.....  .....                                   .....
ACCCTAGAGGTCCCCTTTTTATTTAAAAAGCATGCGGATCCGTCGGAAATACAGGAACGCACGTCTGATGGCCCTTCGCTGGGATGGT    1440
```

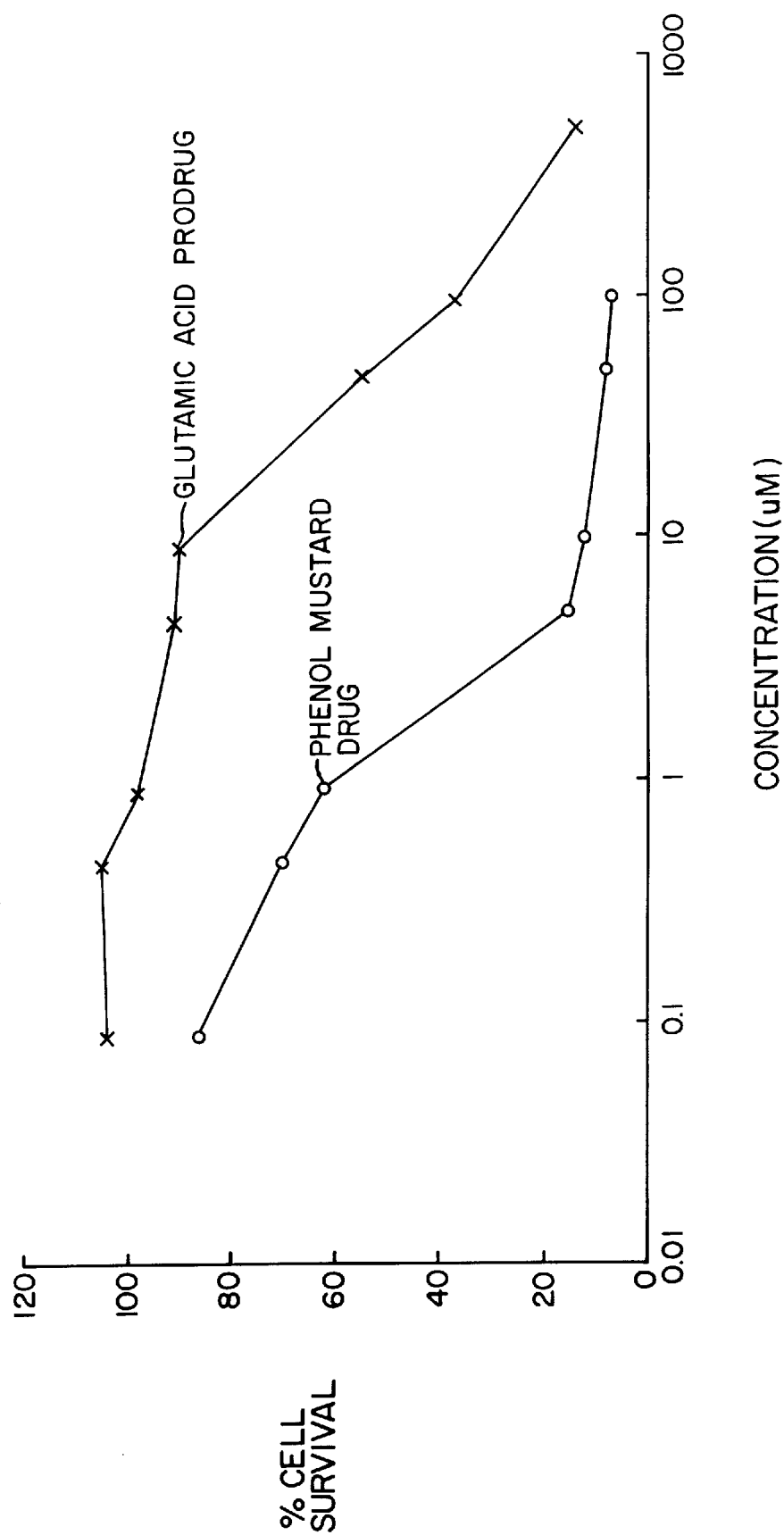
Fig.22. Cytotoxicity of glutamic acid prodrug and phenol mustard drug in LoVo human colorectal tumour cells.

Fig.23.

Growth medium.

| Component | Concentration gl⁻¹ de ionised water |
|---|---|
| Potassium di-hydrogen orthophosphate | 3.0 |
| di-sodium hydrogen orthophosphate | 6.0 |
| Sodium chloride | 0.5 |
| Casein hydrolysate | 2.0 |
| Ammonium sulphate | 10.0 |
| Glycerol | 35.0 |
| Yeast extract | 20.0 |
| Magnesium sulphate heptahydrate | 0.5 |
| Calcium chloride di-hydrate | 0.03 |
| Thiamine | 0.008 |
| Iron sulphate heptahydrate | 0.04 |
| Citric acid | 0.02 |
| Trace element solution (TES)* | 0.5 mll⁻¹ |
| Tetracycline hydrochloride | 0.01 |

* Trace element solution (TES)

| Component | mg per 10ml de-ionised water |
|---|---|
| Aluminium chloride hexahydrate | 2.0 |
| Cobalt chloride hexahydrate | 0.8 |
| Potassium chromium sulphate dodecahydrate | 0.2 |
| Copper chloride dihydrate | 0.2 |
| Boric acid | 0.1 |
| Potassium iodide | 2.0 |
| Manganese sulphate monohydrate | 2.0 |
| Nickel sulphate hexahydrate | 0.09 |
| Sodium molybdate dihydrate | 0.4 |
| Zinc sulphate heptahydrate | 0.4 |

X-Y = Me$_2$NCH$_2$CH$_2$-O-

= H$_2$NCH$_2$CO-NH-

CHEMICAL COMPOUNDS

CROSS-REFERENCES TO RELATED APPLICATIONS

BACKGROUND OF THE INVENTION

1. Field of the Invention

This invention relates to antibody directed enzyme prodrug therapy (ADEPT) using a non-naturally occuring mutant form of a host enzyme, especially a mutant form of ribonuclease.

2. Description of the Related Art

Targeting of drugs selectively to kill cancer cells in a patient has long been a problem for medical research. ADEPT is one approach to overcome the problem. ADEPT uses a tumour selective antibody conjugated to an enzyme. The conjugate is administered to the patient (usually intravenously), allowed to localise at the tumour site(s) and clear from the general circulation. Subsequently a prodrug is administered to the patient which is converted by the enzyme (localised at the tumour sites) into a cytotoxic drug which kills tumour cells. Since one molecule of enzyme can catalyse generation of many cytotoxic drug molecules an amplification effect is produced. Furthermore tumour cells not displaying the antigen recognised by the antibody (tumours usually display microheterogeneity) are also killed by enzymically amplified generation of the cytotoxic drug. A known system uses the procaryotic enzyme carboxypeptidase G2 (CPG2) as the enzyme component (see WO 88/07378). A drawback of systems using procaryotic enzymes is that the normal gut flora may contain procaryotic organisms capable of triggering non-selective cytotoxic drug generation.

A further problem with known systems is that repeated administration of the conjugate results in a host immune response rendering the therapy less effective. The antibody component is generally a mouse monoclonal which can be humanised using known techniques to reduce immunogenicity. However reduction of the immunogenicity of the enzyme component has proved more problematic. This is because the enzyme component must not be present naturally in the human host circulation otherwise premature conversion of prodrug to cytotoxic drug will occur and no selective toxicity to tumours will be observed. Akzo in WO90/02939 have proposed use of human enzymes for ADEPT with selectivity being maintained by choice of a human enzyme not normally present in the circulation such as lysozyme. Akzo have chosen human lysozyme as their enzyme and because of the nature of the substrate requirements [being an endoglycosidase it requires $\beta_{1-4}$ linked polymers of N-acetylglucosamine (NAG-chitin) for cleavage] they are forced into producing prodrugs containing such functionalities. To prevent cell entry they further elaborate the oligomer with taurine residues—relying on the sulphonic acids to prevent cell entry and hence cytotoxicity—20 fold less—FIG. 13 in WO90/02939.

Use of a mammalian enzyme such as alkaline phosphatase (Senter et al: U.S. Pat. No. 4,975,278) or a human enzyme such as beta-glucuronidase (Behringwerke DE 42336237) or lysozyme (Akzo; WO 90/07929) for ADEPT has the advantage that such enzymes should have reduced, or lack, immunogenicity compared with non-mammalian enzymes. A disadvantage of using a mammalian or human enzyme is that it is present endogenously in patients and there will thus be the potential for turnover for prodrug to drug which is not due to the administered antibody-enzyme conjugate. This is likely to lead to enhanced toxicity with this type of ADEPT approach. Prodrugs for alkaline phosphatase are rapidly converted to drugs both in mice (Doyle, T. W. and Vyas, D. M., Cancer Treatment Reviews 17, 127–131, 1990) and in man (Hande et al. Clinical Pharmacology and Therapeutics 53, 233, 1993) in the absence of any administered conjugate due to the widespread distribution of endogenous alkaline phosphatase, thus confirming this is a critical problem for this enzyme. Human data on prodrugs for beta-glucuronidase or lysozyme are not available. Glucuronidase and lysozyme are present in the plasma and in other tissue sites. Akzo report lysozyme is present in milk, tears, saliva, spleen, leukocytes and monocytes. Behringwerke in DE423637 report activated marcophages, granulocytes and platelets secrete glucuronidase. Since these cells are widely distributed throughout the body this could lead to undesirable prodrug activation. Indeed Behringwerke have shown in mice that after administration of a Doxorubicin prodrug relatively high levels of free drug accumulate in the spleen which is a rich source of these cell (see table 3 in DE4236237).

Use of human enzymes in this ADEPT approach is limited by the fact that only enzymes with a predominant intracellular distribution can be used and the prodrugs that are used with them must be kept out of cells to minimise toxicity. This severely limits the number of options to produce an ADEPT system. Lysozyme although being a small enzyme has disadvantages for ADEPT. Lysozyme does not release the active drug but releases a derivative of unknown pharmacological activity. In the example given by Akzo, Dox-(GlcNAc)$_1$ or Dox-(GlcNAc)$_5$ is released rather than free Doxorubicin. Glucuronidase can release the active drug e.g. adriamycin from the glucuronide prodrug and anti-tumour activities have been reported (Bosslet, K et al Cancer Research 54, 2151–59, 1994). However, human glucuronidase is a high molecular weight enzyme (150–300 KDa) and consequently the resulting targeting conjugate is likely to be very large. This is likely to cause problems with penetration into tissues such as a tumour since it is well documented that smaller proteins penetrate more rapidly into solid tumours. In addition glucuronidase is glycosylated and this glycosylation leads to the rapid blood clearance of the antibody-glucuronidase conjugate used in ADEPT. The rapid blood clearance results in little conjugate localising to tumour xenografts. The combination of high molecular weight and rapid blood clearance is likely to lead to poor tumour localisation in patients. Thus glucuronidase is not an ideal enzyme for ADEPT.

The present invention is based on the discovery that a host enzyme (for example human ribonuclease, an enzyme naturally present in the general circulation) can be engineered such that it will recognise a prodrug for ADEPT therapy that is not significantly recognised by natural host enzyme. Since the engineered enzyme is highly similar in terms of amino acid composition to the native host enzyme it advantageously exhibits markedly reduced immunogenicity compared with bacterial enzymes such as CPG2. The engineered enzyme does not occur naturally and thus non-selective triggering of prodrug activation, by natural flora or human enzymes, is advantageously reduced. The approach has the additional advantages that it is applicable to a wide range of human or mammalian enzymes since it is not limited by the natural distribution of the enzyme and prodrugs can be employed that get into cells.

These problems have been addressed in part by International patent application WO 95/13095 (Wellcome Foundation) which was published after the earliest priority date of the present invention. This application proposed ADEPT using mutant mammalian enzymes to activate prodrugs which are not activated by the corresponding native enzyme but did not disclose the presently claimed invention.

It is very surprising that the replacement of a charged residue, one located at or close to the substrate binding or catalytic site of an enzyme, by a residue of opposite charge, produces a mutant enzyme with an intact catalytic centre, and this mutant enzyme differs from the native enzyme solely in possessing a related, complementary but charged inverted substate specificity requirement.

Furthermore the prodrug/drug combinations disclosed in Wellcome (based on methotrexate and melphalan) rely on blockage of active transport mechanisms to prevent cell penetration of the prodrug. This limits the range of prodrug/drug possibilities to those possessing such active transport mechanisms. In contrast the reversed polarity approach disclosed herein allows choice of charge properties of prodrugs (which may or may not also possess active transport properties) to block cell entry of the prodrug and thus enable application of the invention to a wider range prodrug/drug options.

SUMMARY OF THE INVENTION

According to one aspect of the present invention there is provided a matched two component system designed for use in a host in which the components comprise:

(i) a first component that is a targeting moiety capable of binding with a tumour associated antigen, the targeting moiety being linked to a mutated enzyme capable of converting a prodrug into an antineoplastic drug and;

(ii) a second component that is a prodrug convertible under the influence of the enzyme to the antineoplastic drug;

wherein:

the mutated enzyme is a mutated form of a host enzyme in which the natural host enzyme recognises its natural substrate by an ion pair interaction and this interaction is reversed ("reversed polarity") in the design of mutated enzyme and complementary prodrug;

the first component is substantially non-immunogenic in the host and;

the prodrug second component is not significantly convertible into antineoplastic drug in the host by natural unmutated host enzyme.

Preferably the system described above is one in which the first component comprises a mutated enzyme based on an enzyme from the same species as the host for which the system is intended for use.

Preferably the system described above is one in which the targeting moiety is an antibody or a fragment thereof. Preferably the system described above is one in which the antibody fragment is an F(ab')$_2$ fragment.

Preferably the system described above is one in which the mutated enzyme is mutated ribonuclease. Preferably the system described above is one in which the mutated enzyme is human ribonuclease comprising a negatively charged amino acid at position 66. Preferably the system described above is one in which the negatively charged amino acid at position 66 of ribonuclease is Glu.

Another preferred embodiment for the system described above is one in which the mutated enzyme is mutated glucuronidase.

According to another aspect of the present invention there is provided a matched two component system designed for use in a host in which the components comprise:

(i) a first component that is a targeting moiety capable of binding with a tumour associated antigen, the targeting moiety being linked to an enzyme capable of converting a prodrug into an antineoplastic drug and;

(ii) a second component that is a prodrug convertible under the influence of the enzyme to the antineoplastic drug;

wherein:

the enzyme is a mutated form of a host enzyme;

the first component is substantially non-immunogenic in the host and;

the prodrug is not significantly convertible into antineoplastic drug in the host by natural unmutated host enzyme.

The term "the prodrug is not significantly convertible into antineoplastic drug in the host by natural unmutated host enzyme" means that the prodrug does not give undue untargeted toxicity problems on administration to the host.

The term "substantially non-immunogenic" means that the first component can be administered to the host on more than one occasion without causing significant host immune response as would be seen with for example the use of a mouse antibody linked to a bacterial enzyme in a human host.

Preferably the mutated enzyme is based on an enzyme from the same species as the host for which the system is intended for use but the mutated enzyme may be based on a host enzyme from a different species as long as the structure of the enzyme is sufficiently conserved between species so as not to create undue immunogenicity problems.

Preferably the targeting moiety is an antibody, especially an antibody fragment such as for example F(ab')$_2$. Linkage to enzyme may be effected by known methods such as use of heterobifunctional reagents as cross-linkers or by gene fusion or any other suitable method. Antibody may be from the same host (eg use of mouse antibody in mice) or the antibody may be manipulated such that it is not significantly recognised as foreign in the chosen host (eg use of chimeric, CDR grafted or veneered mouse antibodies in humans).

Transplantation of the variable domains of rodent antibodies into the constant domains of human antibodies (Chimeric antibodies) or building the antigen binding loops (CDRs) of rodent antibodies into a human antibody (CDR grafting) have both been shown to greatly decrease the immunogenicity of the rodent antibody in preclinical studies in monkeys and in patients. Even CDR grated antibodies incorporate a large number (>50) of amino acids from the rodent antibody sequence into the human framework. Despite this in monkeys and patients greatly reduced immunogenicity has been reported. This provides evidence that mutating a very limited number of amino acids in the catalytic site of a host enzyme is likely to result in an enzyme with minimal immunogenicity and certainly lower immunogenicity than a non-host enzyme. The reader is directed to the following references: A. Mountain and J. R. Adair. Biotechnology and Genetic Engineering Reviews 10, 1–142, 1992; G. Winter and W. J. Harris, Trends in Pharmacological Sciences, 14, 139–143, 1993; I. I. Singer et al. J. Immunol. 150, 2844–57, 1993; J. Hakimi et al. J. Immunol, 147, 11352–59, 1991 and; J. D. Isacs et al, The Lancet, 340, 748–752, 1992. The constant region domains may be for example human IgA, IgE, IgG or IgM domains. Human IgG2 and 3 (especially IgG2) are preferred by IgG 1 and 4 isotypes may also be used. Human antibodies per se may also be used such as those generated in mice engineered to produce human antibodies.

The host enzyme is mutated (by any suitable method such as for example chemical or biotechnological gene synthesis or targeted mutation) to give a change in mode of interaction between enzyme active site and prodrug compared with the native host enzyme.

Preferably the enzyme mutation is a polarity change in its active site such that it turns over a prodrug with a complementary polarity; the prodrug not being significantly turned over by the unmutated host enzyme. Preferably the natural host enzyme recognises its natural substrate by an ion pair interaction and this interaction is reversed in the design of mutated enzyme and complementary prodrug. Preferably the enzyme is mutated ribonuclease, especially human ribonuclease with reversed polarity (see FIGS. 12–15).

Lysine 66 in human ribonuclease is a positively charged residue which interacts with negatively charged phosphate groups on the natural RNA substrate for the enzyme. The polarity of this residue is reversed for example by genetic engineering (but chemical synthesis is also contemplated) to give a negatively charged residue such as glutamic acid. The resulting 'reversed polarity' enzyme recognises the prodrugs of the present invention which are not significantly recognised by the unmutated host enzyme. Further alternations to residues in the native site region are contemplated to optimise substrate binding the turnover characteristics. Engineered forms of the ribonuclease enzyme represent a further aspect of the present invention. Ribonuclease is an advantageous enzyme due to its low molecular weight (approx. 13600 Da: allowing good tumour penetration after administration) and good stability to heat stress and proteolysis. Preferably the prodrug is a mustard-ribonucleotide of Formula 1 as set out in FIG. 11 wherein:

Q is O or NH (especially NH);

A is a group of formula —X—Y— wherein

Y is $SO_2$, CO or a single bond (preferably CO) with the proviso that when O is oxygen then Y is not $SO_2$;

X is —$(CH_2)_n$— where n=1–4 (preferably n=1 except when Y is a single bond then n is preferably 2) optionally substituted by $C_{1-4}$ alkyl on any carbon atom (R and/or S configurations are contemplated at any chiral atom) or when Y is CO and n=1 then X is optionally substituted on carbon with the side chain of alanine, valine, leucine, isoleucine, methionine, phenylalanine, tryptophan, serine, threonine, cysteine, asparagine, glutamine, lysine, arginine or histidine (R and/or S configurations are contemplated at any chiral atom);

R1 is uracil or cytosine as shown in FIG. 11;

R2 and R3 independently represent H or $C_{1-4}$ alkyl (preferably methyl and especially $R^2=R^3=H$);

R5 and R6 independently represents Cl, mesyl or tosyl (preferably R5=R6=Cl);

R7, R8, R9 and R10 independently represent H, $C_{1-4}$ alkyl (preferably methyl), $C_{1-4}$ alkoxy (preferably methoxy), F or Cl (preferably Cl) and the preferred positions for representing radicals other than H are R8 & R9 but R7=R8=R9=R10=H is especially preferred.

In a preferred embodiment the mustard ribonucleotide is one in which:

Q is NH;

X is —$(CH_2)_n$— where n is 1–4;

Y is —C(O)—;

R1 is uracil or cytosine;

R2 and R3 is H;

R5 and R6 are Cl; and

R7, R8, R9 and R10 are H;

or a salt thereof.

The following individualised compound is especially preferred; O-[(2R,3S,4R,5R)-2-(2-aminoacetamidomethyl)-5-(2,4-dioxo-1,2,3,4-tetrahydropyrimidin-1-yl)-4-hydroxy-2,3,4,5-tetrahydrofuran-3-yl]O-[4-(bis[2-chloroethyl]amino) phenyl] hydrogen phosphate which is shown as the end product in FIG. 7.

Another preferred compound is the cytosine analogue of the end product of FIG. 7.

In this specification the generic term "alkyl" includes both straight-chain and branched-chain alkyl groups. However references to individual alkyl groups such as "propyl" are specific for the straight-chain version only and references to individual branched-chain alkyl groups such as "isopropyl" are specific for the branched-chain version only. An analogous convention applies to other generic terms.

It is to be understood that, insofar as certain of the compounds of Formula 1 may exist in optically active or racemic forms by virtue of one or more asymmetric carbon atoms, the invention includes in its definition any such optically active or racemic form which possesses the property of being a substrate for mutant enzymes of the invention.

They synthesis of optically active forms may be carried out by standard techniques of organic chemistry well known in the art, for example by synthesis from optically active starting materials or by resolution of a racemic form. Similarly, substrate properties against mutant enzymes may be evaluated using standard laboratory techniques.

Point mutations will be referred to as follows: natural amino acid (using the 1 letter nomenclature), position, new amino acid. For example "D253K" means that at position 253 an aspartic acid (D) has been changed to lysine (K). Multiple mutations in one enzyme will be shown between square brackets.

In this specification the term CPB includes the following:
i) mature, pro and prepro forms of the enzyme with or without "tags" (eg c-myc);
ii) any carboxypeptidase with specificity for peptidic substrates having Lys or Arg at the C terminus;

pancreatic and plasma CPB enzymes (the pancreatic enzyme is preferred);

unless indicated otherwise or self evident from the context.

Mutant CPBs of the invention are mutants of any of the above CPBs having the desired property required for the invention. The following mutants of pancreatic HCPB are preferred: D253K, D253R and; especially [G251N.D253R]; corresponding mutations in other CPBs are also contemplated. A mutant CPB of the invention may also comprise other "conservative" mutations (insertions, substitutions and/or deletions) that do not significantly alter the properties of the key mutation. For the purposes of this document a conservative amino acid substitution is a substitution whose probability of occurring in nature is greater than ten times the probability of that substitution occurring by chance (as defined by the computational methods described by Dayhoff et al, Atlas Protein Sequence and Structure, 1971, page 95–96 and FIGS. 9–10).

References on CPBs include the following: Folk J E in The Enzymes Vol III, Academic Press (1971), pg 57; Coll M et al (1991) EMBO Journal 10, 1–9; Eaton D L et al (1991) J Biol Chem 266, 21833–21838; Yamamoto K et al (1992) J Biol Chem 267, 2575–2581; U.S. Pat. No. 5,364,934 (Genentech) and; International Patent Application WO 95/14096 (Eli Lilly).

The compounds of this invention may form salts with various inorganic and organic acids and bases which are also within the scope of the invention. Such salts include ammonium salts, alkali metal salts like sodium and potassium salts, alkaline earth metal salts like the calcium and magnesium salts, salts with organic bases; e.g. dicyclohexylamine salts, N-methyl-D-glucamine, salts with amino acids like arginine, lysine, and the like. Also, salts with organic and inorganic acids may be prepared; e.g., HCl, HBr, $H_2SO_4$, $H_3PO_4$, methanesulfonic, toluenesulfonic, maleic, fumaric and camphorsulfonic. Non-toxic physiologically acceptable salts are preferred, although other salts are also useful; e.g., in isolating or purifying the product.

The salts can be formed by conventional means such as by reacting the free acid or free base forms of the product with one or more equivalents of the appropriate base or acid in a solvent or medium in which the salt is insoluble, or in a solvent such as water which is then removed in vacuo or by freeze-drying or by exchanging the cations of an existing salt for another cation on a suitable ion exchange resin. The compounds of this invention may be utilized in compositions such as tablets, capsules or elixirs for oral administration, suppositories for rectal administration, sterile solutions or suspensions for parenteral or intramuscular administration, and the like.

The compounds of this invention can be administered to patients (animals and humans) in need of such treatment in dosages that will provide optimal pharmaceutical efficacy. Although the dose will vary from patient to patient depending upon the nature and severity of disease, the patient's weight, special diets then being followed by a patient, concurrent medication, and other factors which those skilled in the art will recognize, the dosage range will generally be about 1 to 4000 mg. per patient per day which can be administered in single or multiple doses. Preferably, the dosage range will be about 100 to 400 mg. per patient per day; more preferably about 500 to 3000 mg. per patient per day.

The most effective mode of administration and dosage regimen for the conjugates and prodrugs of this invention in cancer therapy depend on a number of factors such as the severity of disease, the patient's health and response to treatment and the judgement of the treating physician. Accordingly the dosages of the conjugates and prodrugs should be titred to the individual patients. Nevertheless, an effective dose of conjugate is likely to be in the range of 20 to about 200 mg/m$^2$. The effective dose of the prodrug will depend on the particular drug used and the toxicity of the parent drug. Since the prodrug is less cytotoxic than the parent drug the MTD of the parent drug, if known, would provide a starting point. For phenol mustard based prodrugs where clinical data are not available on the parent drug the therapeutic dose range is less certain and would need to be defined by standard animal toxicology studies and dose escalation studies in patients starting at a low dose. However the therapeutic dose is generally in the range 500–2000 mg/m$^2$.

Naturally, these dose ranges can be adjusted on a unit basis as necessary to permit divided daily dosage and, as noted above, the dose will vary depending on the nature and severity of the disease, weight of patient, special diets and other factors.

Typically, these combinations can be formulated into pharmaceutical compositions as discussed below.

About 1 to 100 mg. of compound or mixture of compounds of Formula 1 or a physiologically acceptable salt thereof is compounded with a physiologically acceptable vehicle, carrier, excipient, binder, preservative, stabilizer, flavor, etc., in a unit dosage form as called for by accepted pharmaceutically practice. The amount of active substance in these compositions or preparations is such that a suitable dosage in the range indicated is obtained.

Illustrative of the adjuvants which can be incorporated in tablets, capsules and the like are the following: a binder such as gum tragacanth, acacia, corn starch or gelatin; an excipient such as microcrystalline cellulose; a disintegrating agent such as corn starch, pregelatinized starch, alginic acid and the like; a lubricant such as magnesium stearate; a sweetening agent such as sucrose, lactose or saccharin; a flavoring agent such as peppermint, oil of wintergreen or cherry. When the dosage unit form is a capsule, it may contain, in addition to materials of the above type, a liquid carrier such as fatty oil. Various other materials may be present as coatings or to otherwise modify the physical form of the dosage unit. For instance, tablets may be coated with shellac, sugar or both. A syrup or elixir may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a vehicle such as water for injection, a naturally occuring vegetable oil like sesame oil, coconut oil, peanut oil, cottonseed oil, etc., or a synthetic fatty vehicle like ethyl oleate or the like. Buffers, preservatives, antioxidants and the like can be incorporated as required.

According to another aspect of the present invention there is provided a system as herein defined for use in a method of controlling the growth of neoplastic cells in a host in which the method comprises administration to said host an effective amount of a first component, allowing the first component to clear substantially from the general circulation, and administering an effective amount of a second component. Preferably the components are administered intravenously.

According to another aspect of the present invention there is provided a method of controlling the growth of neoplastic cells in a host in which the method comprises administration to said host an effective amount of a first component as defined above, allowing the first component to clear substantially from general circulation in the host, and administering an effective amount of a second component as defined above.

According to another aspect of the present invention there is provided a pharmaceutical composition comprising an effective tumour localising amount of a first component as herein defined and a pharmaceutically acceptable carrier or diluent. Preferably the composition is suitable for intravenous administration. Preferably the first component is supplied as a dry solid which is reconstituted before use with a suitable diluent.

According to another aspect of the present invention there is provided a pharmaceutical composition comprising an effective antitumour amount of a second component as defined herein and a pharmaceutically acceptable carrier or diluent. Preferably the composition is suitable for intravenous administration. Preferably the second component is supplied as a dry solid which is reconstituted before use with a suitable diluent.

According to another aspect of the present invention there is provided a pharmaceutical composition comprising a first component as defined above.

According to another aspect of the present invention there is provided a pharmaceutical composition comprising a second component as defined above.

Preferred pharmaceutical compositions are sterile (for intravenous administration).

According to another aspect of the present invention there is provided a first component as defined above.

According to another aspect of the present invention there is provided a mutated enzyme as defined above.

According to another aspect of the present invention there is provided plasmid pQR162. Plasmid pQR162 was deposited as deposit reference NCIMB 40678 at NCIMB Limited, 23 St Machar Drive, Aberdeen AB2 1RY, Scotland, UK under the Budapest Treaty on $16^{th}$ Aug. 1994.

E. coli MSD 1646 containing pCG330 (also known as pICI1698) was deposited under the Budapest Treaty on $23^{rd}$ Nov. 1994 with the National Collection of Industrial and Marine Bacteria (NCIMB), 23 St Machar Drive, Aberdeen, Scotland, United Kingdom AB2 1RY: the accession number is NCIMB 40694. NCIMB 40694 is another aspect of the present invention.

Antibody A5B7 was deposited as hybridoma deposit reference 93071411 under the Budapest Treaty on $14^{th}$ July 1993 at ECACC, PHLS Centre for Applied Microbiology & Research, Porton Down, Salisbury, Wiltshire SP4 OJG, UK. A humanised antibody A5B7 in the form of a $F(ab')_2$ is preferred.

Further antibodies useful in ADEPT have been described as follows: Antibody BW 431/26 was described in Haisma, H. J. et al., Cancer Immunol. Immunother., 34: 343–348 (1992). Antibodies L6, 96.5, and 1F5 were described in European Patent 302 473. Antibody 16.88 was described in International Patent Application WO90/07929. Antibody B72.3 was described in European Patent No. 392 745. Antibody CEM231 was described in European Patent No. 382 411. Antibodies HMFG-1 and HMFG-11 (Unipath Ltd. Basingstoke, Hants, United Kingdom) react with a mucin-like glycoprotein molecule on milk fat globule membranes and may be used to target breast and ovarian cancers. Antibody SM3 (Chemicon International Ltd. London, United Kingdom) reacts with core protein of mucin and may be used to target breast and ovarian cancer. Antibodies 85A12 (Unipath Ltd, Basingstoke, Hants, United Kingdom) and ZCEA1 (Pierce Chemical Company, Chester, United Kingdom) react with tumour antigen CEA. Antibody PR4D1 (Serotec, Oxford, United Kingdom) reacts with a colon tumour associated antigen. Antibody E29 (Dako Ltd, High Wycombe, United Kingdom) reacts with epithelial membrane antigen. Antibody C242 is available from CANAG Diagnostics, Gothenberg, Sweden. The reader is also referred to Table 3 on page 208 in International patent application WO 95/13095 (Wellcome) which includes data on various antibodies.

Generally, antibodies useful in ADEPT are poorly internalised by the tumour cells they recognise. This allows the targeted prodrug-activating enzyme to be resident on the cell surface and thus generate active drug at the tumour site from circulating prodrug. Internalisation of antibody may be assayed by known techniques, for example as set out in Jafrezou et al., Cancer Research 52: 1352 (1992) and in Press et al., Cancer Research, 48: 2249 (1988).

Another utility of the present invention is in the use of the first and second components in in vitro diagnostics. For example detection of a particular antigen may be achieved by exposing a diagnostic sample to a first component of the invention comprising a targeting moiety such as an antibody capable of binding with the antigen. Thereafter unbound first component can be removed, for example by washing, then the amount of bound first component can be quantitated by its ability to catalyse turnover of a second component prodrug. Turnover of prodrug can be quantitated by any suitable means such as HPLC. The reader is referred to A Practical Guide to ELISA by D. M. Kemeny, Pergamon Press 1991.

According to another aspect of the present invention there is provided a recombinant murine $F(ab')_2$ fragment of antibody A5B7 wherein the fragment contains 3 inter-chain disulphide bonds between heave chains at the hinge region.

According to another aspect of the present invention there is provided a recombinant murine $F(ab')_2$ fragment of antibody A5B7 having the sequence set out in SEQ ID NO: 25 & 26 for heavy and light chain respectively. Sutter et al in Gene 113 (1992) 223–230 teaches that it is necessary to introduce additional cysteines in the hinge region of the antibody to obtain good dimer formation in recombinant production. Recombinantly produced fragment is distinguished from proteolytically produced material by the absence of whole antibody contaminants. Recombinantly produced material may also have a higher binding affinity for CEA antigen as determined by a Pharmacia Biacore™ instrument.

According to another aspect of the present invention there is provided a method of making a first component as herein described by linking:

a targeting moiety capable of binding with a tumour associated antigen and an enzyme capable of converting a prodrug into an antineoplastic drug wherein the enzyme is a mutated form of a host enzyme. The mutated enzyme and targeting moiety may be linked by conventional methods known in the art such as for example by heterobifunctional reagents. Gene fusion is also contemplated.

The mutated enzyme and targeting moiety may be may be prepared by expression technologies known in the art. Some expression systems involve transforming a host cell with a vector; such systems are well known such as for example in E. coli, yeast and mammalian hosts (see Methods in Enzymology 185, Academic Press 1990). Other systems of expression are also contemplated such as for example transgenic non-human mammals in which the gene of interest, preferably cut our from a vector but with a mammary promoter to direct expressed protein into the animal's milk, is introduced into the pronucleus of a mammalian zygote (usually by microinjection into one of the two nuclei (usually the male nucleus) in the pronucleus) and thereafter implanted into a foster mother. A proportion of the animals produced by the foster mother will carry and express the introduced gene which has integrated into a chromosome. Usually the integrated gene is passed on to offspring by conventional breeding thus allowing ready expansion of stock. Preferably the protein of interest is simply harvested from the milk of female transgenic animals. The reader is directed to the following publications: Simons et al, (1988), Bio/Technology 6:179–183; Wright et al. (1991) Bio/Technology 9:830–834; U.S. Pat. No. 4,873,191 and; U.S. Pat. No. 5,322,775. Manipulation of mouse embryos is described in Hogan et al, "Manipulating the Mouse Embryo; A Laboratory Manual", Cold Spring Harbor Laboratory 1986.

Transgenic plant technology is also contemplated such as for example described in the following publications: Swain W. F. (1991) TIBTECH 9: 107–109; Ma J. K. C. et al (1994) Eur. J. Immunology 24: 131–138; Hiatt A. et al (1992) FEBS Letters 307:71–75; Hein M. B. et al (1991) Biotechnology Progress 7: 455–461; Duering K. (1990) Plant Molecular Biology 15: 281–294.

If desired, host genes can be inactivated or modified using standard procedures as outlined briefly below and as described for example in "Gene Targeting; A Practical Approach", IRL Press 1993. The target gene (or portion thereof) is preferably cloned into a vector with a selection marker (such as Neo) inserted into the gene to disrupt its function. The vector is linearised then transformed (usually by electroporation) into embryonic stem (ES) cells (eg derived from a 129/Ola strain of mouse) and thereafter homologous recombination events take place in a proportion of the stem cells. The stem cells containing the gene disruption are expanded and injected into a blastocyst (such as for example from a C57BL/6J mouse) and implanted into a foster mother for development. Chimeric offspring can be identified by coat colour markers. Chimeras are bread to ascertain the contribution of the ES cells to the germ line by mating to mice with genetic markers which allow a distinction to be made between ES derived and host blastocyst derived gametes. Half of the ES cell derived gametes will carry the gene modification. Offspring are screened (eg by Southern blotting) to identify those with a gene disruption (about 50% of progeny). These selected offspring will be heterozygous and therefore can be bred with another heterozygote and homozygous offspring selected thereafter (about 25% of progeny). Transgenic animals with a gene knockout can be crossed with transgenic animals produced by known techniques such as microinjection of DNA into pronuclei, sphaeroplast fusion (Jakobovits et al. (1993) Nature 362:255–258) or lipid mediated transfection (Lamb et al. (1993) Nature Genetics 5 22–29) of ES cells to yield transgenic animals with an endogenous gene knockout and foreign gene replacement.

ES cells containing a targeted gene disruption can be further modified by transforming with the target gene sequence containing a specific alteration, which is preferably cloned into a vector and linearised prior to transformation. Following homologous recombination the altered gene is introduced into the genome. These embryonic stem cells can subsequently be used to create transgenics as described above.

The term "host cell" in this context includes any procaryotic or eucaryotic cell suitable for expression technology such as for example bacteria, yeasts, plant cells and non-human mammalian zygotes, oocytes, blastocysts, embryonic stem cells and any other suitable cells for transgenic technology. If the context so permits the term "host cell" also includes a transgenic plant or non-human mammal developed from transformed non-human mammalian zygotes, oocytes, blastocysts, embryonic stem cells, plant cells and any other suitable cells for transgenic technology.

According to another aspect of the present invention there is provided a polynucleotide sequence selected from a polynucleotide sequence encoding any of the following:

any first component as defined above; and any mutated enzyme as defined above.

According to another aspect of the present invention there is provided a vector comprising a polynucleotide as defined above.

According to another aspect of the present invention there is provided a cell comprising a polynucleotide as defined above.

BRIEF DESCRIPTION OF THE DRAWINGS

The invention will now be illustrated in the following examples in which:

FIG. 8 depicts oligonucleotide primers FIG. 9 depicts a scheme for synthesis of a uracil based prodrug analogue FIG. 10 depicts a scheme for synthesis of a cytidine based prodrug analogue FIG. 11 depicts chemical formulas

FIG. 13 is a schematic diagram of a prodrug in the active site of a reversed polarity mutant enzyme wherein:

\* represents a reversed polarity residue (Lys 66 in native ribonuclease) and;

X is a positively charged group (attached by reversed polarity residue)

Figure 14:
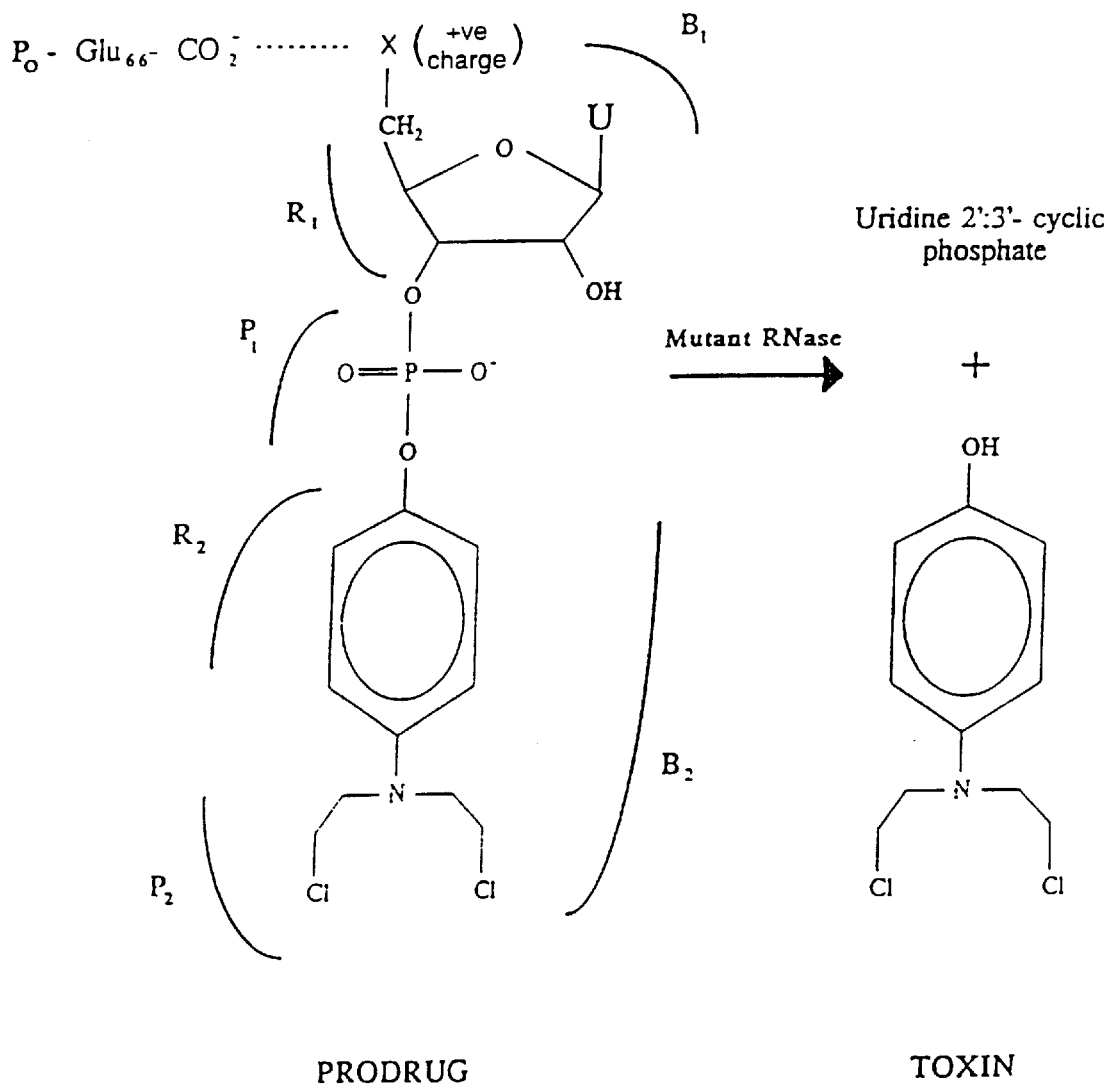

FIG. 14 illustrates cleavage of prodrug by reversed polarity mutant enzyme

FIG. 15 demonstrates the mechanism of action of native human RNase

FIG. 16 depicts the structure of CpA & C>p RNase substrates

Figure 17:
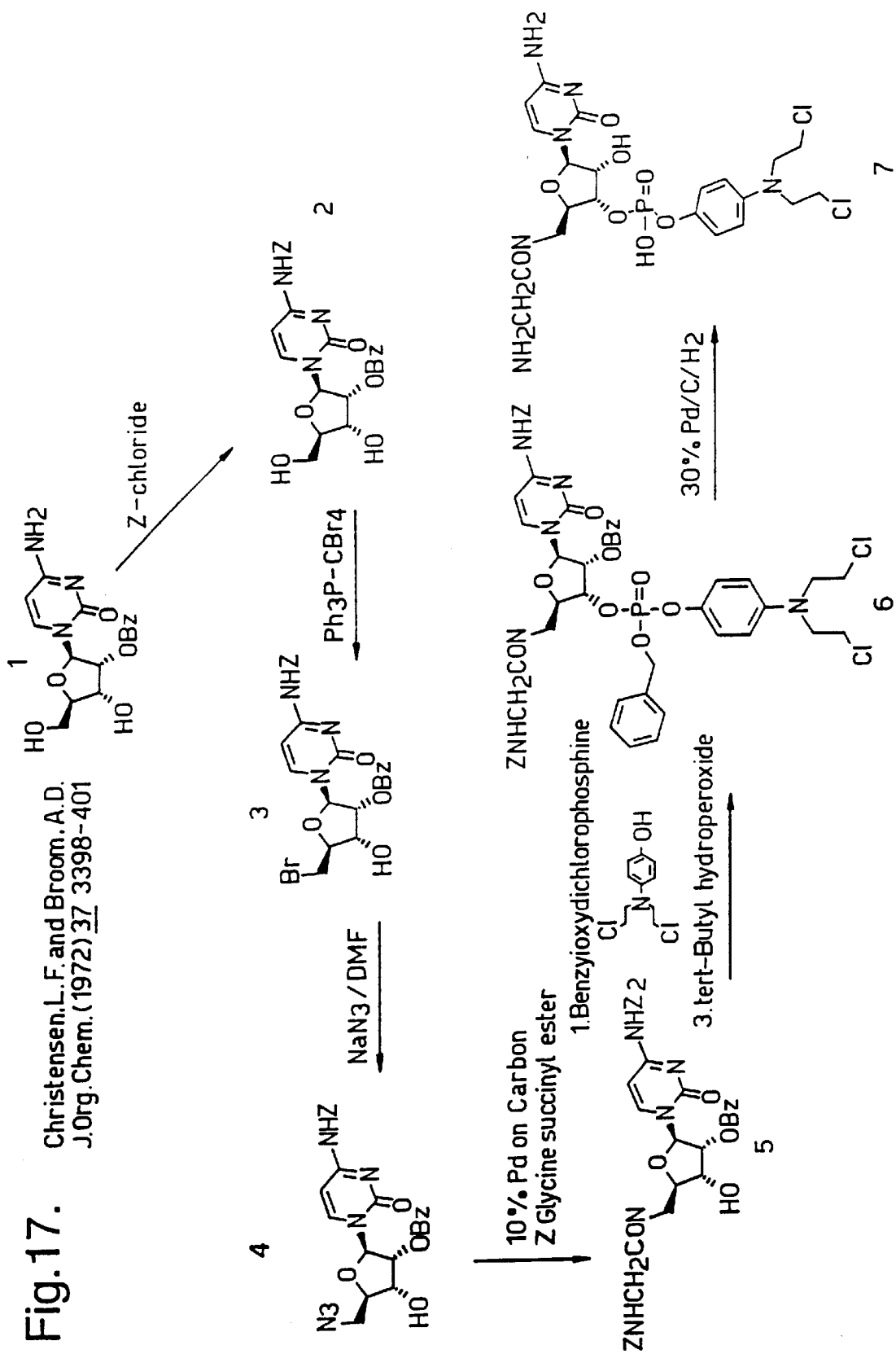

FIG. 17 depicts a scheme for synthesis of a Cytosine based prodrug

Figure 18:
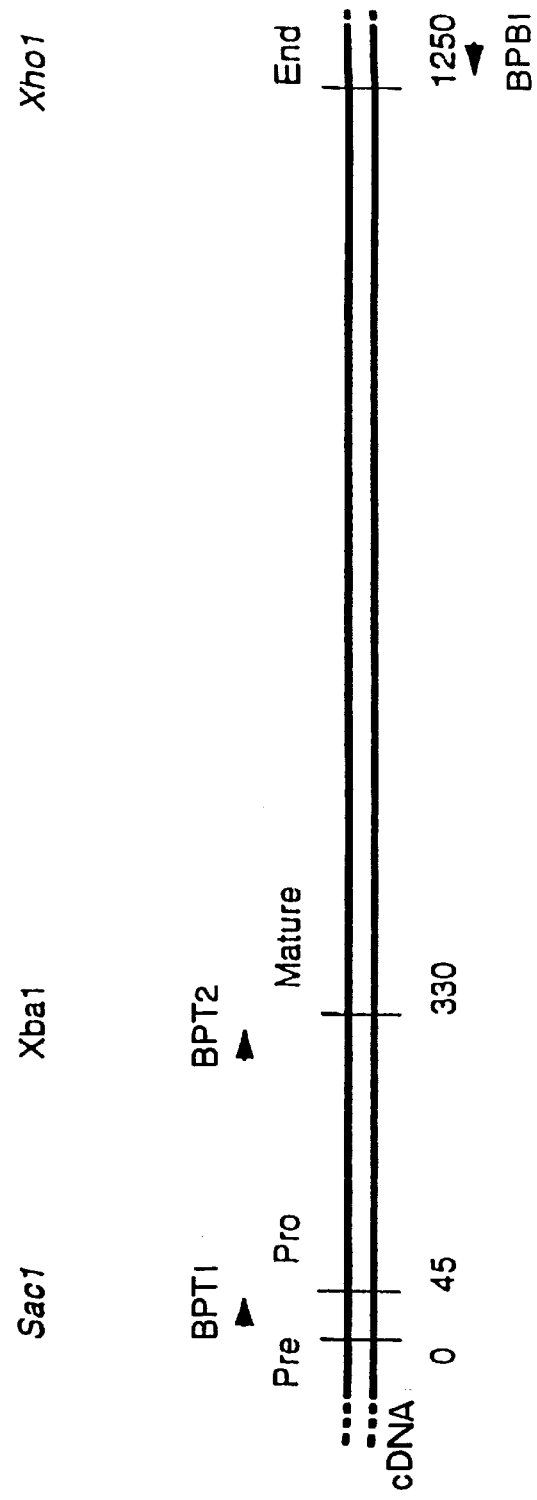

FIG. 18 illustrates pancreatic HCPB cloning.

Figure 19:
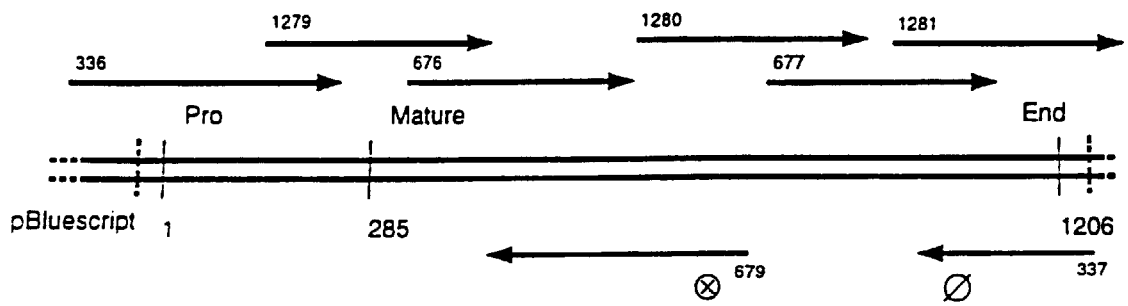

FIG. 19 illustrates pancreatic HCPB sequencing.

Figure 20:
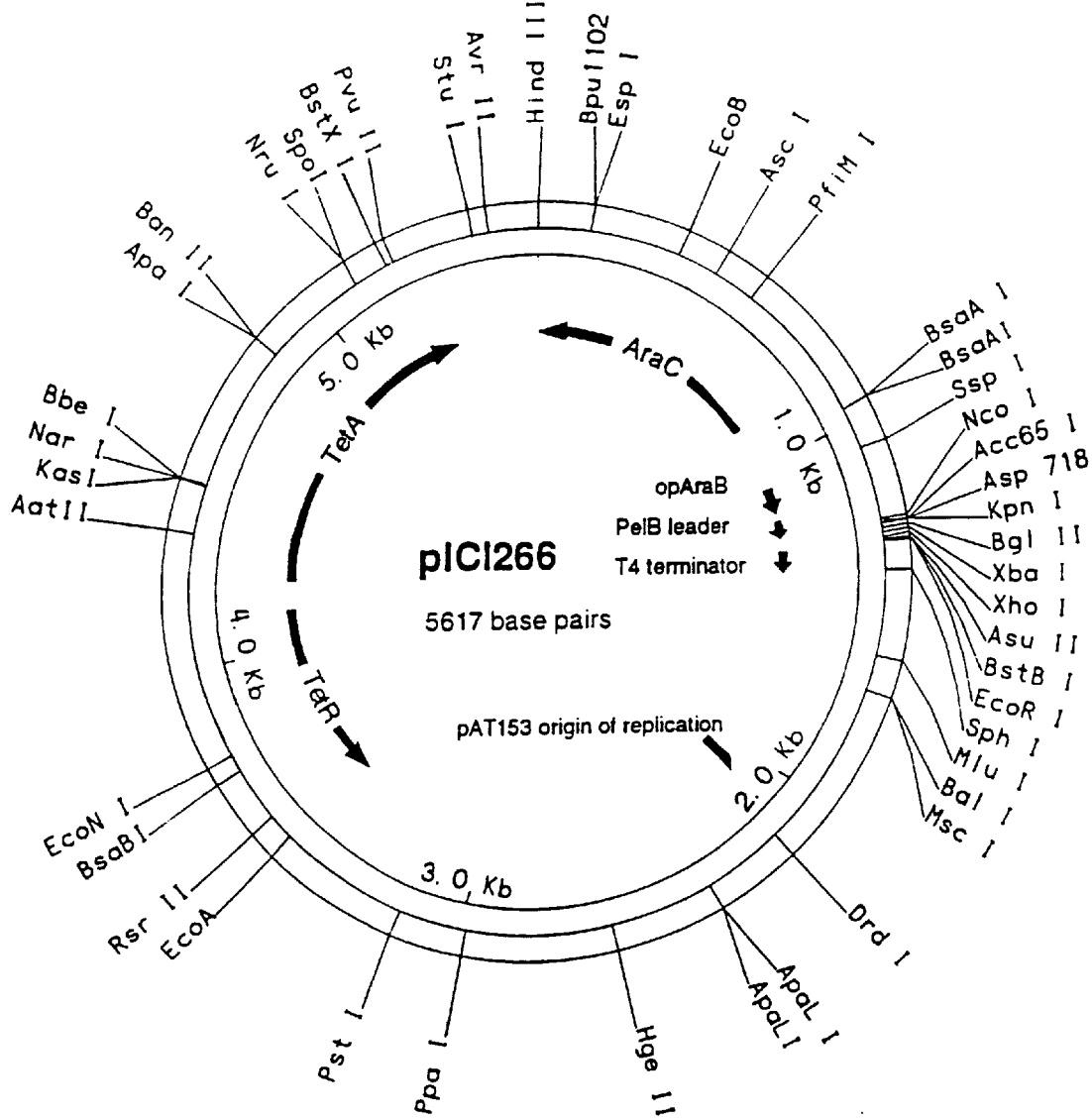

FIG. 20 illustrates vector pICI1266.

FIG. 21 illustrates pICI1266 expression vector gene cloning.

FIG. 22 illustrates cytotoxicity of a prodrug and corresponding drug.

FIG. 23 lists the composition of a growth medium.

Figure 24:
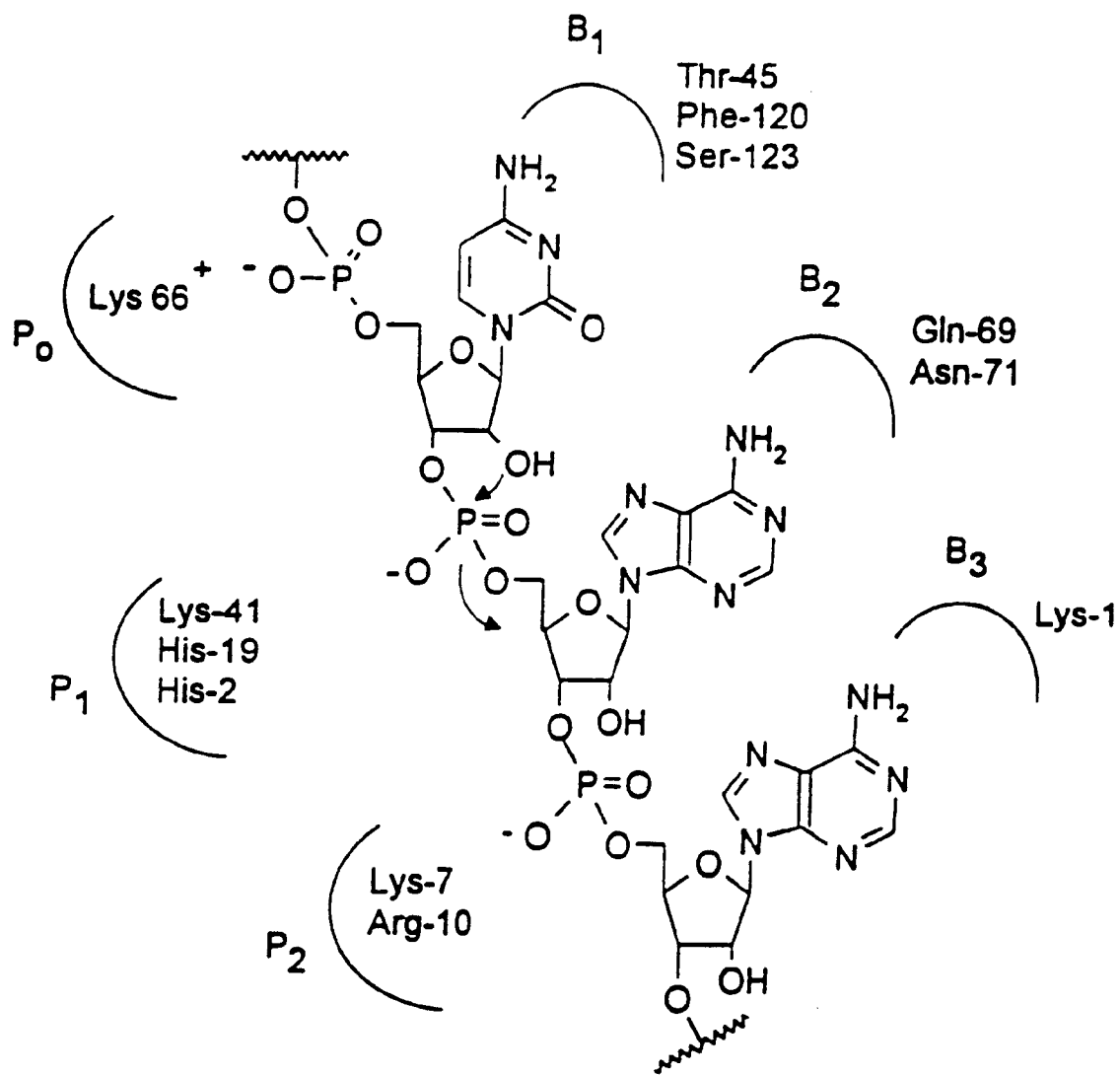

FIG. 24 is a diagram representing the key amino acid interactions between native ribonuclease and a fragment of ribonucleic acid. The positively charged Lys66 at position $P_O$ is shown making an ionic interaction with the negatively charged phospho-diester bond while residues at $P_1$ are important in the catalytic process.

Figure 25:
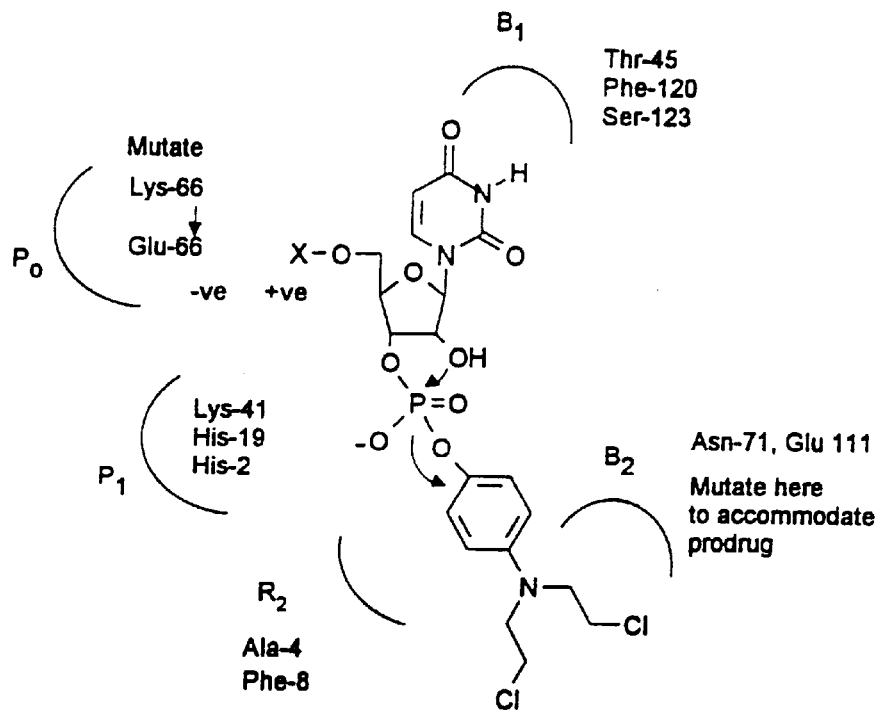

FIG. 25 depicts an interaction between a mustard prodrug and mutant RNAse. In order to avoid turnover by native RNAse the key amino acid at position 66 has been changed to a negatively charged glutamic acid. This Glu-66 makes an ionic interaction with the positively charged "X" moiety in the prodrug thus completing a reverse polarity interaction. It is envisaged that further mutations at positions $R_2$ and $B_2$ would lead to enhanced interaction with the prodrug.

Figure 26:
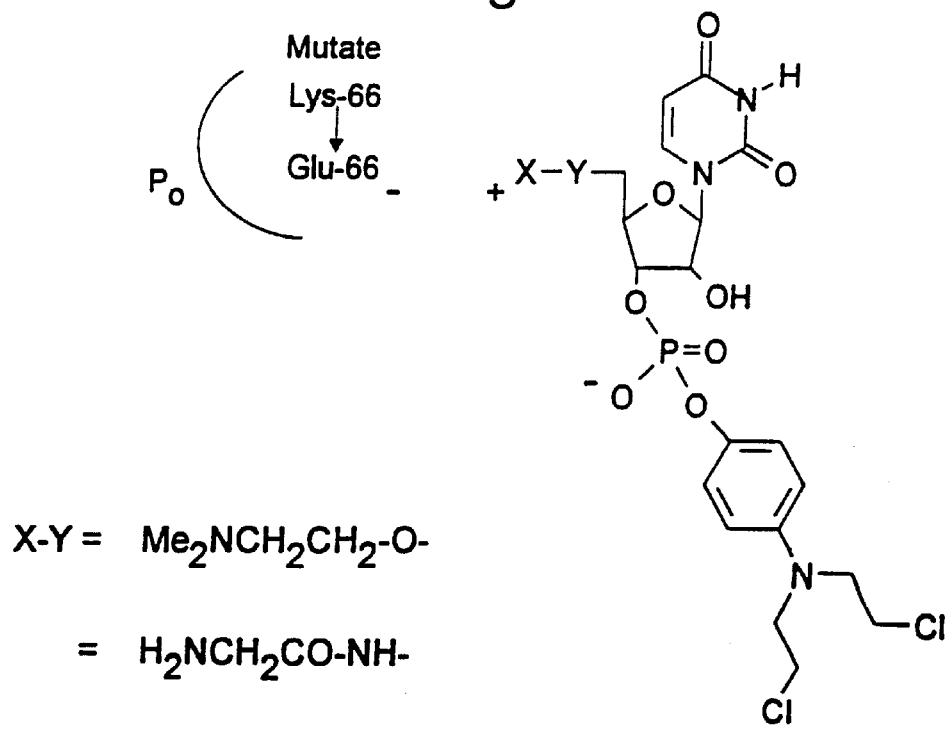

FIG. 26 shows two possible options for the positively charged moiety at position 5' of ribose to affect an interaction with Glu-66 at $P_O$.

FIGS. 27–33 illustrate chemical synthetic procedures.

DESCRIPTION OF THE PREFERRED EMBODIMENTS

Abbreviations

| Description of the Preferred Embodiments | |
|---|---|
| Ac | acetyl |
| ADEPT | antibody directed enzyme prodrug therapy |
| BOC | tert-butoxycarbonyl |
| BP-RNase | bovine pancreatic ribonuclease |
| CPB | carboxypeptidase B |
| DCCI | 1,3-dicyclohexylcarbodiimide |
| DMAP | 4-dimethylaminopyridine |
| DMF | N,N-dimethyl-formamide |
| DMSO | dimethylsulfoxide |
| Et | ethyl |
| EDCI | 1-(3-dimethylaminopropyl)-3-ethyl-carbodiimide |
| HCPB | human CPB |
| HOBT | 1-hydroxybenzotriazole |
| HP-RNase | human pancreatic ribonuclease |
| PCR | polymerase chain reaction |
| TFA | trifluoroacetic acid |
| THF | tetrahydrofuran |

Reference Example 1

Preparation of Recombinant Mature Bovine Pancreatic Ribonuclease

Recombinant bovine pancreatic ribonuclease was prepared from the coding sequence for the bovine pancreatic ribonuclease (BP-RNase) precursor as described by Tarragona-Fiol et al. in Gene (1992) 118, 239–245. The protein was expressed from E. coli under control of the tac promoter from a two cistron expression fragment in pQR163. A plasmid containing the two cistron fragment was designated pQR162 (NCIMB 40678).

Reference Example 2

Preparation of Arg4Ala,Lys6Ala Human Pancreatic Ribonuclease

The coding sequence for the human pancreatic ribonuclease (HP-RNase) gene was obtained from genomic DNA extracted from human buccal epithelial cells utilising the PCR technique as described by Tarragona-Fiol et al. in Protein and Peptide Letters (1994) 1, 76–83. For the preparation of HP-RNase expression of an engineered HP-RNase in E. coli was described. In order to direct the expression of the recombinant human pancreatic enzyme to the periplasmic space of E. coli, the bovine pancreatic RNase signal was fused 5' to the human gene. Initial attempts to express the recombinant enzyme were not successful. Consequently site-directed mutagenesis techniques were used to genetically engineer the HP-RNase gene to enable expression in E. coli. The resultant engineered enzyme shows similar kinetic characteristics to the homologous bovine enzyme.

(a) Cloning of the mature coding sequence for Arg4Ala, Lys6Ala HP-RNase

Restriction enzyme digestions, dephosphorylations, ligations, transformation and small scale plasmid DNA purification was carried out as described by Maniatis et al., (1982) Molecular Cloning. A Laboratory Manual. Cold Spring Harbour, Laboratory, Cold Spring harbour, New York. Oligonucleotides were synthesised using a Cyclone™ DNA synthesiser.

The mature sequence of the HP-RNase gene was obtained from genomic DNA extracted from buccal epithelial cells using the PCR technique. Briefly, epithelial cells were obtained by agitating vigorously 10 ml of 0.9% saline in the mouth for 20 seconds. The suspension of buccal epithelial cells (1.5 ml) was pelleted by centrifugation and resuspended in 100 µl of 10 mM NaCl. 10 mM EDTA. After a further centrifugation the cell pellet was resuspended in 75 µl of 20 mM NaOH and incubated at 100° C. for 30 minutes. The cell debris were pelleted and the supernatant was stored at −20° C. An aliquot (2–3 µl) was normally used as template in PCR incubations. Two primers (SEQ ID NO: 5 and SEQ ID NO: 6; see FIG. 8, primers 1 & 2) complementary to the 5'- and 3'-ends of the mature sequence of HP-RNase were used in a PCR incubation (5 pmol/each), which also contained; human genomic DNA, 0.2 mM dNTPs, Stratagene™ buffer (1×) [10× buffer is 200 mM Tris-HCl (pH 8.2). 100 mM KCl, 60 mM $(NH_4)_2SO_4$, 20 mM $MgCl_2$, 1% Triton™ X-100 and 100 µg/ml nuclease-free BSA] and 2.5 units of pfu polymerase (Stratagene). The PCR incubation was carried out using 30 cycles of denaturation at 92° C. for 30 sec. annealing at 55° C. for 30 sec and extension at 75° C. for 1 min. The resulting PCR products were analysed and separated by agarose gel electrophoresis. The DNA fragment of interest was excised from the agarose gel and the DNA extracted using centrifugal units (Spin-X™, Costar). In order to direct the expression of a complete recombinant enzyme into the periplasmic space of Escherichia coli JM107 cells, the signal sequence of bovine pancreatic RNase was fused to the 5'-end of the human gene, and the coding sequence for the last seven amino acids of HP-RNase plus a termination codon was attached to the 3'-end using the PCR technique. A PCR incubation was then set up containing this PCR derived mature sequence of the HP-RNase gene which lacks the coding sequence for the last 7 amino acids as template, a set of overlapping primers (SEQ ID NO: 7 to 10; see primers 3–6 in FIG. 8) at different concentrations (0.1, 0.5 and 50 pmol from the inner to the outermost primer), 0.2 mM nucleotides, Stratagene buffer (1×. see above) and 2.5 units of pfu polymerase (Stratagene). The incubation was carried out using the same conditions as described above. The PCR products were treated as described above and the fragment of interest excised and extracted from the agarose gel. This fragment was cleaved with EcoRI and ligated into previously digested and dephosphorylated pUC18 to enable double stranded DNA sequencing by the dideoxy 3). The fused gene was then ligated into the expression vector pKK223.3 3; see Example 1). The bovine signal sequence has incorporated a DNA sequence coding for a hexapeptide 5'- to the open reading frame. This is utilised to disrupt the secondary structure of the mRNA produced upon initiation of transcription of the promoter. Induction, expression and purification of the recombinant enzyme was carried out as described above. The analysis of periplasmic proteins obtained after this procedure revealed no product which exhibited recombinant RNase activity.

Figure 3:
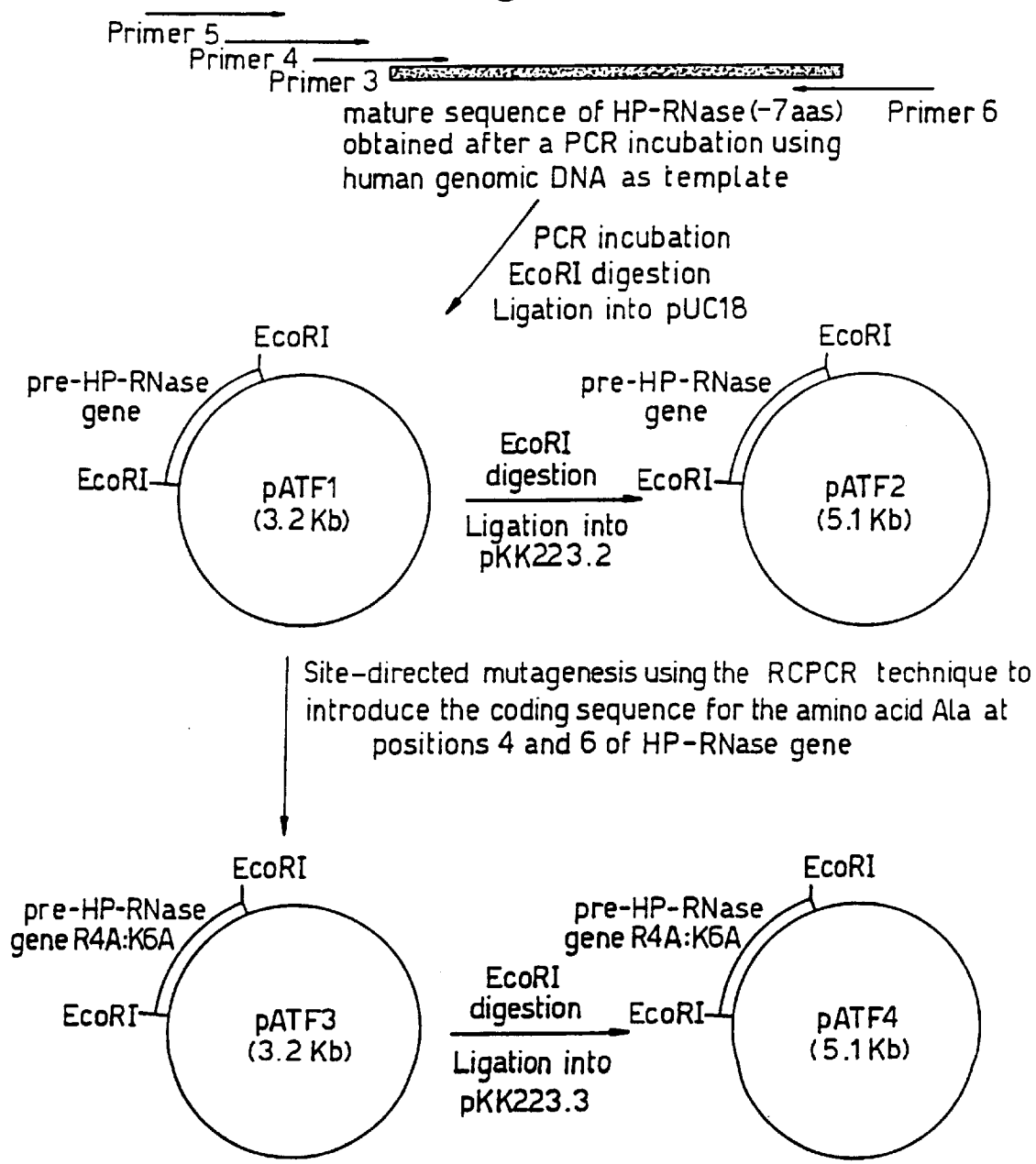
FIG. 3 depicts PCR strategies leading to plasmid pATF4. Primers 3–6 are used in a PCR reaction which (a) incorporates the bovine signal sequence plus the coding sequence for a hexapeptide 5' to the human pancreatic ribonuclease gene, and (b) the coding sequence for the last seven amino acids of the HP-RNase enzyme plus a termination codon. Primers 5 and 6 also incorporate restriction sites for EcoR1.

The lack of expression of the human enzyme in these experiments was unexpected since the bovine signal sequence has been used successfully to direct translocation of the recombinant bovine enzyme to the periplasmic space. Comparison of the N-terminal sequence of the native human and bovine enzymes show differences at positions 4 and 6 where alanine residues in the bovine enzyme are replaced by arginine and lysine residues respectively in the human counterpart. It is known that the presence of positive charged amino acids early in the mature sequence can act as stop transfer signals preventing further translocation. To overcome this problem a strategy was developed to replace the arginine and the lysine at positions 4 and 6 in the human enzyme with alanine residues. Thus the technique of RCPCR (primers used for the introduction of the desired mutation are SEQ ID NO: 11 to 14; see primers E–H in FIG. 8) was used to generate a recombinant clone pATF3 containing the required replacements (see FIG. 3). This plasmid chimera was used as template in double stranded DNA sequencing to verify the incorporation of the coding sequences for alanine residues at positions 4 and 6. Excision with EcoRI and ligation with pKK223.3 produced the chimeric expression vector pATF4 (FIG. 3) which was used to express the engineered human enzyme.

(b) Expression and purification of the recombinant Arg4Ala, Lys6Ala HP-RNase from *E. coli*

Figure 4:
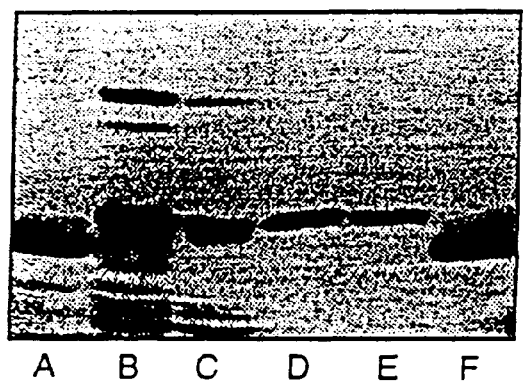
FIG. 4 depicts purity assessment of PAGE of expressed R4A.K6A human pancreatic RNase. Lanes A and F, 2 $\mu$g of RNase A; lanes B and C, different amounts of positively charged proteins from the periplasmic space of *E. coli* cells containing pATF4; lanes D and E, 1 $\mu$g, and 500 ng of the purified HP-RNase.

Transformation of *Escherichia coli* cells with pATF4 and IPTG induction results in the expression of the engineered recombinant human enzyme which is isolated from the periplasmic contents using protocols described above for the production of the homologous bovine enzyme. Engineered recombinant HP-RNase was isolated from the periplasmic contents and purified to homogeneity (see FIG. 4). N-terminus sequencing of the recombinant enzyme has been carried out and indicates that the bovine signal sequences has been cleaved correctly. This also verifies the replacement of Arg-4 and Lys-6 with alanines.

The kinetic characterisation was carried out using CpA and C>p as substrates (FIG. 16). The kinetic parameters Km, kcat, and kcat/Km were compared with the values obtained for commercial and recombinant bovine pancreatic RNase under the same assay conditions (see Tables). The data indicate that the kinetic properties of the engineered HP-RNase enzyme are not significantly different for the homologous bovine counterpart.

| | kcat/Km $(mM^{-1}/s^{-1})$ |
|---|---|
| Kinetic parameters of the different enzymes for CpA as substrate at pH 7.0 | |
| Rec. HP-RNase R4A:K6A | 1700 (480) |
| Rec. BP-RNase | 2800 (370) |
| BP-RNase | 2300 (600) |
| Kinetic parameters of the different enzymes for C > p as substrate at pH 7.0 | |
| Rec. HP-RNase R4A:K6A | 4.2 (0.8) |
| Rec. BP-RNase | 3.9 (0.9) |
| BP-RNase | 2.3 (0.5) |

(n) indicates standard error.

Reference Example 3
Synthesis and isolation of murine A5B7-bovine pancreatic ribonuclease conjugate A particular antibody capable of binding with a tumour associated antigen (CEA) and is particularly suitable for targeting colorectal carcinoma. A5B7 is available from DAKO Ltd., 16 Manor Courtyard, Hughenden Avenue, High Wycombe, Bucks HP13 5RE, England, United Kingdom. Antibody fragments can be prepared from whole IgG antibody by conventional means such as for example F(ab')$_2$ fragments as described by Mariani, M. et al (1991), Molecular Immunology 28, 69–77. In general the antibody (or antibody fragment)-enzyme conjugate should be at least divalent, that is to say capable of binding to at least 2 tumour associated antigens (which may be the same or different). Antibody molecules may be humanised by known methods such as for example by "CDR grafting" as disclosed in EP239400 or by grafting complete variable regions onto human constant regions as disclosed in U.S. Pat. No. 4,816, 567. Humanised antibodies may be useful for reducing immunogenicity of an antibody (or antibody fragment). A humanised version of antibody A5B7 has been disclosed in PCT WO92/01059.

The hybridoma which produces monoclonal antibody A5B7 was deposited with the European Collection of Animal Cell Cultures, Division of Biologics, PHLS Centre for Applied Microbiology and Research, Porton Down, Salisbury, Wiltshire SP4 OJG, United Kingdom. The date of deposit was Jul. 14, 1993 and the accession number is No. 93071411. Antibody A5B7 may be obtained from the deposited hybridoma using standard techniques known in the art such as documented in Fenge C, Fraune E & Schuegerl K in "Production of Biologicals from Animal Cells in Culture" (Spier R E, Griffiths J R & Meignier B, eds) Butterworth-Heinemann, 1991, 262–265 and Anderson B L & Gruenberg M L in "Commercial Production of Monoclonal Antibodies" (Seaver S. ed), Marcel Dekker, 1987, 175–195. The cells may require re-cloning from time to time by limiting dilution in order to maintain good levels of antibody production.

The linker used for derivitisation of murine A5B7 is SATA™ (S-acetyl thioglycollic acid N hydroxy succinimide ester), Sigma (product code A9043).

The linker used for bovine pancreatic ribonuclease (BP-RNase) derivatisation is SMPB (4-(p-maleimidophenyl) butyric acid N-hydroxysuccinimide ester), Sigma (product code M6139).

SATA (Sigma) was dissolved in DMSO (Fisons) at a concentration of 10 mg/ml. To a solution of 50 mg of A5B7 at 5.4 mg/ml in 100 mM phosphate/100 mM NaCl/1 mM EDTA pH7.2 (buffer A) was added 309 µg (30.9 µl) SATA solution (representing a 4 molar excess over A5B7), mixed and allowed to stand at room temperature for 40 mins. The resulting solution was passed down a Sephadex™ G25 column (Pharmacia) (210 ml 2.6×38 cm) to remove excess reagents at room temperature yielding a final concentration of 2.09 mg/ml of derivatised A5B7 (23.5 ml total volume). The SATA derivatised A5B7 was mixed with 1.0 ml 10% v/v 500 mM hydroxylamine HCl/500 mM sodium phosphate/30 mM EDTA pH8.0 to deacetylate the derivatised A5B7, the reaction proceeding for 40 mins at room temperature. The protein concentration was determined by UV absorbance at 280 nm assuming e=1.4 (or by Bradford Protein assay). The linker loading was determined by Ellmans-SH assay and found to be 1.2 linkers/mole A5B7.

BP-RNase (Sigma), was resuspended in 6.0 ml of 100 mM sodium phosphate/100 mM NaCl pH 7.2 (buffer B) to give a concentration of 8.33 mg/ml.

SMPB (Sigma) was dissolved in DMSO (Fisons) at a concentration of 10 mg/ml. A solution of 50 mg BP-RNase was mixed with 6500 mg (650 ml) of the SMPB solution (representing a 5 molar excess over BP-RNase) and allowed to stand at room temperature for 120 mins. Excess reagents were removed by gel permeation chromatography (Sephadex B25 210 ml 2.6×30 cm). The derivatised protein concentration was determined by UV A280 assuming e=0.6. The linker loading was determined by a 'reverse' Ellmans assay, by adding a known amount of 2-mercaptoethanol to the maleimido derivatised BP-RNase and assaying unreacted SH groups.

The conjugation reaction proceded by the addition of equal weights of the deacetylated derivatised A5B7 and derivatised BP-RNase and was diluted with deionised water to a concentration of 1.0 mg/ml and mixed under nitrogen. The reaction was allowed to proceed for 20 hrs at room temperature followed by termination by the addition of 1 mg/ml aqueous glycine.

The crude conjugation was buffer exchanged by dialysis into 50 mM Phosphate pH 8.0 (Buffer C) and the resulting solution applied to a Q Sepharose™ (Pharmacia) column (30 ml 1.6×15 cm) equilibrated in Buffer C. The column was washed in buffer C to remove excess A5B7 and BRNase followed by elution of the conjugate in 0.5M NaCl wash at a flow rate of 1 ml/min.

Purity of the resultant conjugate was determined by SDS-Page and contained a total of 5.75 mg conjugate with the composition 88.4% conjugate and 11.6% free derivatised A5B7 by laser densitometry.

Reference Example 4
Synthesis and isolation of murine A5B7 F(ab')$_2$-bovine pancreatic ribonuclease conjugate The linker used for A5B7 F(ab')$_2$ derivitisation is SATA (S-acetyl thioglycollic acid N hydroxy succinimide ester), Sigma (product code A9043).

The linker used for bovine pancreatic ribonuclease (BP-RNase) derivitisation is SMPB (4-(p-maleimidophenyl) butyric acid N-hydroxysuccinimide ester),Sigma (product code M6139).

SATA (Sigma) was dissolved in DMSO (Fisons) at a concentration of 10 mg/ml. To a solution of 18.20 mg of the F(ab')$_2$ fragment at 2.14 mg/ml in 100 mM phosphate/100 mM NaCl/1 mM EDTA pH7.2 (buffer A) was added 167 μg (16.7 μl) SATA solution [representing a 4 molar excess over A5B7 F(ab')$_2$], mixed and allowed to stand at room temperature for 40 mins. The resulting solution concentrated to 2.0 ml (9 mg/ml) via an Amicon YM10™ (100,000 MW cutoff) membrane followed by removal of excess reagents through a Sephadex G25™ column (Pharmacia) (50 ml 1.6×16 cm) at room temperature yielding a final concentration of 1.04 mg/ml of derivatised A5B7 F(ab')$_2$ (10 ml total volume). The SATA derivatised A5B7 F(ab')$_2$ was mixed with 1.0 ml 10% v/v 500 mM hydroxylamine HCl/500 mM sodium phosphate/30 mM EDTA pH8.0 to deacetylate the derivatised A5B7 F(ab')$_2$, the reaction proceeding for 40 mins at room temperature. The protein concentration was determined by UV absorbance at 280 nm assuming e=1.4 (or by Bradford Protein assay). The linker loading was determined by Ellmans-SH assay and found to be 1.2 linkers/mole Fab$_2$.

BP-RNase (Sigma), was resuspended in 2.0 ml of 100 mM sodium phosphate /100 mM NaCl pH 7.2 (buffer B) to give a concentration of 7.50 mg/ml.

SMPB (Sigma) was dissolved in DMSO (Fisons) at a concentration of 10 mg/ml. A solution of 15 mg BP-RNase was mixed with 1949 mg (1.95 ml) of the SMPB solution (representing a 5 molar excess over BP-RNase) and allowed to stand at room temperature for 120 mins. Excess reagents were removed by gel permeation chromatography (Sephadex G25 50 ml 1.6×16 cm). The derivatised protein concentration was determined by UV A280 assuming e=0.6. The linker loading was determined by a 'reverse' Ellmans assay, by adding a known among of 2-mercaptoethanol to the maleimido derivatised BRNase and assaying unreacted SH groups.

The conjugation reaction proceded by the addition of equal weights of the deacetylated derivatised A5B7 F(ab')$_2$ and derivatised A5B7 F(ab')$_2$ was diluted with deionised water to a concentration of 1.0 mg/ml and mixed under nitrogen. The reaction was allowed to proceed for 20 hrs at room temperature followed by termination by the addition of 1 mg/ml aqueous glycine.

The crude conjugation was buffer exchanged by dialysis into 50 mM Tris pH 8.0 (Buffer C) and 5 ml (6.5 mg) of the resulting solution applied to a Mono Q™ (HR5/5) (Pharmacia) column equilibrated in Buffer C. The column was washed in buffer C to remove excess A5B7 F(ab')$_2$ followed by elution of the conjugate and remaining BP-RNase in a salt gradient (0–0.1M over 20 column volumes) at a flow rate of 1 ml/min. Isolation of conjugate from residual enzyme was achieved by applying pooled fractions containing conjugate on to a S200™ GPC column (Pharmacia) (60 ml 1.6×30 cm) and running in PBS at a flow rate of 1 ml/min.

Purity of the resultant conjugate was determined by SDS-Page and contained a total of 0.70 mg conjugate with the composition 95.5% conjugate and 4.5% free derivatised A5B7 F(ab')$_2$ by laser densitometry.

Murine A5B7 F(ab')$_2$ was made as described in Reference Example 5, or by the following procedure:

The A5B7 antibody, described in Reference Example 3, (780 ml at 5.4 mg/ml) was prepared for digestion by diafiltration versus 7 volumes of 0.1M sodium phosphate, 3 mM EDTA(pH6.4), using an Amicon™ CH$_2$ spiral cartridge apparatus containing 1 30 KDa membrane. The material recovered (3682 mg estimated by ABS@280 nm) was 0.22 μM filtered and stored at 4° C. until use. Crystalline papain suspension (9 ml at 10 mg/ml; Boehringer Mannheim, product code (1080140) was mixed with 0.1M sodium phosphate, 3 mM EDTA (pH6.4) containing 100 mM L-cysteine and left for 30 minutes at 37° C. The excess cysteine was then removed by size exclusion chromatography (Pharmacia G25M™ column size 2.6 cm diameter, 30 cm length total volume approx 160 ml) using 0.1M sodium phosphate, 3 mM EDTA (pH6.4) run at 3 ml/min flow rate. Fractions (1 minute) were collected and monitored by OD280 and a simple DTNB spot test to ensure clearance from free cysteine prior to pooling of reduced papain pool. The concentration of the reduced papain pool was determined (by OD280 assuming E=2.5) as 1.65 mg/ml. volume 32.8 ml. total protein available 54 mg. The digestion was carried out using a 1/60 w/w ratio of reduced papain to A5B7 at 37° C. using all the available papain and 655 ml of the antibody (warmed to 37° C. prior to commencement of the digestion) and at an estimated protein concentration of 4.9 mg/ml. The reaction was quenched with 0.1× total reaction volume of 100 mM N-ethylmaleimide in 50% ethanol after 20 hours. The F(ab')$_2$ was purified from the Fc and trace undigested antibody using a 400 ml Protein A Sepharose FF™ (Pharmacia) column (dimensions 5 cm×20 cm) equilibrated with 25 mM sodium phosphate. 150 mM sodium chloride (pH7.33) until pH and conductivity matched that of the equilibration buffer (19.7 mS at 15° C.) The crude digest was diluted 1:1 with column buffer and split into 2 batches (660 ml and 840 ml) and each loaded at 6.5 ml/min (linear flow rate of 0.33 ml/cm2/min) onto a protein A column. 10 ml fractions were collected. Once loaded the column was washed with equilibration buffer until the absorbance @ 280 nm approached baseline. The initial wash consisted of 50 mM sodium acetate (pH 4.5) followed by an extended 50 mM sodium acetate (pH 4.0) wash then a 50 mM citric acid pH3.5 followed by a final 50 mM citric acid (pH2.8) wash. During the washes the OD280 values were measured and pools taken then neutralised within 30 minutes using disodium hydrogen orthophosphate solution (0.4M). Samples of the pools were analysed by SDS Page (Pharmacia Excel™ gel, coomassie stained). F(ab')$_2$ was eluted by the pH4.0 buffer and undigested A5B7 was eluted in the lowest pH washes. The F(ab')$_2$ pooled samples were diafiltered into 100 mM sodium phosphate. 100 mM sodium chloride, 1 mM EDTA (pH7.2).(Amicon™ CH2 30 KDa membrane, 7 volume diafiltration) and yielded a total of 845 mg F(ab')$_2$ (@ 2 mg/ml).

Reference Example 5

Preparation of recombinant murine A5B7 F(ab')$_2$ in myeloma cells.

This example describes the preparation of cDNA from the A5B7 hybridoma, the isolation of specific Fd and L chain fragments by PCR, determination of the complete DNA sequence of these fragments, the subsequent co-expression in myeloma cells to generate a recombinant F(ab')$_2$ fragment, fermentation of the myeloma cells and purification of the recombinant F(ab')$_2$ protein.

Several methods for production of genetically engineered antibodies in myeloma cells are described in the literature, including Neuberger et al. (1984) Nature 312, 604–608, Williams and Neuberger (1986) Gene 43, 318–324, Wright and Shin (1991) Methods 2, 125–135, Traunecker (1991) Trends in Biotechnology 9, 109–113 and Bebbington et al. (1992) Bio/Technology 10, 169–175. For convenience, this example will use essentially the procedure described by Bebbington et al. based on glutamine synthetase (GS) gene as a selective marker.

a) Preparation of mRNA from hybridoma cells

There are several procedures for the isolation of polyA+ mRNA from eukaryotic cells (Sambrook J., Fritsch E. R., Maniatis T., Molecular Cloning: A Laboratory Manual, Cold Spring Harbor Laboratory Press, Second Edition, 1989, Chapter 8 p3 hereinafter referred to as Maniatis). One such method is provided in kit form by Pharmacia and relies on the lysis of a relatively small number of cell ($10^7$ or less) followed by binding of polyA+mRNA to an oligo dT column. Unwanted cell components are removed by washing with a low salt concentration before eluting the mRNA in high salt solution at elevated temperature.

mRNA was prepared from $10^7$ A5B7 hybridoma cells using the Quickprep™ mRNA kit (Pharmacia Biotechnology Ltd.). The concentration of the mRNA was estimated by scanning a sample from 300–220 nm in a Uvikon 930 spectrophotometer (Kontron™ Instruments) and using a factor 40 µg/ml/unit OD at 260 nm. The mRNA was stored as 2.5 µg aliqouts precipitated in ethanol.

b) cDNA synthesis.

The method used for cDNA synthesis was based on that of Gubler and Hofman which relies on reverse transcription from primed mRNA followed by RNAse H treatment to provide priming and synthesis of the second strand by DNA polymerase I. Other methods for the synthesis of cDNA are reviewed in Maniatis (Chapter 8).

A 5 µg sample mRNA was primed with oligo dT (12–18 mer mixture, Pharmacia Biotechnology Ltd., 0.5 µg) in a 10 µl solution containing 2.5 u placental RNAse inhibitor (Life Technologies Ltd.) made up with RNAse-free water by incubating at 70° C. followed by cooling on ice. First strand cDNA synthesis was then performed by adding 4 µl 5× H-RT buffer (250 mM Tris, pH8.3, 200 mM KCl, 30 mM MgCl$_2$ and 0.5 mg/ml BSA), 2 µl 0.1M DTT (dithiothreitol), 1 µl dNTP mix (dATP, dCTP, dGTP and dTTP at 20 mM), 4 µl Superscript™ Reverse transcriptase (Life Technologies Ltd.) and incubating at 42° C. for 1 hour. For the second strand reaction, 1.5 µl dNTP mix (as above), 92.5 µl RNAse-free water, 30 µl 5× reaction buffer (125 mM Tris, pH7.5, 500 mM KCl, 25 mM MgCl$_2$, 50 mM (NH$_4$)$_2$SO$_4$ and 0.5 mg/ml β-NAD), 1 µl T4 DNA ligase (10 u, Life Technologies Ltd.), 4 µl DNA polymetrase I (40 u, Life Technologies Ltd.) and 1 µl RNase H (2.7 u, Life Technologies Ltd.) were added and incubation continued at 16° C. for a further 2 hours. To ensure that blunt-ended cDNA was prepared a final incubation at 16° C. for 5 minutes after 2 µl T4 DNA polymerase (10 u, Life Technologies Ltd.) was performed. Enzyme activity was then stopped by incubation at 70° C. for 10 minutes.

c) Isolation of antibody gene fragments by PCR

Isolation of A5B7 Fd and L chain fragments was performed using the cDNA as template. The Fd fragment was terminated immediately after the hinge sequence (c-terminal threonine) hereinafter referred to as proteolytic type Fd. By proteolytic Fd we mean in this example it is a recombinant Fd equivalent to a proteolytically produced Fd, described in Reference Example 4.

Material from the first-strand cDNA reaction or after completion of the second strand reaction is suitable as template. The material could be used neat from the completed reaction or as a dilution (up to 1 in 100) in double-distilled water. Oligonucleotides (SEQ ID NO numbers 17–24) were used in the generation of the Fd and L chain fragments. For each antibody fragment, the 5' region oligonucleotide (SEQ ID NO: 17 for Fd fragment and SEQ ID NO: 18 for the L chain) encoded a restriction enzyme site (HindIII for Fd and EcoRI for L chain) a consensus Kozak sequence (GCCGCCACC) to maximise translation initiation and a portion of the natural murine signal sequence. The 3' region oligonucleotide for the proteolytic type Fd fragment (SEQ ID NO: 19 was complementary to the 3' end of the antibody hinge region, encoded mutations to introduce tandem translation termination codons (TAG and TAA) immediately after the hinge and contained an EcoRI restriction enzyme site beyond this sequence. The 3' region of the L chain was determined by an oligonucleotide (SEQ ID NO: 20) complementary to the end of the coding region, introduced an additional translation termination codon (TAA) and an EcoRI restriction site. In addition pairs of partially overlapping and complementary oligonucleotides for each fragment (SEQ ID NO: 21 and 22 for the Fd and SEQ ID NO: 23 and 24 for the L chain) were used to introduce silent mutations into each DNA strand resulting in the removal of a BamHI from the CH1 of the Fd fragment and the VL of the L chain without altering the encoded amino-acid sequence. Each 5' and 3' oligonucleotide was used with the appropriate mutagenic oligonucleotide to generate 2 mutated fragments of each antibody chain. After purification the two fragments were mixed in equal proportions and used as the templates for a second PCR reaction using the relevant 5' and 3' region oligonucleotides. The products of these reactions were the full-length Fd and L chain fragments without internal BamHI sites.

In general, 5 µl of cDNA was added to a 100 µl reaction containing 10 mM Tris-HCl,pH 8.3, 50 mM KCl, 0.1% gelatin, 1.5 mM MgCl$_2$, 1.25 mM each of dATP, dCTP, dGTP and dTTP, 1 µM each of an appropriate oligo pair and 2.5 u Taq DNA polymerase (Amplitaq, Perkin-Elmer Cetus). Each reaction was overlaid with 100 μl mineral oil and incubated at 94° C. for 1.5 minutes, 50 or 55° C. for 1.0 minute and 72° C, for 2.0 minutes for 25 cycles plus 10 minutes at 72° C. Control reactions with no DNA were also set up.

The PCR reactions were analysed by running a 5 μl sample of each on a 0.8% agarose (Sigma Chemical Company Ltd.) gel which was subsequently stained in 1 μg/ml Ethidium Bromide (BDH Laboratory Supplied) solution and the DNA visualised on a UV transilluminator, Bands of the appropriate size were visible in all PCRs with A5B7 cDNA present indicating successful amplification of the fragments of the Fd and L chains. The absence of a DNA band in the control reactions indicted that the reagents used did not contain contaminating DNA.

Each PCR product was purified by use of a Centricon 100™ microconcentrator (Amicon Ltd.). Each reaction was added to a concentrator and the volume increased to 2 ml by addition of double distilled water. The unit was then centrifuged at 500×g (Sorval RT6000B™ benchtop centrifuge with H1000B rotor) for 5 minutes and the "flow-through" discarded. The retentate was diluted to 2 ml again and the unit re-centrifuged. The process was repeated for a third time. This procedure results in the removal of excess oligos and buffer components from the amplified DNA. These purified DNAs were then used directly in subsequent PCR reactions. The appropriate pairs of fragments were mixed in equal proportions and aliquots used in the second PCRs with the respective 5' and 3' oligonucleotides.

d) Subcloning the PCR generated fragments into pBluescript™

The products of the second PCR reactions showed bands of approximately 775 bp and 730 bp consistent with the full-length Fd and L chains respectively. These products were also purified using Centricon 100™ microconcentrators as above. Each DNA product was then precipitated in a 1.5 ml solution containing 50 μl 3M sodium acetate, distilled water to 500 μl and 1 ml of absolute ethanol. The solution was incubated on ice for at least 10 minutes before centrifugation at 11.600×g for 10 minutes (MSE MicroCentaur™). The supernatant was discarded and the pellet washed in 1 ml 70% ethanol (v/v in distilled water) by centrifugation for a further 5 minutes. The supernatant was discarded and the DNA pellet dried under vacuum. Each DNA pellet was resuspended in distilled water. The Fd PCR product was then digested with EcoRI and HindIII in a 200 μl reaction containing 20 mM Tris-acetate. pH 7.9, 10 mM magnesium acetate, 50 mM potassium acetate, 1 mM dithiothreitol (DTT), and 25 u each of HindIII and EcoRI (Promega Corporation). The L chain product was digested with EcoRI in a 30 μl reaction containing 90 mM Tris-HCl, pH7.5, 10 mM magnesium chloride, 50 mM sodium chloride and 10 u EcoRI. Digests were incubated at 37° C. for 1 hr.

The digested fragments were then purified by electrophoresis on a 0.75% SeaPlaque™ GTG agarose gel (FMC BioProducts Ltd) followed by excision of the appropriate bands from the gel. The agarose gel slice was redissolved by incubation at 65° C. for 2 minutes, diluted to a final volume of 450 μl with distilled water and 50 μl 3M sodium acetate added. This solution was extracted with an equal volume of liquified phenol, equilibrated with Tris buffer pH7.6 (Fisons Scientific Equipment) using cetrigugation at 11.600×g for 2 minutes (MSE MicroCentaur™) to separate the aqueous and phenolic phases. The subsequent aqueous phase was re-extracted with a phenol:chloroform mixture (50:50 v:v) and again with chloroform prior to ethanol precipitation as described above. Each purified pellet was resuspended in 10 μl distilled water and a 1 μl sample visualised by electrophoresis on a 0.8% agarose gel to estimate quality and concentration.

pBluescript™ (Stratagene Cloning Systems) was used for initial cloning of Fd and L chain cDNAs. This phagemid vector has unique EcoRI and HindIII cloning sites, Ampicillin resistance gene, and both ColEl and fl replication origins for isolation of either double- or single stranded DNA. 5 μg pBluescript™ KS-DNA was digested to completion with 30 u EcoRI (Promega Corporation) in a 100 μl reaction containing 90 mM Tris-HCl, pH7.5, 10 mM MgCl2, 50 mM NaCl or with EcoRI and HindIII in a 100 μl reaction containing 20 mM Tris-acetate, pH 7.9, 10 mM magnesium acetate, 50 mM potassium acetate, 1 mM dithiothreitol (DTT), and 25 u each of EcoRI and HindIII (Promega Corporation) at 37° C. for 1 hour. 2 μl calf-intestinal alkaline phosphatase (2 u, Bohringer Mannheim) was the added to the EcoRI digested plasmid to remove 5' phosphate groups and incubation continued at 37° C. for a further 30 minutes. Phosphatase activity was destroyed by incubation at 70° C. for 10 minutes. The EcoRI-HindIII cut plasmid was purified from a SeaPlaque GTG agarose gel as described above.

25–50 ng of digested Fd or L chain PCR product was ligated with 50 ng of EcoRI-HindIII or EcoRI/CIP treated pBluescript respectively in 10 μl of a solution containing 30 mM Tris-HCl, pH7.8, 10 mM MgCl2, 10mM DTT, 1 mM ATP and 1.5 u T4 DNA ligase (Promega Corporation) at 16° C. for 2.5 hours. A 1 μl aliquot of each reaction was used to transform 20 μl of competent E. coli DH5α cells (Life Technologies Ltd.) using the protocol provided with the cells. Transformed cells were plated onto L-agar plus 100 μg/ml Ampicillin, 1 mM IPTG and 0.2% X-gal and incubated overnight at 37° C. Clones containing cloned inserts were selected on the basis of producing white colonies on the above medium compared to the blue colour generated by cells containing the parental plasmid.

e) DNA sequence analysis of cDNA clones

The potential Fd and L chain cDNA clones identified by colour selection were picked from the agar plates and used for large scale plasmid DNA preparation. Each clone was used to inoculate 200 ml of L-broth plus 100 μg/ml ampicillin in a 500 ml conical flask. The cultures were incubated, shaking at 37° C. overnight. After growth the cells from each culture were pelleted by centrifugation at 5000×g for 10 minutes in a Sorvall RC5C centrifuge and GS3 rotor at 4° C. The cell pellet from each culture was resuspended in 20 ml TE buffer and re-centrifuged at 2000×g for 10 minutes in a Sorvall RC5C centrifuge and SS-34 rotor in an oak-ridge rube at 4° C. Each washed cell pellet was resuspended in 3 ml ice cold 25% sucrose, 50 mM Tris, pH8.0, and left on ice. Fresh lysozyme solution (1.0 ml at 10 mg/ml) was added, the contents mixed by rolling the tube and incubation on ice continued for 5 minutes. Sodium ethylene diamine tractetate (EDTA) solution (1.0 ml at 0.5 mM, pH8.5) was added and the contents gently mixed. Finally, 5.0 ml of iced Triton X™ solution (0.1% Triton X-100, 62.5 mM EDTA, 50 mM Tris, pH8.0) was added, the contents gently mixed and incubation on ice continued for a further 10 minutes. The cell debris was then pelleted by centrifugation at 39,000×g for 30 minutes in a Sorvall RC5C centrifuge and SS-34 rotor at 4° C. The supernatant containing plasmid DNA was added to 16 g caesium chloride (Boehringer Mannheim) and 150 μl ethidium bromide solution (10 mg/ml) and the volume increased to 18.5 ml by addition of TE buffer. This solution was transferred to an 18.5 ml crimp top, polypropylene centrifuge tube (Sorvall Instruments). The tube was sealed and centrifuged at 180,000×g for 16 hours in a Sorvall TV865B (titanium, vertical) rotor and OTD65B centrifuge at 18° C.

After centrifugation, plasmid DNA was visible as a distinct orange band in the CsCl/EtBR density gradient which had formed. The plasmid DNA was removed from the gradient using a hypodermic syringe to pierce the tube wall. The sample taken from the gradient was diluted 3–4 fold with TE buffer and the DNA precipitated by addition of an equal volume of isopropyl alcohol and incubation on ice for 10 minutes. The precipitated DNA was pelleted by centrifugation at 17,000×g in a Sorvall RC5C centrifuge and SS-34 rotor at 4° C. and the supernatant discarded. The resulting pellet was washed in 70% ethanol (v/v) and re-centrifuged for 5 minutes. The pellet was then dried under vacuum, resuspended in 1.8 ml TE buffer and 200 μl 3M sodium acetate solution and extracted with an equal volume of phenol using centrifugation at 17,000×g for 2 minutes to separate the phases. The aqueous phase was re-extracted against an equal volume of chloroform before precipitating the DNA by addition of an equal volume of ethanol at −20° C. and incubating on ice for 10 minutes. The purified DNA was pelleted as above, washed in 5 ml 70% ethanol and the pellet vacuum dried. The dried pellet was resuspended in 500 μl double-distilled water and DNA concentration estimated by scanning a diluted sample from 300 to 220 nm in a UV spectrophotometer using and extinction coefficient of 50 μg/ml/OD260. A number of proprietary kits, e.g. Qiagen™ (Hybaid Ltd), are also available for plasmid DNA purification.

This purified plasmid DNA was then used for DNA sequence analysis. Double stranded DNA can be used for DNA sequence analysis by the dideoxy chain termination method of Sanger (Proc.Nat.Acad.Sci. USA 74, 1977, p5463) using a proprietary sequencing kit such as the Sequenase™ kit supplied by United States Biochemical Company and used in accordance with the protocols provided.

Aliquots (2–4 μg) of Fd and L chain cDNA clone plasmid DNA were used for DNA sequence analysis. Each aliquot was initially denatured by incubation with 0.2M NaOH, 0.2 mM EDTA in a final volume of 100 μl at room temperature for 10 minutes. The denatured DNA was then precipitated by addition of 10 μl 3M sodium acetate (pH5.0) and 275 μl ethanol and incubation on ice for 10 minutes. The precipitated DNA was recovered as described for plasmid DNA above. The denatured DNA was then primed for sequencing by incubation of each with 0.5 pmoles of an appropriate primer in 10 μl of Sequenase™ reaction buffer (40 mM Tris, pH7.5, 25 mM MgCl$_2$, 50 mM NaCl) containing 10% di-methyl sulphoxide (DMSO) at 65° C. for 2 minutes followed by gradual cooling to below 30° C. These primed templates were then used in sequencing reactions according to the protocols provided with 10% DMSO added to labelling and termination mixtures.

The sequencing reactions were analysed by autoradiography after high resolution electrophoresis on a 6% polyacrylamide: 8M urea denaturing gel (Sanger and Coulson, 1978, FEBS lett. 87, p107).

The complete Fd and L chain sequences of the cloned cDNA are given below (SEQ ID NO: 25 for the proteolytic type Fd chain and SEQ ID NO: 26 for L chain). The plasmid containing the proteolytic type Fd was named pAF1 and the L chain pAF3. The presence of the silent mutation in each fragment for removal of the BamHI site was also confirmed. The DNA sequence indicates that the antibody is an IgGκ isotype when compared to published constant region DNA sequence data (in Kabat, E. A., Wu, T. T., Bilofsky, H., Reid-Milner, M., Perry, H., 1987, Sequences of Proteins of Immunological Interest, Fourth Edition, Public Health Service N.I.H. Washington DC).

f) Subcloning into myeloma expression vectors

To generate vectors capable of Fd and L chain coexpression in myeloma cells, the GS-System™ system (Celltech Biologics) was used (WO 87/04462, WO 89/01036, WO 86/05807 and WO 89/10404).

The procedure requires cloning the Fd chain into the HindIII-EcoRI region of vector pEE6 [this is a derivative of pEE6.hCMV—Stephens and Cockett (1989) Nucleic Acids Research 17, 7110—in which a HindIII site upstream of the hCMV promoter has been converted to a BglII site] and the L chain into the EcoRI site of pEE12 [this vector is similar to pSV2.GS described in Bebbington et al. (1992) Bio/Technology 10, 169–175, with a number of restriction sites originally present in pSV2.GS removed by site-directed mutagenesis to provide unique sites in the multi-linker region]. Subsequently, a BglII-BamHI Fd expression cassette from pEE6 is inserted into the BamHI region of pEE12. Alternatively, a BglII-SalI fragment containing the Fd expression cassette can be inserted into the BamHI-SalI region of the pEE12 plasmid containing the L chain.

To construct the individual vectors (proteolytic Fd in pEE6 and L chain in pEE12), plasmids pAF1 and pEE6 were digested with EcoRI and HindIII and pAF3 and pEE12 were digested with EcoRI as described above. The appropriate vector and insert fragments from each digest were then isolated from Seaplaque™ GTG agarose and ligated together and used to transform competent DH5α cells also as described earlier. The transformed cells were plated onto L agar plus 100 μg/ml ampicillin. Screening of colonies from the transformation was by a PCR method. Colonies were transferred into 200 μl distilled water and mixed by vortexing. The suspended cells were then heated to 100° C. for 1 minute and centrifuged at 11.600×g for 2 minutes prior to using the supernatant in a PCR reaction. In each PCR reaction, an oligo which primes within the CMV promoter (SEQ ID NO: 27) was used with the oligo complementary to the 3' region of either Fd (SEQ ID NO: 19) or L chain (SEQ ID NO: 20) as appropriate. Only clones with the antibody fragment gene inserted in expressing orientation downstream from the CMV promoter will produce specific PCR products of approximately 2.0 kbp in each case. PCR reactions of 20 μl were set up containing 20 pmoles of each oligo (SEQ ID NO: 27 with either SEQ ID NO:19 or 20) 10 mM Tris-HCl, pH8.3, 50 mM KCl, 0.1% gelatin, 1.5 mM MgCl2, 1.25 mM each of dATP, dCTP, dGTP and dTTP and 0.5 u Taq DNA polymerase (Amplitaq™, Perkin-Elmer Cetus). Each reaction was overlaid wit 20 μl mineral oil and incubated at 94° C. for 1.5 minutes, 50° C. for 1.0 minute and 72° C. for 2.0 minutes for 25 cycles plus 10 minutes at 72° C. Control reactions with clones containing the parent plasmids and with no DNA were also set up. The PCR reactions were analysed by agarose gel electrophoresis and potential clones identified by the presence of a 2.0 kbp PCR product. These possible clones were used for large scale plasmid DNA preparation, were characterised by restriction enzyme digestion with EcoRI-HindIII or EcoRI and the sequence of the insertion confirmed by DNA sequence analysis as described above. The isolates were named pAF4 (proteolytic type Fd in pEE6) and pAF6 (L chain in pEE12).

To create the co-expressing vectors, 5–7.5 μg of Fd plasmid pAf4 was digested with 30 u each of BglII (Pharmacia) and BamHI (New England Biolabs) in a solution containing 50mM Tris-HCl, pH7.9, 10 mM magnesium chloride, 150 mM sodium chloride and 1 mM DTT for 1 hour at 37° C. Digestion was confirmed by agarose gel electrophoresis, 5 μg of L chain plasmid pAF6 was digested with 25 units of BamHI (New England Biolabs) in the solution described above by incubating for 1 hour at 37° C. The DNA was then dephosphorylated by the addition of 2 u CIP and incubations at 37° C. for 40 minutes followed by three extractions with 10 μl of Strataclean™ resin (Stratagene Ltd). The Fd expression cassette fragment and major pAF6 plasmid band was then purified from Sea-Plaque™ GTG agarose gels, the appropriate combination ligated together and the ligation used to transform competent DH5α cells all as described previously.

g) Identification of co-expressing vectors.

One hundred colonies from the above transformation were picked in duplicate in batches of 50 onto 9 cm nitrocellulose discs (Schleicher and Schull) laid onto L-agar plus 100 μg/ml ampicillin plates. A third set of plates without filters was streaked to form a master stock of the selected colonies. After overnight incubation at 37° C. the nitrocellulose filters were removed and processed according to the method of Grunstein and Hogness (Maniatis, Chapter 1, p102) to lyse the bacterial cells in situ. The filters were overlaid on 3MM paper (Whatman) soaked in the various reagents—10% SDS for 2 minutes, 3M NaOH, 1M NaCl for 5 minutes and 1M Tris, p6.8 for 2×2 minutes. The filters containing lysed cells were transferred to 3MM paper moistened with 20× SSC (3M NaCl, 0.3M sodium citrate) and the DNA cross-linked to the filters by exposure to UV light in a Spectrolinker™ XL 1500 (Spectronics Corporation) set on optional crosslink (120,000 μJoules). The filters were air dried before being used in probing (see below). The master stock plates were stored at 4° C. until required.

Oligonucleotides specific for Fd and L chains (SEQ ID NO: 22 and 24 respectively) were used to generate specific hybridisation probes for Fd and L chain containing clones. A hybridisation probe can be generated from a synthetic oligonucleotide by the addition of a radio-active 5' phospate group from γ $^{32}$P ATP by the action of T4 polynucleotide kinase. 20 pmoles of the oligonucleotide were added to a 20 μl reaction containing 100 mM Tris, pH7.5, 10 mM MgCl$_2$, 0.1 mM Spermidine, 20 mM DTT, 7.5 μM ATP, 0.5 μM γ$^{32}$P ATP and 2.5 u T4 polynucleotide kinase (Pharmacia Bio-technology Ltd). The reactions were incubated for 30 minutes at 37° C. and then for 10 minutes at 70° C. prior to use in hybridisation. Methods for the generation of hybridisation probes from oligonucleotides are provided in Maniatis (chapter 11). A 10 μl aliquot of the radio-labelled oligo was added to 10 ml of 6×SSC (1M NaCl, 0.1M sodium citrate). 0.1% SDS (sodium dodecyl sulphate) and 0.25% Marvel™ (fat-reduced dried milk powder) which was then used as a probe solution.

The processed filters containing the selected clones (see above) were pre-hybridised in duplicate batches each in 90 ml 6×SSC, 0.1% SDS, 0.25% Marvel™ at 65° C. for 3 hours in a Techne HB-1 hybridisation oven using rotating glass tubes. Each duplicate set was then probed in 10 ml of probe solution (one set with the VH probe and the other with VL) at 65° C. overnight in the same apparatus. After incubation, each set of filters was washed in 100 ml 6×SSC, 0.1% SDS at 65° C. for 15 minutes, 100 ml 3×SSC, 0.1%SDS at 65° C. for 30 minutes and 100 ml 1×SSC. 0.1%SDS at 65° C. for 30 minutes in the same apparatus. The washed filters were then air dried and autoradiographed using Hyperfilm™ MP (Amersham International) in conjunction with a fast tungstate intensifying screen at −70° C. After developing the film in a Kodak automatic film processor, potential F(ab')$_2$ expression clones were identified by hybridisation of both probes. The frequency of clones showing hybridisation with both Fd and L chain specific probes was very low (approximately 2%).

The potential co-expressing clones were picked from the master plates and used for large-scale plasmid DNA preparation. Restriction digestion analysis with the enzymes EcoRI and HindIII was used to confirm the orientation of each expression cassette. Clones with the L and Fd expresion cassettes in tandem orientation (rather than convergent) only were identified. The generation of the co-expressing vector pAF8 (proteolytic Fd and L in pEE12).

h) Transfection of myeloma cells

Several methods exist for the introduction of DNA into eukaryotic cells (Bebbington, C., 1991, Methods, vol 2, p136–145). Electroporation has become a routinely used method more recently, replacing the calcium phosphate-DNA co-precipitation method. NS0 myeloma cells (Methods in Enzymology, 1981, 73B, p3–46, ECACC cat no. 85110503) are a suitable host cell for this work due to the absence of any endogenous secreted antibody protein. It is expected that a proportion of colonies arising in glutamine-free medium after transfection of the Fd and L chain co-expressing plasmids will express functional A5B7 antibody fragments.

Prior to transfection 40 μg of the pAF8 plasmid DNA was linearised by digestion with 200 u SalI (New England Biolabs) in a 400 μl reaction containing 10 mM Tris-HCl, pH7.9, 10 mM magnesium chloride, 150 mM sodium chloride, 1 mM DTT and 100 μg/ml acetylated BSA at 37° C. for 1.75 hour. After digestion each DNA was precipitated in ethanol and resuspended in 50 μl distilled water.

NS0 cells were grown to near confluence in 160 cm$^2$ tissue culture flasks (Nunc or Costar) containing 50 ml non-selective growth medium (Dulbecco's Modified Eagle Medium, Life Technologies Ltd., plus 10% foetal calf serum from an accredited source) incubated at 37° C. in an atmosphere of 5% CO$_2$. Prior to transfection the NS0 cells were resuspended by knocking the flask against a hand or bench and transferred to a 50 ml conical centrifuge tube (Falcon). A sample (40 μl) was taken an used to estimate the cell concentration using a Coulter counter set to count between 10 and 20 μm. The cells were pelleted by centrifugation at 500×g for 5 minutes (Sorval RT6000C benchtop centrifuge) then washed with 45 ml of ice-cold phosphate buffered saline (PBS) and re-centrifuged. The washed cells were resuspended in ice-cold PBS to a concentration of 1.3×10$^7$ cells per ml and stored on ice. Each 50 μl sample of SalI digested plasmid DNA was mixed with 800 μl (10$^7$) NS0 cells in a 0.4 cm pathlength electroporation cuvette (Bio-Rad Laboratories Ltd) avoiding bubbles and the cuvette incubated on ice for 5 minutes. The cuvette was then wiped dry with a tissue and placed in a Gene Pulser™ electroporation equipment (Bio-Rad Laboratories Ltd) and 2 consecutive pulses of 1500 volts at 3 μFarads delivered according to the manufacturer's instructions. After electroporation the cuvettes were returned to ice for 5 minutes before mixing with 30 ml pre-warmed non-selective medium. Approximately 20 ml of this cell suspension was distributed into 4× flat-bottomed 96 well tissue culture plates (Nunc) at 50 μl per well. A further 10 ml was diluted with 30 ml non-selective medium and plated into 5×96 well plates. The diluted suspension was diluted further (10 ml to 40 ml) with non-selective medium and plated in a further 5×96-well plates. The cells were then incubated at 37° C. in 5% CO$_2$ overnight. Glutamine-free selective medium (150 μl, Bebbington et al., (1992) Bio/Technology 10, 169–175) was added to each well of the 96 well plates and the plates returned to the incubator to allow the gradual depletion of glutamine and until colonies were visible using the naked eye.

i) Expansion of cell lines

Colonies were selected from the 96-well plates where 1 colony per well was present. The cells were resuspended by pipetting up and down and 100 μl transferred to a well of a 24-well plate and 1 ml selective medium added to each well. A further 100 μl selective medium was added back to each of the wells in the 96-well plates from which colonies had been removed to provide a back-up source of the cell lines. The 24-well plates were incubated at 37° C. in 5% $CO_2$ until approx 50% confluent with cell growth. At this stage, 100 μl culture supernatant was removed and tested for anti-CEA binding activity in an ELISA assay (see below). Cell lines showing binding activity were expanded further by pipetting up and down and transferring 1 ml to a 25 $cm^2$ tissue culture flask. A further 1 ml of selective medium was added to each flask and the flasks incubated sloping to concentrate the cells towards the bottom of the flask. After several days incubation, 3 ml of selective medium was added to each flask which was then incubated horizontally until the cells achieved 50–75% confluence. At this stage the medium was removed from the cells and the cells washed carefully with 5 ml selective medium which was then discarded and replaced with a further 5 ml of selective medium. The flasks were returned to the incubator for 24 hr. The cells were then harvested by knocking the flask, the cell density counted either using a Coulter counter at 10–20 μm detection limits or using a haemocytometer after staining with trypan blue solution (Life Technologies) and counting viable (unstained) cells under a microscope. The cells were pelleted by centrifugation (~300×g for 5 minutes) and the supernatant removed and stored at 4° C. for use in analysis of antibody fragment expression (see below). The cells were resuspended in 50% dialysed foetal calf medium. 40% glutamine-free DMEM and 10% DMSO to a concentration of $1-2\times10^6$ cell per ml. The cells were then transfered in 1 ml aliquots to screw cap cryotubes (Nuc), frozen at −70° C. overnight and then transferred to liquid nitrogen for long term storage.
Western blot analysis Western blot analysis was performed as described below.

Aliquots (15 μl) of each supernatant sample were mixed with an equal volume of sample buffer (62.5 mM Tris, pH6.8, 1% SDS, 10% sucrose and 0.05% bromophenol blue) with and without reductant (50 mM DTT). The samples were incubated at 100° C. for 15 minutes before electrophoresis on a 8–18% acrylamide gradient gel (Excel™ gel system from Pharmacia Biotechnology Products) in a Multiphor™ II apparatus (LKB Produkter AB) according to the manufacturer's instructions. After electrophoresis, the separated proteins were transferred to a Hybond C-Super™ membrane (Amersham International) using a Novablot™ apparatus (LKB Produkter AB) according to protocols provided by the manufacturer. After blotting, the membrane was air dried.

The presence of antibody fragments was detected by the use of anti-murine F(ab')$_2$ antibody-peroxidase conjugate (ICN Biomedicals, product no. 67-430-1) Whilst this primary antibody is raised against murine F(ab')$_2$ it has been shown to bind primarily to the kappa L chain. The presence of murine A5B7 antibody fragments was visualized using the ECL detection system (Amersham International) according to the protocol provided.

This showed that about 90% of the material present in the cell supernatants was F(ab')$_2$ protein.

k) ELISA analysis

Standard procedures for ELISA assay are available in "Laboratory Techniques in Biochemistry and Molecular Biology" eds. Burdon. R. H. and van Kippenberg, P. H., volume 15, "Practice and Theory of Enzyme Immunoassays". Tijssen, P., 1985. Elsevier Science Publishers B. V. Another source of information is "Antibodies—A Laboratory Manual" Harlow, E. and Lane, D. P. 1988, published by Cold Spring Harbor Laboratory.

The cell supernatants (see above) were used to detect the presence of anti-CEA binding material according to the protocol given below:

l) ANTI-CEA ELISA

1. Prepare coating buffer (1 capsule of Carbonate-Bicarbonate buffer—Sigma C-3041—in 100 ml double distilled water).

2. Add 5 μl of CEA stock solution (0.2 mg/ml. Dako) to 10 ml of coating buffer for each 96 well plate required.

3. Add 100 μl of diluted CEA to each well of a Nunc "Maxisorp™" microtitre plate.

4. Incubate plates at 4° C. overnight (or room temp. for 2 hours).

5. Wash plates 4 times for 5 minutes each with Phosphate buffered saline+0.01% Sodium azide (PBSA).

6. Block plates (after banging dry) with 1% BSA (Sigma A-7888) in PBSA at 150 μl per well. Incubate at room temp. for 2 hours.

7. Wash plates 4 times for 5 minutes each with PBSA.

8. Load samples (culture supernatants) and standards (doubling dilutions of proteolytic A5B7 F(ab')$_2$) as appropriate. Dilute samples in growth medium (or PBS). Include PBSA+1% BSA and diluent as blanks.

9. Incubate at 4° C. overnight.

10. Wash plates 6 times for 5 minutes each with PBSA+0.5% Tween 20.

11. Prepare secondary antibody solution (anti-mouse IgGF(ab')$_2$ from goat, peroxidase conjugated—ICN 67-430-1—at 20 μl in 40 ml PBSA+1% BSA+0.5% Tween 20) and add 100 μl per well.

12. Incubate at room temp. for 2 hours.

13. Wash plates 6 times for 5 minutes each with PBSA+0.5% Tween 20.

14. Prepare developing solution by dissolving 1 capsule of Phosphate-Citrate Perborate buffer (Sigma P-4922) in 100 ml double distilled water. Add 30 mg o-Phenylenediamine Dihydrochloride (OPD, Sigma P-8287) per 100 ml buffer. Add 100 μl per well.

15. Incubate at room temp. in darkness for 15 minutes.

16. Stop reaction by addition of 50 μl per well of 2 M Sulphuric acid.

17. Read OD 490 nm in plate reader.

m) Calculation of Specific Production Rate (SPR)

The amount of anti-CEA binding activity in each sample was determined using the Softmax data handling package. This figure was assumed to give an approximate figure for the amount of A5B7 F(ab')$_2$ fragment present in the cell supernatant taking into account the Western blot analysis data which indicates that the majority of the antibody L chain (>90%) is present as F(ab')$_2$. This figure was then used to calculate a specific production rate in terms of $\mu g/10^6$ cells/24 hours which was used to rank the cell lines according to productivity. SPR calculations for the best cell lines isolated ranged typically from 4 $\mu g/10^6$ cells/24 hours.

Purification of Recombinant A5B7 F(ab)$_2$

The recombinant A5B7 F(ab)$_2$ material was purified from myeloma medium supernatant using a r-Protein A 500 mg cartridge such as for example manufactured by NyGene.

The cartridge was first washed in a citrate buffer at 100 mM citric acid pH2.8 and then equilibrated with 150 mM sodium chloride 10 mM sodium phosphate pH7.4 until the pH of the wash matched that of the equilibration buffer. Both buffers were pre-filtered at 0.45 µm using a Millipore filter.

The myeloma medium (1.8 liters) containing the recombinant A5B7 F(ab)$_2$ was also pre-filtered and diluted 1:1 with the equilibration buffer. This diluted medium was then loaded onto the Protein A cartridge, collecting all the unbound wash. Once loaded the cartridge was washed through with the equilibration buffer until the absorbance at 280 nm returned to baseline.

The buffer was then changed to 100 mM sodium ph4.0 also pre-filtered. This elution buffer was collected as 45 ml fractions. Once the absorbance at 280 nm had again returned to baseline the buffer was changed to 100 mM citric acid pH2.8 in order to wash the column.

Optical density at 280 nm was determined on the fractions and those containing significant absorbance were titrated to ph7.0. and analysed by SDS PAGE.

The fractions containing the recombinant A5B7 F(ab)$_2$ were pooled. This volume was concentrated (Amicon YM10™ membrane) and dialysed into 150 mM sodium chloride. 10 mM sodium phosphate and 3 mM EDTA disodium salt. pH7.4. and stored at 4° C. A total of 73 mg F(ab)$_2$ was obtained at a purity of >90% as judged by non-reducing SDS PAGE.

The myeloma cell supernatant used in the above purification was obtained essentially as described Bebbington et al. (1992) in Bio/Technology 10, 169–175. The GS media (Cat. No. 51435) and supplement (Cat. No. 58672) is available from JRH Biosciences (JRH Biosciences Europe. Hophurst Lane, Crawley Down. W. Susses, U.K., RH10 4FF). At the end of the fermentation procedure, the supernatant was filtered through a 0.45 m filter to remove any particulate matter and stored at 4° C. until purification, typically no longer than 24 hours.

Reference Example 6
Synthesis of Uracil-based Prodrug analogue (see Scheme In FIG. 9)

Compound 7 (5 mg) was dissolved in 0.5 ml hydrochloric acid (0.1 N) to give the desired end product (compound 9). After 0.5 hr at 25° C. in the dark the stock solution was kept on ice and aliquots diluted with buffer for test with mutant RNase.

Compound (7) was prepared from uridine as follows:
2',3'-O-Methoxyethylidene uridine (Compound 1)

Uridine (5 g), p-toluenesulphonic acid monohydrate (1 g) and trimethylorthoacetate (15 ml) were stirred together at 20° C. for 16 hr. The reaction mixture was made slightly basic with methanolic sodium methoxide and then concentrated to a gum. The required product was purified by column chromatography on silica gel (Merck 9385) using chloroform/methanol mixtures as eluant and in the proportion 96:4 (by volume) at first, followed by 92:8.

NMR (DMSOd6): (δ) 11.38 (s.1H); 7.75 (d,1H): 5.95(d) and 5,80(d, total 1H): 5.62(d,1H); 4.70–5.10(m,3H); 4.18(q) and 4.04(q, total 1H); 3.60(m,2H); 3.15(s) and 3.28(s, total 3H); 1.57(s) and 1.49 (s, total 3H).

5'-Azido-5'-deoxy-2',3'-O-methoxyethylideneuridine (Compound 2)

To a solution of 2',3'-O-methoxyethylideneuridine (7.0 g, 23.3 mmol) in dry pyridine (80 ml) at 0° C. was added methanesulphonyl chloride (1.9 ml, 24 mmol). After stirring for 16 hr at 4° C. the solvent was evaporated in vacuo and the residue dissolved in chloroform was washed with water. The organic layer was separated, dried and concentrated to give the crude mesylate.

The crude reaction product was dissolved in dry dimethylformamide (100 ml) and sodium azide (3.25 g, 50 mmol) added. The mixture was stirred at 85° C. for 7 hr and then worked up by evaporation of the solvent in vacuo to give a gum which was dissolved in chloroform and washed with sodium bicarbonate solution. The chloroform extract was separated, dried over anhydrous sodium sulphate and concentrated to give the crude 5'-azido product. The crude azide intermediate was used as starting material for the next step.
3'-O(and 2'-O)-Acetyl-5'-azido-5'-deoxyuridine (Compound 3)

The crude azide (compound 2, above) was dissolved in acetic acid (70%) (100 ml) and after 15 minutes the solvent was removed under reduced pressure. The residue was repeatedly dissolved in absolute ethanol and concentrated to remove last traces of acetic acid. This procedure gave a crude sample of the required product as a mixture of 2' and 3'-regioisomers.

NMR of 2:1 ratio of 2'acetoxy to 3'acetoxy in DMSOd6: (δ) 11.40(s,1H); 7.70(d,1H); 5.60–5.95(m.3H); 5.22(t, 0.33H); 5.03(dd, 0.66H); 4.41 (q,0.66H); 4.24(q,0.33H); 4.14 (q,0.66H); 3.94(m.0.33H); 3.62(m,2H); 2.08(s,0.66H); 2.06(s,0.33H).

3'-O(and 2'-O)-Acetyl-5'-azido-5'-deoxy-2'-O(and 3'-O)-tetrahyropyranyluridine

The crude acetate from the previous reaction was dissolved in dry dichloromethane (80 ml). Dihydropyran (6 ml) plus p-toluenesulphonic acid monohydrate (500 mg) were added to the reaction flask. The mixture was stirred at 25° C. for 3 hr. after which, tlc indicated that starting material had been consumed. The reaction mixture was diluted with dichloromethane, washed with aqueous sodium bicarbonate and the organic layer dried before evaporating under reduced pressure. The crude product (mixture of 2' and 3'-regioisomers) was purified on silica gel column using chloroform/methanol mixtures as eluant (97:3 by volume at first, followed by 95:5).
5'-Amino-5'-deoxy-2'-O(and 3'-O)-tetrahydropyranyluridine (Compound 4)

The azide intermediate from the previous reaction was dissolved in tetrahydrofuran (100 ml) and triphenylphosphine (6.5 g. 25 mmole) was added followed by water (0.45 ml). After stirring for 16 hr at 25° C. concentrated ammonia was added and the reaction continued for a further 24 hr. The reaction mixture was concentrated to dryness and purified by column chromatography (first chloroform/methanol 9:1, followed by chloroform/methanol 1:1) to give the required product as a mixture of 2' and 3' regioisomers.
5'-(N-Benzyloxycarbonylglycyl)amino-5'-deoxy-2'-O(and 3'-O)-tetrahydropyranyluridine (Compound 5)

To a solution of 5'-amino-5'-deoxy-2'-O(and 3'-O)-tetrahydropyranyluridine (3g) in anhydrous tetrahydrofuran is added N-benzyloxycarbonylglycine p-nitrophenyl ester (3.1 g, 9.2 mmol). The solution was stirred for 16 hr at 25° C. concentrated to a gum and purified by column chromatography on silica using chloroform/methanol (96:4) as eluant. The required product was obtained as a mixture of regioisomers (3.6 g, 75% yield).

NMR in DMSOd6:(δ) 11.36(s,1H); 8.02(b,1H); 7.70(two d,1H); 7.32(m,6H); 5.90(d) and 5.70(d, total 1H); 5.444(d) and 5.20(d,total 1H); 5.02(s,2H); 4.75(m,1H); 3.20–4.25 (m, 9H); 1.35–1.80 (m, 6H).
Mass Spectrum (FAB), m/e, 519(M+H+). C24H30N4O9 requires M+,518
3'-O(and 2'-O)-Phosphoramidite derivative of above product To a solution of the product (1.9 g 3.67 mmol) from the previous reaction and diisopropylethylamine (1.5 ml) in dry dichloromethane (30 ml) was added N,N-diisopropylmethylphosphonamidic chloride. After stirring for 5 hr at 25° C. the reaction was diluted with chloroform and washed with aqueous sodium bicarbonate solution. The chloroform extract was separated, dried and concentrated to give a gum. The crude mixture was purified by column chromatography using the following eluants (first chloroform/triethylamine 98:2, followed by chloroform/triethylamine/methanol 96:2:2) to give the required phosphorus containing intermediate (1.9 g).

Fully protected phosphate intermediate (Compound 6)

To a solution of the phosphoramidite (1.9 g. 2.4 mmol) from the above reaction and 4-dipropylaminophenol (0.7 g, 3.6 mmol) in dry acetonitrile (40 ml) was added tetrazole (0.5 g, 7.2 mmole). After stirring for 16 hr at 25° C. in the dark, tetriarybutylhydroperoxide (70%; 0.4 ml) was added. After 15 min the reaction mixture was concentrated, dissolved in chloroform and washed with aqueous sodium bicarbonate. The chloroform layer was separated, dried and then concentrated to a gum. This was purified by column chromatography on silica using ethyl acetate followed by ethyl acetate/methanol (93:7 by volume). Evaporation of appropriate fractions gave the product (1.5 g) as a mixture of the 2 and 3' regioisomers.

NMR in DMSOd6: ($\delta$) 11.43 (s, 1H); 8.10(b, 1H); 7.75(m, 1H); 7.35(s, 5H); 7.00(m. 2H); 6.60(m, 2H); 5.90(m, IH); 5.69(m,1H); 5.17(m) and 4.97(m, total 1H); 5.02 (s, 2H); 4.69(bs) and 4.57(bs, total 1H); 4.53(m) and 4.23 (m, total 1H); 4.08(m, 1H); 3.15–3.85 (m.13H); 1.35–1.75(m,10H); 0.88(t, 6H).

Mass Spectrum (FAB), m/e, 787(M+) and 788 (M++H), $C_{37}H_{50}N_5O_{12}P$ requires M+, 787

THP protected prodrug analogue (Compound 7)

The fully protected intermediate from the preceding reaction (1 mmole) was dissolved in a mixture of ethanol (20 ml)/cyclohexene (10 ml) before addition of 20% palladium on charcoal (150 mg). The mixture was refluxed for 1 hr and then filtered before concentrating under reduced pressure. The resultant gum was purified by column chromatography on silica using chloroform/methanol (9:1) as eluant to give the free glycyl derivative.

The methyl protected phosphate (1 mmole) from the preceding reaction was next dissolved in tertiary butylamine (30 ml). The reaction mixture was refluxed for 16 hr and concentrated before purifying by column chromatography on silica using chloroform/methanol (9:1) followed by chloroform/methanol (7:3) as eluants to give the required THP protected prodrug analogue as a mixture of 2' % 3'regioisomers.

Separation of 2' and 3' regioisomers by High Pressure Liquid Chromatography

The separation was accomplished by HPLC on a Partisil ODS-2 column by isocratic elution with 60:40 methanol/ammonium formate (0.1M). Appropriate fractions were pooled and freeze dried to give the required 3'-linked intermediate (7); see structure in FIG. 9.

NMR in DMSOd6: ($\delta$)8.85(s,1H); 8.25 (s,1H); 7.75(d, 1H); 6.95 (d,2H); 6.5(d,2H); 5.85 (d,1H); 5.6(d,1H); 4.5(m, 2H); 4.3(m,1H); 4.07(m,1H); 3.2–3.6(m,6H); 3.1(m, 4H); 1.2–1.6(m, 10H); 0.8(m,6H).

Reference Example 7

Synthesis of a cytidine prodrug analogue (see scheme, FIG. 10)

The cytidine prodrug analogued (compound 13) was prepared by analogy with the uridine compounds described in Reference Example 6. The procedure described in Reference Example 6 was followed but with compound 7(FIG. 9) replaced by compound 12 (FIG. 10.

Standard work-up: Concentration of reaction mixture in vacuo, dissolve residue in $CHCl_3$, wash the solution with aq $NaHCO_3$, dry on $Na_2SO_4$, filter and concentrate. Purification by flash column chromatography with indicated solvent mixture.

Compound 12 was prepared as follows (see scheme in FIG. 10).

$N^4$-Benzoyl-2',3'-O-methoxyethylidenecytidine (compound 1) was prepared according to D.P.L. Green, T Ravindranathan, C B Reese and R Saffhill, Tetrahedron 26, 1031 (1970)

$N^4$-Benzoyl-5'-O-methanesulfonyl-2',3'-O-methoxyethylidenecytidine (Compound 2) was prepared as follows.

To a stirred solution of $N^4$-benzoyl-2',3'-O-Methoxyethylidenecytidine (9.85 g, 25.0 mmole) in pyridine (100 ml) was added methanesulphonyl chloride (1.9 ml, 25 mmole) at 0° C. After stirring for 16 hr at 25° C. the reaction mixture was worked up by concentrating the solution under vacuo, redissolving in chloroform and washing the organic layer with aqueous sodium bicarbonate. The chloroform layer was separated, dried over sodium sulphate and concentrated to give the product.

3'-O-Acetyl-5'-azido-$N^4$-benzoyl-5'-deoxycytidine (mixture with 2'-0-acetyl isomer) (Compound 3) was prepared as follows.

The crude mesylate (compound 2) was dissolved in anhydrous DMF (100 ml). Sodium azide (3.25 g, 50 mM) was added and the reaction mixture stirred at 80° C. for 7 hr. The reaction was worked up by concentrating the solvent, redissolving in chloroform and washing the chloroform extract with sodium bicarbonate solution. The residue obtained from concentrating the dried chloroform layer was dissolved in 120 ml 70% HOAc. After 15 minutes the solvent was removed in vacuo and the crude product purified by column chromatography (95:5 $CHCl_3$/MdOH followed by 92:8 $CHCl_3$/MeOH). Yield of required product was 6 g.

3'-O-Acetyl-5'-azido-$A^4$-benzoyl-2'-O-tetrahydropyranyl-5'-deoxycytidine (mixture with 3'-O-tetrahydropyrayl isomer) (Compound 4) was prepared as follows.

Compound 3 (6 g) from the above example was dissolved in methylene chloride (100 ml) and dihydropyran (4 ml). After addition of 0.5 g p-toluene sulphonic acid mono hydrate the mixture was stirred for 16 hr at 25° C. A similar work up procedure to that described above gave a crude product which was purified by column chromatography eluting with 98:2 $CHCl_3$/MeOH to give the required product.

5'-Azido-5'-deoxy-2'-O-tetrahydropyranylcytidine (mixture with 3'-O-tetrahydropyranyl isomer) (Compound 5) was prepared as follows.

The acetate (compound 4, 9.0 g, impure) was dissolved in methanol (60 ml) and sodium methoxide (3.5 g) was added. After stirring at 25° for 1 hr the reaction mixture was concentrated and purified by flash column chromatography. Yield 3.7 g.

Note: It is possible to separate the 2' and 3'isomers at this stage (as well as at most of the next steps) by chromatography.

5'-Azido-$N^4$-benzyloxycarbonyl-5'-deoxy-2'-O-tetrahydropyranylcytidine (mixture with 3'-O-tetrahydropyranyl isomer) (Compound 6) was prepared as follows.

The cytidine compound (compound 5, 3.7 g) was dissolved in anhydrous pyridine (80 ml) and a catalytic amount of dimethylamino-pyridine (DMAP) and 2 ml Z-Cl were added. After stirring for 16 hr at 25° C. the reaction was worked up and the product purified using column chromatography on silica and (CHCl$_3$/MeOH, 95:5) as eluant. 2.3 g of product was obtained.

5'-(N-Benzyloxycarbonyl)amino-5'-deoxy-2'-O-tetrahydropyranylcytidine (mixture with 3'-O-tetrahydropyranyl isomer) (Compound 7) was prepared as follows The azide (compound 6, 3.06 g) in THF (30 ml) was stirred with triphenylphosphine (1.7 g) for 24 hr at 50° C. Water (5 ml) was added and stirring continued for another 1 hour at 50° C. Concentration of the reaction mixture and purification on silica column using (first CHCl$_3$/MeOH 9:1, then 1:1 and finally 100% MeOH) gave 0.9 g of the product.

N4-Benzyloxycarbonyl-5'-(N-benzyloxycarbonylglycyl) amino-5'-deoxy-2'-O-tetrahydropyranylcytidine (mixture with 3'-O-tetrahydropyranyl isomer) (Compound 8) was prepared as follows.

The amine (compound 7. 0.9 g) was dissolved in anhydrous dichloromethane (30 ml) and p-nitrophenyl-N-carbobenzyloxy-glycinate (700 mg) was added. After stirring for 16 hr at 25° C., the reaction mixture was concentrated and purified by column chromatography using: (CHCl$_3$/MeOH first in the proportion 97:3, then 95:5). 1 g of the required material was obtained.

N4-Benzyloxycarbonyl-5'-N-(benzyloxycarbonylglycyl) amino-5'-deoxy-2'-O-tetrahydropyranylcytidyl-3'-(N,N-diisopropylmethyl) phosponamidate (mixture with 3' isomer) (Compound 9) was prepared as follows.

The alcohol (compound 8, 1 g) was dissolved in anhydrous dichloromethane (30 ml) and EtN(iPr)$_2$ (1.7 ml) was added, followed by Cl-P(OMe)N(iPr)$_2$(34 ml). After stirring for 6 hrs at 25° C. and work-up the mixture was purified by column chromatography on silica using (first CHCl$_3$/Et$_3$N 98:2, the CHCl$_3$/Et$_3$N/MeOH 97:2:1). 1.1 g product was obtained.

(Methyl)(4-N,N-dipropylaminophenyl)[N4-benzyloxycarbonyl-5'-(N-benzyloxycarbonylglyc yl)amino-5'-deoxy-2'-O-tetrahydropyranylcytidyl-3']-phosphate (mixture with 3' isomer) (Compound 10) was prepared as follows.

The phosphonamidate (compound 9, 1.1 g) was dissolved in anhydrous acetonitrile (30 ml) and 4-N,N-dipropylaminophenol (200 mg) was added followed by tetrazole (420 mg). After stirring at 25° C. for 16 hr, 70% t-butylhydroperoxide (0.3 ml) was added. After 15 minutes the reaction mixture was worked up and the crude product purified by column chromatography on silica eluting with: (first EtOAc, then EtOAc/MeOH 97:3) to give 0.85 g product (Methyl)(4-N,N-dipropylaminophenyl)(5'-deoxy-5'-glycylaminocytidyl-3')- phosphate (mixture with 3' isomer) (Compound 11) was prepared as follows.

The bis-carbobenzyloxy-protected compound (compound 10, 0.85 g) was dissolved in ethanol (30 ml) and cyclohexene (15 ml). Pd-C 20% (400 mg) were added and the stirred mixture heated to reflux for 4 hrs. After filtration the solution was concentrated and the gum purified by column chromatography on silica eluting with: (first CHCl$_3$/MeOH 95:5 then 5:1 and finally 100% MeOH). 100 mg product was obtained.

(4-N,N-dipropylaminophenyl)(5'-deoxy-5'-glycylamino-2'-O-tetrahydropyranylcytidyl-3') hydrogenphosphate. (Compound 12) was prepared as follows.

The phosphate (compound 11. 100 mg) was dissolved in t-butylamine (25 ml) and heated to relfux for 8 hr. After concentration the product was purified by HPLC (Magnum 20 reversed phase column, eluent MeOH/0.1 M ammonium formate in the ratio 60:40)

NMR (DMSOd6):(δ) 9.1 (s, 1H), 7.6 (d, 1H), 7.2 (m, 3H), 6.95 (d, 2H), 6.45 (d, 2H), 5.8(d, 1), 5.72(d, 1H), 4.71 (m, 1H), 4.45 (m, 1H), 4.22 (m, 1H), 4.1 (m, 1H), 3.8 (t, 1H), 3.7–3.15 (m, 2H), 3.51 (s, 2H), 3.35–3.5 (m, 1H), 3.0 (m, 4H), 1.8—1.2 (m, 10H), 0.8 (m, 6H).

Mass Spectrum FABMS [MH+]639

Reference Example 8

Localisation of A5B7 F(ab')$_2$-BP-RNase conjugate to LoVo tumour xenografts

The murine A5B7 F(ab')$_2$-BP-RNase conjugate prepared as described in Reference Example 4, was radioiodinated with carrier-free $^{125}$I using the IODOGEN™ reagent (Pierce and Warriner (UK) Ltd. Chester England) following the manufacturer's recommended method. In vitro retention of >50% immunoreactivity after radioiodination was confirmed by binding to LoVO tumour cells using the method of Lindmo et al. J. Immunol. Meth., 72, 77–89, 1984. Approximately 10 μg of conjugate containing 10 μCi$^{125}$I was injected intravenously into athymic nude mice (nu/nu:Alpk [outbred]) bearing established LoVo tumour xenografts (1×10$^7$ LoVO tumour cells injected subcutaneously 7 days previously). Following injection of conjugate, groups of 3 mice were killed at various time periods later and the tumour, a sample of blood and a range of other tissues were removed, weighted and counted in a gamma counter. The tumour and tissue distribution of the conjugate is shown in below.

| Tumour and tissue localisation of A5B7 F(ab')$_2$-BP-RNase | | | | | |
|---|---|---|---|---|---|
| Tissue | 4 hr | 24 hr | 48 hr | 72 hr | 96 hr |
| Tumour | 2.54 | 3.27 | 1.00 | 0.66 | 0.41 |
| Blood | 6.83 | 1.06 | 0.25 | 0.12 | 0.06 |
| Liver | 1.81 | 0.62 | 0.12 | 0.07 | 0.06 |
| Kidney | 2.76 | 0.55 | 0.23 | 0.18 | 0.11 |
| Lung | 2.85 | 0.28 | 0.15 | 0.09 | 0.08 |

Units=% injected dose/g tissue; results are mean values from 3 mice.

The results clearly show that the A5B7F(ab')$_2$-RNase conjugate specifically localises to the LoVo xenograft. From 24 hr onwards there was more conjugate/g tissue in the tumour compared to any other tissue including the blood. The levels of conjugate in the tumour were similar to those achieved with a A5B7 F(ab')$_2$-CPG2 conjugate (Blakery et al. Br. J. Cancer, 69 supplement XX1, p 14, 1994). These levels with this CPG2 conjugate have been shown sufficient in combination with mustard prodrugs to result in tumour regressions and prolonged growth delays in the LoVo xenograft model (Blakey et al. Br. J. Cancer, 69 supplement XX1, p14, 1994: Blakey et al. Proceedings of the American Association for Cancer Research, 35, p507, 1994).

Reference Example 9

Figure 28:
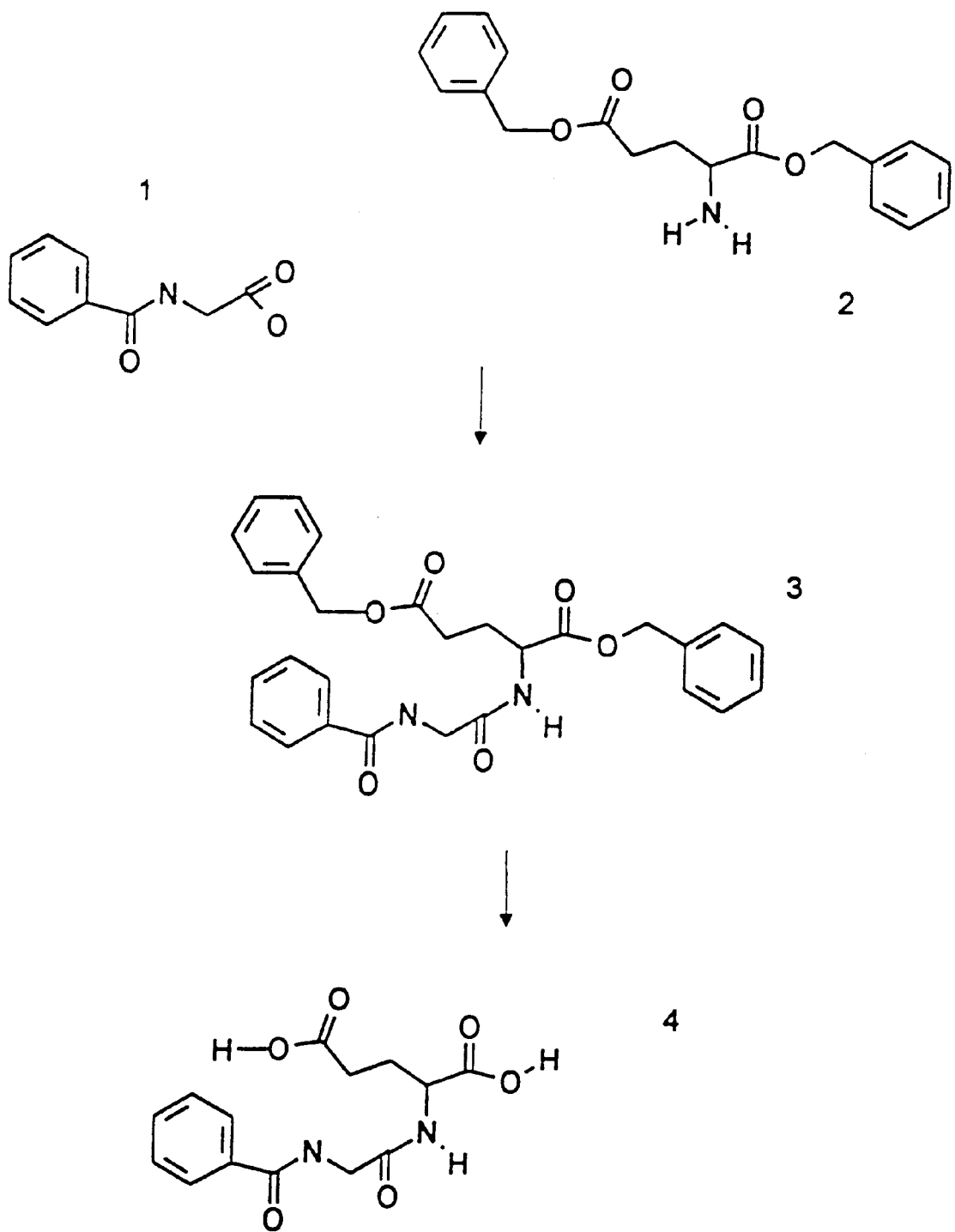
Figure 29:
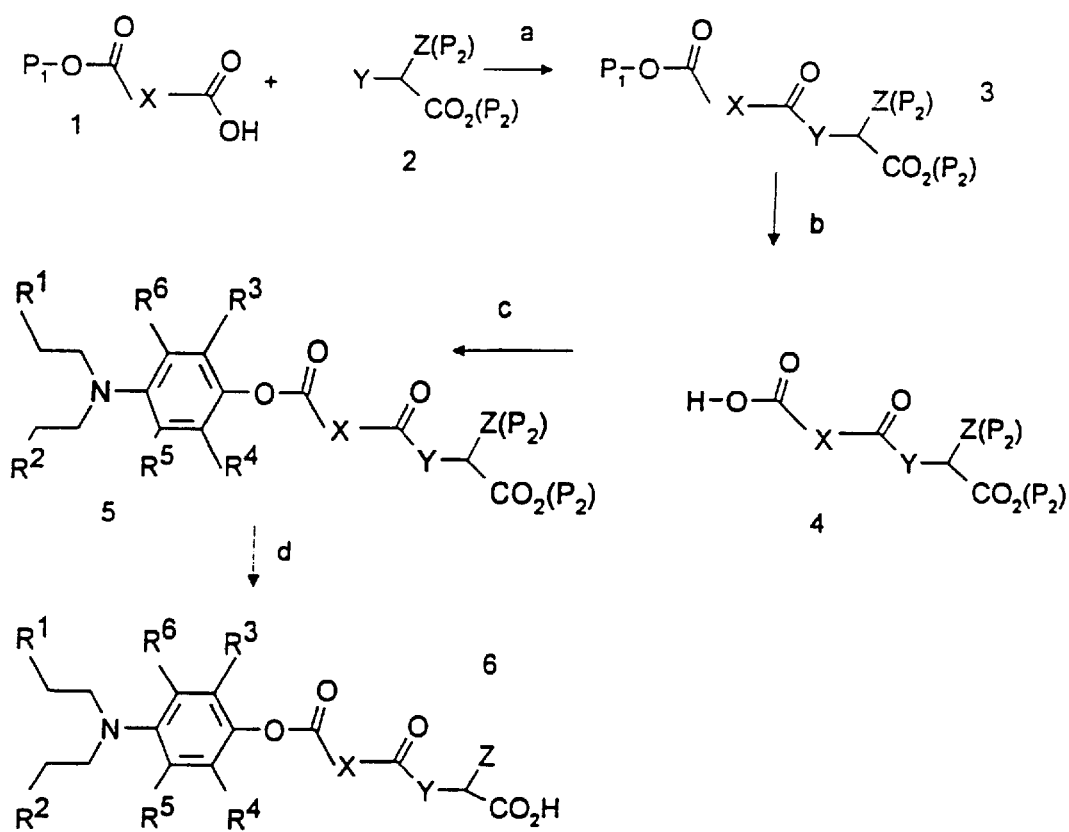
Figure 30:
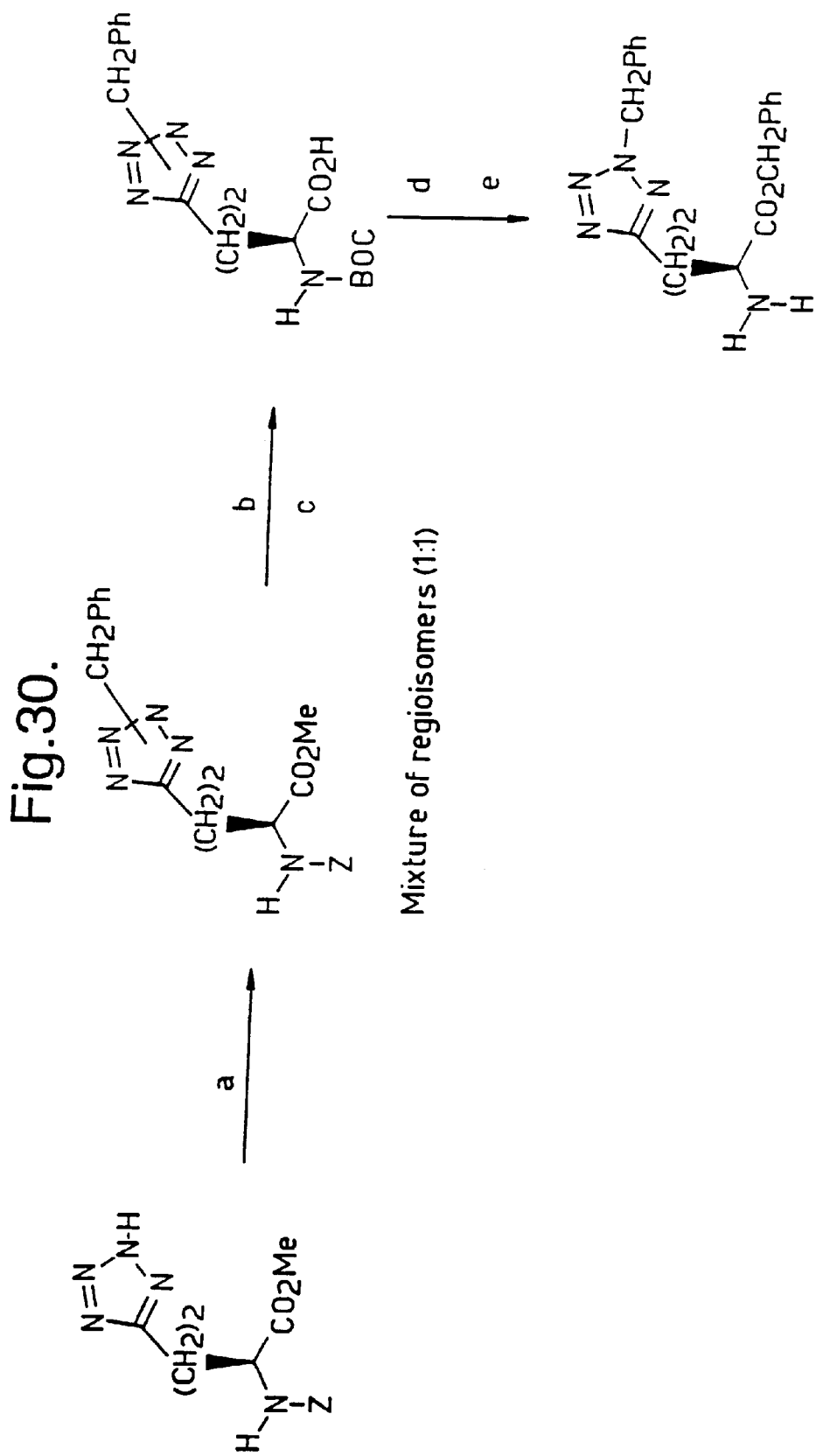
Figure 31:
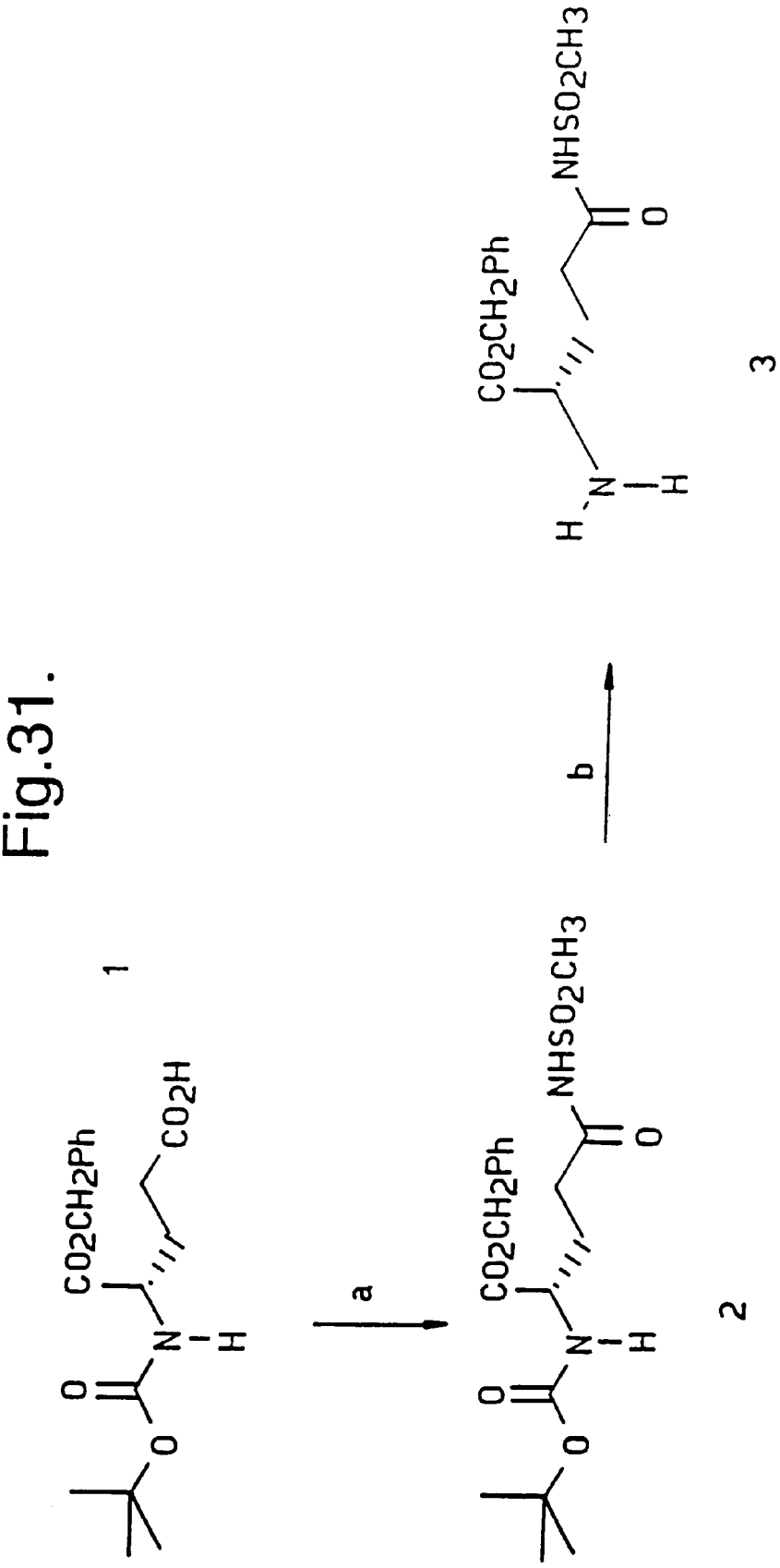
Figure 32:
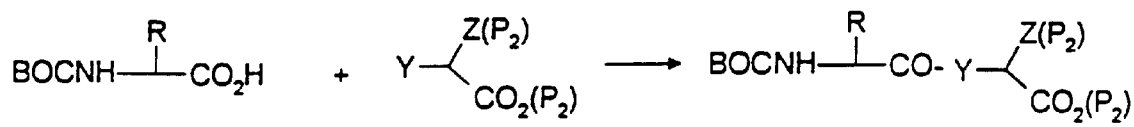
Figure 33:
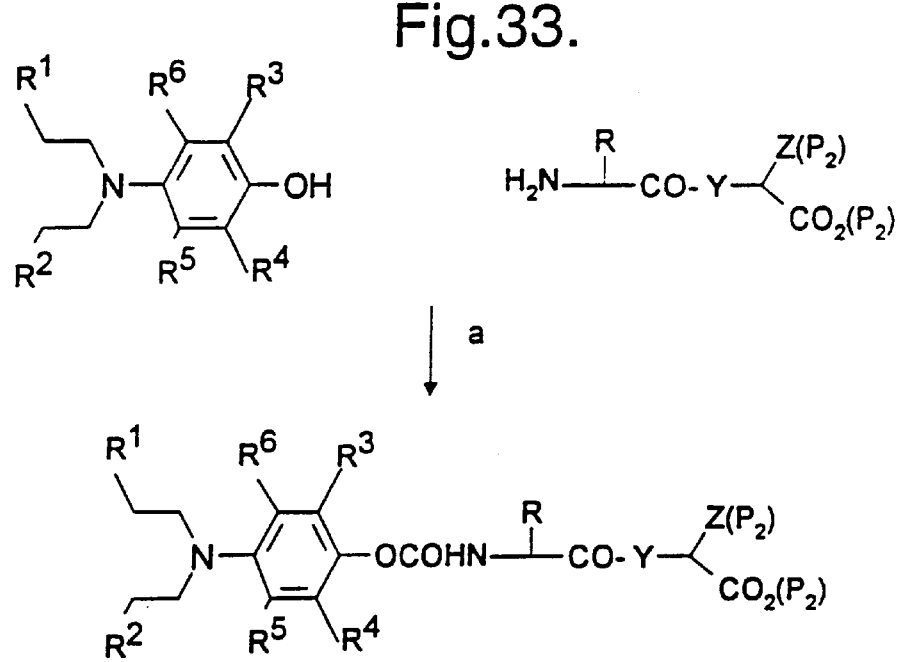

Synthesis of Hippuryl-L-Glutamic Acid (see FIG. 28)

Hippuryl-L-glutamic acid dibenzyl ester (compound 3) (2.06 g, 4.2×10$^{-3}$) moles) and 30% Pd/Carbon (50% moist) (0.77 g) in THF were stirred in an atmosphere of hydrogen for 1.5 hours. The mixture was filtered through Celite™ and the filtrate evaporated to dryness. Trituration with diethyl ether gave the desired end product as a white crystalline solid 1.02 g (78%). Melting point 169°–171° C. 20D=−2.5°

NMR DMSO d6 12.3.2H(broad); 8.7. 1H(t); 8.2 0.1H (t); 7.9.2H (m); 7.5, 3H(m); 4.3, 1H (m); 3.9.2H(m); 2.3. 2H (t); 1.9.2H (m)

The starting material compound 3 was prepared as follow. To a solution of hippuric acid (0.90 g, 5×10$^{-3}$ moles) and L-glutamic acid dibenzyl ester (2.50 g, 5×10$^{-3}$ moles) in DMF (35 ml) was added 1-hydroxybenzotriazole (0.73 g, 5.5×10$^{-3}$ moles), triethylamine (1.4 ml. 9.7×10$^{-3}$ moles) and 1(3-dimethyl-aminopropyl)-3-ethylcarbodiimide. HCl salt (1.05 g, 5.5×10$^{-3}$ moles). The mixture was stirred overnight at room temperature, poured into water (400 ml) and extracted twice with ethyl acetate (100 ml). The combined extracts were washed with saturated sodium bicarbonate solution, water, 2N HCl and water. The organic phase was dried over MgSO$_4$ and evaporated to obtain the desired starting material as a yellow oil. 2.06 g (84%).

NMR DMSO d6 8.7, 1H(t); 8.4 1H(d); 7.9, 2H(m); 7.5. 3H(m); 7.35, 10H(m); 5.15.2H (s); 5.05, 2H(s); 4.4, 1H(m); 3.9.2H(t); 2.0, 4H(m)

Reference Example 10
Synthesis of Hippuryl-L-Aspartic acid

Hippuryl-L-aspartic acid dibenzyl ester (1.28 g, 2.7×10$^{-3}$ moles) and 30% Pd/Carbon (50% moist) (0.51 g) in THF were stirred in an atmopshere of hydrogen for 3 hours. The mixture was filtered through Celite™ and the filtrate evapoated to dryness. Trituration with deithyl ether gave an off-white crystalline solid 0.62 g (78%). Melting point 200°–202° C. 20D=+7.9° NMR DMSO d6 12.5, 2H(broad); 8.7. 1H(t); 8.2. 1H(d); 7.2 .2H(m); 7.5, 3H(m); 4.6. 1H (m); 3.9. 2H(d); 2.7, 2H(m)

The starting material was synthesised as follows. To a solution of hippuric acid (0.90 g, 5×10$^{-3}$ moles) and L-aspartic acid dibenzyl ester (2.31 g, 5×10$^{-3}$ moles) in DMF (35 ml) was added 1-hyhdroxybenzotriazole (0.73 g, 5.5×10$^{-3}$ moles), triethylamine (1.4 ml, 9.7×10$^{-3}$ moles) and 1-(3-dimethyl-aminopropyl)-3-ethylcarbodiimide, HCl salt (1.05 g, 5.5×10$^{-3}$ moles). The mixture was stirred for 4 hours at room temperature then poured into water (450 ml) and extracted twice with ethyl acetate (100 ml). The extract was washed with saturated sodium bicarbonate solution, water, 2N HCl and water. The organic phase was dried over MgSO$_4$ and evaporated to dryness to obtain the desired starting material as a yellow oil. 1.90 g (80%)
NMR DMSO d6 8.7, 1H, (t); 8.45, 1H, (d); 7.9, 2H(m); 7.5.3H(m); 7.3, 10H (m); 5.15, 2H (s); 5.05. 2H(s); 4.8. 1H(m); 3.9.2H(m); 2.92H(m)

Reference Example 11
Enzymic activity of recombinant HCPB against Hipp-Art.

Purified human CPB, produced as described in Reference Example 20, was assayed for its ability to convert hippuryl-L-arginine (Hipp-Arg) to hippuric acid using a spectrophotometric assay.

The Km and kcat for native HCPB were determined by measuring the initial rate of conversion of Hipp-Arg to hippuric acid at 254 nM using a range of Hipp-Arg concentrations (0.75–0.125 mM) Tris HCl buffer, pH 7.5 using 1 cm path length cuvettes in a total volume of 1.0 ml using a Perkin Elmer Lambda 2 spectophotometer. Km and Vmax values were calculated using the ENZFITTER™ software programme (Biosoft™, Perkin Elmer). Kcat was calculated form Vmax by dividing by the enzyme concentration in the reaction mixture.

The results for human CPB against Hipp-Arg were:
Km=0.18 mM
kcat=65 s$^{-1}$

The results demonstrate that the recombinant HCPB is enzymatically active and can cleave the amide bond in Hipp-Arg to release Hippuric acid.

Figure 27:
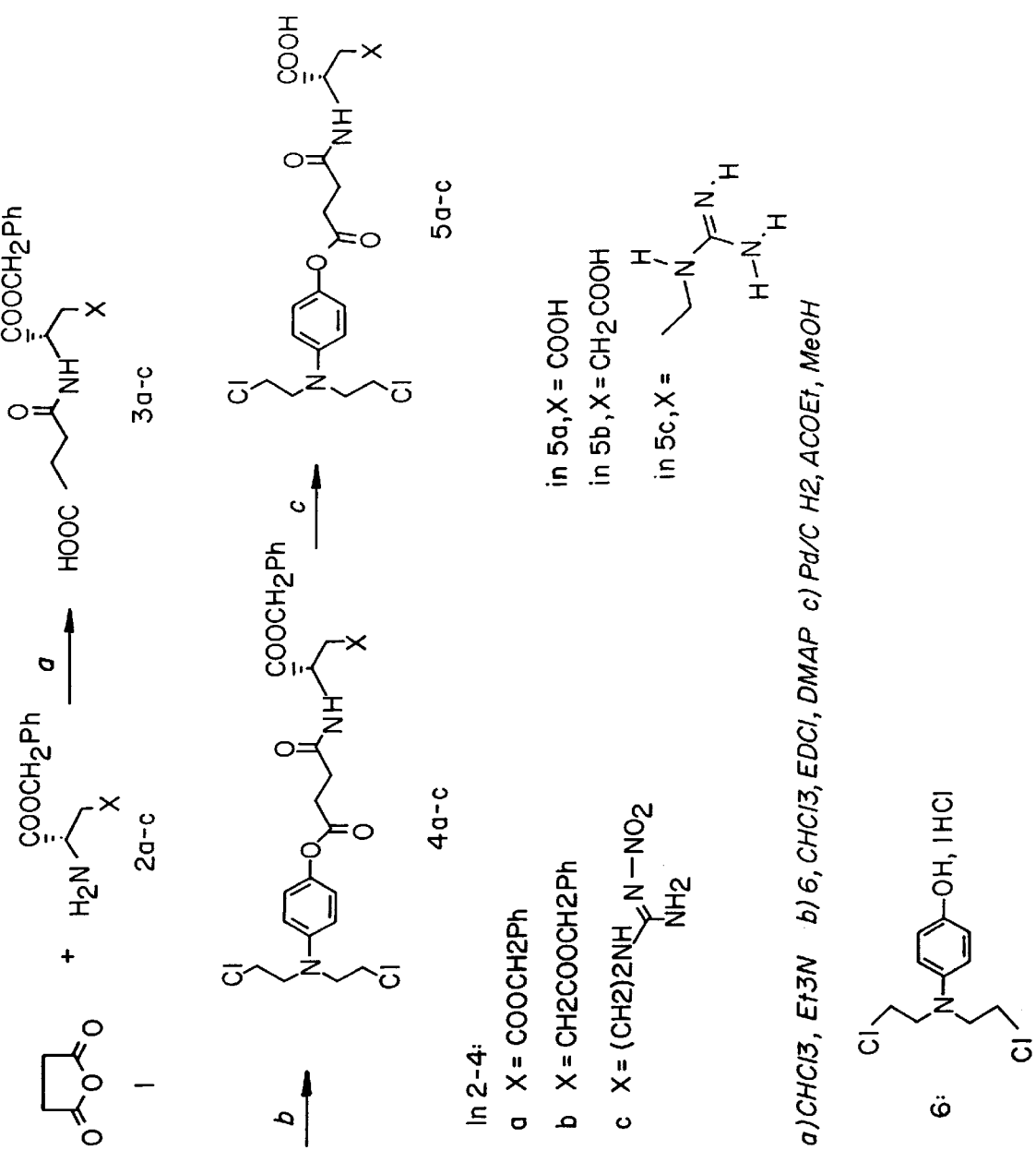

Reference Example 12
Synthesis of an Arginine mustard prodrug (see FIG. 27)

(2S),2-(3-{4-[bis-(2-chlorethyl)-amino)-phenoxycarbonyl}-propionyl-amino)-5-guanidino-pentoic acid (compound 5c, FIG. 27)

A solution of (2S),2-{4-[bis-(2-chloroethyl)-amino)-phenoxycarbonyl}-propionyl-amino)-5-(2-nitro)-guanidino-pentoic acid benzyl ester (compound 4c, FIG. 27)(275 mg; 0.44 mmol) in ethyl acetate/MeOH (1/1: V/V) (8 ml) containing 10% Pd/C (200 mg) was hydrogenated in a Paar apparatus at 80 psi for 6 h. After filtration the organic layer was evaporated. The resulting oil was recrystallised using CH$_2$Cl$_2$/diethyl ether to give the desired compound 5c as a white solid (180 mg), yield 84%.

1HNMR(CD3OD): 1.55—1.7 (m, 3H); 1.8–1.9 (m, 1H); 2.6–2.7 (m, 2H); 2.75–2.85 (m, 1H); 2.9–2.95 (m, 1H); 3.1–3.2 (m, 2H); 3.6–3.7 (m, 4H); 3.7–3.8 (m, 4H); 4.3 (dd, 1H); 6.75 (dd. 2H); 6.95 (dd, 2H).

MS(ESI): 512–514 (MNa)+

Anal (C$_{20}$H$_{29}$N$_5$O$_4$Cl$_2$ 1.5 H$_2$O): Calc. C: 47.91 H: 6.43 N:13.97, Found C: 47.7 H:6.21 N:14.26.

Starting material compound 4c was prepared as follows. To a solution of (2S), 2-amino-5-(2-nitro)-guanidino-pentoic acid benzyl ester (compound 2c) (654 mg; 1 mmol) in CHCl$_3$ (10 ml) was added dihydro-furan-2.5-dione (compound 1)(120 mg; 2 mmol) followed by triethylamine (202 mg; 2 mmol) dropwise. After stirring for 2 h at room temperature, the solvent was evaporated and the crude residue was dissolved in water, pH was adjusted to 2.5 with 2N HCl. The aqueous layer was extracted with ethyl acetate. The organic layer was washed with brine, dried (MgSO$_4$) and evaporated to give (2S),2-(3-carboxy-propionylamino)-5-(2-nitro)-guanidino-pentoic acid benzyl ester (compound 3c). The resulting solid was triturated with diethylether and filtered off: 280 mg (68%).

1HNMR (CD$_3$OD): 1.52–1.68(m, 2H); 1.7–1.8(m, 1H); 1.85–1.95(m, 1H); 2.45–2.7(m, 4H); 3.15–3.3 (m, 2H); 4.5 (m, 1H); 5.15 (dd, 2H); 7.25–7.4 (m, 5H)

MS(ESI): 432[MNa]+

To a suspension of compound 3c (204 mg; 0.5 mmol) in CHCl$_3$ (5 ml) was added 4-[bis(2-chlorethyl)amino]-phenol (compound 6)(135 mg; 0.5 mmol), EDCI (19 mg; 0.5 mmol) followed by DMAP (18 mg; 0.75 mmol). After stirring at room temperature for 6h, the solvent was evaporated. The residue was partitioned between ethyl acetate and water and the aqueous phase acidifed to pH=3 with 2N HCl. After extraction with ethyl acetate, the organic layer was washed with brine, dried (MgSO$_4$) and evaporated. The residue was purified by flash chromatography using CH$_2$Cl$_2$/MeOH(95/5: V/V) as eluant to give the desired starting material 4c as a white foam (281 mg) yield: 90%.

4c: 1HNMR(CD3OD): 1.55–1.7 (m, 2H); 1.7–1.8(m, 1H); 1.85–1.95 (m, 1H); 2.55–2.75(m, 2H); 2.8–2.9(m, 2H); 3.15–3.25 (m, 2H); 3.6–3.7(m, 4H); 3.7–3.8(m, 4H); 4.5(dd, 1H); 5.15 (dd, 2H); 6.7(d, 2H); 6.95(d, 2H); 7.32(m, 5H)

MS(ESI):647–649[MNa]+

Reference Example 13
Synthesis of succinic acid mono-{4-[N,N-bis(2-chloroethyl) amino]-phenyl} ester (also called "intermediate" herein)

To a suspension of succinic anhydride (225 mg, 2.25 mmol) in CHCl3 (10 ml) was added under stirring. 4-[N,N-bis(2-chloroethyl)-amino]phenol (compound 6, FIG. 27; 203 mg, 0.75 mmol) followed by triethylamine (75 mg, 0.75 mmol). The mixture was stirred overnight and the solvent evaporated. The crude residue was dissolved in EtOAC/Et$_2$O/H$_2$O and under stirring the pH was adjusted to 3. The organic layer was washed with water, brine, dried (MgSO$_4$), and evapoarated. The resulting oil was crystallised from Et$_2$O/hexane and the white solid was filtered off and dried under vacuum to obtain the desired end product (210 mg; yield 83%). Melting point 98°–100° C.

MS(ESI): 356–358[MNa]+

1H NMR (CDCl3): 2.8(dd, 2H); 2.9(dd,2H); 3.65(dd, 4H); 3.75(dd, 4H); 6.65(d,2H); 7.0 (d, 2H)

Analysis (C$_{14}$H$_{17}$Cl$_2$O$_4$N0.2H$_2$O): Calc. % C: 49.78 H: 5.19 N:4.15, Found % C: 49.9 H: 5.3 N:4.2

Reference Example 14

Cloning of human pancreatic carboxypeptidase B (HCPB)

Standard molecular biology techniques, such as restriction enzyme digestion, ligation, kinase reactions, dephosphorylation, polymerase chain reaction (PCR), bacterial transformations, gel electrophoresis, buffer preparation and DNA generation, purification and isolation, were carried out as described by Maniatis et al., (1989) Molecular Cloning, A Laboratory Manual; Second edition; Cold Spring Harbor Laboratory, Cold Spring Harbor, New York, or following the recommended procedures of manufacturers of specific products. In most cases enzymes were purchased from New England BioLabs, but other suppliers, and equivalent procedures may be used. Oligonucleotide sequences were prepared in an Applied Biosystems 380A DNA synthesiser from 5'-dimethoxytrityl base-protected nucleoside-2-cyanoethyl-N,N'-di-isopropyl-phosphoramidites and protected nucleoside linked to controlled-pore glass supports on a 0.2 $\mu$mol scale, according to the protocols supplied by Applied Biosystems Inc.

The coding sequence for human pancreatic carboxypeptidase B was obtained from a human pancreatic cDNA library cloned in the $\lambda$gt10 vector (Clontech. Human pancreas 5'STRETCH cDNA, HL1163a) using PCR technology, and cloned into the plasmid vector pBluescript™II KS+ (Stratagene).

Typically, an aliquot of the cDNA library (5 $\mu$l at a titre of >10$^8$pfu/ml) was mixed with 100pMols of two oligonucleotide primers. BPT1 and BPB1. (SEQ ID NO:46 and SEQ ID NO: 47), dNTPs to a final concentration of 200 $\mu$M. Taq polymerase reaction buffer, and 2.5U of Taq polymerase in a final volume of 100 $\mu$l. The mixture was heated at 94° C. for 10 minutes prior to addition to the Taq enzyme, and the PCR incubation was carired out using 30 cycles of 94° C. for 1.5 minutes. 50° C. for 2 minutes, and 72° C. for 2 minutes, followed by a single incubation of 72° C. for 9.9 minutes at the end of the reaction.

The two oligonucleotide primers were designed to allow PCR extension from the 5' of the gene from BPT1 (SEQ ID NO:46), between the start of the pre-sequence and the start of the pro-sequence, and PCR extension back from the 3' end of the gene from BPB1 (SEQ ID NO: 47), as shown in FIG. 18. BPT1 and BPB1 are also designed to introduce unique restriction sites, SacI and XhoI respectively, into the PCR product.

An aliquot of the PCR product was analysed for DNA of the correct size (about 1250 base pairs) by agarose gel electrophoresis and found to contain predominantly a band of the correct size. The remainder of the product from the reaction mix was purified and separated from excess reagents using a Centricon™100 microconcentrator column (Amicon), followed by DNA isolation by ethanol/sodium acetate precipitation, centrifugation, vacuum drying and re-suspension in distilled water. The isolated DNA was restriction digested with enzymes SacI and XhoI, and a band of the correct size (about 1250 base pairs) purified and isolated from agarose gel electrophoresis using excision and glass-milk (Geneclean™, Stratec Scientific, or other similar product.)

pBluescript™II KS+ double stranded DNA (Stratagene) was restriction digested with SacI enzyme, and the product dephosphorylation treated with calf intestinal alkaline phosphatase to remove 5'phosphoryl groups and reduce re-ligation and vector background following transformation. The DNA product was purified from enzyme reaction contaminants using glass-milk, and then restriction digested with XhoI enzyme. DNA of the correct size (about 2850 base pairs) was purified and isolated by agarose gel electrophoresis using excision and glass-milk (Geneclean™, Stratec Scientific, or other similar product).

Aliquots of both restricted and purified DNA samples were checked for purity and concentration estimation using agarose gel electrophoresis compared with known standards. From these estimates ligation mixes were prepared to clone the HCPB gene into the vector, using a molar ratio of about 1 vector to 2.5 insert (1 pBluescript™II KS+ to 2.5 HCPB PCR product), and a final DNA concentration of about 2.5 ng/$\mu$l, in the presence of T4 DNA ligase, 1 mM ATP and enzyme buffer.

Following the ligation reaction the DNA mixture was used to transform *E. coli* strain DH5$\alpha$ (Gibco-BRL, maximum efficiency competent cells). Cell aliquots were plated on L-agar nutrient media containing 100 $\mu$g/ml ampicillin as selection for plasmid vector, and incubated over-night at 37° C. Colonies containing plasmids with inserts of interest were identified by hybridisation.

About 200 colonies were picked and plated onto duplicate sterile nitro-cellulose filters (Schleicher and Schull), pre-wet on plates of L-agar nutrient media containing 100 $\mu$g/ml ampicillin as selection for plasmid vector, and incubated over-night at 37° C. One duplicate plate is stored at 4° C., and acts as a source of live cells for the colonies, the other plate is treated to denature and fix the DNA from the individual colonies to the nitro-cellulose. The nitro-cellulose filter is removed from the agar plate and placed in succession onto Whatman™ filter papers soaked in:

1. 10% SDS for 2 minutes
2. 0.5 M NaOH, 1.5 M NaCl for 7 minutes
3. 0.5 M NaOH, 1.5 M NaCl for 4 minutes
4. 0.5 M NaOH, 1.5 M NaCl for 2 minutes
5. 0.5 M Tris pH7.4, 1.5 M NaCl for 2 minutes
6. 2×SSC (standard saline citrate) for 2 minutes.

The filter is then placed on a Whatman™ filter paper soaked in 10×SSC and the denatured DNA is crossed linked to the nitro-cellulose by ultra violet light treatment (Spectrolinker™ XL-1500 UV crosslinker). The filters are then allowed to air dry at room temperature, and are then pre-hybridised at 60° C. for one hour in a solution of 6×SSC with gentle agitation (for example using a Techne HB-1D hybridizer). Pre-hybridization blocks non-specific DNA binding sites on the filters.

In order to determine which colonies contain DNA inserts of interest the DNA crosslinked to the nitro-cellulose filter is hybridised with a radio-labelled $^{32}$P-DNA probe prepared from HCPB PCR product of the pancreatic cDNA library (see above). About 50 ng of DNA was labelled with 50 $\mu$Ci of $^{32}$P-dCTP (~3000Ci/mMol) using T7 DNA polymerase in a total volume of 50 $\mu$l (Pharmacia T7 Quickprime kit), and the reaction allowed to proceed for 15 minutes at 37° C. The labelled probe is then heated to 95° C. for 2 minutes, to denature the double stranded DNA, immediately added to 10 ml of 6×SSC at 60° C. and this solution used to replace the pre-hybridisation solution on the filters. Incubation with gentle agitation is continued for about 3 hours at 60° C. After this time the hybridisation solution is drained off, and the filters washed twice at 60° C. in 2×SSC for 15 minutes each time. Filters were then gently blotted dry, covered with cling film (Saran™ wrap or similar), and exposed against X-ray film (for example Kodak Xomat™-AR5) over-night at room temperature. Following development of the film, colonies containing inserts of interest were identified as those which gave the strongest exposure (darkest spots) on the X-ray film. In this series of experiments about 15% of the colonies gave positive hybridisation. From this 12 colonies were chosen from further screening. These colonies were picked from the duplicate filter, streaked and maintained on L-agar nutrient media containing 100 μg/ml ampicillin, and grown in L-broth nutrient media containing 100 μg/ml ampicillin.

The selected isolates were checked by PCR for inserts of the correct size, using primers BPT1 and BPT1, (SEQ ID NO:46 and SEQ ID NO:47), and for priming with an internal primer BPT2(SEQ ID NO:48) and BPB1. BPT2 is designed to prime at the end of the pro-sequence, prior to the start of the mature gene and to introduce an Xbal restriction site.

For PCR screening colonies of the selected isolate were picked and dispersed into 200 μl of distilled water and heated at 100° C. for 10 minutes in a sealed Eppendorf™ tube. The suspensions were then centrifuged for 10 minutes in a microfuge to pellet cell debris, and 1 μl of the supernatant used as the DNA template in PCR screening. Typically, 1 μl of supernatant was mixed with 20 pmols of two oligonucleotide primers, BPT1 and BPB1, or BPT2 and BPB1, dNTPs to a final concentration of 200 μM. Taq polymerase reaction buffer, and 0.5 U of Taq polymerase in a final volume of 20 μl. The PCR incubation was carried out using 25 cycles of 94° C. for 1.5 minutes. 50° C. for 2 minutes, and 72° C. for 2 minutes, followed by a single incubation of 72° C. for 9.9 minutes at the end of the reaction.

The PCR products were analysed for DNA of the correct size (about 1250 base pairs from primers BPT1 to BPB1, and about 900 base pairs from primers BPT2 to BPB1, see FIG. 18) by agarose gel electrophoresis. Ten of the twelve clones gave PCR DNA products of the correct size. Six of the ten clones were then taken for plasmid DNA preparation (using Qiagen Maxi™ kits, from 100 ml of over-night culture at 37° C. in L-broth with 100 μg/ml ampicillin). These plasmid DNA preparations were then sequenced over the region of PCR product insert using an USB Sequenase™ DNA sequencing kit, which incorporates bacteriophage T7 DNA polymerase. Each clone was sequenced using eight separate oligonucleotide primers, known as 676, 336, 337, 679, 677, 1280, 1279 and 1281 (SEQ ID NO: 48 to 55). The positioning of the sequencing primers within the HCPB sequence is shown diagramatically in FIG. 19, primers 336, 1279, 676, 1280, 677 and 1281 being 'forward', and 337 and 679 'backwards'.

Five of the six clones were found to have identical sequence (SEQ ID NO:56) of 1263 base pairs between and including the SacI and XhoI restriction sites, and this sequence was used in further experiments. The translation of the DNA sequence into its polypeptide sequence is shown in SEQ ID NO: 57, and is numbered 1 from the start of the mature protein sequence. Amino acid numbered –95 marks the start of the putative pro-enzyme sequence. Only part of the enzyme secretion leader sequence (pre-sequence) is present in the cloned PCR generated DNA. The polypeptide sequence shows an aspartate residue at position 253, which when the whole sequence is aligned with other mammalian carboxypeptidase A and B sequences indicates a B type specificity (see amino acids numbered 255 by Catasus L. et al. Biochem J., 287, 299–303, 1992, and discussion). However, the cysteine residue at position 135 in the cloned sequence is not observed in other published human pancreatic carboxypeptidase B sequences, as highlighted by Yamamoto et al. in the Journal of Biology Chemistry, 267, 2575–2581, 1992, where she shows a gap in her sequence following the position numbered 244, when aligned with other mammalian pancreatic carboxypeptidase B amino acid sequences. Also shown on FIG. 19 are the approximate sites of the aspartate amino acid residue in the enzyme recognition site, and the cysteine residue at position 135 of the mature enzyme.

One of the clones was deposited on Nov. 23, 1995 with the National Collection of Industrial and Marine Bacteria Limited (23 St. Machar Drive, Aberdeen AB2 1RY, Scotland) and has the designation NCIMB 40694. The plasmid from this clone is known as pICI1698.

Reference Example 15

Expression of mature HCPB-(His)$_6$-c-Mye from *E. coli*

In order to achieve the expression of mature HCPB from *E. coli* the mature gene from pICI1698 was transferred into a plasmid vector which allows controlled secretion of protein products into the periplasm of the bacteria. This secretion vector, known as pICI266, in a bacterial host MSD522 suitable for controlled expression, has been deposited on Oct. 11, 1993 with the National Collection of Industrial and Marine Bacteria Limited (Aberdeen AB2 IRY, Scotland) and has the designation NCIMB 40589. A plasmid map of pICI266 is shown in FIG. 20. The plasmid has genes for tetracycline resistance and induction (TetA and TetR), and AraB operator and promoter sequence for inserted gene expression, and an AraC gene for expression control. The promoter sequence is followed by the PelB translation leader sequence which directs the polypeptide sequence following it to the periplasm. The site of gene cloning has several unique restriction sites and is followed by a phage T4 transcription terminator sequence. The DNA sequence in this region and the features for gene cloning are shown diagramatically in FIG. 21.

For the cloning of the mature HCPB sequence into pICI266 it was decided to generate HCPB DNA by PCR, and to make some alterations to the codon usage at the start of the mature gene to introduce *E. coli* preferred codons. Also, to help with detection and purification of the expression construct a C-term peptide tag, known as (His)$_6$-c-myc was added to the enzyme. The tag consists of 6 histidines, a tri-peptide linker (EPE) and a peptide sequence (EQKLISEEDL) from c-myc which is recognised by the antibody 9E10 (as published by Evan et al. Mol Cell Biol, 5, 129–136, 1985, and available from Cambridge Research Biochemicals and other antibody suppliers). The C-term is completed by the addition of an Asparagine. The 6 histidine residues should allow the purification of the expressed protein on a metal chelate column (for example Ni-NTA Agarose from Qiagen). In addition the PCR primers are used to introduce unique restriction sites at the 5' (FspI) and 3' (EcoRI) of the gene to facilitate the introduction of the PCR product into the expression vector. The sequence of the two primers, known as FSPTS1 and 6HIS9E10R1BS1, are shown in SEQ ID NO: 58 and 59.

To generate a modified gene for cloning into pICI266, PCRs were set up using 100 pMols of primers FSPTS1 and 6HIS9E10R1BS1 in the presence of approximately 5 ng of pICI1698 DNA, dNTPs to a final concentration of 200 μM. Taq polymerase reaction buffer, and 2.5 U of Taq polymerase in a final volume of 100 μl. The mixture was heated at 94° C. for 10 minutes prior to addition to the Taq enzyme, and the PCR incubation was carried out using 30 cycles of 94° C. for 1.5 minutes. 50° C. for 2 minutes, and 72° C. for 2 minutes, followed by a single incubation of 72° C. for 9.9 minutes at the end of the reaction. An aliquot of the PCR product was analysed for DNA of the correct size (about 1000 base pairs) by agarose gel electrophoresis and found to contain predominantly a band of the correct size. The remainder of the product from the reaction mix was purified and separated from excess reagents using a Centricon™ 100 microconcentrator column (Amicon), followed by DNA isolation by ethanol/sodium acetate precipitation, centrifugation, vacuum drying and re-suspension in distilled water. The isolated DNA was restriction digested with enzymes FspI and EcoRI, and a band of the correct size (about 1000 base pairs) purified and isolated from agarose gel electrophoresis using excision and glass-milk (Geneclean™, Stratec Scientific, or other similar product).

pICI266 double stranded DNA, prepared using standard DNA technology (Qiagen plasmid kits or similar), was restriction digested with KpnI enzyme, being very careful to ensure complete digestion. The enzyme was then inactivated by heating at 65° C. for 10 minutes, and then cooling on ice. The 3' over-hang generated by the KpnI was then enzymatically digested by the addition of T4 DNA polymerase as recommended by the supplier (New England BioLabs), in the presence of dNTPs and incubation at 16° C. for 15 minutes. The reaction was stopped by inactivating the enzyme by heating at 70° C. for 15 minutes. The DNA product was purified from enzyme reaction contaminants using glass-milk, an aliquot checked for yield by agarose gel electrophoresis, and the remainder restriction digested with EcoRI enzyme. Again care was taken to ensure complete restriction digest. DNA of the correct size (about 5600 base pairs) was purified and isolated by agarose gel electrophoresis using excision and glass-milk (Geneclean™, Stratec Scientific, or other similar product).

Aliquots of both restricted and purified DNA samples were checked for purity and concentration estimation using agarose gel electrophoresis compared with known standards. From these estimates ligation mixes were prepared to clone the HCPB gene into the vector, using a molar ratio of about 1 vector to 2.5 inset (1 pICI266 to 2.5 HCPB PCR product), and a final DNA concentration of about 2.5 ng/μl, in the presence of T4 DNA ligase, 1 mM ATP and enzyme buffer, using conditions suitable for the ligation of blunt ended DNA (FspI to T4 DNA polymerase treated KpnI).

Following the ligation reaction the DNA mixture was used to transform E. coli strain DN5= (Gibco-BRL, maximum efficiency competent cells). Cell aliquots were plated on L-agar nutrient media containing 10 μg/ml tetracycline as selection for plasmid vector, and incubated over-night at 37° C. Colonies containing plasmids with inserts of interest were identified by hybridisation.

About 350 colonies were picked and plated onto duplicate sterile nitro-cellulose filters (Schleicher and Schull), pre-wet on plates of L-agar nutrient media containing 10 μg/ml tetracycline as selection for plasmid vector, and incubated over-night at 37° C. One duplicate plate is stored at 4° C., and acts as a source of live cells for the colonies, the other plate is treated to denature and fix the DNA from the individual colonies to the nitro-cellulose. The nitro-cellulose filter is removed from the agar plate and place in succession onto Whatman™ filter papers soaked in:

1. 10% SDS for 2 minutes
2. 0.5M NaOH, 1.5M NaCl for 7 minutes
3. 0.5M NaOH, 1.5M NaCl for 4 minutes
4. 0.5M NaOH, 1.5M NaCl for 2 minutes
5. 0.5M Tris pH 7.4, 1.5M NaCl for 2 minutes
6. 2×SSC (standard saline citrate) for 2 minutes The filter is then placed on a Whatman filter paper soaked in 10×SSC and the denatured DNA is crossed linked to the nitro-cellulose by ultra violet light treatment (Spectrolinker XL-1500 UV crosslinker). The filters are then allowed to air dry at room temperature, and are then pre-hybridised at 60° C. for one hour in a solution of 6×SSC with gentle agitation (for example using a Techne HB-1D hybridizer™). Pre-hybridization blocks non-specific DNA binding sites on the filters.

In order to determine which colonies contain DNA inserts of interest, the DNA crosslinked to the nitro-cellulose filter is hybridised with a radio-labelled 32P-DNA probe prepared from HCPB PCR product of the pancreatic cDNA library (see above). About 50 ng of DNA was labelled with 50 μCi of 32P-dCTP (~3000Ci/mMol) using T7 DNA polymerase in a total volume of 50 μl (Pharmacia T7 Quickprime™ kit), and the reaction allowed to proceed for 15 minutes at 37° C. The labelled probe is then heated to 95° C. for 2 minutes, to denature the double stranded DNA, immediately added to 10 ml of 6×SSC at 60° C., and this solution used to replace the pre-hybridisation solution on the filters. Incubation with gentle agitation is continued for about 3 hours at 60° C. After this time the hybridisation solution is drained off, and the filters washed twice at 60° C. in 2×SSC for 15 minutes each time. Filters were then gently blotted dry, covered with cling film (Saran™ wrap or similar), and exposed against X-ray film (for example Kodak Xomat™-AR5) over-night at room temperature. Following development of the film, colonies containing inserts of interest were identified as those which gave the strongest exposure (darkest spots) on the X-ray film. In this series of experiments about 50% of the colonies gave positive hybridisation. From this 12 colonies were chosen for further screening. These colonies were picked from the duplicate filter, streaked and maintained on L-agar nutrient media containing 10 μg/ml tetracycline, and grown in L-broth nutrient media containing 10 μg/ml tetracycline.

The selected isolates were checked by PCR for inserts of the correct size, using primers FSPTS1 and 6HIS9E10R1BS1, (SEQ ID NO: 58 and SEQ ID NO: 59), and for priming with an internal primer BPB2 (SEQ ID NO: 51) and FSPT1. BPB2 is designed to prime within the mature gene and generate a fragment of about 430 base pairs.

FOR PCR screening colonies of the selected isolates were picked and dispersed into 200 μl of distilled water and heated at 100° C. for 10 minutes in a sealed Ependorph tube. The suspensions were then centrifuged for 10 minutes in a microfuge to pellet cell debris, and 1 μl of the supernatant used as the DNA template in PCR screening. Typically, 1 μl of supernatant was mixed with 20 pMols of two oligonucleotide primers, FSPT1 and 6HIS9E10R1BS1, or FSPT1 and BPB2, dNTPs to a final concentration of 200 μM. Taq polymerase reaction buffer, and 0.5 U of Taq polymerase in a final volume of 20 μl. The PCR incubation was carried out using 25 cycles of 94° C. for 1.5 minutes, 50° C. for 2 minutes, and 72° C. for 2 minutes, followed by a single incubation of 72° C. for 9.9 minutes at the end of the reaction.

The PCR products were analysed for DNA of the correct size (about 1000 base pairs from primers FSPTS1 to 6HIS9E10R1BS1, and about 430 base pairs from primers FSPTS1 to BPB2) by agarose gel electrophoresis. All twelve clones gave PCR DNA products of the correct size. Six of the clones were then taken for plasmid DNA preparation (using Qiagen Maxi™ kits, from 100 ml of over-night culture at 37° C. in L-broth with 10 μg/ml tetracycline). These plasmid DNA preparations were then sequenced over the region of PCR product insert using an USB Sequenase™ DNA sequencing kit, which incorporates bacteriphase T7 DNA polymerase. Alternatively the DNA was sequenced using an automated DNA sequencing service (using ABI sequencing equipment). The clones were sequenced using several separate oligonucleotide primers. Three of the primers, known as 1504, 1590 and 1731, were used to check the cloning junctions between the expression vector and the inserted gene (SEQ ID NO: 60, 61 and 62), as well as giving sequence data from the start and end of the inserted gene. Other primers, including those known as 679, 677, 1802, and 1280 (SEQ ID NO: 51, 52, 63 and 53) were used to confirm the remainder of the inserted gene sequence. This plasmid containing the modified mature HCPB gene is known as pICI1712. The confirmed sequence of the cloned gene, showing amino acid translation, from the start of the PelB sequence to the end of the $(His)_6$-c-myc tag is shown as SEQ ID NO: 64 with DNA numbering starting from 1 in the first codon of PelB, and peptide numbering starting from 1 in the mature HCPB.

To obtain controlled expression of the modified HCPB the pICI1712 plasmid DNA was transformed into calcium chloride transformation competent E. coli expression strains. Included amongst these strains were a number which were incapable of growing with arabinose as the major carbon source, and were chromosome deleted for the arabinose (Ara) operon. A preferred strain is known as MSD213 (strain MC1000 of Casadaban et al. Journal of Molecular Biology, v138, 179–208, 1980), and has the partial genotype, F-Ara Δ(Ara-Leu) ΔLacX74 GalV GalK StrR. Another preferred stain is known as MSD525 (strain MC1061) and has the genotype. AraD139 Δ(Ara Leu)7697 ΔLac74 GalU HsdR RpsL. E. coli strains of similar genotype, suitable for controlled expression of genes from the AraB promoter in plasmid pICI266, may be obtained from The E. coli Genetic Stock Centre, Department of Biology, Yale University, Conn., U.S.A. Selection for transformation was on L-agar nutrient media containing 10 μg/ml tetracycline, over night at 37° C. Single colonies were picked from the transformation plates, purified by streaking and maintained on L-agar nutrient media containing 10 μg/ml tetracycline, and grown in L-broth nutrient media containing 10 μg/ml tetracycline.

All pICI1712 transformed expression strains were treated in the same manner to test for expression of the cloned HCPB gene.

1. A single colony was used to inoculate 10 ml of L-broth nutrient media containing 10 μg/ml tetracycline in a 25 ml Universal container, and incubated over night at 37° C. with shaking.
2. 75 ml of L-broth nutrient media containing 10 μg/ml tetracycline pre-warmed to 37° C. in a 250 ml conical flask was inoculated with 0.75 ml (1% v/v) of the over-night culture. Incubation was continued at 37° C. with shaking, and growth monitored by light absorbance at 540 nm. Induction of cloned protein expression was required during exponential growth of the culture, and this was taken as between 0.4 and 0.6 O.D. at 540 nm, and generally took 90 to 150 minutes from inoculation.
3. When the cells had reached the required optical density the cultures were allowed to cool to approximately 30° C. by placing the flasks at room temperature for 30 minutes. Arabinose was then added to a final concentration of 1% (w/v), and incubation continued at 30° C. with shaking for 4 to 6 hours.
4. After incubation a final optical density measurement is taken, and the cells were harvested by centrifugation.

The final O.D. measurement is used to calculate the the volume of protein acrylamide gel (Laemmli) loading buffer that is used to resuspend the cell pellet. For O.D. less than 1 a volume of 10 μl is used for each 0.1 O.D. unit, and for an O.D. greater than 1 a volume of 15 μl is used for each 0.1 O.D. unit. The Laemmli loading buffer consists of 0.125M Tris-HCl pH 6.8, containing 2% SDS, 2% β-mercaptoethanol, 10% glycerol and 0.1% Bromophenol blue.

5. Following re-suspension the samples were denatured by heating at 100° C. for 10 minutes, and then centrifuged to separate the viscous cell debris from the supernatant. Expression samples, usually 20 μl of the supernatant, typically were loaded onto 17% SDS acrylamide gels for electrophoretic separation of the proteins. Duplicate gels were generally prepared so that one could be stained for total protein (using Coomassie or similar stain and standard conditions), and the other could be processed to indicate specific products using Western analysis.

For Western analysis proteins in the run gel were transferred to nylon membrane (Problot™, Applied Biosystems for example), using a semi-dry electrophoresis blotting apparatus (Bio-rad or similar). Before, and during processing care was taken to ensure that the membrane remained damp. After and during processing care was taken to ensure that the blocked with a solution of 5% low fat milk powder (Marvel™ or similar) in phosphate buffered saline (PBS) at room temperature with gentle agitation for 5 hours. The membrane was then washed 3 times at room temperature with gentle agitation for 5 minutes each time in PBS containing 0.05% Tween 20. The washed membrane was then incubated with the primary antibody, monoclonal 9E10 mouse anti-c-myc peptide (see above), at a suitable dilution (typically 1 in 10,000 for ascites for 1 in 40 for hybridoma culture supernatant) in PBS containing 0.5% Tween 20 and 0.5% low fat milk powder, at room temperature with gentle agitation over night. The membrane was then washed 3 times at room temperature with gentle agitation for at least 5 minutes each time in PBS containing 0.05% Tween 20. The washed membrane was then incubated with the secondary antibody, horseradish peroxidase labelled anti-mouse IgG (typically raised in goat, such as A4416 from Sigma), at a suitable dilution (typically 1 in 10,000) in PBS containing 0.05% Tween 20 and 0.5% low fat milk powder, at room temperature with gentle agitation for at least three hours. The membrane was then washed 3 times at room temperature with gentle agitation for at least 10 minutes each time in PBS containing 0.05% Tween 20. The membrane was then processed using the Amersham ECL™ Western detection kit methodology, and exposed against Amersham Hyperfilm™ ECL for 30 seconds in the first instance, and then for appropriate times to give a clear image of the expressed protein bands. Other methods of similar sensitivity for the detection of peroxidase labelled proteins on membranes may be used.

Good expression of the cloned tagged HCPB in pICI266 (PICI1712) was demonstrated in E.coli strains MSD213 and MSD525 by the Coomassie stained gels showing an additional strong protein band at about 35,000 Daltons when compared to vector (PICI266) alone clones, and a band of the same size giving a strong signal by Western analysis detection of the c-myc peptide tag.

Reference Example 16
Expression of mature HCPB from E. coli

The method of cloning and expressing the mature HCPB in E. coli was very similar to the method described in Reference Example 1.5 Again pICI266 was used as the cloning vector, but in this case the starting material for PCR of the mature HCPB gene was plasmid pICI1712, the tagged gene in the expression vector. Two oligonucleotides, known as 2264 and 2265 (SEQ ID NO: 65 and 66) were used in the PCR reactions (instead of primers FSPTS1 and 6HIS9E10R1BS1), using similar conditions to Reference Example 15, but using pICI1712 DNA instead of pICI1698. The first, top strand, oligonucleotide, 2264, was designed to prime on pICI1712 and to include the NcoI restriction enzyme site in the PelB leader sequence, and to continue to the start of the inserted mature HCPB gene (DNA bases 36 and 66 inclusive in SEQ ID NO:64). The second, bottom strand, oligonucleotide, 2256, was designed to prime at the end of the mature HCPB gene, prior to the start of the $(His)_6$-c-myc tag sequence (complementary to DNA bases 965 to 987 inclusive in SEQ ID NO: 64), and to introduce translation termination codons (complementary to TAA TAA) at the end of the gene followed by and EcoRI (GAATTC) restriction enzyme site and fill-in bases. This oligo primes back into the gene in the PCR to isolate the mature gene sequence.

An aliquot of the PCR product was analysed for DNA of the correct size (about 970 base pairs) by agarose gel electrophoresis and found to contain predominantly a band of the correct size. The remainder of the product from the reaction mix was purified in a similar manner to Reference Example 15. The isolated DNA was restriction digested with enzymes NcoI and EcoRI, and a band of the correct size (about 94- 0 base pairs) purified in a similar manner to Reference Example 15.

pICI266 double stranded DNA, prepared in a similar manner to Reference Example 15, was restriction digested with NcoI and EcoRI enzymes, being very careful to ensure complete digestion. DNA of the correct size (about 5600 base pairs) was purified in a similar manner to Reference Example 15.

Aliquots of both restricted and purified DNA samples were checked for purity and concentration estimation using agarose gel electrophoresis compared with known standards. From these estimates ligation mixes were prepared to clone the HCPB gene into the pICI266 vector in a similar manner to Reference Example 15.

Following the ligation reaction the DNA mixture was used to transform E. coli strain DH5α, colonies were picked and tested by hybridisation, in a similar manner to Reference Example 15.

Six of the clones were then taken for plasmid DNA preparation, which were then sequenced over the region of PCR product in a similar manner to Reference Example 15. The clones were sequenced using six separate oligonucleotide primers known as 1504, 1802, 679, 1280, 677 and 1731 (SEQ ID NO: 60, 63, 51, 53, 52 and 62). From the sequencing results a clone containing a plasmid with the required mature HCPB gene sequence was selected, and is known as pICI1736.

The confirmed sequence of the cloned gene, showing amino acid translation, from the start of the PelB sequence to the EcoRI restriction site is shown as SEQ ID NO: 67 with DNA numbering starting from 1 in the first codon of PelB, and peptide numbering starting from 1 in the mature HCPB.

To obtain controlled expression of the mature HCPB, the pICI1736 plasmid DNA was transformed into calcium chloride transformation competent E. coli expression strains in a similar manner to Reference Example 15. All pICI1736 transformed expression strains were treated in a similar manner to reference Example 15 to test for expression of the cloned HCPB gene. However, in this case the 9E10 monoclonal antibody specific for the c-myc peptide tag cannot be used in the Western analysis, as the mature HCPB has no C-terminal tag. Therefore, the primary antibody was an anti-bovine carboxypeptidase. A raised in rabbit (from Biogenesis) which had previously been shown to cross-react with purified human pancreatic carboxypeptidase B. The secondary antibody was an anti-rabbit IgG antibody labelled with horseradish peroxidase and raised in goat (Sigma A9169 or similar).

Expression of the cloned mature HCPB in pICI266 (pICI1736) was demonstrated in E. coli strains MSD213 and MSD525 by the Coomassie stained gels showing an additional protein band at about 34,000 daltons when compared to vector (pICI266) alone clones. A band of the same size gave a signal by Western analysis detection using the anti-bovine carboxypeptidase A.

Reference Example 17

Expression of mature HCPB from COS cells

A gene encoding preHCPB was generated by PCR from PICI1698 (Reference Example 14). The PCR was set up with template pICI1689 (10 μg) and oligos SEQ ID NO: 34 and SEQ ID NO: 35 (100 pMoles of each) in buffer (100 μl) containing 10 mM Tris-HCl (pH 8.3). 50 mM KCL, 1.5 mM $MgCl_2$, 0.125 mM each of dATP, dCTP, dGTP and dTTP and 2.5 u Taq DNA polymerase (Amplitaq. Perkin-Elmer Cetus). The reaction was overlaid with mineral oil (100 μl) and incubated at 94° C. for 1 min. 53° C. for 1 min and 72° C. for 2.5 min for 25 cycles, plus 10 min at 72° C. The PCR product of 985 bp was isolated by electrophoresis on a 1% agarose (Agrarose type I. Sigma A-6013) gel followed by excision of the band from the gel and isolation of the DNA fragment by use of Geneclean™ (Geneclean II kit. Stratech Scientific Ltd. or Bio 101 Inc.). The Geneclean kit contains 1) 6M sodium iodide 2) a concentrated solution of sodium chloride. Tris and EDTA for making a sodium chloride/ethanol/water wash; 3) Glassmilk™- a 1.5 ml vial containing 1.25 ml of a suspension of a specially formulated silica matrix in water.

This is a technique for DNA purification based on the method of Vogelstein and Gillespie published in Proceedings of the National Academy of Sciences U.S.A. (1979) Vol 76, p 615. Alternatively any of the methods described in "Molecular Cloning - laboratory manual" Second Edition, Sambrook, Fritsch and Maniatis (Cold Spring Harbor Laboratory, 1989) can be used. Briefly, the Geneclean procedure is as follows. To 1 volume of gel slice is added 3 volumes of sodium iodide solution from the kit. The agarose is melted by heating the mix at 55° C. for 10 min than Glassmilk (5–10 μl) is added, mixed well and left to stand for 10 min at ambient temperature. The glassmilk is spun down and washed 3 times with NEW WASH (500 μl) from the kit. The wash buffer is removed from the Glassmilk which is to dry in air. The DNA is eluted by incubating the dried Glassmilk with water (5–10 μl) at 55° C. for 5–10 min. The aqueous supernatant containing the eluted DNA is recovered by centrifugation. The elution step can be repeated and supernatants pooled.

The preHCPB gene was digested for 1 h at 37° C. with EcoRI and HindIII in a 100 μl reaction containing 100 mM Tris-HCl (pH 7.5), 10 mM magnesium chloride, 50 mM NaCl, 0.025% triton X-100, and 25 u of each HindIII and EcoRI (New England Biolabs). The digested fragment was purified by agarose gel electrophoresis and GeneClean as described above for the uncut fragment and cloned into pBluescript™ (Stratagene Cloning Systems).

pBluescript™ KS+DNA (5 μg) was digested to completion with EcoRI and HindIII (25 u each) in a 100 μl reaction as described above. Calf-intestinal alkaline phosphatase (1 μl; New England Biolabs. 10 u/μl) was the added to the digested plasmid to remove 5' phosphate groups and incubation continued at 37° C. for a further 30 minutes. Phosphatase activity was destroyed by incubation at 70° C. for 10 minutes. The EcoRI-HindIII cut plasmid was purified from an agarose gel as described above. The EcoRI-HindIII digested preHCPB gene (50 mg) was ligated with the above cut plasmid DNA in 20 μl of a solution containing 30 mM Tris-Hcl (pH 7.8), 10 mM MgCl$_2$, 10 mM DTT, 1 mM ATP, 50 μg/ml BSA and 400 u T4 DNA ligase (New England Biolabs, Inc) at 25° C. for 4 h. A 1 μl aliquot of the reaction was used to transform 20 μl of competent E. coli DH5α cells (MAX efficiency DH5α competent cells. Life Technologies Ltd) using the protocol provided with the cells. Transformed cells were plated onto L-agar plus 100 μg/ml Ampicillin. Potential preHCPB clones were identified by PCR. Each clone was subjected to PCR as described above for preparation of the preHCPB gene except that the mix with the cells was incubated at 94° C. (hot start procedure) for 5 min prior to 25 cycles of PCR and oligos SEQ ID NO: 36 and 37 replaced oligos SEQ ID NO: 34 and 35. A sample (10 μl) of the PCR reaction was analysed by electrophoresis on a 1% agarose gel. Clones containing the preHCPB gene were identified by the presence of a 1.2 kb PCR product. Clones producing the 1.2 kb were used for large scale plasmid DNA preparation and the sequence of the insert confirmed by DNA sequence analysis. The plasmid containing the preHCPB gene in pBluescript™ was named pMF15.

To generate vectors capable of expressing HCPB in eukaryotic cells the GS-System™ (Celltech Biologics) was used (WO 87/04462, WO 89/01036, WO 86/05807 and WO 89/10404). The procedure requires cloning the preHCPB gene into the HindIII-EcoRI region of vector pEE12 [this vector is similar to pSV2.GS described in Bebbington et al. (1992) Bio/Technology 10, 169–175, with a number of restriction sites originally present in pSV2.GS removed by site-directed mutagenesis to provide unique sites in the multi-linker region]. To construct the expression vector, plasmids pEE12 and pMF15 were digested with EcoRI and HindIII as described above. The appropriate vector (from pEE12) and insert (from pMF15) from each digest were isolated from a 1% agarose gel and ligated together and used to transform competent DH5α cells. The transformed cells were were plated onto L agar plus ampicillin (100 μg/ml). Colonies were screened by PCR as described above, with oligos which prime within the CMV promoter (SEQ ID NO: 38) and in the HCPB gene (SEQ ID NO: 39). Clones producing a 1.365 kb PCR product were used for large scale plasmid DNA preparation and the sequence of the insert confirmed by DNA sequence analysis. The plasmid containing the preHCPB sequence in pEE12 was named pMF48.

A second eukaryotic expression plasmid, pEE12 containing the prepro sequence of preproHCPB was prepared as described above. Oligos SEQ ID NO: 40 and 41 were used in the initial PCR to isolate a gene for the prepro sequence from pMF18 (described in Reference Example 19). In this case the PCR was performed with a hot start procedure by first incubating the mix without Taq DNA polymerase for 5 min at 94° C. Taq DNA polymerase (2.5 u) was then added and the PCR continued through the 25 cycles as described above. The 360 bp fragment was clone into pBluescript to give pMF66 and subsequently into pEE12 (screening by PCR with SEQ ID NO: 40 and 41 to give pMF67.

For expression in eukaryotic cells, vectors containing genes capable of expressing preHCPB and the prepro sequence were cotransfected into COS-7 cells. COS cells are an African green monkey kidney cell line. CV-1 transformed with an origin-defective SV40 virus and have been widely used for short-term transient expression of a variety of proteins because of their capacity to replicate circular plasmids containing an SV40 origin or replication to very high copy number. There are two widely available COS cells clones, COS-1 and COS-7. The basic methodology for transfection of COS cells is described by Bebbington in Methods: A Companion to Methods in Enzymology (1991) 2, 141. For expression of HCPB, the plasmid vectors pMF48 and pMF67 (4 μg of each) were used to transfect the COS-7 cells (2×10e5) in a six-well culture plate in 2 ml Dulbecco's Modified Eagle's Medium (DMEM) containing 10% heat inactivated foetal calf serum (FCS) by a method known as lipofection-cationic lipid-mediated delivery of polynucleotides [Felgner et al. in Methods: A Companion to Methods in Enzymology (1993) 5, 67–75]. The cells were incubated at 37° C. in a CO2 incubator for 20 h. The mix of plasmid DNA in serum-free medium (200 μl; OPTI-MEM Reduced Serum Medium; GibcoBRL Cat. No. 31985) was mixed gently with LIPOFECTIN reagent (12 μl; GibcoBRL Cat. No. 18292-011) and incubated at ambient temperature for 15 min. The cells were washed with serum-free medium (2 ml; OPTI-MEM). Serum-free medium (600 μl; OPTI-MEM) was added to the DNA/LIPOFECTIN and the mix overlaid onto the cells which were incubated at 37° C. for 6 h in a CO$_2$ incubator. The DNA containing medium was replaced with normal DMEM containing 10% FCS and the cells incubated as before for 72 h. Cell supernatants (250 μl) were analysed for HCPB activity against Hipp-Arg (5 h assay) as described in Reference Example 11. COS cell supernatants which had been treated with LIPOFECTIN reagent, but without plasmid DNA, hydrolysed 1.2% of the substrate, whereas the COS cell supernatants transfected with the mix of plasmids expressing preHCPB and prepro sequence hydrolysed 61% of the Hipp-Art substrate. COS cells transfected with only the preHCPB plasmid hydrolysed Hipp-Art at the level seen for COS cells which had been treated with LIPOFECTIN reagent alone.

LIPOFECTIN Reagent is a 1:1 (w/w) liposome formulation of the cationic lipid N-[1-(2,3-dioleyloxy)propyl]-n.n.n-trimethylammonium chloride (DOTMA) and dioleoyl phosphatidylethanolamine (DOPE) in membrane filtered water. It binds sponaneously with DNA to form a lipid-DNA complex—see Felgner et al. in Proc. Natl. Acad. Sci. U.S.A. (1987) 84, 7431.

Reference Example 18
Expression of proHCPB from E. coli

The method of cloning and expressing the pro-HCPB in E. coli was very similar to the method described in Reference Example 15. Again pICI266 was used as the cloning vector, and the starting material for PCR of the pro-HCPB gene was plasmid pICI1698 (as described in Reference Example 14). Two oligonucleotides, known as 2310 and 2265 (SEQ ID NO: 68 and 66) were used in the PCR reactions (instead of primers FSPTS1 and 6HIS9E10R1BS1), using similar conditions to Reference Example 15.

The first, top strand, oligonucleotide, 2310, was designed to prime on pICI1698, and to add the NcoI restriction enzyme site from the PelB leader sequence (DNA bases 51 to 66 inclusive in SEQ ID NO: 64) to the start of the inserted pro-HCPB gene (DNA bases 40 to 57 inclusive in SEQ ID NO: 56). The second, bottom strand, oligonucleotide, 2265, was designed to prime at the end of the mature HCPB gene, prior to the start of the (His)$_6$-c-myc tag sequence (complementary to DNA bases 965 to 987 inclusive in SEQ ID NO: 64), and to introduce translation termination condons (complementary to TAA TAA) at the end of the gene followed by an EcoRI (GAATTC) restriction enzyme site and fill-in bases. This oligo primes back into the gene in the PCR to isolate the pro-gene sequence.

An aliquot of the PCR product was analysed for DNA of the correct size (about 1240 base pairs) by agarose gel electrophoresis and found to contain predominantly a band of the correct size. The remainder of the product from the reaction mix was purified in a similar manner to Reference Example 15. The isolated DNA was restriction digested with enzymes NcoI and EcoRI, and a band of the correct size (about 1210 base pairs) purified in a similar manner to Reference Example 15.

pICI266 double stranded DNA, prepared in a similar manner to Reference Example 15, was restriction digested with NcoI and EcoRI enzymes, being very careful to ensure complete digestion. DNA of the correct size (about 5600 base pairs) was purified in a similar manner to Reference Example 15.

Aliquots of both restricted and purified DNA samples were checked for purity and concentration estimation using agarose gel electrophoresis compared with known standards. From these estimates ligation mixes were prepared to clone the pro-HCPB gene into the pICI266 vector in a similar manner to Reference Example 15.

Following the ligation reaction the DNA mixture was used to transform *E. coli* strain DH5α, colonies were picked and tested by hybridisation, in a similar manner to Reference Example 15.

Four positive hybridisation isolates were checked by PCR for inserts of the correct size, using primers 2310 and 2265, (SEQ ID NO: 68 and 66), and for priming with a pair of internal primers 1279 (SEQ ID NO: 54) and 679 (SEQ ID NO: 51) in a similar manner to Reference Example 15. The PCR products were analysed for DNA of the correct size (about 1200 base pairs from primers 2310 to 2265, and about 580 base pairs from primers 1279 to 679) by agarose gel electrophoresis. All clones gave PCR DNA products of the correct size.

All four of the clones were then taken for plasmid DNA preparation, and were then sequenced over the region of PCR product in a similar manner to Reference Example 15. The clones were sequenced using six separate oligonucleotide primers known as 1504, 1802, 679, 1281, 1590 and 1592 (SEQ ID NO: 60, 63, 51, 55, 69 and 70). From the sequencing results a clone containing a plasmid with the required pro-HCPB gene sequence was selected, and is known as pICI1738.

The confirmed sequence of the cloned pro-HCPB gene in pICI1738, showing amino acid translation, from the start of the PelB sequence to the EcoRI restriction site is shown as SEQ ID NO: 71 with DNA numbering starting from 1 in the first codon of PelB, and peptide numbering starting from 1 in the mature HCPB.

To obtain controlled expression of the pro-HCPB the pICI1738 plasmid DNA was transformed into calcium chloride transformation competent *E. coli* expression strains in a similar manner to Reference Example 1.5 All pICI1738 transformed expression strains were treated in a similar manner to Reference Example 15 to test for expression of the cloned HCPB gene. However, in this case the 9E10 monoclonal antibody specific for the c-myc peptide tag cannot be use in the Western analysis, as the pro-HCPB has no C-terminal tag. Therefore, the primary antibody was an anti-bovine carboxypeptidase A raised in rabbit (from Biogenesis) which had previously been shown to cross-react with purified human pancreatic carboxypeptidase B. The secondary antibody was an anti-rabbit IgG antibody labelled with horseradish peroxidase and raised in goat (Sigma A0545 or similar).

Expression of the cloned pro-HCPB in pICI266 (pICI1738) was demonstrated from *E. coli* by the Coomassie stained gels showing an additional protein band at about 40,000 Daltons when compared to vector (PICI266) alone clones, and clones produced the tagged HCPB (Reference Example 15). A band of the same size gave a signal by Western analysis detection using the anti-bovine carboxypeptidase A.

Reference Example 19

Expression of proHCPB from COS cells

A gene for preproHCPB was prepared by PCR as described in Reference Example 17 using as template pICI1689 and oligos SEQ ID NO 34 and 40 to give a 1270 bp PCR product. The gene was digested with EcoRI and HindIII and cloned initially into pBluescript KS+ (to give pMF18) then into pEE12 in DH5α (to give pMR49) as described in Reference Example 17. Plasmid pEE12 was transfected into COS-7 cells by use of LIPOFECTIN reagent as described in Reference Example 17 and cell supernatants (250 µl) assayed for HCPB activity against Hipp-Arg (5 h assay), as described in Reference Example 11, following activation with trypsin (700 µg/ml) in 50 mM Tris-Hcl (pH 7.6). 150 mM NaCl at 4° C. for 1 h. Under these condition, complete hydrolysis of the Hipp-Arg substrate was achieved, whereas supernatant from COS cells which had been treated with LIPOFECTIN reagent alone (without plasmid DNA) when activated with trypsin hydrolysed 30% of the Hipp-Arg substrate.

Reference Example 20

Purification of native HCPB

A system has been determined for the initial purification of the native and the different mutant enzymes via two routes. The preferred route is described first.

Recombinant *E. coli* cell paste containing the recombinant enzyme was taken from storage at −70° C. and allowed to thaw. The weight of cell paste was measured in grams and the paste resuspended with the addition of buffer A (200 mM Tris (hydroxymethyl)aminomethane hydrochloride (TRIS-HCl), 20% sucrose ($C_{12}H_{22}O_{11}$), pH 8.0 to a volume equal to the initial weight of the cell paste. The cell suspension was incubated at room temperature for 20 minutes with occasional gentle mixing before an equal volume of distilled water was added and thoroughly mixed in. The cell suspension was again incubated at room temperature for 20 minutes with occasional gentle mixing. The resulting crude osmotic shockate was clarified by centrifugation at 98000×g for 90 minutes at 4° C. after which the supernatant was decanted off from the pelleted insoluble fraction. Deoxyribonuclease 1 was added to the supernatant to a final concentration of 0.1 mg/ml. The mixture was incubated at room temperature, with continuous shaking, until the vicosity was reduced enough for it to be loaded on to a Carboxypeptidase Inhibitor CNBr activated sepharose affinity column, prepared according to instructions with the CNBr activated Sepharose 4B from Pharmacia and carboxypeptidase inhibitor from potato tuber (c-0279, Sigma). The supernatant was adjusted to pH 8.0 and loaded onto the affinity column, pre-equilibrated with 10 mM TRIS-HCl, 500 mM sodium chloride, pH 8.0. After loading the supernatant the column was washed until the absorbance of the flow through was back to baseline before the bound material was eluted from the column by elution buffer (100 mM sodium carbonate, 500 mM sodium chloride, pH 11.4). The eluted fractions were frozen at −20° C. whilst those containing the recombinant carboxypeptidase were determined by western blot analysis using an anti- c-me tag antibody (9E10), followed by an anti-mouse -horse raddish peroxidase conjugate (a-9044, sigma) that gave a colour reaction with exposure to 4-chloro-naphthol and hydrogen peroxide.

Fractions containing the recombinant carboxypeptidase B were pooled, concentrated and the pH adjusted to pH 7.5 before being snap-frozen and stored at −20° C. Further purification of the pooled sample, utilising known methods such as ion exchange and gel permeation chromatography may performed if required.

The second route involves the total lysis of the *E. coli* as opposed to a periplasmic shock, as used in the preferred route.

Recombinant *E. coli* cell paste containing the recombinant enzyme was taken and resuspended in lysis buffer (50 mM TRIS-HCl, 15% Sucrose, pH 8.0). Lysozyme was added to a concentration of 1 mg/ml and at the same time lithium dodecyl sulphate (LDS) was added (80 μl of a 25% solution per 25 ml of suspension). The suspension was incubated on ice for 30 minute with occasional shaking, followed by the addition deoxyribonuclease 1 to a concentration of 1 mg/ml and again the suspension was incubated on ice for 30 minutes with occasion shaking.

The suspension was subsequently divided in to 20 ml volumes and sonicated to complete the disruption of the cells for 10×30 sec bursts with 30 sec intervals between bursts. Sonicated suspensions were centrifuged at 98,000×g for 90 minutes at 4° C. after which the supernatant was decanted off from the pelleted insoluble fraction. The supernatant was adjusted to pH 8.0 and loaded on to the affinity column, pre-equilibrated with 10 mM TRIS-HCl, 500 mM sodium chloride, pH 8.0. After loading the supernatant the column was washed until the absorbance of the flow through was back to baseline before the bound material was eluted from the column by elution buffer (100 mM sodium carbonate, 500 mM sodium chloride, pH 11.4). The eluted fractions were frozen at −20° C. whilst those containing the recombinant carboxypeptidase were determined by western blot analysis using an anti- c-myc tag antibody (9E10), followed by an anti-mouse -horse raddish peroxidase conjugate (a-9044, sigma) that gave a colour reaction with exposure to 4-chloronaphthol and hydrogen peroxide. Fractions containing the recombinant carboxypeptidase B were pooled, concentrated and the pH adjusted to pH 7.5 before being snap-frozen and stored at −20° C. Further purification of the pooled sample, utilizing known methods such as ion exchange and gel permeation chromatography may performed if required.

Samples of the pooled material from both routes, analysed by SDS-PAGE and Coomassie stained nitrocellulose blot provided Coomassie stained bands at the correct molecular weight for the recombinant carboxypeptidase B's. These bands sequenced by an automated protein/peptide sequencer using the Edman degradation technique gave positive matches for the particular recombinant carboxypeptidase B being purified.

Reference Example 21
Expression of murine A5B7 F(ab')$_2$-HCPB fusion protein from COS cells This example describes the preparation of cDNA from the A5B7 hybridoma, the isolation of specific Fd and light chain fragments by PCR, determination of the complete DNA sequence of these fragments, the subsequent preparation of an Fd-HCPB fusion gene and a co-expression vector capable of producing both light chain and Fd-HCPB fusion protein in eukaryotic cells, expression of the F(ab')2-HCPB from COS cells by co-transfection with a prepro sequence from HCPB.

The procedure described in Reference Example 5 is repeated as far as item (e).

f) Preparation of Fd-HCPB fusion DNA sequence

A gene encoding the C-terminal region of the Fd sequence, from the NcoI site in SEQ ID NO: 25 (position 497) was joined to the HCPB sequence by PCR. In this process DNA for an 8 amino-acid linker sequence (VPEVSSVF) was introduced. Plasmid pAF1 (described in Reference Example 5) was subjected to PCR (hot start procedure) as described in Reference Example 17 with oligos SEQ ID NO: 42 and 43 to give a 338 bp product. Similarly, pICI1698 was subjected to PCR with oligos SEQ ID NO: 44 to 34 to give a 998 bp product. Both products were isolated by agarose gel electrophoresis and Geneclean™ as described in Reference Example 17 and used (0.2 ng each in 50 μl total volume) in a second hot start PCR with 10 cycles for 1 min at 94° C. and 4 min at 63° C. followed by 2 min at 94° C. Flanking oligos (SEQ ID NO: 42 and 34; 100 pM each) were added in 50 μl buffer with Amplitaq (2.5 u). After heating to 94° C. for 3 min, the mix was subjected to 25 cycles of 1.5 min at 94° C., 2 min at 55° C. and 2 min at 72° C. followed by 10 min at 72° C. The product was a band at 1336 bp, isolated at described previously, then cut with EcoRI and HindIII and cloned into pBluescript™ in DH5α (clones were screened by PCR with oligos SEQ ID NO: 36 and 37) to give pMF35 To make the complete Fd-HCPB fusion sequence, plasmids pAF1 and pMF35 were cut (10 μg of each) with NcoI and EcoRI for 2 h in buffer (100 μl) containing 50 mM potassium acetate, 20 mM Tris-acetate (pH 7.9), 10 mM MgCl$_2$. 1 mM DTT. EcoRI (40 u) and NcoI (20 u). The vector fragment (3.4 kb) from pAF1 was isolated and treated with calf intestinal alkaline phosphatase as described in Reference Example 17 and ligated to the purified 1.2 kb fragment from pMF35. The resulting vector was cloned in DH5α (screened by PCR with oligos SEQ ID NO: 36 and 37 for a 1.922 bp insert) and named pMF39. The EcoRI-HindIII fragment from pMF39 was cloned into pEE6 [this is a derivative of pEE6.hCMV—Stephens and Cockett (1989) Nucleic Acids Research 17, 7110—in which a HindIII site upstream of the hCMV promoter has been converted to a BglII site] in DH5α (screened by PCR with oligos SEQ ID NO: 38 and 39 for a 2.200 bp, approximately, insert) to give pMF43.

To make the co-expression vector, pMF43 (10 μg) was cut with BglII (20 u) and SalI (40 U) in buffer (100 μl) containing 10 mM Tris-HCl (pH 7.9), 150 mM NaCl, 10 mM MgCl$_2$, 1 mM DTT and BSA (100 μg/ml) and the 4348 bp fragment isolated by agarose gel electrophoresis and purified with Geneclean™ as described previously. Similarly, pAF6 (described in e) in Reference Example 5) was cut with BamHI (40 u) and SalI (40 u) and the 7.8 kb vector fragment isolated and ligated to the BglII-SalI fragment from pMF43 and cloned into DH5α. Colonies were screened by PCR with 2 sets of oligos (SEQ ID NO: 18 and 45, and SE ID NO: 17 and 39). Clones giving PCR products of 360 bp and 1.3 kp respectively were characterised by DNA sequencing. A clone with correct sequence was named pMF53—light chain/Fd-HCPB co-expression vector in DH5α.

g) Expression of A5B7 F(ab')$_2$-HCPB in COS cells

The procedure described in Reference Example 17 for co-transfection of COS-7 cells with the plasmid encoding the prepro sequence (pMF67) was repeated with pMF48 replaced by pMF53. COS cell supernatants were examined for HCPB activity as described in Reference Examples 11 and 17. COS cell supernatants which had been treated with LIPOFECTIN reagent, but without plasmid DNA, hydrolysed 1.2% of the substrate, whereas the COS cell supernatants transfected with the mix of plasmids expressing light chain/Fd-HCPB and prepro sequence hydrolysed 34% of the Hipp-Arg substrate. COS cells transfected with only pMF53 plasmid hydrolysed Hipp-Arg at the level seen for COS cells which had been treated with LIPOFECTIN reagent alone. By Western analysis (see h below) bands of approximately 80 kDa and 160 kDa were visible, corresponding to Fab'-HCPB and F(ab')$_2$-(HCPB)$_2$ respectively. In a CEA ELISA assay (see i and j below) cell supernatants (see above) were used to detect the presence of CEA binding material according to the protocol given in j.

h) Western blot analysis

Western blot analysis was performed as described below.

Aliquots (20 μl) of each supernatant sample were mixed with an equal volume of sample buffer (62.5 mM Tris, pH 6.8, 1% SDS, 10% sucrose and 0.05% bromophenol blue) with and without reductant. The samples were incubated at 65° C. for 10 minutes before electrophoresis on a 8–18% acrylamide gradient gel (Excel™ gel system from Pharmacia Biotechnology Products) in a Multiphor™ II apparatus (LKB Produkter AB) according to the manufacturer's instructions. After electrophoresis, the separated proteins were transfered to a Hybond™ C-Super membrane (Amersham International) using a Novablot™ apparatus (LKB Produkter AB) according to protocols provided by the manufacturer. After blotting, the membrane was air dried.

The presence of antibody fragments were detected by the use of an anti-murine F(ab')$_2$ antibody-peroxidase conjugate (ICN Biomedicals, product no. 67-430-1). The presence of murine A5B7 antibody fragments was visualised using the ECL™ detection system (Amersham International) according to the protocol provided.

i) ELISA analysis

Standard procedures for ELISA assay are available in "Laboratory Techniques in Biochemistry and Molecular Biology" eds. Burdon, R. H. and van Kippenberg, P. H., volume 15. "Practice and Theory of Enzyme Immunoassays", Tijssen, P., 1985, Elsevier Science Publishers B. V., Another source of information is "Antibodies—A Laboratory Manual" Harlow, E. and Land, D. P. 1988, published by Cold Spring Harbor Laboratory.

j) ANTI-CEA ELISA

1. Prepare coating buffer (1 capsule of Carbonate-Bicarbonate buffer—Sigma C-3041—in 100 ml double distilled water).
2. Add 5 μl of CEA stock solution (1 mg/ml. Dako) to 10 ml of coating buffer for each 96 well plate required.
3. Add 100 μl of diluted CEA to each well of a Nunc "Maxisorp™" microtitre plate—50 ng/well/100 μl.
4. Incubate plates at 4° C. overnight (or room temp. for 2 hours).
5. Wash plates 4 times for 5 minutes each with Phosphate buffered saline—0.01% Sodium azide (PBSA)+0.05% Tween 20.
6. Block plates (after banging dry) with 1% BSA (Sigma A-7888) in PBSA containing 0.05% Tween 20 at 200 μl per well. Incubate at room temp. for 2 hours.
7. Wash plate 4 times for 5 minutes each with PBSA containing 0.05% Tween 20.
8. Load samples (culture supernatants) and standards (doubling dilutions of proteolytic A5B7 F(ab')$_2$) as appropriate. Dilute samples in growth medium (or PBS). Includes PBSA+1% BSA and diluent as blanks).
9. Incubate at ambient temperature for 3 H.
10. Wash plates 6 times for 5 minutes each with PBSA+0.5% Tween 20.
11. Prepare secondary antibody solution (anti-mouse IgG F(ab')$_2$, from goat, peroxidase conjugated—ICN 67-430-1—at 20 μl in 40 ml PBSA+1% BSA+0.5% Tween 20) and add 100 μl per well.
12. Incubate at room temp. for 1 h.
13. Wash plates 6 times for 5 minutes each with PBSA+0.5% Tween 20.
14. Prepare developing solution by dissolving 1 capsule of Phosphate-Citrate Perboate buffer (Sigma P-4922) in 100 ml double distilled water. Add 30 mg o-Phenylenediamine Dihydrochloride (OPD, Sigma P-8287) per 100 ml buffer. Add 150 μl per well.
15. Stop reaction by addition of 50 μl per well of 2M Sulphuric acid.
17. Read OD 490 nm in plate reader.

Example 1

Preparation of bovine Lys66Glu pancreatic ribonuclease (a) Construction of a RNase gene sequence containing the substitution in the codon 66 (Lus→Glu) via recombinant circle polymerase chain reaction (RCPCR).

A plasmid containing the pre-sequence coding for bovine pancreatic RNase (pQR162: NCIMB No 40678 and described in Tarragona-Fiol et al., Gene (1992) 118, 239–245) was used in a PCR incubation as template. Primers for PCR incubations were synthesised by the phosphite-triester method using cyanoethyl phosphoramidites on a Cyclone™ DNA synthesiser (Milligen/Millipore). The primers were designed such that when they are used in PCR incubations, the products generated are double-stranded, linear DNA molecules which upon combination, denaturation and re-annealing form double-stranded DNA with discrete, cohesive, single stranded ends in addition to the original blunt ended products. These ends will anneal to form recombinant circles of DNA. These molecules are then ready for transformation into competent E. coli cells.

Two PCR incubations, one with oligonucleotides SEQ ID NO: 1 and SEQ ID NO: 2 (see primers A & B in FIG. 8) and the other with oligonucleotides SEQ ID NO: 3 and SEQ ID NO: 4 (see primers C & D in FIG. 8), were allowed to undergo 25–30 cycles of 1.5 min at 92° C. 1.5 min at 55° C. and 6 min at 75° C. with a final 10 min at 75° C. in a Techne PHC-1 thermal cycler. The reaction contained pQR162 as template (10 ng), 50 pmol/primer, 5 μl of 10×Buffer 1 [200 mM Tris-HCl (pH 8.2), 100 mM KCl, 60 mM (NH$_4$)$_2$SO$_4$, 20 mM MgCl$_2$, 1% Triton X-100 and 100 μg/ml nuclease-free BSA] and 2.5 U of pfu polymerase (a thermostable polymerase from Pyrococcus furiosus, Stratagene) in a total volume of 50 μl, overlaid with the same volume of paraffin oil to prevent evaporation.

PCR products were analysed on a 1% agarose gel. The DNA fragment generated from each PCR incubation (approx. 3.1 kb) was removed from the gel and the DNA separated from the agarose by centrifugation (Spin-X™, Costar). The two extracted DNA fragments were precipitated with ethanol and resuspended in 20 μl of water. Aliquots from each (10 μl) were combined in a total volume of 50 μl containing 10 mM Tris/HCl pH 8.8, 10 mM NaCl and 1 mM Na$_2$ EDTA. The combined DNA fragments were denatured for 5 min at 92° C. and re-annealed for 2 hours at 55–57° C. The recombinant circles thus formed were used to transform an aliquot of competent cells.

Figure 1:
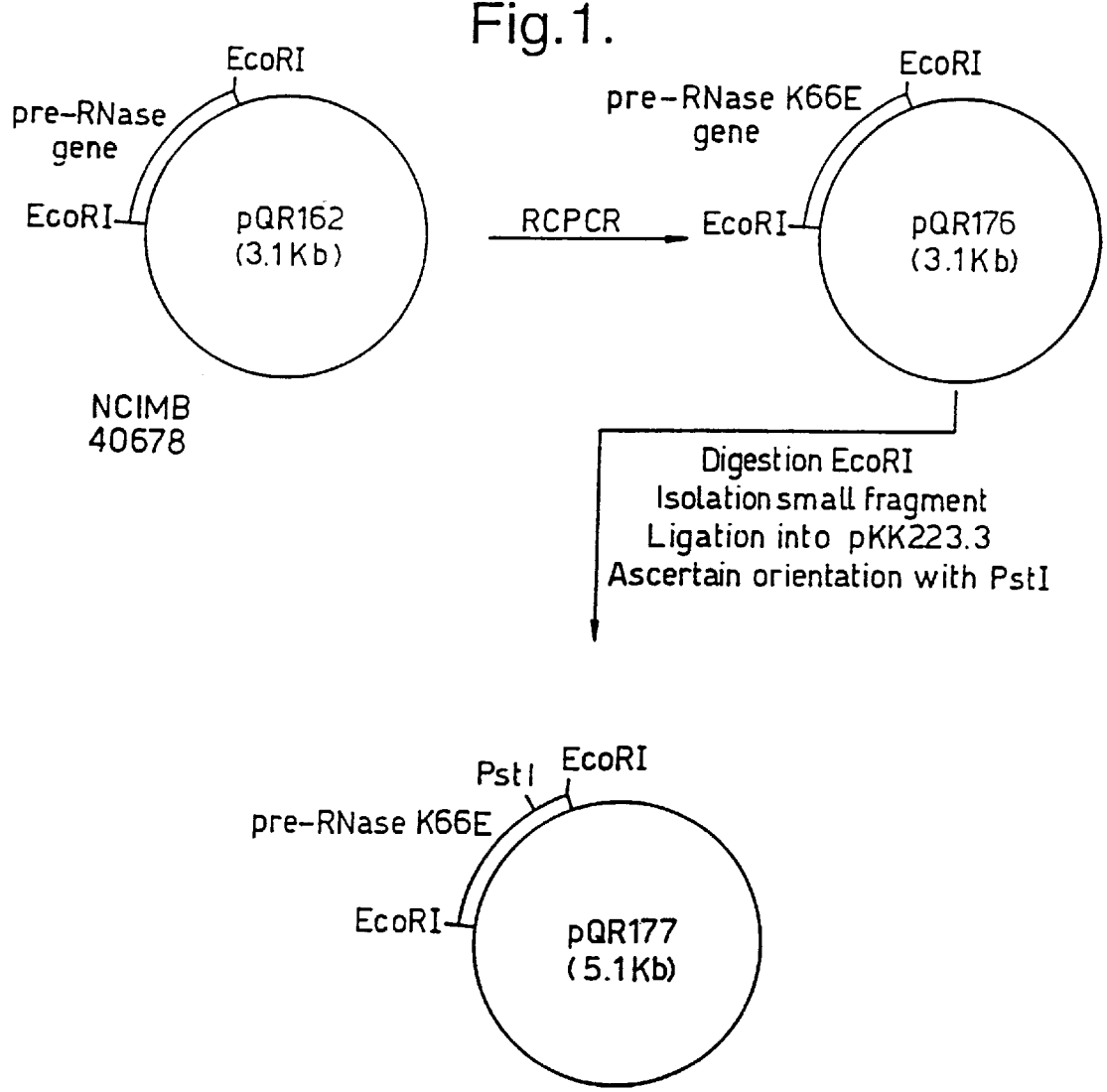
FIG. 1 depicts construction of plasmid pQR177

Mini-preps for the isolation of plasmids were carried out [Maniatis et al. (1982) Molecular Cloning. A Laboratory Manual. Cold Spring Harbour, Laboratory, Cold Spring harbour. N.Y.] and used as templates for double stranded DNA sequencing using the dideoxy chain termination method [Sanger et al., (1977) Proc. Natl. Acad. Sci. USA 74, 5463–5467]. A plasmid containing the altered coding sequence without any mis-incorporation was designated pQR176. This was digested in a total volume of 20 µl containing 20 U of EcoRI and reaction buffer. The DNA fragment having the altered coding sequence was obtained from an agarose gel as described above and ligated to previously digested and dephosphorylated pKK223.3 [Pharmacia Biotech: this vector contains the tac promoter, regulated by the lac repressor and induced by the addition of isopropyl-β-D-thiogalactoside (IPTG)); Brosius and Holy, Proc. Natl. Acad. Sci. USA (1984) 81, 6929] in a total volume of 20 µl containing 20 U of T4 DNA ligase and reaction buffer. The ligated products were used to transform an aliquot of *E. coli* competent cells. Restriction enzyme analysis of plasmids obtained from the different recombinant colonies were carried out to ascertain size and orientation of the inserts with respect to the tac promoter. The correct construct was named pQR177 (FIG. 1).

(b) Production and purification of Lys66Glu bovine pancreatic RNase

The strategy for the production and purification of the engineered sequence follows protocols developed for the expression of bovine pancreatic ribonuclease A in *E. coli* (Tarragona-Fiol et al., Gene 1992). This system utilises the natural signal sequence of bovine pancreatic ribonuclease to direct the production of ribonuclease or its engineered mutants to the periplasm of *E. coli*. The oxidative environment of the periplasm facilitates the correct folding of the protein resulting in the expression of fully active recombinant RNase. The high net positive charge of the recombinant or engineered mutants facilitates the rapid purification from engodenous periplasmic proteins. Expression and subsequent purification to homogeneity of mutant proteins takes place in 48 hours from inoculation of the medium. The plasmid pQR177 contains two Ribosome Binding Sites (RBS), one provided by the tac promoter of the vector and the other, for translation of the second cistron, is contained within the coding sequence of the first cistron. The mRNA produced upon IPTG induction of *Escherichia coli* cells harbouring pQR177 is bicistronic and starts from the tac promoter. The first cistron encodes a 6-aa peptide (Met-Phe-Leu-Glu-Asp-Asp). The stop codon of the first cistron and the start codon of the second cistron overlap such that ribosomes will continue translation of the mRNA and produce pre-RNase. The synthesised precursor form of RNase is translocated to the periplasm and N-terminal sequencing has shown that the signal sequence is correctly cleaved. The oxidative environment of the periplasm allows the correct folding of RNase to form the native enzyme as evidenced by the recovery of fully active enzyme. *Escherichia coli* [pQR177] cells were grown in 5 liters of media containing 100 µg Ap/ml for 8 hrs at 28° C. When cells were in the exponential phase of growth, IPTG was added to a final concentration of 0.5 mM and growth of cells was continued overnight at 28° C. with shaking. The release of the periplasmic proteins was carried out using a modified spheroplast/osmotic shock procedure. Cells from an overnight culture (5 liters) were pelleted by centrifugation at 8300×g (average) for 10 min at 10° C. The cell pellet was resuspended in 60 ml of 200 mM Tris-HCl pH 7.5/20% (w/v) sucrose (RNase free)/1 mM Na$_2$EDTA. The suspension was left for 30 min at room temperature. An osmotic shock was obtained by adding an equal volume of sterile water and mixing thoroughly. The mixture was left for a further 30 min at room temperature. Spheroplasts were pelleted by centrifugation at 100000×g (average) for 90 min at 10° C.

Figure 2:
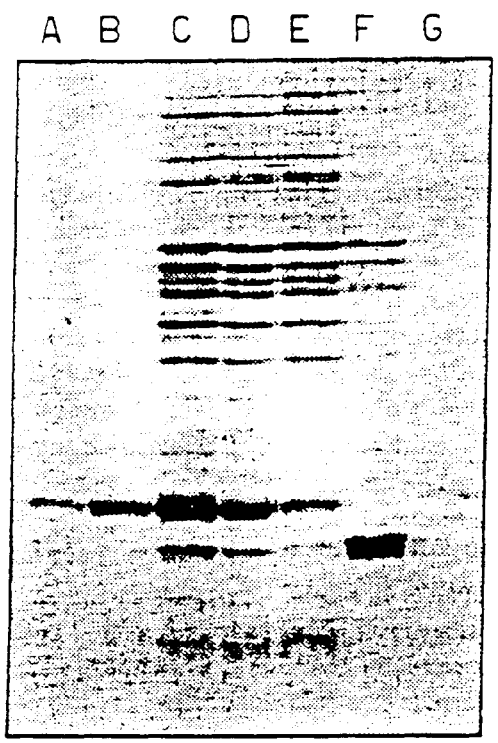
FIG. 2 depicts purification of bovine ribonuclease. Assessment of purity of recombinant RNase on a silver stained 0.1% SDS-16% polyacrylamide gel. Lanes A and G correspond to commercial RNase (M, 13700). Lanes C-E contain positively charged proteins obtained after isocratic elution of the periplasmic extract from *Escherichia coli* [pQR163] cultures and induced with different concentrations of IPTG (0.5, 2 and 0 mM respectively). Lane F, as lanes 3 to 5 but the culture contained *Escherichia coli* [pKK223.3] cells (control). Lane B, purified recombinant RNase after ion-exchange chromatography.

Cation exchange chromatography (S-Sepharose™ FF) was used to obtain all the positively charged proteins from the periplasmic extract. Buffer A was 50 mM MES, pH 6.5 and Buffer B. 50 mM MES, 1 M NaCl, pH 6.5. Recombinant RNase was purified from the pool of positively charged proteins by cation exchange chromatography (Mono-S™, Pharmacia-LKB) on a gradient of 17.5 mM NaCl/min. Assessment of the purity of recombinant RNase by PAGE-SDS electrophoresis and silver staining clearly shows that this combination of techniques results in purification of the protein to homogeneity (see FIG. 2). RNase activity of the recombinant enzyme was estimated on the hydrolysis of cytidylyl-3',5'-adenosine (CpA) and cytidine-2',3'-cyclic monophosphate (C>p) showing an equal specific activity to that of the commercial enzyme (see Table). Protein concentration was determined measuring the OD at 278 (OD278 nm=0.71 is equivalent to 1 mg/ml of RNase). Kinetic measurements were carried out by monitoring the increase (C>p hydrolysis) in absorbance with time at 286 nm [Witzel and Barnard (1962) Biochem. Biophys. Res. Commun. 7, 295–299]. The initial velocity and substrate concentration values were used to determine the parameters $K_m$ and $k_{cat}$ and their standard errors by a computational method based on the analysis described by Wilkinson (1961) Biochem. J. 80, 324–332. Differences between these parameters obtained using different ribonucleases were assessed using the Student t-test. The rate of hydrolysis of C>p was measured at room temperature in cuvettes of 0.1 cm path length (Hellma) in a total volume of 250 µl. Reactions contained varying concentrations of C>p in 0.1 M (1,3-bis [tris(hydroxymethyl)-methylamino]propane) pH 7.0, 50 mM NaCl (I=0.1) and were initiated by the addition of the enzyme (see Table). The data indicates that the kinetic properties of the engineered Lys66Glu RNase enzyme are not significantly different to the commercial bovine enzyme.

TABLE

|  | kcat/Km (mM$^{-1}$ s$^{-1}$) |
| --- | --- |
| BP-RNase | 3.4 (0.9) |
| Lys66Glu BP-RNase | 4.7 (0.1) |

Example 2

Preparation Arg4Ala,Lys6Ala,Lys66Glu human pancreatic ribonuclease

Plasmid pATF3 (described in Reference Example 2, contains the Arg4Ala,Lys6Ala HP-RNase gene) and was used as template (2 ng) in a PCR incubation containing the primer SEQ ID NO: 15 and 16 (5 pmol/each), nucleotides (0.2 mM), PCR buffer and 2.5 units of pfu polymerase. After 5 min of initial denaturation at 92° C. 30 cycles were carried out of denaturation (92° C., 1 min), annealing (55° C., 1 min) and extension (75° C., 1 min). The PCR fragment was gel extracted as described in Example 1 and digested with EcoRI (10–15 units) at 37° C. for 1 hour. After heat inactivation of the enzyme, the EcoRI fragment was ligated into EcoRI digested and dephosphorylated pUC18. The resulting plasmid was named pATFZ1. Plasmid pATFZ1 was used to confirm the DNA sequence of the mutated HP-RNase gene.

Figure 5:
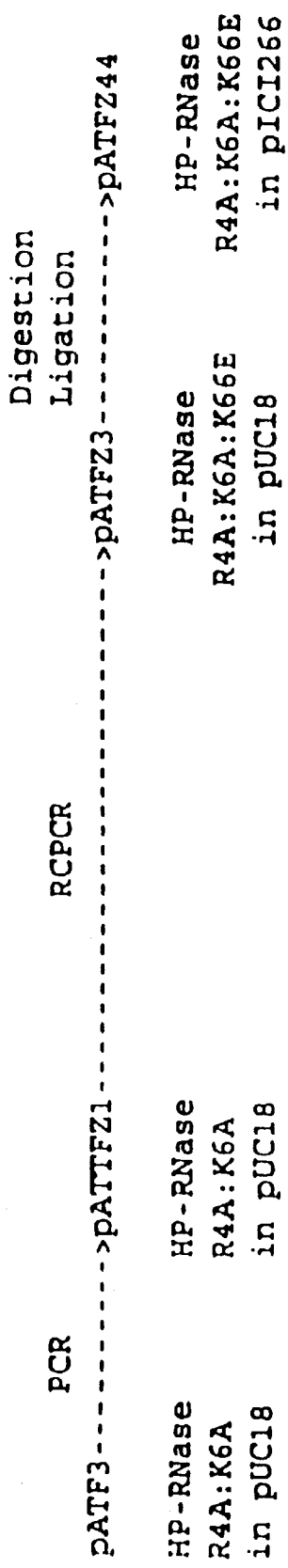
FIG. 5 depicts recombinant circle PCR generation of pATFZ44

To generate the Arg4Ala,Lys6Ala,Lys66Glu HP-RNase, pATFZ1 was used as template in RCPCR incubations as described in Example 1 but with oligonucleotide primers SEQ ID NO: 30 to 33 replacing SEQ ID NO: 1 to 4 respectively). The resulting plasmid was called pATFZ3. The gene for Arg4Ala,Lys6Ala,Lys66Glu HP-RNase was excised from pATFZ3 by digestion with EcoRI and NcoI (10–15 units of each) and ligated to previously digested (EcoRI and NcoI) and dephosphorylated pICI266 (NCIMB 40589) for expression studies. Ligations, expression and purification, were carried out as the example described in Example 1, except that a double digestion with NcoI and EcoRI was used to excised the fragment from pATFZ3, as described above, and was ligated to previously dephosphorylated and digested (with EcoRI and NcoI) pICI266 and, the induction was carried out with 1% arabinose (instead of IPTG). The resulting construct was called pATFZ44 (see FIG. 5). Expression and purification of the mutant enzyme was as described in Example 1, but with induction with 1% arabinose instead of IPTG.

Example 3

Figure 7:
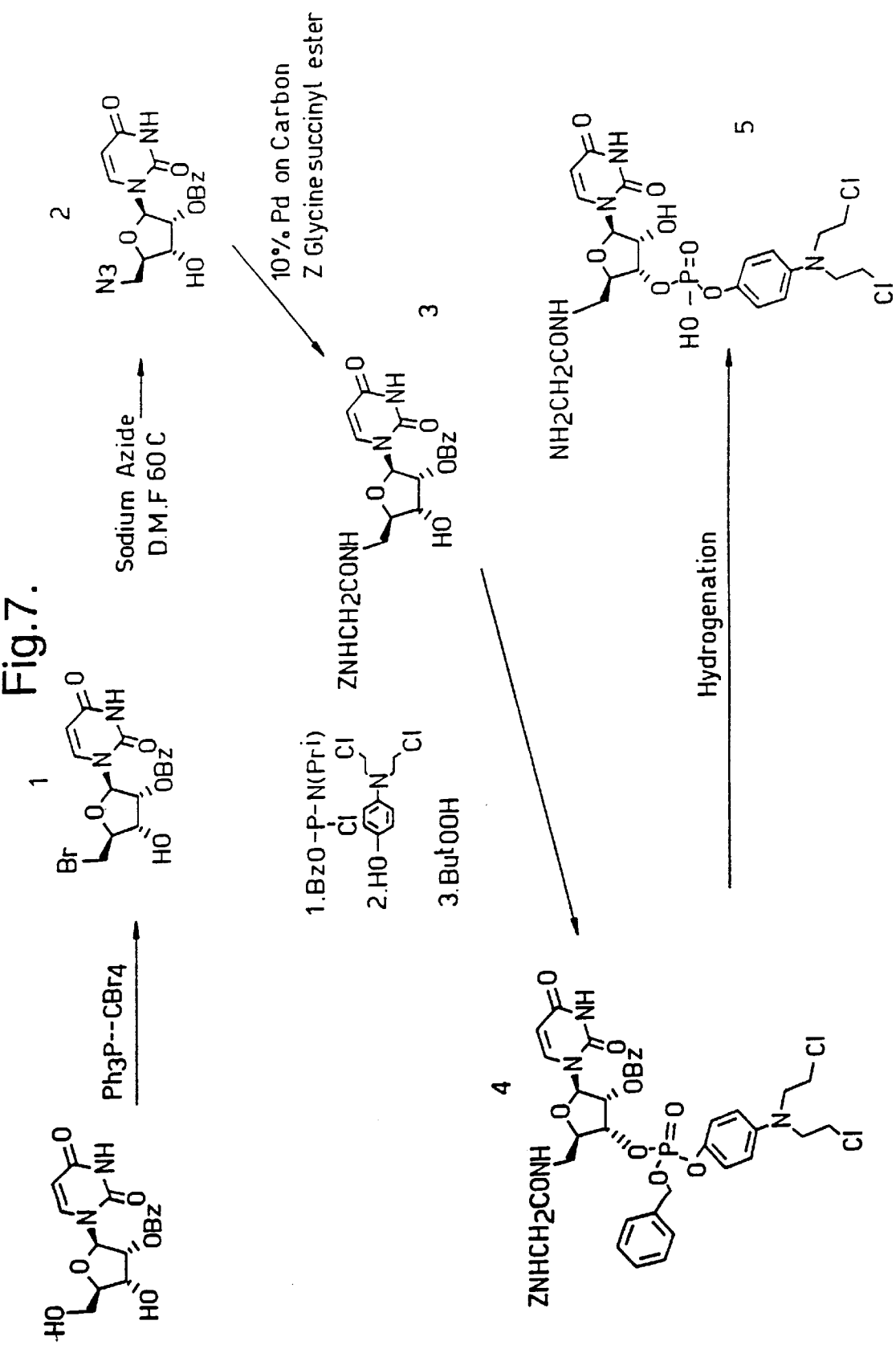
FIG. 7 depicts a scheme for synthesis of uracil based prodrug
Figure 12:
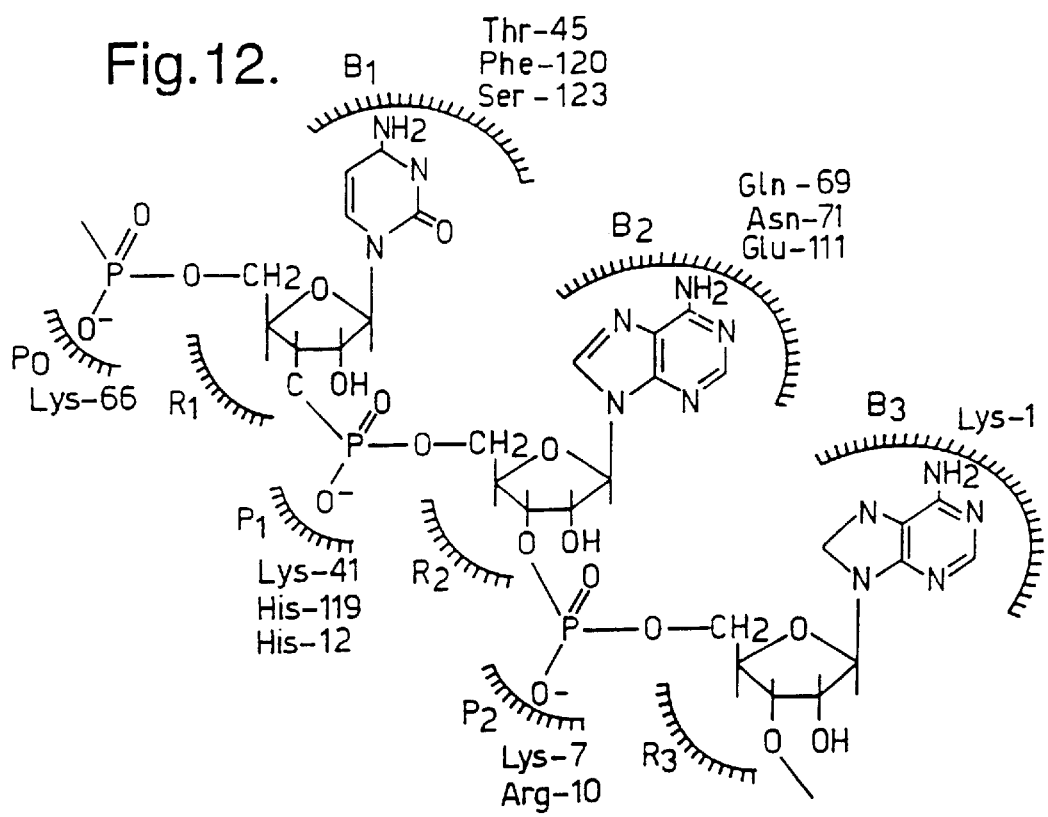
FIG. 12 is a schematic diagram of the active site of ribonuclease A—substrate complex wherein B, R, and P indicate binding subsites for base, ribose and phosphate, respectively. $B_1$ is specific for pyrimidines and $B_2$ "prefers" purines. 3'-Pyrimidine mononucleotides bind to $B_1R_{1P1}$. 5'-Purine mononucleotides bind to $B_2R_{2P1}$. 3'-AMP binds to $B_2R_{2P}2$. The phosphate group of the phosphodiester bond hydrolysed by the enzyme binds to $p_1$. The residues known to be involved in each site are indicated.
Figure 13:
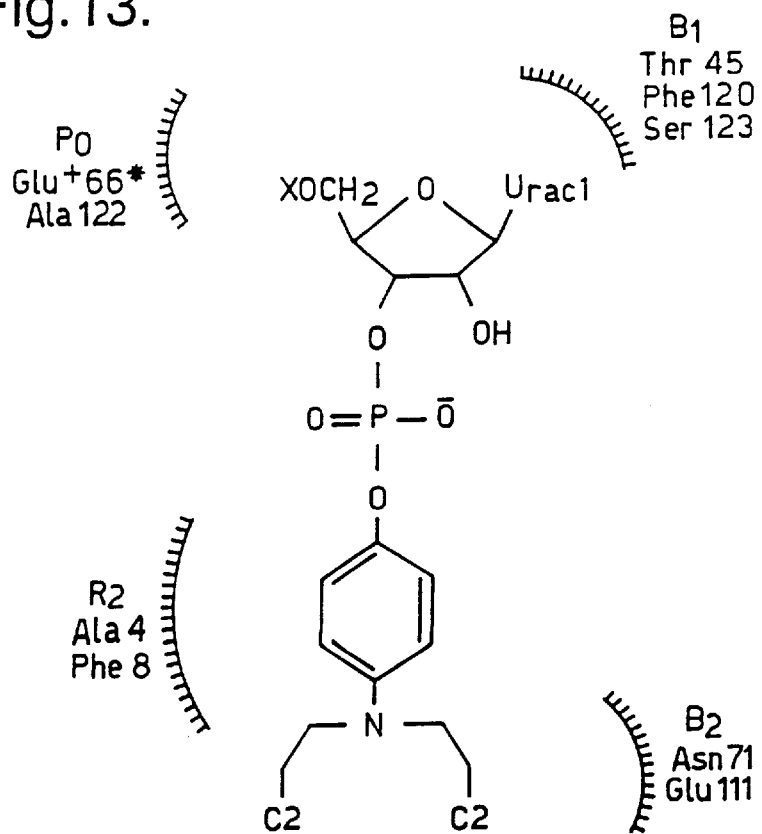

Preparation of O-[(2R,3,R4R,5R)-2-(2-aminoacetamidomethyl)-5-(2,4-dioxo-1,2,3,4-tetrahydropyrimidin-1-yl)-4-hydroxy-2,3,4,5-tetrahydrofuran-3-yl]O-[4-(bis[2-chloroethyl]amino) phenoxy] hydrogen phosphate (which is shown as the end product in FIG. 7).

Compound 4 (FIG. 7: 31 mg, 0.034 mM) was dissolved in 0.01M HCl in N,N-dimethylformamide (DMF) and 30% palladium on carbon catalyst (60 mg) added as a suspension in dimethylformamide. The mixture was stirred under an atmosphere of hydrogen for 2 hrs 45 mins. After filtration through Celite™ the filtrate was evaporated to dryness at <30° C. The crude product was suspended in dry dichloromethane and the mixture centrifuged. The supernatant dichloromethane layer was discarded. The process was repeated and finally the solid residue dried to give the desired product 9.4 mg (compound 5, FIG. 7).

NMR data DMSO, d4 Acetic (δ) 3,3 (1H, m); 3.5 (3H, m); 3.62 (8H, s); 4.05 (1H, m); 4.25 (1H, m); 4.53 (1H, m); 5.62 (1H, d); 5.72 (1H, d); 6.63 (2H, d); 7.05 (2H, d); 7.63 (1H, d).

Compound 4 was made by the following procedure.

2'-O-Benzyl-5'-bromo-5'-deoxyuridine (compound 1, FIG. 7)

To a mixture of 2'-O-benzyluridine [Wagner et al. (1974), J. Org. Chem. 39, 24–30] (334 mg 1 mM) carbon tetrabromide (500 mg) and DMF (4 ml) at 20° C. under Argon was added over 5 mins a solution of triphenylphosphine (340 mg) in DMF (2 ml). The mixture was stirred at 20° C. for 2 hrs, poured into water (60 ml) and extracted twice with ethyl acetate. The combined organic extracts were washed with water, dried, and evaporated to an oil. This oil was chromatographed on 20 g of Merck silica gel (Art. 9385). Elution with 5% methanol in toluene gave 2'-O-benzyl-5'-bromo-5'-deoxyuridine (160 mg, 40%).

NMR (DMSO d6) δ 11.4 (s1H); 7.6 (d1H); 7.3 (m5H); 5.95 (d1H); 5.6 (dd1H); 4.6 (q2H); 4.0–4.2 (m3H); 3.6–3.8 (m2H)

5'-Azido-2'-O-benzyl-5'-deoxyuridine (compound 2, FIG. 7)

2'-O-Benzyl-5'-bromo-5'-deoxyuridine (4.3 g) was dissolved in DMF (86 ml) and sodium azide (7 g) added. The mixture was stirred and heated at 60° C. for 45 mins. After cooling and decanting from unreacted sodium azide the DMF was evaporated to dryness. The residue was dissolved in ethyl acetate and washed twice with water, dried and evaporated to dryness. The residue was chromatographed on Merck silica gel (Art. 9385). Elution with 10% methanol in toluene gave 1.5 g of pure 5'-azido-2'-O-benzyl-5'-deoxyuridine.

NMR (DMSO d6) δ 11.4 (s1H); 7.6 (d1H); 7.3 (m5H); 5.9 (d1H); 5.6 (d1H); 5.4 (d1H); 4.65 (q2H); 3.9–4.2 (m3H); 3.6 (d2H).

2'-O-Benzyl-5'-carbobenzoxyglycylamino-5'-deoxyuridine (compound 3, FIG. 7)

To a mixture of 5'-azido-2'-O-benzyl-5'-deoxyuridine (1.5 g), tetrahydroguran (25 ml) and benzyloxycarbonyl glycine N-hydroxysuccinyl ester (1.3 g) was added 10% platinum on carbon (50% moist with water) (1.5 g). The mixture was stirred under an atmosphere of hydrogen for 4 hours. After filtration through Celite™ the filtrate was evaporated to dryness. The residue was dissolved in ethyl acetate and washed with 5% citric acid soln. (x2) water, sodium bicarbonate soln. (x2) dried and evaporated to dryness. The residue was triturated with 1:1 ether/ethyl acetate to give a solid (960 mg) (42%).

NMR (DMSO d6) δ 11.3 (s1H); 8.0 (t1H); 7.6 (d1H); 7.4 (m10H); 5.9 (d1H); 5.6 (d1H); 5.4 (d1H); 5.0 (s2H); 4.6 (q.2H); 4.0 (m2H); 3.9 (m1H); 3.6 (d2H); 3.5 (m2H)

Preparation of compound 4 (FIG. 7)

a) Benzyloxydichlorophosphine [Scott et al. (1990), J. Org. Chem. 55, 4904–4911] (135 mg, 0.64 mM) was dissolved in dry dichloromethane (4.0 mls), the solution was cooled to –20° C. and a mixture of diisopropylamine (0.091 ml, 0.64 mM) and dissopropylethylamine (0.11 ml, 0.64 mM) dissolved in dry dichloromethane (2.0 ml) was added. The solution was stirred at –20° C. for 45 min and then allowed to warm to room temperature over 30 min and then stirred at room temp. for a further 30 min. This solution was then added dropwise to a solution of 2'-O-benzyl-5'-carbobenzoxyblycylamino-5'-deoxyuridine (280 mg, 0.53 mM) and diisopropylethylamine (0.336 ml, 2.14 mM) in dichloromethane (3.0 ml) cooled to 0° C. The solution was stirred 10 mins at 0° C. and at room temperature for 2 hours. The reaction mixture was then diluted with dichloromethane washed with saturated sodium bicarbonate (x2), dried and evaporated to an oil. The oil was azeotroped with toluene (2x) ready for the next reaction.

b) The crude product from the previous stage was dissolved in dry dichloromethane (2.5 ml) and a solution of 4-N,N-bis-(2-chloroethyl)aminophenol (125 mg, 0.534 mM) in dry dichloromethane (3.0 ml) was added. A solution of 0.46M tetrazole in dry acetonitrile (3.2 ml) was then added and the solution stirred at room temp. for 2 hrs. After this time 70% t-butyl hydroperoxide solution in water (0.11 ml. 0.801 mM) was added and the solution stirred a further 1 hour at room temperature. The reaction mixture was diluted with dichloromethane and washed with saturated sodium bicarbonate (1x), dilute sodium bisulphite (1x), saturated sodium chloride (1x), dried and evaporated to dryness. The crude product was chromatographed on Merck silica gel (ART 9385) elution with 2% methanol, in dichloromethane and then 3.5% methanol in dichloromethane gave the pure product 118 mg.

NMR data. DMSOd6 (δ) Mixture of diastereoisomers 3.37 1H (m); 3.42 2H (d); 3.67 8H (d); 4.12 1H (m); 4.33 1H (m); 4.56 2H (m); 5.0 2H (s); 5.14 3H (m); 5.59 1H (d); 5.91 1H (d); 6.64 2H (dd); 7.05 2H (t); 7.28 15H (m); 7.45 1H (t); 7.62 1H (dd); 8.13 1H (brs); 11.35 1H (s).

Example 4

Synthesis and isolation of murine A5B7 F(ab')$_2$-Lys66Glu bovine pancreatic ribonuclease conjugate The procedure described in Reference Example 4 is repeated but with bovine pancreatic ribonuclease replaced by Lys66Glu bovine pancreatic ribonuclease (described in Example 1).

Example 5
Synthesis and isolation of murine A5B7 F(ab')$_2$-Arg4Ala, Lys6Ala,Lys66Glu human pancreatic ribonuclease conjugate The procedure described in Reference Example 4 is repeated but with bovine pancreatic ribonuclease replaced by Arg4Ala,Lys6Ala,Lys66Glu human pancreatic ribonuclease (described in example 2).

Example 6
Synthesis and isolation of humanised A5B77 F(ab')$_2$-Arg4Ala,Lys6Ala,Lys66Glu human pancreatic ribonuclease conjugate The procedure described in Example 5 is repeated but with murine A5B7 F(ab')$_2$ replaced by humanised A5B7 F(ab')$_2$.

The humanised A5B7 F(ab')$_2$ is made by the following procedure. The procedure described in Reference Example 5 is followed from step f) therein but the murine sequences for Fd and light chain, as shown in SEQ ID NO: 25 and 26 respectively, are replaced by the humanised sequences shown in SEQ ID NO: 28 and 29 respectively.

The humanised sequences shown in SEQ ID NO: 28 and 29 may be prepared by a variety of methods including those described by Edwards (1987) Am. Biotech. Lab. 5, 38–44, Jayaraman et al. (1991) Proc. Natl. Acad. Sci. USA 88, 4084–4088. Foguet and Lubbert (1992) Biotechniques 13, 674–675 and Pierce (1994) Biotechniques 16, 708.

Example 7
In vitro cytotoxicity of uracil based prodrug of Example 3, corresponding drug and, prodrug plus mutant enzyme Arg4Ala,Lys6Ala,Lys66Glu Human Pancreatic-RNase (HP-RNase).

Figure 6:
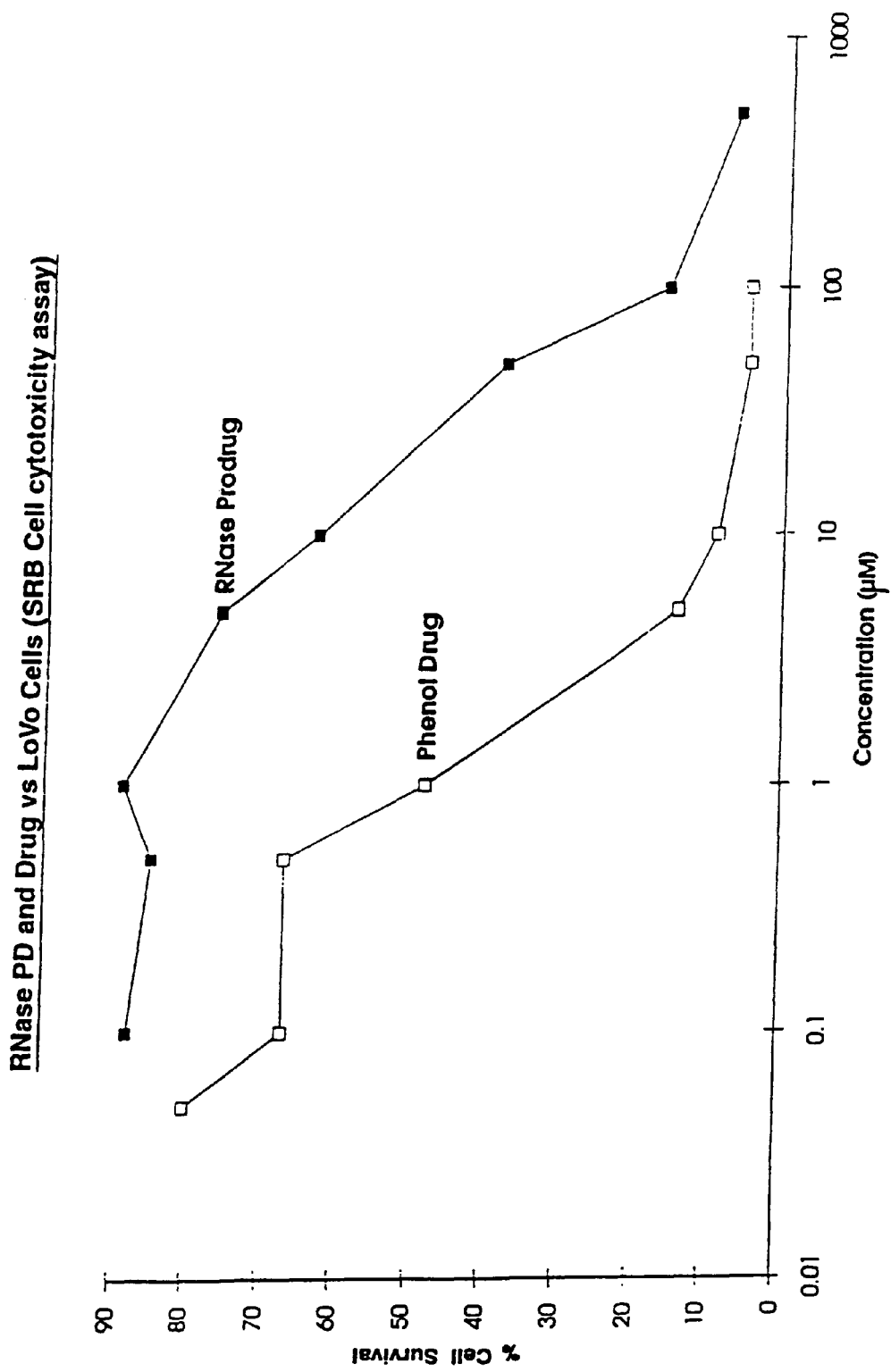
FIG. 6 depicts a comparison of toxicity against LoVo cells between a prodrug and corresponding drug

The differential cytotoxicity to tumour cells of the RNase prodrug and corresponding drug has been demonstrated by the following means. LoVo colorectal tumour cells were incubated with prodrug or drug over a final concentration range of $5 \times 10^{-4}$ to $5 \times 10^{-8}$M in 96 well (2,500 cells/well) microtitre plates for 1 hr at 37° C. The cells were then washed and incubated for a further three days at 37° C. TCA was then added to the wells and after washing to remove dead cells, the amount of cellular protein adhering to the plates was assessed by addition of SRB dye as described by P. Skehan et al., J. Natl. Cancer Inst. 82, 1107 (1990). Potency of the compounds was assessed by the concentration required to inhibit cell growth by 50% (IC50). Upon treatment of LoVo cells with the drug an IC50 of approximately 1 μM was seen. In contrast the prodrug was much less cytotoxic with an IC50 of approximately 30 μM (FIG. 6). Thus the RNase prodrug is approximately 30 fold less cytotoxic to tumour cells than the drug generated by cleavage with the mutant RNase.

If either free Arg4Ala,Lys6Ala,Lys66Glu HP-RNase (10 μg enzyme) or A5B7 F(ab')$_2$-Arg4Ala,Lys6Ala,Lys66Glu HP-RNase conjugate (10 μg enzyme) is added to the assay wells containing the prodrug cytotoxicity can be seen which is comparable to that of the active drug thus demonstrating conversion of the prodrug by the mutant enzyme to release the more potent drug.

These studies demonstrate the activity of a conjugate of mutant human RNase to convert a relatively inactive prodrug into a potent cytotoxic drug capable of killing tumour cells in an ADEPT system.

Example 8
Anti-tumour activity of RNase prodrug and antibody-mutant RNase conjugate in xenografted mice The anti-tumour efficacy of the RNase prodrug and Arg4Ala,Lys6Ala,Lys66Glu HP-RNase conjugate (or Lys66Glu bovine pancreatic RNase) can be demonstrated in the following model. LoVo tumour cells ($10^7$) are injected subcutaneously into athymic nude mice. When the tumours are 4–5 mm in diameter the conjugate is administered iv at doses between 10–100 mg/kg. Following localisation of the conjugate to the tumours and allowing a suitable time interval for residual conjugate to clear from the bloodstream and normal tissues (1–4 days) the prodrug is administered either iv or ip to the mice in dose ranging between 100–1000 mg/kg. The combination of conjugate and prodrug cause the tumours to row significantly slower than untreated control tumours or tumours treated with either the same dose of conjugate or prodrug alone. These studies demonstrate that the Arg4Ala,Lys6Ala,Lys66Glu HP-RNase conjugate in combination with the prodrug result in anti-tumour activity.

Example 9
Clinical dosing in patients

The most effective mode of administration and dosage regimen for the conjugates and prodrugs of this invention in cancer therapy depend on a number of factors such as the severity of disease, the patient's health and response to treatment and the judgement of the treating physician. Accordingly the dosages of the conjugates and prodrugs should be titred to the individual patients. Nevertheless, an effective dose of conjugate is likely to be in the range of 20 to about 200 mg/m$^2$. The effective dose of the prodrug will depend on the particular drug used and the toxicity of the parent drug. Since the prodrug is less cytotoxic than the parent drug the MTD of the parent drug, if known, would provide a starting point. For phenol mustard based prodrugs where clinical data is not available on the parent drug the therapeutic dose range is less certain and would need to be defined by standard animal toxicology studies and dose escalation studies in patients starting at a low dose. However the therapeutic dose may be in range 500–2000 mg/m$^2$.

Example 10
Enzyme kinetics of the uracil based prodrug of Example 3 (RNase prodrug) versus native and mutant Lys66Glu bovine pancreatic RNase The absorbancies of RNase prodrug and corresponding phenol mustard drug were scanned from 200 nm to 350 nm using a spectrophotometer (Perkin Elmer Lambda 2) and the wavelength was selected were the absorbance difference (due to cleavage of the phosphate linkage) between prodrug and drug was maximal. This absorbance was 256 nm. The km and Vmax were then determined by measuring the initial rate of conversion of prodrug to drug at this wavelength using a range of prodrug concentrations (0.2–2 mM) and RNase enzyme concentrations (5–80 μg/ml). Measurements were carried out at 37° C. in 0.025M Tris-HCL plus 0.01% Brig-35 buffer pH7.5 in cuvettes of 0.1 cm path length (Hellma) in a total volume of 250 μL. Kcat was calculated from the Vmax by dividing by the amount of RNase in the reaction mixture. The enzymic activity of both enzymes against the standard substrate Cytidine2'3' Cyclic monophosphate (C>p) was measured by determining the absorbance change at 284 nm and using a range of C>p concentrations (0.5–6 mM) and RNase enzyme concentrations (5–35 μg/ml). The results are shown in below.

Kcat/Km enzyme kinetics for RNase prodrug and C>p with bovine native and mutant Lys66Glu RNase.

| Substrate | BP-RNase | Lys66GluBP-RNase |
|---|---|---|
| | (kcat/Km mM$^{-1}$s$^{-1}$) | |
| RNase Prodrug (Example 3) | 0.37 | 18 |
| C > p | 3.0 | 3.0 |

The results show that both native and mutant bovine RNase turn over the standard substrate C>p at a similar rate. In contrast, the mutant RNase hydrolyses the prodrug much faster than the native enzyme does. Thus, introducing the mutation of Lys66Glu in RNase has not compromised the ability of the bovine enzyme to cleave the phosphate bond but has produced an enzyme which can specifically cleave the RNase Prodrug (Example 3) to release active drug.

Example 11
Enzyme kinetics of uracil based prodrug of Example 3 (RNase prodrug) versus native and Arg4Ala,Lys6Ala, Lys66Glu human pancreatic RNase The enzyme kinetic measurements with native HP-RNase and Arg4Ala,Lys6Ala,Lys66Glu HP-RNase were carried out as described in example 10 except that the buffer used was 0.1 M 1,3-bis[tris(hydroxymethyl)-methylamino]-propane, pH 7.0, 50 mM NaCl. The results are shown below.
Keat/Km enzyme kinetics for RNase prodrug and C>p with native HP-RNase and Arg4Ala,Lys6Ala,Lys66Glu HP-RNase.

| Substrate | HP-RNase | Arg4Ala,Lys6Ala,Lys66Glu HP-RNase |
|---|---|---|
| RNase prodrug (Example 3) | 0.2 | 3.6 |
| C > p | 1.2 | 1.2 |

Units=keat/Km mM-$^1$s-$^1$

The results show that both the native and mutant human enzymes turn over the standard substrate C>p at a similar rate. In contrast, the mutant human RNase hydrolyses the RNase prodrug much faster than the native enzyme. Thus, introducing the mutation Lys66Glu into human pancreatic RNase has also not compromised the ability of the human enzyme to cleave the phosphate bond but has produced an enzyme which can specificaly cleave the RNase prodrug to release active drug.

Example 12
Synthesis of cytosine based prodrug (see Scheme in FIG. 17)

The procedure described in Example 3 is followed but with compound 6 (FIG. 17) replacing compound 4 (FIG. 7). Compound 6 (FIG. 17) is prepared as described for compound 4 (FIG. 7) but with N$^4$-benzyloxycarbonyl-2'-O-benzylcytidine replacing 2'-O-benzyluridine.

N$^4$-Benzyloxycarbonyl-2'-O-benzylcytidine (compound 2, FIG. 17) is prepared from 2'-O-benzylcytidine [Christensen and Broom (1972), J. Org. Chem. 37, 3398–3401] by the procedure used to prepare compound 6 in Reference Example 7.

Example 13
Enzyme activity of bovine Lys66Glu pancreatic RNase on Uridine and Cytidine based prodrug analogues of Reference Examples 6 and 7 respectively The experiment was performed in a manner analagous to that described in Example 10 but the assays were performed at 25° C. The results are shown below.
Keat/Km enzyme kinetics for RNase prodrug analogues and C>p with bovine native and mutant Lys66Glu RNase.

| Substrate | BP-RNase | Lys66GluBP-RNase |
|---|---|---|
| | (kcat/Km mM$^{-1}$s$^{-1}$) | |
| RNase Prodrug analogue (Ref Ex 6) | 1(0.2) | 25(6) |
| RNase Prodrug analogue (Ref Ex 7) | 5.5(0.3) | 109(11) |
| C > p | 3.0 | 3.0 |

The results show that both native and mutant bovine RNase turn over the standard substrate C>p at a similar rate. In contrast, the mutant RNase hydrolyses the prodrug analogues much faster than the native enzyme does. Thus, introducing the mutation of Lys66Glu in RNase has not compromised the ability of the bovine enzyme to cleave the phosphate bond but has produced an enzyme which can specifically cleave the RNase prodrug analogues (Reference Examples 6 & 7) to indicate release of active drugs with appropriate prodrugs.

Example 14
Typical pharmaceutical compositions containing a prodrug compound of the invention A: Dry Filled Capsules Containing 50 mg of Active Ingredient Per Capsule

| Ingredient | Amount per capsule (mg) |
|---|---|
| Compound | 50 |
| Lactose | 149 |
| Magnesium stearate | 1 |
| Capsule (size No 1) | 200 |

The compound can be reduced to a No. 60 powder and the lactose and magnesium sterate can then be passed through a No. 60 blotting cloth onto the powder. The combined ingredients can then be mixed for about 10 minutes and filled into a No. 1 dry gelatin capsule.

B: Tablet

A typical tablet would contain compound (25 mg), pregelatinized starch USP (82 mg), microcrystaline cellulose (82 mg) and magnesium stearate (1 mg).

C: Suppository

Typical suppository formulations for rectal administration can contain compound (0.08–1.0 mg), disodium calcium edetate (0.25–0.5 mg), and polyethylene glycol (775–1600 mg). Other suppository formulations can be made by substituting, for example butylated hydroxytoluene (0.04–0.08 mg) for the disodium calcium edetate and a hydrogenated vegetable oil (675–1400 mg) such as Suppocire L, Wecobee FS, Wecobee M, Witepsols, and the like, for the polyethylene glycol.

D: Injection

A typical injectible formulation would contain compound (10 mg) benzylalcohol (0.01 ml) and water for injection (1.0 ml).

Example 15
Cloning and expression of D253K HCPB-(His)$_6$-c-Myc from E. coli

The method of cloning and expressing the D253K-HCPB in E. coli was very similar to the method described in Reference Example 15. Again pICI266 was used as the cloning vector, and the starting material for PCR of the pro-HCPB gene was plasmid pICI1698 (as described in Reference Example 14). However, in this case site directed mutagenesis was used during the PCR amplification of the gene to change the codon at amino acid position 253 in the mature gene from Aspartate to Lysine (GAC to AAA), the D253K change. Two PCR mixtures were prepared, in a manner similar to that described in Reference Example 15. In the first reaction primers were FSPTS1 (SEQ ID NO: 58) and 1398 (SEQ ID NO: 72). In the second reaction primers were 6HIS9E10R1BS1 (SEQ ID NO: 59) and 1397 (SEQ ID NO: 73). In both reactions the starting DNA was pICI1698. Primers 1398 and 1397 (SEQ ID NO: 72 and 73) are designed to anneal around amino acid codon 253, introduce the GAC to AAA change in the DNA sequence, and produce complementary sequence at the ends of the two PCR products. The other two primers, FSPTS1 and 6HIS9E10R1BS1 (SEQ ID NO: 58 and 59) are described in Reference Example 15. Aliquots of the two PCR reactions were analysed for DNA of the correct size (about 750 and 250 base pairs) and estimation of concentration by Agarose gel electrophoresis, and found to contain predominantly bands of the correct size. Another PCR was then set up using approximately 4 ng of each of the first two PCR products, in the presence of dNTPs to a final concentration of 200 $\mu$M. Taq polymerase reaction buffer, 2U of Taq polymerase in a final volume of 80 $\mu$l. The mixture was heated at 94° C. for 10 minutes prior to the addition of the Taq enzyme, and PCR incubation was carried out using 10 cycles of 94° C. for 1 minute and 63° C. for 4 minutes. On completion of these cycles the reaction mix was made up to 120 $\mu$l by the addition of 120 pmols of each end primer, FSPTS1 and 6HIS9E10R1BS1 (SEQ ID NO: 58 and 59), additional dNTPs (approximately an extra 100 $\mu$M), Taq polymerase reaction buffer, and 4U of Taq polymerase. The mixture was heated at 94° C. for 10 minutes prior to addition of Taq enzyme, and the PCR incubation was carried out using 30 cycles of 94° C. for 1.5 minutes, 50° C. for 2 minutes, and 72° C. for 2 minutes, followed by a single incubation of 72° C. for 9.9 minutes at the end of the reaction.

An aliquot of the PCR product was analysed for DNA of the correct size (about 1000 base pairs) by agarose gel electrophoresis and found to contain predominantly a band of the correct size. The remainder of the product from the reaction mix was purified in a similar manner to Reference Example 15. The isolated DNA was restriction digested with enzymes Fsp1 and EcoRI, and a band of the correct size (about 1000 base pairs) purified in a similar manner to Reference Example 15.

pICI266 double stranded DNA, prepared in a similar manner to Reference Example 15, was restriction digested with KpnI enzyme, and blunt-end treated with T4 DNA polymerase being very careful to ensure complete digestion. The purified DNA was then digested with restriction enzyme EcoRI. DNA of the correct size (about 5600 base pairs) was purified in a similar manner to Reference Example 15.

Aliquots of both restricted and purified DNA samples were checked for purity and concentration estimation using agarose gel electrophoresis compared with known standards. From these estimates ligation mixes were prepared to clone the HCPB gene into the pICI266 vector in a similar manner to Reference Example 15.

Following the ligation reaction the DNA mixture was used to transform E. coli strain DH5α. colonies were picked and tested by hybridisation, in a similar manner to Reference Example 15.

Six positive hybridisation isolates were checked by PCR for inserts of the correct size, using primers FSP1TS1 and 6HIS9E10R1BS1 (SEQ ID NO: 58 and 59), and for priming with an internal primer FSPTS1 (SEQ ID NO: 58) and 679 (SEQ ID NO: 51) in a similar manner to Reference Example 15. The PCR products were analysed for DNA of the correct size (about 1000 base pairs from primers FSPTS1 to 6HIS9R10R1BS1, and about 430 base pairs from primers FSPTS1 to 679) by agarose gel electrophoresis. All clones gave PCR DNA products of the correct size.

All six of the clones were then taken for plasmid DNA preparation, and two were sequenced over the region of PCR product in a similar manner to Reference Example 15. The clones were sequenced using eight separate oligonucleotide primers known as 1281, 677, 1504, 679, 1802, 1590, 1280 and 1731 (SEQ ID NO: 55, 52, 60, 51, 63, 61, 53 and 62). From the sequencing results a clone containing a plasmid with the required D253K-HCPB gene sequence was selected, and is known as pICI1713.

The confirmed sequence of the cloned D253K-HCPB gene in pICI1713, showing amino acid translation, from the start of the PelB sequence to the EcoRI restriction site is shown as SEQ ID NO: 74 with DNA numbering starting from 1 in the first codon of PelB, and peptide numbering starting from 1 in the mature HCPB.

To obtain controlled expression of the D253K-HCPB, the pICI1713 plasmid DNA was transformed into calcium chloride transformation competent E. coli expression strains in a similar manner to Reference Example 15. All pICI1713 transformed expression strains were treated in a similar manner to Reference Example 15 to test for expression of the cloned D253K-HCPB gene. In this case the 9E10 monoclonal antibody specific for the C-myc peptide tag was used in the Western analysis, as the D253K-HCPB has the C-terminal (His)$_6$-c-myc tag in a similar manner to Reference Example 15.

Expression of the cloned tagged D253K-HCPB in pICI266 (pICI1713) was demonstrated from E. coli by the Coomassie stained gels showing a strong protein band at about 35,000 Daltons when compared to vector (pICI266) alone clones, and clones producing the tagged HCPB (Reference Example 15). A band of the same size gave a strong signal by Western analysis detection of the c-myc-tag.

Example 16

Cloning and expression of D253R HCPB-(His)-$_6$-c-Myc from E. coli

The method of cloning and expressing the D253R-HCPB in E. coli was very similar to the method described in Reference Example 16. Again pICI266 was used as the cloning vector, and the starting material for PCR of the pro-HCPB gene was plasmid pICI1712 (as described in Reference Example 15. However, in this case site directed mutagenesis was used during the PCR amplification of the gene to change the codon at amino acid position 253 in the mature gene from Aspartate to Arginine (GAC to CGC), the D253R change. Two PCR mixtures were prepared, in a manner similar to that described in Reference Examples 15 and 16. In the first reaction primers were 2264 (SEQ ID NO: 65) and 2058 (SEQ ID NO: 75). In the second reaction primers were 6HIS9E10R1BS1 (SEQ ID NO: 59) and 2054 (SEQ ID NO: 76). In both reactions the starting DNA was pICI1712.

Primers 2058 and 2054 (SEQ ID NO: 75 and 76) are designed to anneal around amino acid codon 253, introduce the GAC to CGC change in the DNA sequence, and produce complementary sequence at the ends of the two PCR products. The other two primers, 2264 and 6HIS9E10R1BS1 (SEQ ID NO: 65 and 59) are described in Reference Examples 15 and 16. Aliquots of the two PCR reactions were analysed for DNA of the correct size (about 750 and 250 base pairs) and estimation of concentration by Agarose gel electrophoresis, and found to contain predominantly bands of the correct size. Another PCR was then set up using approximately 4 ng of each of the first two PCR products, in the presence of dNTPs to a final concentration of 200 μM. Taq polymerase reaction buffer, 2U of Taq polymerase in a final volume of 80 μl. The mixture was heated at 94° C. for 10 minutes prior to the addition of the Taq enzyme, and PCR incubation was carried out using 10 cycles of 94° C. for 1 minute and 63° C. for 4 minutes. On completion of these cycles the reaction mix was made up to 120 μl by the addition of 120 pmols of each end primer, 2264 and 6HIS9E10R1BS1 (SEQ ID NO: 65 and 59), additional dNTPs (approximately an extra 100 μM), Taq polymerase reaction buffer, and 4U of Taq polymerase. The mixture was heated at 94° C. for 10 minutes prior to addition of Taq enzyme, and the PCR incubation was carried out using 30 cycles of 94° C. for 1.5 min. 50° C. for 2 min. and 72° C. for 2 min. followed by a single incubation of 72° C. for 9.9 min at the end of the reaction.

An aliquot of the PCR product was analysed for DNA of the correct size (about 1000 base pairs) by agarose gel electrophoresis and found to contain predominantly a band of the correct size. The remainder of the product from the reaction mix was purified in a similar manner to Reference Example 15. The isolated DNA was restriction digested with enzymes NcoI and EcoRI, and a band of the correct size (about 1000 base pairs) purified in a similar manner to Reference Example 15.

pICI266 double stranded DNA, prepared in a similar manner to Reference Example 15, was restriction digested with NcoI and EcoRI enzymes, being very careful to ensure complete digestion. DNA of the correct size (about 5600 base pairs) was purified in a similar manner to Reference Example 15.

Aliquots of both restricted and purified DNA samples were checked for purity and concentration estimation using agarose gel electrophoresis compared with known standards. From these estimates ligation mixes were prepared to clone the HCPB gene into the pICI266 vector in a similar manner to Reference Example 15.

Following the ligation reaction the DNA mixture was used to transform *E. coli* strain DH5α, colonies were picked and tested by hybridisation, in a similar manner to Reference Example 15.

Three of the clones were then taken for plasmid DNA preparation, and were sequenced over the region of PCR product in a similar manner to Reference Example 15. The clones were sequenced using nine separate oligonucleotide primers known as 1281, 677, 1504, 679, 1802, 1590, 1280, 1731 and 1592 (SEQ ID NO: 55, 52, 60, 51, 63, 61, 53, 62 and 70). From the sequencing results a clone containing a plasmid with the required D253R-HCPB gene sequence was selected, and is known as pICI1746.

The confirmed sequence of the cloned D253R-HCPB gene cloned in pICI1746, showing amino acid translation, from the start of the PelB sequence to the EcoRI restriction site is shown as SEQ ID NO: 77 with DNA numbering starting from 1 in the first codon of PelB, and peptide numbering starting from 1 in the mature HCPB.

To obtain controlled expression of the D253R-HCPB the pICI1746 plasmid DNA was transformed into transformation competent *E. coli* expression strains in a similar manner to Reference Example 15. All pICI1746 transformed expression strains were treated in a similar manner to Reference Example 15 to test for expression of the cloned D253R-HCPB gene. In this case the 9E10 monoclonal antibody specific for the C-myc peptide tag was used in the Western analysis, as the D253R-HCPB has the C-terminal (His)$_6$-c-myc tag in a similar manner to Reference Example 15.

Expression of the cloned tagged D253R-HCPB in pICI266 (pICI1746) was demonstrated from *E. coli* by the Coomassie stained gels showing a strong protein band at about 35,000 Daltons when compared to vector (pICI266) alone clones, and clones producing the tagged HCPB (Reference Example 15). A band of the same size gave a strong signal by Western analysis detection of the c-myc tag.

Purification is achieved using methodology analogous to that set out below in Example 17.

Example 17

Purification of mutant D253K HCPB-(His)$_6$-c-Myc proteins from *E. coli*

First a 20 liter fermentation process for carboxypeptidase B analogue D253K in a cell paste is described. *E. coli* K12 strain MSD 1924 was transformed with plasmid pZen 1713 (pICI 1713; see Example 15 above) and the resultant strain MSD 2230 (MSD 1924 pZen 1713) was stored in glycerol freezing mix at −80° C.

MSD 2230 was streaked onto agar plates containing L-tetracycline (10 μgml-$^1$) medium to separate single colonies after overnight growth at 37° C. Six single colonies of MSD 2230 were removed from the surface of the L-tetracycline (10 μgml-$^1$) agar, resuspended in a 10 ml L-tetracycline (10 μgml-$^1$) broth and 100 μl of this culture was immediately inoculated into each of six 250 ml Erlenmeyer flasks containing 75 ml of L-tetracycline (10 μgml-$^1$) broth. After growth for 15–16 hours at 37° C. on a reciprocating shaker (300 rpm) the contents of the flasks were pooled and used to inoculate a single fermenter (U30D vessel, B. Braun, Melsungen, Germany) containing 15 liters of the growth medium described in FIG. 23.

The fermentation was performed at a temperature of 37° C. and pH of 6.7 and pH of 6.7 which was automatically controlled to the set point by the addition of 6M sodium hydroxide or 2M sulphuric acid. The dissolved oxygen tension (dOT) set point was 50% air saturation and it was maintained by the automatic adjustment of the fermenter stirrer speed between 200 and 1000 rpm. The air flow to the fermenter was maintained at 20 standard liters per minute which corresponds to 1.3 vessel volumes per minute (vvm) by a Tylan mass flow controller.

4.5 Hours following inoculation, a solution of yeast extract (225 gl-$^1$) was fed into the fermenter at a rate of 190–210 mlh-$^1$ for 28.5 hours. 1.5 hours after the yeast extract feed was started, the fermentation temperature set point was reduced to 25° C. When this temperature was attained, approximately 1 hour later, expression of the carboxypeptidase analogue D253K was induced with a single shot addition of 50% arabinose to give a final concentration in the fermenter vessel of 0.5%. 1–2 hours following induction, a mixture of glycerol (714 gl-$^1$) and ammonium sulphate (143 gl-$^1$) was fed into the fermenter at 45–55 mlh-$^1$ until harvest. The fermentation was continued under these conditions until ca. 75 hours post fermenter inoculation when the culture was harvested by transferring aliquots of the fermenter contents into 1 liter centrifuge bottles. The spent medium was separated from the bacterial cells by centrifugation in a Sorvall RC-3B centrifuge (7.000×g, 4° C. 30 min.). This process typically yields a final dry weight of ca.20 gl-$^1$.

The cell paste was purified as follows. Recombinant *E. coli* cell paste containing the recombinant enzyme, D253K HCPB, was taken from storage at −70° C. and allowed to thaw. The weight of cell paste was measured and found to be 309 grams. The paste was resuspended with the addition of buffer A [200 mM Tris (hydroxymethyl)aminomethane hydrochloride (TRIS-HCl), 20% sucrose, pH 8.0] to give a resuspended volume of 320 ml. The cell suspension was incubated at room temperature for 20 minutes with occasional gentle mixing before an equal volume of distilled water, at room temperature, was added and throughly mixed in. The cell suspension was again incubated at room temperature for 20 minutes with occasional gentle mixing.

The resulting crude osmotic shockate was clarified by centrifugation at 98000×g for 90 minutes at 4° C. after which the supernatant was decanted off from the pelleted insoluble fraction, giving a clarified volume of 240 ml. Deoxyribonuclease 1 (24 mg) was dissolved in distilled water (5 ml) and added to the supernatant. The mixture was incubated at room temperature, with continuous shaking for 30 minutes to reduce the vicosity of the supernatant enough for it to be loaded on to a Carboxypeptidase Inhibitor CNBr activated Sepharose™ affinity column, prepared according to instructions with the CNBr activated Sepharose™ 4B from Pharmacia and carboxypeptidase inhibitor from potato tuber (c-0279, Sigma). The supernatant was diluted 1:1 with 10 mM TRIS-HCl, 500 mM sodium chloride, pH 8.0 (Buffer B), adjusted to pH 8.0 and loaded over night, on to the Carboxypeptidase inhibitor affinity column at 0.5 ml/min. The column was pre-equilibrated with buffer B at 4° C. After loading the supernatant, the column was washed until the absorbance of the flow through was back to baseline before the bound material was eluted from the column by elution buffer (100 mM sodium carbonate. 500 mM sodium chloride, pH 11.4) at 4° C., with 1 ml fractions being collected. The eluted fractions were frozen at −20° C. after samples were taken to determine those containing the recombinant carboxypeptidase. This was accomplished by Western blot analysis using an anti-c-myc tag antibody (9E10), followed by an anti-mouse-horseradish peroxidase conjugate (a-9044, sigma) that gave a colour reaction with exposure to 4-chloro-naphthol and hydrogen peroxide.

Fractions 11 to 44 determined to contain the recombinant carboxypeptidase B. These were pooled, the pH adjusted to pH 7.5 and concentrated using a Milliport Centifugal Ultrafree™ −20 (10,000 molecular weight cut off) before being snap-frozen and stored at −20° C. The purification detailed here provided 4.7 mg of D253K mutant carboxypeptidase at a purity of 80% in a volume of 0.95 ml.

Example 18

Synthesis of an aspartic acid phenol mustard prodrug (compound 5a, FIG. 27) (2S),2-(3-{4-[bis-(2-chloroethyl)-amino)-phenoxycarbonyl}-propionyl-amino)-succinic acid Analagous methodology to that set out in Reference Example 12 was used.

(2S),2-(3-{4-[bis-(2-chloroethyl)-amino)-phenoxycarbonyl}-propionylamino)-succinic acid dibenzyl ester (4a) was hydrogenated for 2 h at 80 psi to give the desired end product 5a (yield 86%).

5a: 1HNMR (CD3OD): 2.65–2.75 (t,2H); 2.8–2.9 (m,4H); 3.7–3.75 (m,4H); 3.8–3.85 (m, 4H); 4.75 (t,1H); 6.7–6.8 (m,2H); 7.0–7.1 (m,2H).

MS (ESI): 471–473 (MNa)+

Anal. ($C_{18}H_{22}N_2O_7Cl_2$1.4$H_2O$): Calc. % C: 45.56 H: 5.27 N: 5.90, Found % C: 45.79 H: 5.60 N: 5.91

Starting material compound 4a was prepared as follows.

(2S),2-amino-succinic acid dibenzyl ester (Compound 2a) was reacted with compound 1 to give (2S),2-(3-carboxypropionylamino)-succinic acid dibenzyl ester (compound 3a) after recrystallisation with diethyl ether/hexane: (Yield: 80%).

3a: 1HNMR (CDCl3): 2.42–2.6 (m,2H); 2.6–2.75 (m,2H); 2.85 (dd,2H); 3.1 (dd,1H); 4.9 (dd,1H); 5.05 (dd, 2H); 5.15 (s,2H); 6.7 (d,1H); 7.25–7.5 (m,10H).

MS (ESI): 436 [MNa]+

Anal. ($C_{22}H_{23}NO_7$0.4$H_2O$): Calculated % C: 62.82 H: 5.70 N: 3.33, Found % C: 63.2 H: 5.75 N: 2.9

Compound 3a was reacted to give the desired starting material 4a (yield 78%) stirring was maintained for 3 h at room temperature and purification was achieved by flash chromatography using diethyl ether/hexane (70/30 V/V as eluent).

4a: 1HNMR (CDCl3): 2.55–2.65 (m,2H); 2.8–2.9 (m,2H); 2.9 (dd,1H); 3.1 (dd,1H); 3.6 (dd, 4H); 3.7 (dd,4H); 4.9 (dd,1H); 5.05 (dd,2H); 5.15 (s,2H); 6.58 (d,1H); 6.65 (d,2H); 6.95 (d,2H); 7.25–7.4 (m,10H).

MS (ESI): 651–653 (MNa)+

Example 19

Synthesis of a glutamic acid phenol mustard prodrug (5b; FIG. 27) (2S),2-(3-{4-[bis-(2-chloroethyl)-amino)-phenoxycarbonyl}-propionyl-amino)-pentanedioic acid Analagous methodology to that set out in Reference Example 12 was used.

(2S),2-(3-{4-[bis-(2-chloroethyl)-amino)-phenoxycarbonyl}-propionylamino)-pentanedioic acid dibenzyl ester (4b) was hydrogenated for 3 h at 60 psi to give the desired end product 5b (yield: 93%).

5b: 1HNMR (CD3OD): 1.9–2.0 (m,1H); 2.1–2.2 (m,1H); 2.35–2.45 (m,2H); 2.55–2.7 (m, 2H); 2.8–2.9 (m,2H); 3.65–3.7 (m,4H); 3.72–3.8 (m,4H); 4.4–4.5 (m,1H); 6.75 (d,2H); 6.95 (d,2H).

MS (ESI): 485–487 (MNa)+

Starting material compound 4b was prepared as follows.

(2S),2-amino-pentanedioic acid dibenzyl ester (2b) was reacted to give (2S),2-(3-carboxypropionylamino)-pentanedioic acid dibenzyl ester (3b) (Yield: quantitative)

3b: 1HNMR (CDCl3): 2.0–2.1 (m,1H); 2.2–2.3 (m,1H); 2.3–2.5 (m,4H); 2.6–2.7 (m, 2H); 4.65 (dd,1H); 5.05 (s,2H); 5.15 (s,2H); 6.5 (d,1H); 7.3–7.4 (m,10H).

MS (ESI): 450 [MNa]+

3b was reacted to give the desired starting material 4b (yield: 82%).

4b: 1HNMR (CDCl3): 1.95–2.05 (m,1H); 2.2–2.3 (m,1H); 2.3–2.5 (m,2H); 2.6 (dt,2H); 2.8–3.0 (m,2H); 3.6 (dd,4H); 3.7 (dd,4H); 4.7 (dd,1H); 5.1 (s,2H); 5.2 (s,2H); 6.3 (d,1H); 6.6 (d,2H); 6.95 (d,2H); 7.3–7.4 (m,10H).

MS (ESI): 665–667 (MNa)+

Example 20

Assay of activity of mutant human CPB and native human CPB against Hipp-Asp and Hipp-Glu prodrug analogues Purified mutants of human CPB (D253K and D253R: Examples 15–17) and native human CPB, produced as described in Reference Example 20, were assayed for their ability to convert either hippuryl-L-aspartic acid (Hipp-Asp—Reference Example 10), hippuryl-L-glutamic acid (Hipp-Glu—Reference Example 9) or hippuryl-L-arginine (Sigma Chemical Company—cat no. H6625) to hippuric acid using a HPLC based assay.

The reaction mixture (250 µl) contained 4 µg human CPB (native or mutant) and 0.5 mM Hipp-Asp or Hipp-Glu in 0.025M Tris-HCL, pH 7.5. Samples were incubated for 5 h at 37° C. The reactions were terminated by the addition of 250 µl of 80% methanol, 20% distilled water, 0.2% trifluoro acetic acid and the amount of hippuric acid generated was quantified by HPLC.

HPLC analysis was carried out using a Hewlett Packard 1090 Series 11 (with diode array) HPLC system. Samples (50 µl) were injected onto a Hichrom HiRPB column (25 cm) and separated using a mobile phase of 40% methanol, 60% distilled water, 0.1% trifluoro acetic acid at a flow rate of 1 ml/min. The amount of product (hippuric acid) produced was determined from calibration curves generated with known amounts of hippuric acid (Sigma-H6375). The results are shown in the Table and are expressed as the percentage conversion of substrate into product in 5 hr at 37° C. with 4 μg enzyme.

Conversion of Hipp-Asp and Hipp-Glu by mutant and native human CPB

|  | Hipp-Asp | Hipp-Glu | Hipp-Arg |
|---|---|---|---|
|  | (% conversion to Hippuric acid) | | |
| Native CPB | 0 | 0 | 100 |
| D253K mutant CPB | 78 | 91 | <2 |
| D253R mutant CPB | 72 | 52 | 3 |

The data show that introduction of either a lysine or arginine residue at position 253 in human CPB instead of the aspartate residue present in the native enzyme changes the substrate specificity of the enzyme so that it is capable of conversion of either Hipp-Asp or Hipp-Glu. In contrast, the native enzyme is unable to convert either of these compounds into Hippuric acid but does convert Hipp-art to hippuric acid. The best activity was seen with the D253K mutant and the Hipp-Glu substrate.

Example 21
Determination of Km and kcat of D253K mutant HCPB with Hipp-Asp and Hipp-Glu Purified D253K HCPB, produced as described in Example 17, was assayed against Hipp-Asp (Reference Example 10) and Hipp-Glu (Reference Example 9) to determine Km and kcat for these substrates. Hipp-Glu and Hipp-Asp were diluted in range 0.25–8.0 mM and 0.25–5.0 mM respective in 0.025M Tris-HCL buffer, pH 7.5. Where necessary substrate samples were adjusted to pH 7.5 with 1M NaOH.

D253K HCPB (4 μg/ml for Hipp-Asp and 0.5 μg/ml for Hipp-Glu) was added to these substrates (500 μl reaction volume) to start the reaction. Samples were incubated for 5 h at 37° C. Reactions were terminated by the addition of 500 μl methanol/distilled water (80/20) containing 0.2% TFA. The amount of hippuric acid produced was quantified by HPLC as described in Example 20.

Km and Vmax values were calculated using the ENZFITTER software programme (Biosoft. Perkin Elmer). kcat was calculated from Vmax by dividing by the enzyme concentration in the reaction mixture (using a molecular weight for HCPB of 34 KDa). The results are shown in the Table.

Km and kcat data for Hipp-Asp and Hipp-Glu with D253K mutant HCPB

|  | Km (mM) | kcat (s$^{-1}$) | kcat/Km (mM$^{-1}$s$^{-1}$) |
|---|---|---|---|
| Hipp-Asp | 2.7 | 0.26 | 0.1 |
| Hipp-Glu | 5.3 | 3.8 | 0.7 |

The data confirm that replacing aspartate with a lysine residue at position 253 in human CPB results in an enzyme which can convert both Hipp-Asp and Hipp-Glu into hippuric acid with reasonable enzyme kinetics. The kcat/Km is approximately 7 fold greater with the Hipp-Glu compared to the Hipp-Asp substrate.

Example 22
Assay of activity of mutant HCPB and native HCPB against glutamic acid prodrug Purified D253K HCPB and native human CPB, produced as described in Example 17 and Reference Example 20 respectively, were assayed for their ability to enzymatically cleave glutamic acid from a glutamic acid prodrug (Example 18). Cleavage liberates an intermediate (Reference Example 13) which self collapses non-enzymatically to release the active phenol mustard drug. Conversion of the glutamic acid prodrug to intermediate was measured using a HPLC based assay.

Prodrug was diluted in the range 0.25–5.0 nM in 0.025M Tris-HCL buffer, pH 7.5. Where necessary prodrug samples were adjusted to pH 7.5 with 1M NaOH. D253K mutant HCPB or native HCPB, both at a final concentration of 0.25 mg/ml, were added to the these substrates (250 μl reaction volume prewarmed to 37° C. for 2 min) to start the reaction. Samples were incubated for 4 minutes at 37° C. The reaction was terminated by the addition of 250 μl 98.8% MeCN, 0.2% TFA and the samples placed on ice. The amount of intermediate produced was then quantified by HPLC.

HPLC separation was carried out as described in Example 20 except that a mobile phase of MeCN/distilled water (55/45 V/V) containing 0.1% TFA was used to achieve separation of the prodrug (retention time 4.9 minutes) and intermediate (retention time 8.4 minutes). The amount of intermediate produced was quantified from calibration curves generated with known amounts of the intermediate.

The amount of intermediate formed at 5.0 mM and 0.25 mM prodrug with native and mutant (D253K) HCPB in replicate samples is shown in the Table.

Conversion of prodrug to intermediate by native and mutant (D253K) HCPB

| Prodrug concentration | Intermediate concentration(mM) | |
|---|---|---|
| (mM) | Native HCPB | Mutant HCPB |
| 5.0 | 0.0 | 0.023.0.022 |
| 0.25 | 0.0 | 0.005.0.005 |

Km, Vmax and kcat values for the mutant human enzyme (D253K) and the prodrug were calculated from the amount of intermediate produced over a range of substrate concentrations (0.25–5.0 mM) using the ENZFITTER™ software described in Example 21.

The results for the D253K mutant HCPB were:
Km=1.25 mM
Vmax=1.17×10$^{-4}$ mMsec$^{-1}$
kcat=0.016 sec$^{-1}$ The data show that introduction of a lysine residue at position 253 in human CPB instead of the aspartate residue present in the native enzyme changes the substrate specificity of the enzyme so that it is capable of conversion of the glutamic acid prodrug into its self-collapsing intermediate. In contrast, the native enzyme is unable to convert the prodrug to its intermediate. Since the prodrug is relatively non-cytotoxic (Example 23) and the intermediate is non-enzymatically broken down to release free phenol mustard drug which kill tumour cells (Example 23) these results demonstrate that mutation of active site residues of CPB can yield a mutant human enzyme capable of converting a relatively non-cytotoxic prodrug into a potent cytotoxic drug capable of killing tumour cells.

Example 23
Cytotoxicity of glutamic acid prodrug and phenol mustard drug in LoVo human colorectal tumour cells The differential cytotoxicity to tumour cells of the glutamic acid prodrug and corresponding phenol mustard drug has been demonstrated by the following means.

LoVo colorectal tumour cells were incubated with prodrug or drug over a final concentration range of 5×10$^{-4}$ to 5×10$^{-8}$M in 96-well (2,500 cells/well) microtitre plates for 1 h at 37° C. The cells were then washed and incubated for a further three days at 37° C. TCA was then added to the wells and, after washing to remove dead cells, the amount of cellular protein adhering to the plates was assessed by addition of SRB dye as described by P. Skehan et al, J. Natl. Cancer Inst. 82, 1107 (1990). Potency of the compounds was assessed by the concentration required to inhibit cell growth by 50% (IC50).

Upon treatment of LoVo cells with the phenol mustard drug an IC50 of approximately 1 μM was seen. In contrast the glutamic acid prodrug was much less cytotoxic with an IC50 of approximately 50 μM (FIG. 22). Thus the mutant CPB glutamic acid prodrug is approximately 50 fold less cytotoxic to tumour cells than the phenol mustard drug.

If 100 μg of mutant HCPB (D253K) produced as described in Example 17 is added to the assay wells containing the glutamic acid prodrug cytotoxicity can be seen which is comparable to that of the active drug thus demonstrating conversion of the prodrug by the mutant enzyme to release the more potent drug. Addition of 100 μg of native human CPB to each well does not significantly enhance the cytotoxicity of the glutamic acid prodrug. These studies demonstrate the potential of the mutant human CPB enzyme (D253K) to selectively convert a relatively inactive prodrug into a potent cytotoxic drug capable of killing tumour cells.

Example 24
Preparation of humanised A5B7 F(ab')$_2$-D253K HCPB fusion protein

The procedure described in Reference Example 21 is repeated but with murine A5B7 light chain and Fd sequences replace by sequences for humanised A5B7, and with the HCPB sequence replaced by D253K sequence. The fusion protein is expressed from COS cells by co-transfection with the HCPB prepro sequence as described in Reference Example 21. Large-scale expression of the fusion protein is performed by transiently introducing the plasmid vectors (750 μg of each) into COS-7 cells (11) essentially as described in Reference Example 21. The product is purified either by passing the supernatant containing the fusion protein over immobilised protein A and elution of the bound fusion protein with high pH buffer or by passing the supernatant containing the fusion protein over immobolised carboxypeptidase inhibitor, following the route used for the purification of the recombinant carboxypeptidase enzyme, and elution with the same high pH as used with the enzyme in Example 12. Both these routes may involve further purification of the fusion protein by either gel permeation chromatography, ion exchange chromatography, hydrophobic interaction chromatography singly, or a combination of them.

The procedure described in Reference Example 21 is repeated but the murine sequences for Fd and light chain, as shown in SEQ ID NO: 25 and 26 respectively, are replaced by the humanised sequences shown in SEQ ID NO: 28 and 29 respectively. The HCPB sequence in Reference Example 21 is replaced by the D253K sequence [described in Example 15, but without the (His)$_6$.c-Myc tags]. The template for PCR in Reference Example 21 (pICI1698) is replaced by pICI1713 (described in Example 15).

The humanised sequences shown in SEQ ID NO: 28 and 29 are prepared by a variety of methods including those described by Edwards (1987) Am. Biotech. Lab. 5, 38–44. Jayaraman et al. (1991) Proc. Natl. Acad. Sci. USA 88, 4084–4088, Foguet and Lubbert (1992) Biotechniques 13, 674–675 and Pierce (1994) Biotechniques 16, 708.

Example 25
Shake flask fermentation for preparation of D253K HCPB

E. coli strain MSD 213 was transformed with plasmid pICI 1713 (see Example 15) and the resultant strain MSD 213 pZen 1713 stored as a glycerol stock at −80° C. An aliquot of MSD 213 pZen 1713 was streaked onto agar plates of L-tetracycline to separate single colonies after overnight growth at 37° C. A single colony of MSD 213 pZen 1713 was removed and inoculated into a 250 ml Erlenmeyer flask containing 75 ml of L-tetracycline broth. After growth for 16 h at 37° C. on a reciprocating shaker the contents of the flask were used to inoculate to OD550=0.1 each of nine 2L Erlenmeyer flasks containing 600 ml of L-tetracycline broth. The flasks were then incubated at 20° C. on a reciprocal shaker until growth, estimated by measuring the optical density of the culture, reached OD550= 0.5. At this point heterologous protein production was induced by adding L-arabinose to the cultures to a final concentration of 0.01% w/v and the incubation continued at 20° C. as described above for a further 42 h. The spent medium was separated from the bacterial cells by centrifugation in a Sorvall RC-3B centrifuge (7000× g, 4° C., 30 min) and the cell paste stored at −70° C.

Example 26
Use of ADEPT in autologous bone marrow transplantation

Autologous bone marrow transplantation involves removal of a portion of the patient's own marrow before giving the patient intensive radiochemotherapy. The bone marrow is returned to the patient on completion of the treatment. In some cancers, such as leukaemias and lymphomas of B- and T-cell lineage and carinomas of breast, lung and colon, malignant cells infiltrate the marrow and should be eliminated before reinfusing the marrow to optimise survival. Antibody-toxin conjugates have been used previously to eliminate these tumour cells for autologous bone marrow (Blakey, D. C. et al. Prog. Allerby vol 45, 50, 1988).

ADEPT could be used for this purpose especially if a short-lived reactive mustard alkylating agent is used as the drug component. Thus autologous bone marrow containing tumour cells could be incubated with an appropriate antibody-enzyme conjugate. Following binding of the conjugate selectively to the tumour cells residual conjugate would be washed away. Prodrug would then be added and drug would be generated adjacent to antigen positive tumour cells resulting in selective tumour cell killing. Normal bone marrow cells could be protected by optimising the dilution of the bone marrow to ensure that sufficient distance existed between the site of generation of drug on tumour cells and the bone marrow cells so that the drug became inactivated due to chemical decomposition before it reached the bone marrow cells. Addition of protein to act as a nucleophile for the reactive mustard drug could also be used to minimise normal bone marrow damage.

Example 27
Use of mutate Glucuronidase for reverse polarity ADEPT

Human glucuronidase is another enzyme where the 'reverse polarity' concept can be used to produce a specific human enzyme capable of cleaving a prodrug to release an active drug. Bosslet et al (Cancer Res. 54, 2151, 1994) have already described an adriamycin-glucuronide prodrug for native human glucuronidase and have described the synthesis of a range of alternative prodrugs releasing a range of drugs (Bosslet in patent application AU-50225/93). Endogenous native glucuronidase present in blood and tissue will potentially turn over these prodrugs to release active drug in the absence of antibody-glucuronidase conjugate and thus reduce the specificity of the approach. Cheng and Touster (J.B.C. 247, 2650, 1972) have reported that there is a positively charged amino acid in the active site of glucuronidase that reacts with the negatively charged carboxyl group on the glucuronide ring.

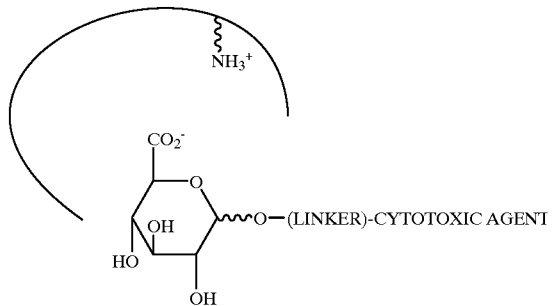

The linker could be either a direct linkage between the glucuronide and the cytotoxic agent or a self imolating linker which for example could be of the type described by Bosslet et al (Cancer Res. 54, 2151, 1994 and Patent Au-A-50225/93). If the negatively charged carboxyl group on the glucuronide ring is replaced with a positive charged group R where, for example, $R=L—CH_2—NH_2$ or $L—CH_2—NHR'$ (where $R'=C_{1-4}$ alkyl and $L=[CH_2]_{0-3}$ or other suitable linkers) then the positive charged prodrug should no longer be a substrate for native glucuronidase. If the positive charge residue in the active site of glucuronidase is then converted to a negative charged amino acid e.g. glutamate or aspartate this mutant glucuronidase will now turn over the positively charged prodrug selectively in a manner analogous to the RNase and CPB examples. Thus the reverse polarity concept can be extended to human glucuronidase and positively charged glucuronide based prodrugs.

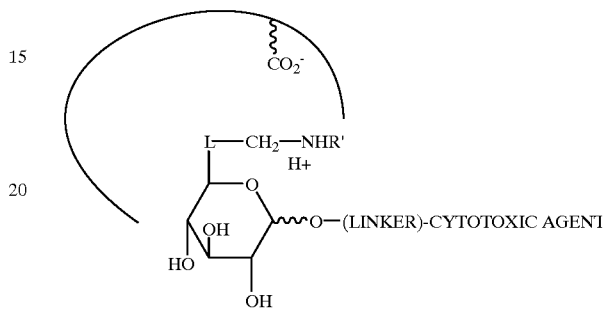

SEQUENCE LISTING (1) GENERAL INFORMATION:

(iii) NUMBER OF SEQUENCES: 77

(2) INFORMATION FOR SEQ ID NO:1:

(i) SEQUENCE CHARACTERISTICS:
      (A) LENGTH: 30 bases
      (B) TYPE: nucleic acid
      (C) STRANDEDNESS: single
      (D) TOPOLOGY: linear (xi) SEQUENCE DESCRIPTION: SEQ ID NO:1:

GGTCTGCCCA TTCTCGCAGG CAACATTTTT                                    30

(2) INFORMATION FOR SEQ ID NO:2:

(i) SEQUENCE CHARACTERISTICS:
      (A) LENGTH: 30 bases
      (B) TYPE: nucleic acid
      (C) STRANDEDNESS: single
      (D) TOPOLOGY: linear (xi) SEQUENCE DESCRIPTION: SEQ ID NO:2:

TGCTACCAGA GCTACTCCAC CATGAGCATC                                    30

(2) INFORMATION FOR SEQ ID NO:3:

(i) SEQUENCE CHARACTERISTICS:
      (A) LENGTH: 30 bases
      (B) TYPE: nucleic acid
      (C) STRANDEDNESS: single
      (D) TOPOLOGY: linear (xi) SEQUENCE DESCRIPTION: SEQ ID NO:3:

AATGTTGCCT GCGAGAATGG GCAGACCAAT                                    30

(2) INFORMATION FOR SEQ ID NO:4:

(i) SEQUENCE CHARACTERISTICS:
        (A) LENGTH: 29 bases
        (B) TYPE: nucleic acid
        (C) STRANDEDNESS: single
        (D) TOPOLOGY: linear (xi) SEQUENCE DESCRIPTION: SEQ ID NO:4:

CTGGGAGCAC ACGGCCTGGA CATCAGCCA                                    29

(2) INFORMATION FOR SEQ ID NO:5:

(i) SEQUENCE CHARACTERISTICS:
        (A) LENGTH: 31 bases
        (B) TYPE: nucleic acid
        (C) STRANDEDNESS: single
        (D) TOPOLOGY: linear (xi) SEQUENCE DESCRIPTION: SEQ ID NO:5:

CGCGCGAATT CGGGTCCAGC CTTCCCTGGG C                                 31

(2) INFORMATION FOR SEQ ID NO:6:

(i) SEQUENCE CHARACTERISTICS:
        (A) LENGTH: 31 bases
        (B) TYPE: nucleic acid
        (C) STRANDEDNESS: single
        (D) TOPOLOGY: linear (xi) SEQUENCE DESCRIPTION: SEQ ID NO:6:

GGCCGGAATT CCATCAAAGT GGACTGGCAC A                                 31

(2) INFORMATION FOR SEQ ID NO:7:

(i) SEQUENCE CHARACTERISTICS:
        (A) LENGTH: 45 bases
        (B) TYPE: nucleic acid
        (C) STRANDEDNESS: single
        (D) TOPOLOGY: linear (xi) SEQUENCE DESCRIPTION: SEQ ID NO:7:

CGCTGTTGGT CCTGGTGCTG CTGCTGGTGC GGGTCCAGCC TTCCC                  45

(2) INFORMATION FOR SEQ ID NO:8:

(i) SEQUENCE CHARACTERISTICS:
        (A) LENGTH: 45 bases
        (B) TYPE: nucleic acid
        (C) STRANDEDNESS: single
        (D) TOPOLOGY: linear (xi) SEQUENCE DESCRIPTION: SEQ ID NO:8:

TGATGGCTCT GAAGTCCCTG GTCCTGTTGT CGCTGTTGGT CCTGG                  45

(2) INFORMATION FOR SEQ ID NO:9:

(i) SEQUENCE CHARACTERISTICS:
        (A) LENGTH: 46 bases
        (B) TYPE: nucleic acid
        (C) STRANDEDNESS: single
        (D) TOPOLOGY: linear (xi) SEQUENCE DESCRIPTION: SEQ ID NO:9:

GCGCGAATTC ATGTTCTTGG AGGATGATTG ATGGCTCTGA AGTCCC                 46

(2) INFORMATION FOR SEQ ID NO:10:

(i) SEQUENCE CHARACTERISTICS:
            (A) LENGTH: 48 bases
            (B) TYPE: nucleic acid
            (C) STRANDEDNESS: single
            (D) TOPOLOGY: linear (xi) SEQUENCE DESCRIPTION: SEQ ID NO:10:

CGCGGAATTC CTAGGTAGAG TCTTCAACAG AAGCATCAAA GTGGACTG                48

(2) INFORMATION FOR SEQ ID NO:11:

(i) SEQUENCE CHARACTERISTICS:
            (A) LENGTH: 33 bases
            (B) TYPE: nucleic acid
            (C) STRANDEDNESS: single
            (D) TOPOLOGY: linear (xi) SEQUENCE DESCRIPTION: SEQ ID NO:11:

AAGGAATCCG CTGCCGCTAA ATTCCAGCGG CAG                                33

(2) INFORMATION FOR SEQ ID NO:12:

(i) SEQUENCE CHARACTERISTICS:
            (A) LENGTH: 30 bases
            (B) TYPE: nucleic acid
            (C) STRANDEDNESS: single
            (D) TOPOLOGY: linear (xi) SEQUENCE DESCRIPTION: SEQ ID NO:12:

GGAAGGCTGG ACCCGCACCA GCAGCAGCAC                                    30

(2) INFORMATION FOR SEQ ID NO:13:

(i) SEQUENCE CHARACTERISTICS:
            (A) LENGTH: 33 bases
            (B) TYPE: nucleic acid
            (C) STRANDEDNESS: single
            (D) TOPOLOGY: linear (xi) SEQUENCE DESCRIPTION: SEQ ID NO:13:

CTGGAATTTA GCGGCAGCGG ATTCCTTGCC CAG                                33

(2) INFORMATION FOR SEQ ID NO:14:

(i) SEQUENCE CHARACTERISTICS:
            (A) LENGTH: 30 bases
            (B) TYPE: nucleic acid
            (C) STRANDEDNESS: single
            (D) TOPOLOGY: linear (xi) SEQUENCE DESCRIPTION: SEQ ID NO:14:

CATATGGACT CAGACAGTTC CCCCAGCAGC                                    30

(2) INFORMATION FOR SEQ ID NO:15:

(i) SEQUENCE CHARACTERISTICS:
            (A) LENGTH: 39 bases
            (B) TYPE: nucleic acid
            (C) STRANDEDNESS: single
            (D) TOPOLOGY: linear (xi) SEQUENCE DESCRIPTION: SEQ ID NO:15:

GTGTGAATTC CCATGGCGAA GGAATCCGCT GCCGCTAAA                          39

(2) INFORMATION FOR SEQ ID NO:16:

(i) SEQUENCE CHARACTERISTICS:

(A) LENGTH: 34 bases
            (B) TYPE: nucleic acid
            (C) STRANDEDNESS: single
            (D) TOPOLOGY: linear (xi) SEQUENCE DESCRIPTION: SEQ ID NO:16:

GTGTGAATTC CTAGGTAGAG TCTTCAACAG AAGC                                   34

(2) INFORMATION FOR SEQ ID NO:17:

(i) SEQUENCE CHARACTERISTICS:
            (A) LENGTH: 50 bases
            (B) TYPE: nucleic acid
            (C) STRANDEDNESS: single
            (D) TOPOLOGY: linear (xi) SEQUENCE DESCRIPTION: SEQ ID NO:17:

ATATAAAGCT TGCCGCCACC ATGAAGTTGT GGCTGAACTG GATTTTCCTT                  50

(2) INFORMATION FOR SEQ ID NO:18:

(i) SEQUENCE CHARACTERISTICS:
            (A) LENGTH: 48 bases
            (B) TYPE: nucleic acid
            (C) STRANDEDNESS: single
            (D) TOPOLOGY: linear (xi) SEQUENCE DESCRIPTION: SEQ ID NO:18:

ATCGAATTCG CCGCCACCAT GGATTTTCAA GTGCAGATTT TCAGCTTC                    48

(2) INFORMATION FOR SEQ ID NO:19:

(i) SEQUENCE CHARACTERISTICS:
            (A) LENGTH: 45 bases
            (B) TYPE: nucleic acid
            (C) STRANDEDNESS: single
            (D) TOPOLOGY: linear (xi) SEQUENCE DESCRIPTION: SEQ ID NO:19:

TGAGAATTCT TACTATGTAC ATATGCAAGG CTTACAACCA CAATC                       45

(2) INFORMATION FOR SEQ ID NO:20:

(i) SEQUENCE CHARACTERISTICS:
            (A) LENGTH: 35 bases
            (B) TYPE: nucleic acid
            (C) STRANDEDNESS: single
            (D) TOPOLOGY: linear (xi) SEQUENCE DESCRIPTION: SEQ ID NO:20:

GCGCCGAATT CTTATTAACA CTCATTCCTG TTGAA                                  35

(2) INFORMATION FOR SEQ ID NO:21:

(i) SEQUENCE CHARACTERISTICS:
            (A) LENGTH: 30 bases
            (B) TYPE: nucleic acid
            (C) STRANDEDNESS: single
            (D) TOPOLOGY: linear (xi) SEQUENCE DESCRIPTION: SEQ ID NO:21:

GACCTGGAAC TCTGGATCTC TGTCCAGCGG                                        30

(2) INFORMATION FOR SEQ ID NO:22:

(i) SEQUENCE CHARACTERISTICS:
            (A) LENGTH: 30 bases
            (B) TYPE: nucleic acid (C) STRANDEDNESS: single
            (D) TOPOLOGY: linear (xi) SEQUENCE DESCRIPTION: SEQ ID NO:22:

AGGTGTGCAC ACCGCTGGAC AGAGATCCAG                                                30

(2) INFORMATION FOR SEQ ID NO:23:

(i) SEQUENCE CHARACTERISTICS:
            (A) LENGTH: 30 bases
            (B) TYPE: nucleic acid
            (C) STRANDEDNESS: single
            (D) TOPOLOGY: linear (xi) SEQUENCE DESCRIPTION: SEQ ID NO:23:

TGGTACCAGC AGAAGCCAGG TTCCTCCCCC                                                30

(2) INFORMATION FOR SEQ ID NO:24:

(i) SEQUENCE CHARACTERISTICS:
            (A) LENGTH: 30 bases
            (B) TYPE: nucleic acid
            (C) STRANDEDNESS: single
            (D) TOPOLOGY: linear (xi) SEQUENCE DESCRIPTION: SEQ ID NO:24:

GGATTTGGGG GAGGAACCTG GCTTCTGCTG                                                30

(2) INFORMATION FOR SEQ ID NO:25:

(i) SEQUENCE CHARACTERISTICS:
            (A) LENGTH: 777 base pairs
            (B) TYPE: nucleic acid
            (C) STRANDEDNESS: single
            (D) TOPOLOGY: linear (xi) SEQUENCE DESCRIPTION: SEQ ID NO:25:

```
CTT GCC GCC ACC ATG AAG TTG TGG CTG AAC TGG ATT TTC CTT GTA            48
                Met Lys Leu Trp Leu Asn Trp Ile Phe Leu Val
                 1               5                      10

ACA CTT TTA AAT GGT ATC CAG TGT GAG GTG AAG CTG GTG GAG TCT GGA        96
Thr Leu Leu Asn Gly Ile Gln Cys Glu Val Lys Leu Val Glu Ser Gly
            15                  20                  25

GGA GGC TTG GTA CAG CCT GGG GGT TCT CTG AGA CTC TCC TGT GCA ACT       144
Gly Gly Leu Val Gln Pro Gly Gly Ser Leu Arg Leu Ser Cys Ala Thr
        30                  35                  40

TCT GGG TTC ACC TTC ACT GAT TAC TAC ATG AAC TGG GTC CGC CAG CCT       192
Ser Gly Phe Thr Phe Thr Asp Tyr Tyr Met Asn Trp Val Arg Gln Pro
    45                  50                  55

CCA GGA AAG GCA CTT GAG TGG TTG GGT TTT ATT GGA AAC AAA GCT AAT       240
Pro Gly Lys Ala Leu Glu Trp Leu Gly Phe Ile Gly Asn Lys Ala Asn
60                  65                  70                  75

GGT TAC ACA ACA GAG TAC AGT GCA TCT GTG AAG GGT CGG TTC ACC ATC       288
Gly Tyr Thr Thr Glu Tyr Ser Ala Ser Val Lys Gly Arg Phe Thr Ile
                80                  85                  90

TCC AGA GAC AAA TCC CAA AGC ATC CTC TAT CTT CAA ATG AAC ACC CTG       336
Ser Arg Asp Lys Ser Gln Ser Ile Leu Tyr Leu Gln Met Asn Thr Leu
            95                 100                 105

AGA GCT GAG GAC AGT GCC ACT TAT TAC TGT ACA AGA GAT AGG GGG CTA       384
Arg Ala Glu Asp Ser Ala Thr Tyr Tyr Cys Thr Arg Asp Arg Gly Leu
        110                 115                 120

CGG TTC TAC TTT GAC TAC TGG GGC CAA GGC ACC ACT CTC ACA GTC TCC       432
Arg Phe Tyr Phe Asp Tyr Trp Gly Gln Gly Thr Thr Leu Thr Val Ser
    125                 130                 135
```

```
TCA GCC AAA ACG ACA CCC CCA TCT GTC TAT CCA CTG GCC CCT GGA TCT        480
Ser Ala Lys Thr Thr Pro Pro Ser Val Tyr Pro Leu Ala Pro Gly Ser
140                 145                 150                 155

GCT GCC CAA ACT AAC TCC ATG GTG ACC CTG GGA TGC CTG GTC AAG GGC        528
Ala Ala Gln Thr Asn Ser Met Val Thr Leu Gly Cys Leu Val Lys Gly
                160                 165                 170

TAT TTC CCT GAG CCA GTG ACA GTG ACC TGG AAC TCT GGA TCT CTG TCC        576
Tyr Phe Pro Glu Pro Val Thr Val Thr Trp Asn Ser Gly Ser Leu Ser
    175                 180                 185

AGC GGT GTG CAC ACC TTC CCA GCT GTC CTG CAG TCT GAC CTC TAC ACT        624
Ser Gly Val His Thr Phe Pro Ala Val Leu Gln Ser Asp Leu Tyr Thr
190                 195                 200

CTG AGC AGC TCA GTG ACT GTC CCC TCC AGC ACC TGG CCC AGC GAG ACC        672
Leu Ser Ser Ser Val Thr Val Pro Ser Ser Thr Trp Pro Ser Glu Thr
205                 210                 215

GTC ACC TGC AAC GTT GCC CAC CCG GCC AGC AGC ACC AAG GTG GAC AAG        720
Val Thr Cys Asn Val Ala His Pro Ala Ser Ser Thr Lys Val Asp Lys
220                 225                 230                 235

AAA ATT GTG CCC AGG GAT TGT GGT TGT AAG CCT TGC ATA TGT ACA TAG        768
Lys Ile Val Pro Arg Asp Cys Gly Cys Lys Pro Cys Ile Cys Thr
                240                 245                 250

TAA GAA TTC                                                            777
```

(2) INFORMATION FOR SEQ ID NO:26:

(i) SEQUENCE CHARACTERISTICS:
(A) LENGTH: 732 base pairs
(B) TYPE: nucleic acid
(C) STRANDEDNESS: single
(D) TOPOLOGY: linear (xi) SEQUENCE DESCRIPTION: SEQ ID NO:26:

```
GAA TTC GCC GCC ACC ATG GAT TTT CAA GTG CAG ATT TTC AGC TTC CTG        48
                Met Asp Phe Gln Val Gln Ile Phe Ser Phe Leu
                1               5                   10

CTA ATC AGT GCT TCA GTC ATA ATG TCC AGA GGA CAA ACT GTT CTC TCC        96
Leu Ile Ser Ala Ser Val Ile Met Ser Arg Gly Gln Thr Val Leu Ser
            15                  20                  25

CAG TCT CCA GCA ATC CTG TCT GCA TCT CCA GGG GAG AAG GTC ACA ATG       144
Gln Ser Pro Ala Ile Leu Ser Ala Ser Pro Gly Glu Lys Val Thr Met
        30                  35                  40

ACT TGC AGG GCC AGC TCA AGT GTA ACT TAC ATT CAC TGG TAC CAG CAG       192
Thr Cys Arg Ala Ser Ser Ser Val Thr Tyr Ile His Trp Tyr Gln Gln
45                  50                  55

AAG CCA GGT TCC TCC CCC AAA TCC TGG ATT TAT GCC ACA TCC AAC CTG       240
Lys Pro Gly Ser Ser Pro Lys Ser Trp Ile Tyr Ala Thr Ser Asn Leu
60                  65                  70                  75

GCT TCT GGA GTC CCT GCT CGC TTC AGT GGC AGT GGG TCT GGG ACC TCT       288
Ala Ser Gly Val Pro Ala Arg Phe Ser Gly Ser Gly Ser Gly Thr Ser
                80                  85                  90

TAC TCT CTC ACA ATC AGC AGA GTG GAG GCT GAA GAT GCT GCC ACT TAT       336
Tyr Ser Leu Thr Ile Ser Arg Val Glu Ala Glu Asp Ala Ala Thr Tyr
            95                  100                 105

TAC TGC CAA CAT TGG AGT AGT AAA CCA CCG ACG TTC GGT GGA GGC ACC       384
Tyr Cys Gln His Trp Ser Ser Lys Pro Pro Thr Phe Gly Gly Gly Thr
        110                 115                 120

AAG CTG GAA ATC AAA CGG GCT GAT GCT GCA CCA ACT GTA TCC ATC TTC       432
Lys Leu Glu Ile Lys Arg Ala Asp Ala Ala Pro Thr Val Ser Ile Phe
125                 130                 135

CCA CCA TCC AGT GAG CAG TTA ACA TCT GGA GGT GCC TCA GTC GTG TGC       480
Pro Pro Ser Ser Glu Gln Leu Thr Ser Gly Gly Ala Ser Val Val Cys
140                 145                 150                 155
```

```
TTC TTG AAC AAC TTC TAC CCC AAA GAC ATC AAT GTC AAG TGG AAG ATT          528
Phe Leu Asn Asn Phe Tyr Pro Lys Asp Ile Asn Val Lys Trp Lys Ile
            160                 165                 170

GAT GGC AGT GAA CGA CAA AAT GGC GTC CTG AAC AGT TGG ACT GAT CAG          576
Asp Gly Ser Glu Arg Gln Asn Gly Val Leu Asn Ser Trp Thr Asp Gln
        175                 180                 185

GAC AGC AAA GAC AGC ACC TAC AGC ATG AGC AGC ACC CTC ACG TTG ACC          624
Asp Ser Lys Asp Ser Thr Tyr Ser Met Ser Ser Thr Leu Thr Leu Thr
        190                 195                 200

AAG GAC GAG TAT GAA CGA CAT AAC AGC TAT ACC TGT GAG GCC ACT CAC          672
Lys Asp Glu Tyr Glu Arg His Asn Ser Tyr Thr Cys Glu Ala Thr His
    205                 210                 215

AAG ACA TCA ACT TCA CCC ATT GTC AAG AGC TTC AAC AGG AAT GAG TGT          720
Lys Thr Ser Thr Ser Pro Ile Val Lys Ser Phe Asn Arg Asn Glu Cys
220                 225                 230                 235

TAA TAA GAA TTC                                                          732

(2) INFORMATION FOR SEQ ID NO:27:

(i) SEQUENCE CHARACTERISTICS:
        (A) LENGTH: 30 bases
        (B) TYPE: nucleic acid
        (C) STRANDEDNESS: single
        (D) TOPOLOGY: linear (xi) SEQUENCE DESCRIPTION: SEQ ID NO:27:

TCGCTATTAC CATGGTGATG CGGTTTTGGC                                          30

(2) INFORMATION FOR SEQ ID NO:28:

(i) SEQUENCE CHARACTERISTICS:
        (A) LENGTH: 777 BASE PAIRS
        (B) TYPE: nucleic acid
        (C) STRANDEDNESS: single
        (D) TOPOLOGY: linear (xi) SEQUENCE DESCRIPTION: SEQ ID NO:28:

AAG CTT GCC GCC ACC ATG AAG TTG TGG CTG AAC TGG ATT TTC CTT GTA           48
                Met Lys Leu Trp Leu Asn Trp Ile Phe Leu Val
                  1               5                  10

ACA CTT TTA AAT GGT ATC CAG TGT GAG GTG CAG CTG CTG GAG TCT GGA           96
Thr Leu Leu Asn Gly Ile Gln Cys Glu Val Gln Leu Leu Glu Ser Gly
            15                  20                  25

GGA GGA CTG GTG CAG CCT GGA GGA TCT CTG AGA CTG TCT TGT GCA ACA          144
Gly Gly Leu Val Gln Pro Gly Gly Ser Leu Arg Leu Ser Cys Ala Thr
        30                  35                  40

TCT GGA TTC ACC TTC ACA GAC TAC TAC ATG AAT TGG GTG AGA CAG GCA          192
Ser Gly Phe Thr Phe Thr Asp Tyr Tyr Met Asn Trp Val Arg Gln Ala
    45                  50                  55

CCT GGA AAG GGA CTC GAG TGG CTG GGC TTC ATC GGA AAT AAG GCA AAT          240
Pro Gly Lys Gly Leu Glu Trp Leu Gly Phe Ile Gly Asn Lys Ala Asn
60                  65                  70                  75

GGA TAC ACA ACA GAG TAC TCT GCA TCT GTG AAG GGA AGA TTC ACA ATT          288
Gly Tyr Thr Thr Glu Tyr Ser Ala Ser Val Lys Gly Arg Phe Thr Ile
                80                  85                  90

TCC AGA GAC AAG AGC AAG TCC ACA CTG TAC CTG CAG ATG AAT ACA CTG          336
Ser Arg Asp Lys Ser Lys Ser Thr Leu Tyr Leu Gln Met Asn Thr Leu
            95                 100                 105

CAG GCA GAG GAC TCT GCA ATT TAC TAC TGT ACA AGA GAC AGA GGA CTG          384
Gln Ala Glu Asp Ser Ala Ile Tyr Tyr Cys Thr Arg Asp Arg Gly Leu
        110                 115                 120

AGA TTC TAC TTC GAC TAC TGG GGA CAG GGA ACA CTG GTG ACA GTG TCT          432
```

```
Arg Phe Tyr Phe Asp Tyr Trp Gly Gln Gly Thr Leu Val Thr Val Ser
    125             130                 135

TCT GCT AGC ACC AAG GGA CCA TCG GTC TTC CCC CTG GCC CCC TGC TCC        480
Ser Ala Ser Thr Lys Gly Pro Ser Val Phe Pro Leu Ala Pro Cys Ser
140             145                 150                 155

AGG AGC ACC TCC GAG AGC ACA GCC GCC CTG GGC TGC CTG GTC AAG GAC        528
Arg Ser Thr Ser Glu Ser Thr Ala Ala Leu Gly Cys Leu Val Lys Asp
                160                 165                 170

TAC TTC CCC GAA CCG GTG ACG GTG TCG TGG AAC TCA GGC GCT CTG ACC        576
Tyr Phe Pro Glu Pro Val Thr Val Ser Trp Asn Ser Gly Ala Leu Thr
            175                 180                 185

AGC GGC GTG CAC ACC TTC CCG GCT GTC CTA CAG TCC TCA GGA CTC TAC        624
Ser Gly Val His Thr Phe Pro Ala Val Leu Gln Ser Ser Gly Leu Tyr
        190                 195                 200

TCC CTC AGC AGC GTC GTG ACG GTG CCC TCC AGC AAC TTC GGC ACC CAG        672
Ser Leu Ser Ser Val Val Thr Val Pro Ser Ser Asn Phe Gly Thr Gln
    205                 210                 215

ACC TAC ACC TGC AAC GTA GAT CAC AAG CCC AGC AAC ACC AAG GTG GAC        720
Thr Tyr Thr Cys Asn Val Asp His Lys Pro Ser Asn Thr Lys Val Asp
220                 225                 230                 235

AAG ACA GTT GAG CGC AAA TGT TGT GTC GAG TGC CCA CCG TGC CCG TAA        768
Lys Thr Val Glu Arg Lys Cys Cys Val Glu Cys Pro Pro Cys Pro
                240                 245                 250

TAG GAA TTC                                                            777

(2) INFORMATION FOR SEQ ID NO:29:

(i) SEQUENCE CHARACTERISTICS:
        (A) LENGTH: 732 BASE PAIRS
        (B) TYPE: nucleic acid
        (C) STRANDEDNESS: single
        (D) TOPOLOGY: linear (xi) SEQUENCE DESCRIPTION: SEQ ID NO:29:

GAA TTC GCC GCC ACC ATG GAT TTT CAA GTG CAG ATT TTC AGC TTC CTG         48
                    Met Asp Phe Gln Val Gln Ile Phe Ser Phe Leu
                     1               5                  10

CTA ATC AGT GCT TCA GTC ATA ATG TCC AGA GGA CAG ACT GTA CTC ACT         96
Leu Ile Ser Ala Ser Val Ile Met Ser Arg Gly Gln Thr Val Leu Thr
            15                  20                  25

CAG AGT CCA AGT AGT CTC AGT GTA AGT GTA GGT GAT AGG GTA ACT ATG        144
Gln Ser Pro Ser Ser Leu Ser Val Ser Val Gly Asp Arg Val Thr Met
        30                  35                  40

ACT TGT AGG GCC AGT AGT AGT GTA ACT TAT ATC CAT TGG TAT CAG CAG        192
Thr Cys Arg Ala Ser Ser Ser Val Thr Tyr Ile His Trp Tyr Gln Gln
    45                  50                  55

AAA CCA GGT CTC GCC CCA AAA AGT TGG ATC TAT GCC ACT AGT AAC CTC        240
Lys Pro Gly Leu Ala Pro Lys Ser Trp Ile Tyr Ala Thr Ser Asn Leu
60                  65                  70                  75

GCC AGT GGT GTA CCA TCT AGA TTC AGT GGT AGC GGT AGT GGT ACT GAT        288
Ala Ser Gly Val Pro Ser Arg Phe Ser Gly Ser Gly Ser Gly Thr Asp
                80                  85                  90

TAT ACT CTC ACT ATC AGT AGT CTC CAG CCA GAA GAT ATC GCC ACT TAC        336
Tyr Thr Leu Thr Ile Ser Ser Leu Gln Pro Glu Asp Ile Ala Thr Tyr
            95                 100                 105

TAT TGC CAG CAT TGG AGT AGT AAA CCA CCA ACT TTC GGT CAG GGT ACT        384
Tyr Cys Gln His Trp Ser Ser Lys Pro Pro Thr Phe Gly Gln Gly Thr
        110                 115                 120

AAA GTA GAA GTA AAA CGT ACT GTG GCT GCA CCA TCT GTC TTC ATC TTC        432
Lys Val Glu Val Lys Arg Thr Val Ala Ala Pro Ser Val Phe Ile Phe
    125                 130                 135
```

| | | | | | | | | | | | | | | |
|---|---|---|---|---|---|---|---|---|---|---|---|---|---|---|
| CCG | CCA | TCT | GAT | GAG | CAG | TTG | AAA | TCT | GGA | ACT | GCC | TCT | GTT | GTG | TGC | 480 |
| Pro | Pro | Ser | Asp | Glu | Gln | Leu | Lys | Ser | Gly | Thr | Ala | Ser | Val | Val | Cys |
| 140 | | | | | 145 | | | | | 150 | | | | | 155 |

| CTG | CTG | AAT | AAC | TTC | TAT | CCC | AGA | GAG | GCC | AAA | GTA | CAG | TGG | AAG | GTG | 528 |
| Leu | Leu | Asn | Asn | Phe | Tyr | Pro | Arg | Glu | Ala | Lys | Val | Gln | Trp | Lys | Val |
| | | | | | 160 | | | | | 165 | | | | | 170 |

| GAT | AAC | GCC | CTC | CAA | TCG | GGT | AAC | TCC | CAG | GAG | AGT | GTC | ACA | GAG | CAG | 576 |
| Asp | Asn | Ala | Leu | Gln | Ser | Gly | Asn | Ser | Gln | Glu | Ser | Val | Thr | Glu | Gln |
| | | | 175 | | | | | 180 | | | | | 185 | | |

| GAC | AGC | AAG | GAC | AGC | ACC | TAC | AGC | CTC | AGC | AGC | ACC | CTG | ACG | CTG | AGC | 624 |
| Asp | Ser | Lys | Asp | Ser | Thr | Tyr | Ser | Leu | Ser | Ser | Thr | Leu | Thr | Leu | Ser |
| | | 190 | | | | | 195 | | | | | 200 | | | |

| AAA | GCA | GAC | TAC | GAG | AAA | CAC | AAA | GTC | TAC | GCC | TGC | GAA | GTC | ACC | CAT | 672 |
| Lys | Ala | Asp | Tyr | Glu | Lys | His | Lys | Val | Tyr | Ala | Cys | Glu | Val | Thr | His |
| 205 | | | | | 210 | | | | | 215 | | | | | |

| CAG | GGC | CTG | AGT | TCG | CCC | GTC | ACA | AAG | AGC | TTC | AAC | AGG | GGA | GAG | TGT | 720 |
| Gln | Gly | Leu | Ser | Ser | Pro | Val | Thr | Lys | Ser | Phe | Asn | Arg | Gly | Glu | Cys |
| 220 | | | | | 225 | | | | | 230 | | | | | 235 |

| TAA | TAG | GAA | TTC | | | | | | | | | | | | | 732 |

(2) INFORMATION FOR SEQ ID NO:30:

(i) SEQUENCE CHARACTERISTICS:
        (A) LENGTH: 30 bases
        (B) TYPE: nucleic acid
        (C) STRANDEDNESS: single
        (D) TOPOLOGY: linear (xi) SEQUENCE DESCRIPTION: SEQ ID NO:30:

AAGGTCACCT GCGAAAACGG GCAGGGCAAC                                              30

(2) INFORMATION FOR SEQ ID NO:31:

(i) SEQUENCE CHARACTERISTICS:
        (A) LENGTH: 25 bases
        (B) TYPE: nucleic acid
        (C) STRANDEDNESS: single
        (D) TOPOLOGY: linear (xi) SEQUENCE DESCRIPTION: SEQ ID NO:31:

CTGGAAACAG ACATTCTGGA CATCT                                                    25

(2) INFORMATION FOR SEQ ID NO:32:

(i) SEQUENCE CHARACTERISTICS:
        (A) LENGTH: 30 bases
        (B) TYPE: nucleic acid
        (C) STRANDEDNESS: single
        (D) TOPOLOGY: linear (xi) SEQUENCE DESCRIPTION: SEQ ID NO:32:

GCCCTGCCCG TTTTCGCAGG TGACCTTTTC                                              30

(2) INFORMATION FOR SEQ ID NO:33:

(i) SEQUENCE CHARACTERISTICS:
        (A) LENGTH: 26 bases
        (B) TYPE: nucleic acid
        (C) STRANDEDNESS: single
        (D) TOPOLOGY: linear (xi) SEQUENCE DESCRIPTION: SEQ ID NO:33:

TGCTACAAGA GCAACTCCAG CATGCA                                                   26

(2) INFORMATION FOR SEQ ID NO:34:

(i) SEQUENCE CHARACTERISTICS:
         (A) LENGTH: 41 bases
         (B) TYPE: nucleic acid
         (C) STRANDEDNESS: single
         (D) TOPOLOGY: linear (xi) SEQUENCE DESCRIPTION: SEQ ID NO:34:

CTCTAGGAAT TCTTATTAGT ACAGGTGTTC CAGGACGTAG C            41

(2) INFORMATION FOR SEQ ID NO:35:

(i) SEQUENCE CHARACTERISTICS:
         (A) LENGTH: 108 bases
         (B) TYPE: nucleic acid
         (C) STRANDEDNESS: single
         (D) TOPOLOGY: linear (xi) SEQUENCE DESCRIPTION: SEQ ID NO:35:

CTTG CCGCCACCAT GTTGGCAGTC TTGGTTCTGG TGACTGTGGC CCTGGCATCT    60

GCTGCAACAG GACACAGTTA TGAGAAGTAC AACAAGTGGG AAACGATA          108

(2) INFORMATION FOR SEQ ID NO:36:

(i) SEQUENCE CHARACTERISTICS:
         (A) LENGTH: 16 bases
         (B) TYPE: nucleic acid
         (C) STRANDEDNESS: single
         (D) TOPOLOGY: linear (xi) SEQUENCE DESCRIPTION: SEQ ID NO:36:

AACAGCTATG ACCATG                                        16

(2) INFORMATION FOR SEQ ID NO:37:

(i) SEQUENCE CHARACTERISTICS:
         (A) LENGTH: 17 bases
         (B) TYPE: nucleic acid
         (C) STRANDEDNESS: single
         (D) TOPOLOGY: linear (xi) SEQUENCE DESCRIPTION: SEQ ID NO:37:

GTAAAACGAC GGCCAGT                                       17

(2) INFORMATION FOR SEQ ID NO:38:

(i) SEQUENCE CHARACTERISTICS:
         (A) LENGTH: 30 bases
         (B) TYPE: nucleic acid
         (C) STRANDEDNESS: single
         (D) TOPOLOGY: linear (xi) SEQUENCE DESCRIPTION: SEQ ID NO:38:

TCGCTATTAC CATGGTGATG CGGTTTTGGC                         30

(2) INFORMATION FOR SEQ ID NO:39:

(i) SEQUENCE CHARACTERISTICS:
         (A) LENGTH: 23 bases
         (B) TYPE: nucleic acid
         (C) STRANDEDNESS: single
         (D) TOPOLOGY: linear (xi) SEQUENCE DESCRIPTION: SEQ ID NO:39:

CAGACTCTGC AGCAGGTCCA CAG                                23

(2) INFORMATION FOR SEQ ID NO:40:

(i) SEQUENCE CHARACTERISTICS:
    (A) LENGTH: 54 bases
    (B) TYPE: nucleic acid
    (C) STRANDEDNESS: single
    (D) TOPOLOGY: linear (xi) SEQUENCE DESCRIPTION: SEQ ID NO:40:

CCCAAGCTTG CCGCCACCAT GTTGGCACTC TTGGTTCTGG TGACTGTGGC CCTG         54

(2) INFORMATION FOR SEQ ID NO:41:

(i) SEQUENCE CHARACTERISTICS:
        (A) LENGTH: 39 bases
        (B) TYPE: nucleic acid
        (C) STRANDEDNESS: single
        (D) TOPOLOGY: linear (xi) SEQUENCE DESCRIPTION: SEQ ID NO:41:

CTCATAACTG AATTCTTATT AACGAACCCG GCTATCAAA         39

(2) INFORMATION FOR SEQ ID NO:42:

(i) SEQUENCE CHARACTERISTICS:
        (A) LENGTH: 34 bases
        (B) TYPE: nucleic acid
        (C) STRANDEDNESS: single
        (D) TOPOLOGY: linear (xi) SEQUENCE DESCRIPTION: SEQ ID NO:42:

GGATCTGCTG CCCAAGCTTA CTCCATGGTG ACCC         34

(2) INFORMATION FOR SEQ ID NO:43:

(i) SEQUENCE CHARACTERISTICS:
        (A) LENGTH: 80 bases
        (B) TYPE: nucleic acid
        (C) STRANDEDNESS: single
        (D) TOPOLOGY: linear (xi) SEQUENCE DESCRIPTION: SEQ ID NO:43:

CTTCTCATAA CTGTGTCCTG TTGCGAACAC GCTGCTCACC TCGGGCACTG TACATAT         60

AGGCTTACAA CCACAATCCC         80

(2) INFORMATION FOR SEQ ID NO:44:

(i) SEQUENCE CHARACTERISTICS:
        (A) LENGTH: 78 bases
        (B) TYPE: nucleic acid
        (C) STRANDEDNESS: single
        (D) TOPOLOGY: linear (xi) SEQUENCE DESCRIPTION: SEQ ID NO:44:

GGTTGTAAGC CTTGCATATG TACAGTGCCC GAGGTGAGCA GCGTGTTCGC AACAGGA         60

AGTTATGAGA AGTACAAC         78

(2) INFORMATION FOR SEQ ID NO:45:

(i) SEQUENCE CHARACTERISTICS:
        (A) LENGTH: 27 bases
        (B) TYPE: nucleic acid
        (C) STRANDEDNESS: single
        (D) TOPOLOGY: linear (xi) SEQUENCE DESCRIPTION: SEQ ID NO:45:

CCGTTTGATC TCGAGCTTGG TGCCTCC         27

(2) INFORMATION FOR SEQ ID NO:46:

(i) SEQUENCE CHARACTERISTICS:
        (A) LENGTH: 20 bases
        (B) TYPE: nucleic acid
        (C) STRANDEDNESS: single
        (D) TOPOLOGY: linear (xi) SEQUENCE DESCRIPTION: SEQ ID NO:46:

```
GTTGGAGCTC TTGGTTCTGG                                              20
```

(2) INFORMATION FOR SEQ ID NO:47:

(i) SEQUENCE CHARACTERISTICS:
        (A) LENGTH: 22 bases
        (B) TYPE: nucleic acid
        (C) STRANDEDNESS: single
        (D) TOPOLOGY: linear xi) SEQUENCE DESCRIPTION: SEQ ID NO:47:

```
CAAGGCCTCG AGCTTTCTCA AC                                           22
```

(2) INFORMATION FOR SEQ ID NO:48:

(i) SEQUENCE CHARACTERISTICS:
        (A) LENGTH: 21 bases
        (B) TYPE: nucleic acid
        (C) STRANDEDNESS: single
        (D) TOPOLOGY: linear xi) SEQUENCE DESCRIPTION: SEQ ID NO:48:

```
GTTTGATTCT AGAGTTCGTG C                                            21
```

(2) INFORMATION FOR SEQ ID NO:49:

(i) SEQUENCE CHARACTERISTICS:
        (A) LENGTH: 22 bases
        (B) TYPE: nucleic acid
        (C) STRANDEDNESS: single
        (D) TOPOLOGY: linear xi) SEQUENCE DESCRIPTION: SEQ ID NO:49:

```
TTGTAAAACG ACGGCCAGTG AG                                           22
```

(2) INFORMATION FOR SEQ ID NO:50:

(i) SEQUENCE CHARACTERISTICS:
        (A) LENGTH: 24 bases
        (B) TYPE: nucleic acid
        (C) STRANDEDNESS: single
        (D) TOPOLOGY: linear xi) SEQUENCE DESCRIPTION: SEQ ID NO:50:

```
GAAACAGCTA TGACCATGAT TACG                                         24
```

(2) INFORMATION FOR SEQ ID NO:51:

(i) SEQUENCE CHARACTERISTICS:
        (A) LENGTH: 23 bases
        (B) TYPE: nucleic acid
        (C) STRANDEDNESS: single
        (D) TOPOLOGY: linear xi) SEQUENCE DESCRIPTION: SEQ ID NO:51:

```
CAGACTCTGC AGCAGGTCCA CAG                                          23
```

(2) INFORMATION FOR SEQ ID NO:52:

```
        (i) SEQUENCE CHARACTERISTICS:
            (A) LENGTH: 19 bases
            (B) TYPE: nucleic acid
            (C) STRANDEDNESS: single
            (D) TOPOLOGY: linear xi) SEQUENCE DESCRIPTION: SEQ ID NO:52:

GGACCTGCTG CAGAGTCTG                                                   19

(2) INFORMATION FOR SEQ ID NO:53:

(i) SEQUENCE CHARACTERISTICS:
            (A) LENGTH: 21 bases
            (B) TYPE: nucleic acid
            (C) STRANDEDNESS: single
            (D) TOPOLOGY: linear xi) SEQUENCE DESCRIPTION: SEQ ID NO:53:

GCCTGTGCTC AATATTGATG G                                                21

(2) INFORMATION FOR SEQ ID NO:54:

(i) SEQUENCE CHARACTERISTICS:
            (A) LENGTH: 23 bases
            (B) TYPE: nucleic acid
            (C) STRANDEDNESS: single
            (D) TOPOLOGY: linear xi) SEQUENCE DESCRIPTION: SEQ ID NO:54:

CCGTGTTAAA GCAGAAGATA CTG                                              23

(2) INFORMATION FOR SEQ ID NO:55:

(i) SEQUENCE CHARACTERISTICS:
            (A) LENGTH: 23 bases
            (B) TYPE: nucleic acid
            (C) STRANDEDNESS: single
            (D) TOPOLOGY: linear xi) SEQUENCE DESCRIPTION: SEQ ID NO:55:

GCTACTGTGA AGAACTTGC CTC                                               23

(2) INFORMATION FOR SEQ ID NO:56:

(i) SEQUENCE CHARACTERISTICS:
            (A) LENGTH: 1263 bases
            (B) TYPE: nucleic acid
            (C) STRANDEDNESS: single
            (D) TOPOLOGY: linear (xi) SEQUENCE DESCRIPTION: SEQ ID NO:56:

GAGCTCTTGG TTCTGGTGAC TGTGGCCCTG GCATCTGCTC ATCATGGTGG TGAGCACT         60

GAAGGCGAGA AGGTGTTCCG TGTTAACGTT GAAGATGAAA ATCACATTAA CATAATC         120

GAGTTGGCCA GCACGACCCA GATTGACTTC TGGAAGCCAG ATTCTGTCAC ACAAATC         180

CCTCACAGTA CAGTTGACTT CCGTGTTAAA GCAGAAGATA CTGTCACTGT GGAGAAT         240

CTAAAGCAGA ATGAACTACA ATACAAGGTA CTGATAAGCA ACCTGAGAAA TGTGGTG         300

GCTCAGTTTG ATAGCCGGGT TCGTGCAACA GGACACAGTT ATGAGAAGTA CAACAAG         360

GAAACGATAG AGGCTTGGAC TCAACAAGTC GCCACTGAGA ATCCAGCCCT CATCTCT         420

AGTGTTATCG GAACCACATT TGAGGGACGC GCTATTTACC TCCTGAAGGT TGGCAAA         480

GGACAAAATA AGCCTGCCAT TTTCATGGAC TGTGGTTTCC ATGCCAGAGA GTGGATT         540

CCTGCATTCT GCCAGTGGTT TGTAAGAGAG GCTGTTCGTA CCTATGGACG TGAGATC         600
```

```
GTGACAGAGC TTCTCGACAA GTTAGACTTT TATGTCCTGC CTGTGCTCAA TATTGAT      660

TACATCTACA CCTGGACCAA GAGCCGATTT TGGAGAAAGA CTCGCTCCAC CCATACT      720

TCTAGCTGCA TTGGCACAGA CCCCAACAGA AATTTTGATG CTGGTTGGTG TGAAATT      780

GCCTCTCGAA ACCCCTGTGA TGAAACTTAC TGTGGACCTG CCGCAGAGTC TGAAAAG      840

ACCAAGGCCC TGGCTGATTT CATCCGCAAC AAACTCTCTT CCATCAAGGC ATATCTG      900

ATCCACTCGT ACTCCCAAAT GATGATCTAC CCTTACTCAT ATGCTTACAA ACTCGGT      960

AACAATGCTG AGTTGAATGC CCTGGCTAAA GCTACTGTGA AGAACTTGC CTCACT       1020

GGCACCAAGT ACACATATGG CCCGGGAGCT ACAACAATCT ATCCTGCTGC TGGGGG      1080

GACGACTGGG CTTATGACCA AGGAATCAGA TATTCCTTCA CCTTTGAACT TCGAGA      1140

GGCAGATATG GCTTTCTCCT TCCAGAATCC CAGATCCGGG CTACCTGCGA GGAGAC      1200

CTGGCAATCA GTATGTTGC CAGCTACGTC CTGAACACC TGTACTAGTT GAGAAA        1260

GAG                                                                 1263
```

(2) INFORMATION FOR SEQ ID NO:57:

(i) SEQUENCE CHARACTERISTICS:
        (A) LENGTH: 415 amino acids
        (B) TYPE: amino acid
        (D) TOPOLOGY: linear (ii) MOLECULE TYPE: protein (xi) SEQUENCE DESCRIPTION: SEQ ID NO:57:

```
Glu Leu Val Leu Val Thr Val Ala Leu Ala Ser Ala His His Gly
        -105                -100                 -95

Gly Glu His Phe Glu Gly Glu Lys Val Phe Arg Val Asn Val Glu Asp
         -90                 -85                 -80

Glu Asn His Ile Asn Ile Ile Arg Glu Leu Ala Ser Thr Thr Gln Ile
         -75                 -70                 -65

Asp Phe Trp Lys Pro Asp Ser Val Thr Gln Ile Lys Pro His Ser Thr
-60                  -55                 -50                 -45

Val Asp Phe Arg Val Lys Ala Glu Asp Thr Val Thr Val Glu Asn Val
                 -40                 -35                 -30

Leu Lys Gln Asn Glu Leu Gln Tyr Lys Val Leu Ile Ser Asn Leu Arg
         -25                 -20                 -15

Asn Val Val Glu Ala Gln Phe Asp Ser Arg Val Arg Ala Thr Gly His
         -10                  -5                   1

Ser Tyr Glu Lys Tyr Asn Lys Trp Glu Thr Ile Glu Ala Trp Thr Gln
 5                   10                  15                  20

Gln Val Ala Thr Glu Asn Pro Ala Leu Ile Ser Arg Ser Val Ile Gly
                  25                  30                  35

Thr Thr Phe Glu Gly Arg Ala Ile Tyr Leu Leu Lys Val Gly Lys Ala
                  40                  45                  50

Gly Gln Asn Lys Pro Ala Ile Phe Met Asp Cys Gly Phe His Ala Arg
                  55                  60                  65

Glu Trp Ile Ser Pro Ala Phe Cys Gln Trp Phe Val Arg Glu Ala Val
 70                  75                  80

Arg Thr Tyr Gly Arg Glu Ile Gln Val Thr Glu Leu Leu Asp Lys Leu
85                   90                  95                 100

Asp Phe Tyr Val Leu Pro Val Leu Asn Ile Asp Gly Tyr Ile Tyr Thr
                 105                 110                 115

Trp Thr Lys Ser Arg Phe Trp Arg Lys Thr Arg Ser Thr His Thr Gly
```

```
                    120                 125                 130
Ser Ser Cys Ile Gly Thr Asp Pro Asn Arg Asn Phe Asp Ala Gly Trp
        135                 140                 145

Cys Glu Ile Gly Ala Ser Arg Asn Pro Cys Asp Glu Thr Tyr Cys Gly
150                 155                 160

Pro Ala Ala Glu Ser Glu Lys Glu Thr Lys Ala Leu Ala Asp Phe Ile
165                 170                 175                 180

Arg Asn Lys Leu Ser Ser Ile Lys Ala Tyr Leu Thr Ile His Ser Tyr
                185                 190                 195

Ser Gln Met Met Ile Tyr Pro Tyr Ser Tyr Ala Tyr Lys Leu Gly Glu
            200                 205                 210

Asn Asn Ala Glu Leu Asn Ala Leu Ala Lys Ala Thr Val Lys Glu Leu
            215                 220                 225

Ala Ser Leu His Gly Thr Lys Tyr Thr Tyr Gly Pro Gly Ala Thr Thr
        230                 235                 240

Ile Tyr Pro Ala Ala Gly Gly Ser Asp Asp Trp Ala Tyr Asp Gln Gly
245                 250                 255                 260

Ile Arg Tyr Ser Phe Thr Phe Glu Leu Arg Asp Thr Gly Arg Tyr Gly
                265                 270                 275

Phe Leu Leu Pro Glu Ser Gln Ile Arg Ala Thr Cys Glu Glu Thr Phe
            280                 285                 290

Leu Ala Ile Lys Tyr Val Ala Ser Tyr Val Leu Glu His Leu Tyr
        295                 300                 305
```

(2) INFORMATION FOR SEQ ID NO:58:

(i) SEQUENCE CHARACTERISTICS:
        (A) LENGTH: 35 bases
        (B) TYPE: nucleic acid
        (C) STRANDEDNESS: single
        (D) TOPOLOGY: linear (xi) SEQUENCE DESCRIPTION: SEQ ID NO:58:

GCCGGGTTTG CGCAACTGGT CACTCTTACG AGAAG     35

(2) INFORMATION FOR SEQ ID NO:59:

(i) SEQUENCE CHARACTERISTICS:
        (A) LENGTH: 88 bases
        (B) TYPE: nucleic acid
        (C) STRANDEDNESS: single
        (D) TOPOLOGY: linear (xi) SEQUENCE DESCRIPTION: SEQ ID NO:59:

CCGGAATTCT TATTAGTTCA GGTCCTCCTC AGAGATCAGC TTCTGCTCCT CGAACTCATG     60

GTGGTGATGG TGGTGGTACA GGTGTTCC     88

(2) INFORMATION FOR SEQ ID NO:60:

(i) SEQUENCE CHARACTERISTICS:
        (A) LENGTH: 22 bases
        (B) TYPE: nucleic acid
        (C) STRANDEDNESS: single
        (D) TOPOLOGY: linear (xi) SEQUENCE DESCRIPTION: SEQ ID NO:60:

TTAGCGGATC CTGCCTGACG GT     22

(2) INFORMATION FOR SEQ ID NO:61:

(i) SEQUENCE CHARACTERISTICS:

```
        (A) LENGTH: 23 bases
        (B) TYPE: nucleic acid
        (C) STRANDEDNESS: single
        (D) TOPOLOGY: linear (xi) SEQUENCE DESCRIPTION: SEQ ID NO:61:

GGCTGGATTC TCAGTGGCGA CTT                                                 23

(2) INFORMATION FOR SEQ ID NO:62:

(i) SEQUENCE CHARACTERISTICS:
        (A) LENGTH: 20 bases
        (B) TYPE: nucleic acid
        (C) STRANDEDNESS: single
        (D) TOPOLOGY: linear (xi) SEQUENCE DESCRIPTION: SEQ ID NO:62:

ACCTCTAGGG TCCCCAATTA                                                     20

(2) INFORMATION FOR SEQ ID NO:63:

(i) SEQUENCE CHARACTERISTICS:
        (A) LENGTH: 23 bases
        (B) TYPE: nucleic acid
        (C) STRANDEDNESS: single
        (D) TOPOLOGY: linear (xi) SEQUENCE DESCRIPTION: SEQ ID NO:63:

CAAGTCGCCA CTGAGAATCC AGC                                                 23

(2) INFORMATION FOR SEQ ID NO:64:

(i) SEQUENCE CHARACTERISTICS:
        (A) LENGTH: 1053 bases
        (B) TYPE: nucleic acid
        (C) STRANDEDNESS: single
        (D) TOPOLOGY: linear (xi) SEQUENCE DESCRIPTION: SEQ ID NO:64:
```

| | | | | | | | | | | | | | | | | |
|---|---|---|---|---|---|---|---|---|---|---|---|---|---|---|---|---|
| ATG | AAA | TAC | CTA | TTG | CCT | ACG | GCA | GCC | GCT | GGA | TTG | TTA | TTA | CTC | GCT | 48 |
| Met | Lys | Tyr | Leu | Leu | Pro | Thr | Ala | Ala | Ala | Gly | Leu | Leu | Leu | Leu | Ala | |
| | | -20 | | | | -15 | | | | -10 | | | | | | |
| GCC | CAA | CCA | GCC | ATG | GCG | GCA | ACT | GGT | CAC | TCT | TAC | GAG | AAG | TAC | AAC | 96 |
| Ala | Gln | Pro | Ala | Met | Ala | Ala | Thr | Gly | His | Ser | Tyr | Glu | Lys | Tyr | Asn | |
| | -5 | | | -1 | | | | | 5 | | | | | | 10 | |
| AAG | TGG | GAA | ACG | ATA | GAG | GCT | TGG | ACT | CAA | CAA | GTC | GCC | ACT | GAG | AAT | 144 |
| Lys | Trp | Glu | Thr | Ile | Glu | Ala | Trp | Thr | Gln | Gln | Val | Ala | Thr | Glu | Asn | |
| | | | | 15 | | | | | 20 | | | | | 25 | | |
| CCA | GCC | CTC | ATC | TCT | CGC | AGT | GTT | ATC | GGA | ACC | ACA | TTT | GAG | GGA | CGC | 192 |
| Pro | Ala | Leu | Ile | Ser | Arg | Ser | Val | Ile | Gly | Thr | Thr | Phe | Glu | Gly | Arg | |
| | | | | 30 | | | | | 35 | | | | | 40 | | |
| GCT | ATT | TAC | CTC | CTG | AAG | GTT | GGC | AAA | GCT | GGA | CAA | AAT | AAG | CCT | GCC | 240 |
| Ala | Ile | Tyr | Leu | Leu | Lys | Val | Gly | Lys | Ala | Gly | Gln | Asn | Lys | Pro | Ala | |
| | | 45 | | | | | 50 | | | | | 55 | | | | |
| ATT | TTC | ATG | GAC | TGT | GGT | TTC | CAT | GCC | AGA | GAG | TGG | ATT | TCT | CCT | GCA | 288 |
| Ile | Phe | Met | Asp | Cys | Gly | Phe | His | Ala | Arg | Glu | Trp | Ile | Ser | Pro | Ala | |
| | | 60 | | | | | 65 | | | | | 70 | | | | |
| TTC | TGC | CAG | TGG | TTT | GTA | AGA | GAG | GCT | GTT | CGT | ACC | TAT | GGA | CGT | GAG | 336 |
| Phe | Cys | Gln | Trp | Phe | Val | Arg | Glu | Ala | Val | Arg | Thr | Tyr | Gly | Arg | Glu | |
| 75 | | | | | 80 | | | | | 85 | | | | | 90 | |
| ATC | CAA | GTG | ACA | GAG | CTT | CTC | GAC | AAG | TTA | GAC | TTT | TAT | GTC | CTG | CCT | 384 |
| Ile | Gln | Val | Thr | Glu | Leu | Leu | Asp | Lys | Leu | Asp | Phe | Tyr | Val | Leu | Pro | |
| | | | | 95 | | | | | 100 | | | | | 105 | | |
| GTG | CTC | AAT | ATT | GAT | GGC | TAC | ATC | TAC | ACC | TGG | ACC | AAG | AGC | CGA | TTT | 432 |
| Val | Leu | Asn | Ile | Asp | Gly | Tyr | Ile | Tyr | Thr | Trp | Thr | Lys | Ser | Arg | Phe | |

```
                    110                 115                 120
TGG AGA AAG ACT CGC TCC ACC CAT ACT GGA TCT AGC TGC ATT GGC ACA         480
Trp Arg Lys Thr Arg Ser Thr His Thr Gly Ser Ser Cys Ile Gly Thr
        125                 130                 135

GAC CCC AAC AGA AAT TTT GAT GCT GGT TGG TGT GAA ATT GGA GCC TCT         528
Asp Pro Asn Arg Asn Phe Asp Ala Gly Trp Cys Glu Ile Gly Ala Ser
    140                 145                 150

CGA AAC CCC TGT GAT GAA ACT TAC TGT GGA CCT GCC GCA GAG TCT GAA         576
Arg Asn Pro Cys Asp Glu Thr Tyr Cys Gly Pro Ala Ala Glu Ser Glu
155                 160                 165                 170

AAG GAG ACC AAG GCC CTG GCT GAT TTC ATC CGC AAC AAA CTC TCT TCC         624
Lys Glu Thr Lys Ala Leu Ala Asp Phe Ile Arg Asn Lys Leu Ser Ser
                175                 180                 185

ATC AAG GCA TAT CTG ACA ATC CAC TCG TAC TCC CAA ATG ATG ATC TAC         672
Ile Lys Ala Tyr Leu Thr Ile His Ser Tyr Ser Gln Met Met Ile Tyr
            190                 195                 200

CCT TAC TCA TAT GCT TAC AAA CTC GGT GAG AAC AAT GCT GAG TTG AAT         720
Pro Tyr Ser Tyr Ala Tyr Lys Leu Gly Glu Asn Asn Ala Glu Leu Asn
        205                 210                 215

GCC CTG GCT AAA GCT ACT GTG AAA GAA CTT GCC TCA CTG CAC GGC ACC         768
Ala Leu Ala Lys Ala Thr Val Lys Glu Leu Ala Ser Leu His Gly Thr
    220                 225                 230

AAG TAC ACA TAT GGC CCG GGA GCT ACA ACA ATC TAT CCT GCT GCT GGG         816
Lys Tyr Thr Tyr Gly Pro Gly Ala Thr Thr Ile Tyr Pro Ala Ala Gly
235                 240                 245                 250

GGC TCT GAC GAC TGG GCT TAT GAC CAA GGA ATC AGA TAT TCC TTC ACC         864
Gly Ser Asp Asp Trp Ala Tyr Asp Gln Gly Ile Arg Tyr Ser Phe Thr
                255                 260                 265

TTT GAA CTT CGA GAT ACA GGC AGA TAT GGC TTT CTC CTT CCA GAA TCC         912
Phe Glu Leu Arg Asp Thr Gly Arg Tyr Gly Phe Leu Leu Pro Glu Ser
            270                 275                 280

CAG ATC CGG GCT ACC TGC GAG GAG ACC TTC CTG GCA ATC AAG TAT GTT         960
Gln Ile Arg Ala Thr Cys Glu Glu Thr Phe Leu Ala Ile Lys Tyr Val
        285                 290                 295

GCC AGC TAC GTC CTG GAA CAC CTG TAC CAC CAC CAT CAC CAC CAT GAG        1008
Ala Ser Tyr Val Leu Glu His Leu Tyr His His His His His His Glu
    300                 305                 310

TTC GAG GAG CAG AAG CTG ATC TCT GAG GAG GAC CTG AAC TAA TAA            1053
Phe Glu Glu Gln Lys Leu Ile Ser Glu Glu Asp Leu Asn
315                 320                 325
```

(2) INFORMATION FOR SEQ ID NO:65:

(i) SEQUENCE CHARACTERISTICS:
        (A) LENGTH: 31 bases
        (B) TYPE: nucleic acid
        (C) STRANDEDNESS: single
        (D) TOPOLOGY: linear (xi) SEQUENCE DESCRIPTION: SEQ ID NO:65:

GTTATTACTC GCTGCCCAAC CAGCCATGGC G                        31

(2) INFORMATION FOR SEQ ID NO:66:

(i) SEQUENCE CHARACTERISTICS:
        (A) LENGTH: 41 bases
        (B) TYPE: nucleic acid
        (C) STRANDEDNESS: single
        (D) TOPOLOGY: linear (xi) SEQUENCE DESCRIPTION: SEQ ID NO:66:

CTCTAGGAAT TCTTATTAGT ACAGGTGTTC CAGGACGTAG C              41

(2) INFORMATION FOR SEQ ID NO:67:

(i) SEQUENCE CHARACTERISTICS:
        (A) LENGTH: 999 bases
        (B) TYPE: nucleic acid
        (C) STRANDEDNESS: single
        (D) TOPOLOGY: linear (xi) SEQUENCE DESCRIPTION: SEQ ID NO:67:

```
ATG AAA TAC CTA TTG CCT ACG GCA GCC GCT GGA TTG TTA TTA CTC GCT        48
Met Lys Tyr Leu Leu Pro Thr Ala Ala Ala Gly Leu Leu Leu Leu Ala
        -20             -15             -10

GCC CAA CCA GCC ATG GCG GCA ACT GGT CAC TCT TAC GAG AAG TAC AAC        96
Ala Gln Pro Ala Met Ala Ala Thr Gly His Ser Tyr Glu Lys Tyr Asn
    -5               1              5              10

AAG TGG GAA ACG ATA GAG GCT TGG ACT CAA CAA GTC GCC ACT GAG AAT       144
Lys Trp Glu Thr Ile Glu Ala Trp Thr Gln Gln Val Ala Thr Glu Asn
                15              20              25

CCA GCC CTC ATC TCT CGC AGT GTT ATC GGA ACC ACA TTT GAG GGA CGC       192
Pro Ala Leu Ile Ser Arg Ser Val Ile Gly Thr Thr Phe Glu Gly Arg
            30              35              40

GCT ATT TAC CTC CTG AAG GTT GGC AAA GCT GGA CAA AAT AAG CCT GCC       240
Ala Ile Tyr Leu Leu Lys Val Gly Lys Ala Gly Gln Asn Lys Pro Ala
        45              50              55

ATT TTC ATG GAC TGT GGT TTC CAT GCC AGA GAG TGG ATT TCT CCT GCA       288
Ile Phe Met Asp Cys Gly Phe His Ala Arg Glu Trp Ile Ser Pro Ala
    60              65              70

TTC TGC CAG TGG TTT GTA AGA GAG GCT GTT CGT ACC TAT GGA CGT GAG       336
Phe Cys Gln Trp Phe Val Arg Glu Ala Val Arg Thr Tyr Gly Arg Glu
75              80              85              90

ATC CAA GTG ACA GAG CTT CTC GAC AAG TTA GAC TTT TAT GTC CTG CCT       384
Ile Gln Val Thr Glu Leu Leu Asp Lys Leu Asp Phe Tyr Val Leu Pro
                95             100             105

GTG CTC AAT ATT GAT GGC TAC ATC TAC ACC TGG ACC AAG AGC CGA TTT       432
Val Leu Asn Ile Asp Gly Tyr Ile Tyr Thr Trp Thr Lys Ser Arg Phe
            110             115             120

TGG AGA AAG ACT CGC TCC ACC CAT ACT GGA TCT AGC TGC ATT GGC ACA       480
Trp Arg Lys Thr Arg Ser Thr His Thr Gly Ser Ser Cys Ile Gly Thr
        125             130             135

GAC CCC AAC AGA AAT TTT GAT GCT GGT TGG TGT GAA ATT GGA GCC TCT       528
Asp Pro Asn Arg Asn Phe Asp Ala Gly Trp Cys Glu Ile Gly Ala Ser
    140             145             150

CGA AAC CCC TGT GAT GAA ACT TAC TGT GGA CCT GCC GCA GAG TCT GAA       576
Arg Asn Pro Cys Asp Glu Thr Tyr Cys Gly Pro Ala Ala Glu Ser Glu
155             160             165             170

AAG GAG ACC AAG GCC CTG GCT GAT TTC ATC CGC AAC AAA CTC TCT TCC       624
Lys Glu Thr Lys Ala Leu Ala Asp Phe Ile Arg Asn Lys Leu Ser Ser
                175             180             185

ATC AAG GCA TAT CTG ACA ATC CAC TCG TAC TCC CAA ATG ATG ATC TAC       672
Ile Lys Ala Tyr Leu Thr Ile His Ser Tyr Ser Gln Met Met Ile Tyr
            190             195             200

CCT TAC TCA TAT GCT TAC AAA CTC GGT GAG AAC AAT GCT GAG TTG AAT       720
Pro Tyr Ser Tyr Ala Tyr Lys Leu Gly Glu Asn Asn Ala Glu Leu Asn
        205             210             215

GCC CTG GCT AAA GCT ACT GTG AAA GAA CTT GCC TCA CTG CAC GGC ACC       768
Ala Leu Ala Lys Ala Thr Val Lys Glu Leu Ala Ser Leu His Gly Thr
    220             225             230

AAG TAC ACA TAT GGC CCG GGA GCT ACA ACA ATC TAT CCT GCT GCT GGG       816
Lys Tyr Thr Tyr Gly Pro Gly Ala Thr Thr Ile Tyr Pro Ala Ala Gly
235             240             245             250

GGC TCT GAC GAC TGG GCT TAT GAC CAA GGA ATC AGA TAT TCC TTC ACC       864
```

―continued

```
Gly Ser Asp Asp Trp Ala Tyr Asp Gln Gly Ile Arg Tyr Ser Phe Thr
            255                 260                 265

TTT GAA CTT CGA GAT ACA GGC AGA TAT GGC TTT CTC CTT CCA GAA TCC       912
Phe Glu Leu Arg Asp Thr Gly Arg Tyr Gly Phe Leu Leu Pro Glu Ser
            270                 275                 280

CAG ATC CGG GCT ACC TGC GAG GAG ACC TTC CTG GCA ATC AAG TAT GTT       960
Gln Ile Arg Ala Thr Cys Glu Glu Thr Phe Leu Ala Ile Lys Tyr Val
            285                 290                 300

GCC AGC TAC GTC CTG GAA CAC CTG TAC TAA TAA GAA TTC                   999
Ala Ser Tyr Val Leu Glu His Leu Tyr
            305                 310
```

(2) INFORMATION FOR SEQ ID NO:68:

(i) SEQUENCE CHARACTERISTICS:
        (A) LENGTH: 34 bases
        (B) TYPE: nucleic acid
        (C) STRANDEDNESS: single
        (D) TOPOLOGY: linear (xi) SEQUENCE DESCRIPTION: SEQ ID NO:68:

CCAACCAGCC ATGGCGCATC ATGGTGGTGA GCAC                                 34

(2) INFORMATION FOR SEQ ID NO:69:

(i) SEQUENCE CHARACTERISTICS:
        (A) LENGTH: 23 bases
        (B) TYPE: nucleic acid
        (C) STRANDEDNESS: single
        (D) TOPOLOGY: linear (xi) SEQUENCE DESCRIPTION: SEQ ID NO:69:

GGCTGGATTC TCAGTGGCGA CTT                                             23

(2) INFORMATION FOR SEQ ID NO:70:

(i) SEQUENCE CHARACTERISTICS:
        (A) LENGTH: 21 bases
        (B) TYPE: nucleic acid
        (C) STRANDEDNESS: single
        (D) TOPOLOGY: linear (xi) SEQUENCE DESCRIPTION: SEQ ID NO:70:

GGAGAAAGCC ATATCTGCCT G                                               21

(2) INFORMATION FOR SEQ ID NO:71:

(i) SEQUENCE CHARACTERISTICS:
        (A) LENGTH: 1284 bases
        (B) TYPE: nucleic acid
        (C) STRANDEDNESS: single
        (D) TOPOLOGY: linear (xi) SEQUENCE DESCRIPTION: SEQ ID NO:71:

```
ATG AAA TAC CTA TTG CCT ACG GCA GCC GCT GGA TTG TTA TTA CTC GCT       48
Met Lys Tyr Leu Leu Pro Thr Ala Ala Ala Gly Leu Leu Leu Leu Ala
-117        -115                -110                -105

GCC CAA CCA GCC ATG GCG CAT CAT GGT GGT GAG CAC TTT GAA GGC GAG       96
Ala Gln Pro Ala Met Ala His His Gly Gly Glu His Phe Glu Gly Glu
        -100                -95                 -90

AAG GTG TTC CGT GTT AAC GTT GAA GAT GAA AAT CAC ATT AAC ATA ATC       144
Lys Val Phe Arg Val Asn Val Glu Asp Glu Asn His Ile Asn Ile Ile
-85             -80                 -75                 -70

CGC GAG TTG GCC AGC ACG ACC CAG ATT GAC TTC TGG AAG CCA GAT TCT       192
Arg Glu Leu Ala Ser Thr Thr Gln Ile Asp Phe Trp Lys Pro Asp Ser
            -65                 -60                 -55
```

```
GTC ACA CAA ATC AAA CCT CAC AGT ACA GTT GAC TTC CGT GTT AAA GCA    240
Val Thr Gln Ile Lys Pro His Ser Thr Val Asp Phe Arg Val Lys Ala
            -50             -45             -40

GAA GAT ACT GTC ACT GTG GAG AAT GTT CTA AAG CAG AAT GAA CTA CAA    288
Glu Asp Thr Val Thr Val Glu Asn Val Leu Lys Gln Asn Glu Leu Gln
        -35             -30             -25

TAC AAG GTA CTG ATA AGC AAC CTG AGA AAT GTG GTG GAG GCT CAG TTT    336
Tyr Lys Val Leu Ile Ser Asn Leu Arg Asn Val Val Glu Ala Gln Phe
    -20             -15             -10

GAT AGC CGG GTT CGT GCA ACA GGA CAC AGT TAT GAG AAG TAC AAC AAG    384
Asp Ser Arg Val Arg Ala Thr Gly His Ser Tyr Glu Lys Tyr Asn Lys
-5               1               5                  10

TGG GAA ACG ATA GAG GCT TGG ACT CAA CAA GTC GCC ACT GAG AAT CCA    432
Trp Glu Thr Ile Glu Ala Trp Thr Gln Gln Val Ala Thr Glu Asn Pro
            15              20              25

GCC CTC ATC TCT CGC AGT GTT ATC GGA ACC ACA TTT GAG GGA CGC GCT    480
Ala Leu Ile Ser Arg Ser Val Ile Gly Thr Thr Phe Glu Gly Arg Ala
        30              35              40

ATT TAC CTC CTG AAG GTT GGC AAA GCT GGA CAA AAT AAG CCT GCC ATT    528
Ile Tyr Leu Leu Lys Val Gly Lys Ala Gly Gln Asn Lys Pro Ala Ile
    45              50              55

TTC ATG GAC TGT GGT TTC CAT GCC AGA GAG TGG ATT TCT CCT GCA TTC    576
Phe Met Asp Cys Gly Phe His Ala Arg Glu Trp Ile Ser Pro Ala Phe
60              65              70              75

TGC CAG TGG TTT GTA AGA GAG GCT GTT CGT ACC TAT GGA CGT GAG ATC    624
Cys Gln Trp Phe Val Arg Glu Ala Val Arg Thr Tyr Gly Arg Glu Ile
            80              85              90

CAA GTG ACA GAG CTT CTC GAC AAG TTA GAC TTT TAT GTC CTG CCT GTG    672
Gln Val Thr Glu Leu Leu Asp Lys Leu Asp Phe Tyr Val Leu Pro Val
        95              100             105

CTC AAT ATT GAT GGC TAC ATC TAC ACC TGG ACC AAG AGC CGA TTT TGG    720
Leu Asn Ile Asp Gly Tyr Ile Tyr Thr Trp Thr Lys Ser Arg Phe Trp
    110             115             120

AGA AAG ACT CGC TCC ACC CAT ACT GGA TCT AGC TGC ATT GGC ACA GAC    768
Arg Lys Thr Arg Ser Thr His Thr Gly Ser Ser Cys Ile Gly Thr Asp
125             130             135

CCC AAC AGA AAT TTT GAT GCT GGT TGG TGT GAA ATT GGA GCC TCT CGA    816
Pro Asn Arg Asn Phe Asp Ala Gly Trp Cys Glu Ile Gly Ala Ser Arg
140             145             150             155

AAC CCC TGT GAT GAA ACT TAC TGT GGA CCT GCC GCA GAG TCT GAA AAG    864
Asn Pro Cys Asp Glu Thr Tyr Cys Gly Pro Ala Ala Glu Ser Glu Lys
            160             165             170

GAG ACC AAG GCC CTG GCT GAT TTC ATC CGC AAC AAA CTC TCT TCC ATC    912
Glu Thr Lys Ala Leu Ala Asp Phe Ile Arg Asn Lys Leu Ser Ser Ile
        175             180             185

AAG GCA TAT CTG ACA ATC CAC TCG TAC TCC CAA ATG ATG ATC TAC CCT    960
Lys Ala Tyr Leu Thr Ile His Ser Tyr Ser Gln Met Met Ile Tyr Pro
    190             195             200

TAC TCA TAT GCT TAC AAA CTC GGT GAG AAC AAT GCT GAG TTG AAT GCC    1008
Tyr Ser Tyr Ala Tyr Lys Leu Gly Glu Asn Asn Ala Glu Leu Asn Ala
205             210             215

CTG GCT AAA GCT ACT GTG AAA GAA CTT GCC TCA CTG CAC GGC ACC AAG    1056
Leu Ala Lys Ala Thr Val Lys Glu Leu Ala Ser Leu His Gly Thr Lys
220             225             230             235

TAC ACA TAT GGC CCG GGA GCT ACA ACA ATC TAT CCT GCT GCT GGG GGC    1104
Tyr Thr Tyr Gly Pro Gly Ala Thr Thr Ile Tyr Pro Ala Ala Gly Gly
            240             245             250

TCT GAC GAC TGG GCT TAT GAC CAA GGA ATC AGA TAT TCC TTC ACC TTT    1152
Ser Asp Asp Trp Ala Tyr Asp Gln Gly Ile Arg Tyr Ser Phe Thr Phe
        255             260             265
```

```
GAA CTT CGA GAT ACA GGC AGA TAT GGC TTT CTC CTT CCA GAA TCC CAG    1200
Glu Leu Arg Asp Thr Gly Arg Tyr Gly Phe Leu Leu Pro Glu Ser Gln
            270                 275                 280

ATC CGG GCT ACC TGC GAG GAG ACC TTC CTG GCA ATC AAG TAT GTT GCC    1248
Ile Arg Ala Thr Cys Glu Glu Thr Phe Leu Ala Ile Lys Tyr Val Ala
        285                 290                 300

AGC TAC GTC CTG GAA CAC CTG TAC TAA TAA GAA TTC                    1284
Ser Tyr Val Leu Glu His Leu Tyr
305                 310
```

(2) INFORMATION FOR SEQ ID NO:72:

(i) SEQUENCE CHARACTERISTICS:
        (A) LENGTH: 25 bases
        (B) TYPE: nucleic acid
        (C) STRANDEDNESS: single
        (D) TOPOLOGY: linear (xi) SEQUENCE DESCRIPTION: SEQ ID NO:72:

```
GGTCATAAGC CCAGTCTTTA GAGCC                                          25
```

(2) INFORMATION FOR SEQ ID NO:73:

(i) SEQUENCE CHARACTERISTICS:
        (A) LENGTH: 27 bases
        (B) TYPE: nucleic acid
        (C) STRANDEDNESS: single
        (D) TOPOLOGY: linear (xi) SEQUENCE DESCRIPTION: SEQ ID NO:73:

```
CCTGCTGCTG GGGGCTCTAA AGACTGG                                        27
```

(2) INFORMATION FOR SEQ ID NO:74:

(i) SEQUENCE CHARACTERISTICS:
        (A) LENGTH: 1059 bases
        (B) TYPE: nucleic acid
        (C) STRANDEDNESS: single
        (D) TOPOLOGY: linear (xi) SEQUENCE DESCRIPTION: SEQ ID NO:74:

```
ATG AAA TAC CTA TTG CCT ACG GCA GCC GCT GGA TTG TTA TTA CTC GCT     48
Met Lys Tyr Leu Leu Pro Thr Ala Ala Ala Gly Leu Leu Leu Leu Ala
        -20                 -15                 -10

GCC CAA CCA GCC ATG GCG GCA ACT GGT CAC TCT TAC GAG AAG TAC AAC     96
Ala Gln Pro Ala Met Ala Ala Thr Gly His Ser Tyr Glu Lys Tyr Asn
        -5                   1                   5              10

AAG TGG GAA ACG ATA GAG GCT TGG ACT CAA CAA GTC GCC ACT GAG AAT    144
Lys Trp Glu Thr Ile Glu Ala Trp Thr Gln Gln Val Ala Thr Glu Asn
            15                  20                  25

CCA GCC CTC ATC TCT CGC AGT GTT ATC GGA ACC ACA TTT GAG GGA CGC    192
Pro Ala Leu Ile Ser Arg Ser Val Ile Gly Thr Thr Phe Glu Gly Arg
                30                  35                  40

GCT ATT TAC CTC CTG AAG GTT GGC AAA GCT GGA CAA AAT AAG CCT GCC    240
Ala Ile Tyr Leu Leu Lys Val Gly Lys Ala Gly Gln Asn Lys Pro Ala
            45                  50                  55

ATT TTC ATG GAC TGT GGT TTC CAT GCC AGA GAG TGG ATT TCT CCT GCA    288
Ile Phe Met Asp Cys Gly Phe His Ala Arg Glu Trp Ile Ser Pro Ala
        60                  65                  70

TTC TGC CAG TGG TTT GTA AGA GAG GCT GTT CGT ACC TAT GGA CGT GAG    336
Phe Cys Gln Trp Phe Val Arg Glu Ala Val Arg Thr Tyr Gly Arg Glu
75                  80                  85                  90

ATC CAA GTG ACA GAG CTT CTC GAC AAG TTA GAC TTT TAT GTC CTG CCT    384
Ile Gln Val Thr Glu Leu Leu Asp Lys Leu Asp Phe Tyr Val Leu Pro
```

```
                 95                 100                 105
GTG CTC AAT ATT GAT GGC TAC ATC TAC ACC TGG ACC AAG AGC CGA TTT    432
Val Leu Asn Ile Asp Gly Tyr Ile Tyr Thr Trp Thr Lys Ser Arg Phe
            110                 115                 120

TGG AGA AAG ACT CGC TCC ACC CAT ACT GGA TCT AGC TGC ATT GGC ACA    480
Trp Arg Lys Thr Arg Ser Thr His Thr Gly Ser Ser Cys Ile Gly Thr
            125                 130                 135

GAC CCC AAC AGA AAT TTT GAT GCT GGT TGG TGT GAA ATT GGA GCC TCT    528
Asp Pro Asn Arg Asn Phe Asp Ala Gly Trp Cys Glu Ile Gly Ala Ser
            140                 145                 150

CGA AAC CCC TGT GAT GAA ACT TAC TGT GGA CCT GCC GCA GAG TCT GAA    576
Arg Asn Pro Cys Asp Glu Thr Tyr Cys Gly Pro Ala Ala Glu Ser Glu
155             160                 165                 170

AAG GAG ACC AAG GCC CTG GCT GAT TTC ATC CGC AAC AAA CTC TCT TCC    624
Lys Glu Thr Lys Ala Leu Ala Asp Phe Ile Arg Asn Lys Leu Ser Ser
            175                 180                 185

ATC AAG GCA TAT CTG ACA ATC CAC TCG TAC TCC CAA ATG ATG ATC TAC    672
Ile Lys Ala Tyr Leu Thr Ile His Ser Tyr Ser Gln Met Met Ile Tyr
            190                 195                 200

CCT TAC TCA TAT GCT TAC AAA CTC GGT GAG AAC AAT GCT GAG TTG AAT    720
Pro Tyr Ser Tyr Ala Tyr Lys Leu Gly Glu Asn Asn Ala Glu Leu Asn
            205                 210                 215

GCC CTG GCT AAA GCT ACT GTG AAA GAA CTT GCC TCA CTG CAC GGC ACC    768
Ala Leu Ala Lys Ala Thr Val Lys Glu Leu Ala Ser Leu His Gly Thr
220             225                 230

AAG TAC ACA TAT GGC CCG GGA GCT ACA ACA ATC TAT CCT GCT GCT GGG    816
Lys Tyr Thr Tyr Gly Pro Gly Ala Thr Thr Ile Tyr Pro Ala Ala Gly
235             240                 245                 250

GGC TCT AAA GAC TGG GCT TAT GAC CAA GGA ATC AGA TAT TCC TTC ACC    864
Gly Ser Lys Asp Trp Ala Tyr Asp Gln Gly Ile Arg Tyr Ser Phe Thr
            255                 260                 265

TTT GAA CTT CGA GAT ACA GGC AGA TAT GGC TTT CTC CTT CCA GAA TCC    912
Phe Glu Leu Arg Asp Thr Gly Arg Tyr Gly Phe Leu Leu Pro Glu Ser
            270                 275                 280

CAG ATC CGG GCT ACC TGC GAG GAG ACC TTC CTG GCA ATC AAG TAT GTT    960
Gln Ile Arg Ala Thr Cys Glu Glu Thr Phe Leu Ala Ile Lys Tyr Val
            285                 290                 295

GCC AGC TAC GTC CTG GAA CAC CTG TAC CAC CAC CAT CAC CAC CAT GAG   1008
Ala Ser Tyr Val Leu Glu His Leu Tyr His His His His His His Glu
300                 305                 310

TTC GAG GAG CAG AAG CTG ATC TCT GAG GAG GAC CTG AAC TAA TAA GAA   1056
Phe Glu Glu Gln Lys Leu Ile Ser Glu Glu Asp Leu Asn
315             320                 325

TTC                                                               1059
```

(2) INFORMATION FOR SEQ ID NO:75:

(i) SEQUENCE CHARACTERISTICS:
        (A) LENGTH: 25 bases
        (B) TYPE: nucleic acid
        (C) STRANDEDNESS: single
        (D) TOPOLOGY: linear (xi) SEQUENCE DESCRIPTION: SEQ ID NO:75:

GGTCATAAGC CCAGTCGCGA GAGCC                                                     25

(2) INFORMATION FOR SEQ ID NO:76:

(i) SEQUENCE CHARACTERISTICS:
        (A) LENGTH: 27 bases
        (B) TYPE: nucleic acid
        (C) STRANDEDNESS: single (D) TOPOLOGY: linear (xi) SEQUENCE DESCRIPTION: SEQ ID NO:76:

CCTGCTGCTG GGGGCTCTCG CGACTGG                                                27

(2) INFORMATION FOR SEQ ID NO:77:

(i) SEQUENCE CHARACTERISTICS:
        (A) LENGTH: 1059 bases
        (B) TYPE: nucleic acid
        (C) STRANDEDNESS: single
        (D) TOPOLOGY: linear (xi) SEQUENCE DESCRIPTION: SEQ ID NO:77:

ATG AAA TAC CTA TTG CCT ACG GCA GCC GCT GGA TTG TTA TTA CTC GCT   48
Met Lys Tyr Leu Leu Pro Thr Ala Ala Ala Gly Leu Leu Leu Leu Ala
        -20             -15             -10

GCC CAA CCA GCC ATG GCG GCA ACT GGT CAC TCT TAC GAG AAG TAC AAC   96
Ala Gln Pro Ala Met Ala Ala Thr Gly His Ser Tyr Glu Lys Tyr Asn
    -5               1               5                      10

AAG TGG GAA ACG ATA GAG GCT TGG ACT CAA CAA GTC GCC ACT GAG AAT  144
Lys Trp Glu Thr Ile Glu Ala Trp Thr Gln Gln Val Ala Thr Glu Asn
                15              20              25

CCA GCC CTC ATC TCT CGC AGT GTT ATC GGA ACC ACA TTT GAG GGA CGC  192
Pro Ala Leu Ile Ser Arg Ser Val Ile Gly Thr Thr Phe Glu Gly Arg
            30              35              40

GCT ATT TAC CTC CTG AAG GTT GGC AAA GCT GGA CAA AAT AAG CCT GCC  240
Ala Ile Tyr Leu Leu Lys Val Gly Lys Ala Gly Gln Asn Lys Pro Ala
            45              50              55

ATT TTC ATG GAC TGT GGT TTC CAT GCC AGA GAG TGG ATT TCT CCT GCA  288
Ile Phe Met Asp Cys Gly Phe His Ala Arg Glu Trp Ile Ser Pro Ala
        60              65              70

TTC TGC CAG TGG TTT GTA AGA GAG GCT GTT CGT ACC TAT GGA CGT GAG  336
Phe Cys Gln Trp Phe Val Arg Glu Ala Val Arg Thr Tyr Gly Arg Glu
75              80              85              90

ATC CAA GTG ACA GAG CTT CTC GAC AAG TTA GAC TTT TAT GTC CTG CCT  384
Ile Gln Val Thr Glu Leu Leu Asp Lys Leu Asp Phe Tyr Val Leu Pro
            95              100             105

GTG CTC AAT ATT GAT GGC TAC ATC TAC ACC TGG ACC AAG AGC CGA TTT  432
Val Leu Asn Ile Asp Gly Tyr Ile Tyr Thr Trp Thr Lys Ser Arg Phe
            110             115             120

TGG AGA AAG ACT CGC TCC ACC CAT ACT GGA TCT AGC TGC ATT GGC ACA  480
Trp Arg Lys Thr Arg Ser Thr His Thr Gly Ser Ser Cys Ile Gly Thr
            125             130             135

GAC CCC AAC AGA AAT TTT GAT GCT GGT TGG TGT GAA ATT GGA GCC TCT  528
Asp Pro Asn Arg Asn Phe Asp Ala Gly Trp Cys Glu Ile Gly Ala Ser
        140             145             150

CGA AAC CCC TGT GAT GAA ACT TAC TGT GGA CCT GCC GCA GAG TCT GAA  576
Arg Asn Pro Cys Asp Glu Thr Tyr Cys Gly Pro Ala Ala Glu Ser Glu
155             160             165             170

AAG GAG ACC AAG GCC CTG GCT GAT TTC ATC CGC AAC AAA CTC TCT TCC  624
Lys Glu Thr Lys Ala Leu Ala Asp Phe Ile Arg Asn Lys Leu Ser Ser
            175             180             185

ATC AAG GCA TAT CTG ACA ATC CAC TCG TAC TCC CAA ATG ATG ATC TAC  672
Ile Lys Ala Tyr Leu Thr Ile His Ser Tyr Ser Gln Met Met Ile Tyr
            190             195             200

CCT TAC TCA TAT GCT TAC AAA CTC GGT GAG AAC AAT GCT GAG TTG AAT  720
Pro Tyr Ser Tyr Ala Tyr Lys Leu Gly Glu Asn Asn Ala Glu Leu Asn
        205             210             215

GCC CTG GCT AAA GCT ACT GTG AAA GAA CTT GCC TCA CTG CAC GGC ACC  768
Ala Leu Ala Lys Ala Thr Val Lys Glu Leu Ala Ser Leu His Gly Thr
        220             225             230

```
AAG TAC ACA TAT GGC CCG GGA GCT ACA ACA ATC TAT CCT GCT GCT GGG  816
Lys Tyr Thr Tyr Gly Pro Gly Ala Thr Thr Ile Tyr Pro Ala Ala Gly
235             240             245             250

GGC TCT CGC GAC TGG GCT TAT GAC CAA GGA ATC AGA TAT TCC TTC ACC  864
Gly Ser Arg Asp Trp Ala Tyr Asp Gln Gly Ile Arg Tyr Ser Phe Thr
            255             260             265

TTT GAA CTT CGA GAT ACA GGC AGA TAT GGC TTT CTC CTT CCA GAA TCC  912
Phe Glu Leu Arg Asp Thr Gly Arg Tyr Gly Phe Leu Leu Pro Glu Ser
        270             275             280

CAG ATC CGG GCT ACC TGC GAG GAG ACC TTC CTG GCA ATC AAG TAT GTT  960
Gln Ile Arg Ala Thr Cys Glu Glu Thr Phe Leu Ala Ile Lys Tyr Val
        285             290             300

GCC AGC TAC GTC CTG GAA CAC CTG TAC CAC CAC CAT CAC CAC CAT GAG  1008
Ala Ser Tyr Val Leu Glu His Leu Tyr His His His His His His Glu
        305             310             315

TTC GAG GAG CAG AAG CTG ATC TCT GAG GAG GAC CTG AAC TAA TAA GAA  1056
Phe Glu Glu Gln Lys Leu Ile Ser Glu Glu Asp Leu Asn
320             325             330

TTC                                                              1059
```

Notes on Sequence Listings

In this specification the sequence numbers referred to in the specification correspond to the sequence listing directly included with the specification (which was not prepared using Patentin software). It is also necessary to supply a Patentin generated sequence listing and this has been done on filing this application and the contents thereof are specifically incorporated by this reference.

Because the Patentin software generates an extra sequence (containing just amino acid sequence) when a nucleic acid sequence contains a coding region (CDS) this created a discrepancy between the Patentin and Non-Patentin generated numbering of SEQ ID NOS. A table submitted with the Patentin generated sequence listing sets out a comparison of the 2 sets SEQ ID NOS. The diskette version of the sequence listing corresponds to the Patentin generated version.

The reader should also be aware of the following "bug" in the Patentin software version 1.30 as currently available. In sequences containing CDS regions, sometimes sequence numbering for amino acids continues on from an earlier CDS (rather than starting from the beginning). This bug affects the amino acid numbering in SEQ ID NOS 27 30 & 32 in the Patentin generated sequence listing.

We claim:

1. A two component system adapted for therapeutic treatment of a host, having:
   (i) a first component comprising a targeting moiety which is an antibody or a fragment thereof, capable of binding with a tumour associated antigen, the targeting moiety being linked to a mutated enzyme capable of converting a prodrug into an antineoplastic drug and;
   (ii) a second component comprising a prodrug convertible under the influence of the mutated enzyme to the antineoplastic drug; wherein:
   the mutated enzyme is a mutated form of a natural host enzyme, which natural host enzyme recognizes its natural substrate by an ion pair interaction with said substrate, and wherein the mutated enzyme and prodrug have structures such that the polarity of the mutated enzyme/prodrug ion pair interaction is reversed relative to the natural host enzyme/natural substrate ion pair interaction;
   the first component is substantially non-immunogenic in the host and;
   the prodrug second component is not significantly convertible into antineoplastic drug in the host by natural unmutated host enzyme.

2. The system according to claim 1 in which the first component comprises a mutated enzyme based on a natural enzyme from the same species as the host for which the system is adapted to therapeutically treat.

3. The system according to claim 1 in which the targeting moiety is an antibody fragment.

4. The system according to claim 3 in which the targeting moiety is an F(ab')$_2$ fragment.

5. The system according to claim 1 in which the mutated enzyme is mutated ribonuclease.

6. The system according to claim 5 in which the mutated enzyme is human ribonuclease comprising a negatively charged amino acid at position 66.

7. The system according to claim 6 in which the negatively charged amino acid at position 66 is Glu.

8. The system according to claim 1 in which the mutated enzyme is mutated glucuronidase.

9. The system according to claim 1 wherein the second component comprises a mustard-ribonucleotide of Formula 1

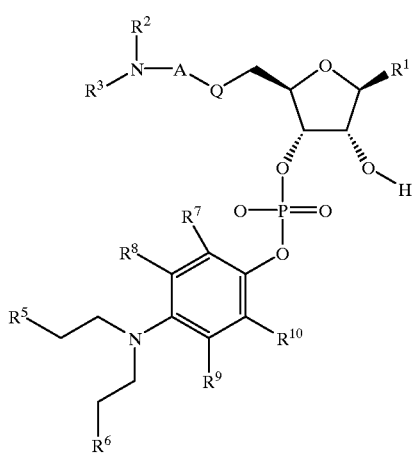

wherein:
Q is O or NH;
a is a group of formula —X—Y—, with Y next to Q, wherein
Y is $SO_2$, CO or a single bond with the proviso that when Q is oxygen then Y is not $SO_2$; and
X is —$(CH_2)_n$—, where n=1–4, which is optionally substituted by $C_{1-4}$alkyl on any carbon atom or when Y is CO and n=1 then X is optionally substituted on carbon with the side chain of alanine, valine, leucine, isoleucine, methionine, phenylalanine, tryptophan, serine, threonine, cysteine, asparagine, glutamine, lysine, arginine or histidine;
$R^1$ is uracil or cytosine;
$R^2$ and $R^3$ independently represent H or $C_{1-4}$alkyl;
$R^5$ and $R^6$ independently represent Cl, mesyl or tosyl; and
$R^7$, $R^8$, $R^9$ and $R^{10}$ independently represent H, $C_{1-4}$alkyl, $C_{1-4}$alkoxy, F or Cl; or a salt thereof.

10. The system according to claim 9 wherein the second component comprises a mustard-ribonucleotide in which:
Q is NH;
X is —$(CH_2)_n$— where n is 1–4;
Y is —C(O)—;
$R^1$ is uracil or cytosine;
$R^2$ and $R^3$ are H;
$R^5$ and $R^6$ are Cl; and
$R^7$, $R^8$, $R^9$ and $R^{10}$ are H; or a salt thereof.

11. The system according to claim 1 wherein the second component comprises the compound O—[(2R,3S,4R,5R)-2-(aminoacetamidomethyl)-5-(2,4-dioxo-1,2,3,4-tetrahydropyrimidin-1-yl)-4-hydroxy,2,3,4,5-tetrahydrofuran-3-yl]O-[4-(bis[2-chloroethyl]amino)phenoxyl]hydrogen phosphate or a salt thereof.

12. A composition comprising a targeting moiety which is an antibody or fragment thereof, capable of binding with a tumour associated antigen, the targeting moiety being linked to a mutated enzyme capable of converting a prodrug into an antineoplastic drug,
wherein the mutated enzyme is a mutated form of a natural host enzyme, which natural host enzyme recognizes its natural substrate by an ion pair interaction with said substrate, and
wherein the mutated enzyme and prodrug have structures such that the polarity of the mutated enzyme/prodrug ion pair interaction is reversed relative to the natural host enzyme/natural substrate ion pair interaction;
which composition is substantially non-immunogenic in the host.

13. The composition according to claim 12 in which the mutated enzyme is based on a natural enzyme from the same species as the host for which the pharmaceutical composition is adapted to therapeutically treat.

14. The composition according to claim 12 in which the targeting moiety is an antibody fragment.

15. The composition according to claim 14 in which the targeting moiety is an F(ab')$_2$ fragment.

16. The composition according to claim 12 in which the mutated enzyme is mutated ribonuclease.

17. The composition according to claim 16 in which the mutated enzyme is human ribonuclease comprising a negatively charged amino acid at position 66.

18. The composition according to claim 17 in which the negatively charged amino acid at position 66 is Glu.

19. The composition according to claim 12 in which the mutated enzyme is mutated glucuronidase.

20. A mustard-ribonucleotide of Formula 1

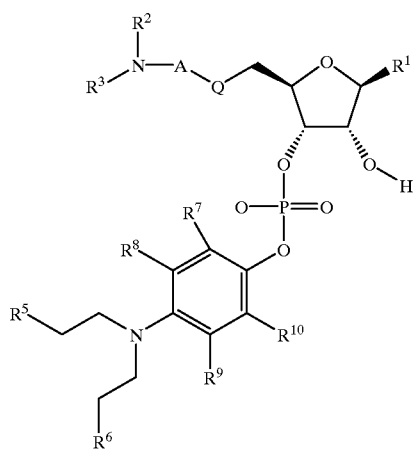

wherein:
Q is O or NH;
A is a group of formula —X—Y—, with Y next to Q, wherein
Y is $SO_2$, CO or a single bond with the proviso that when Q is oxygen then Y is not $SO_2$; and
X is —$(CH_2)_n$—, where n=1–4, which is optionally substituted by $C_{1-4}$alkyl on any carbon atom or when Y is CO and n=1 then X is optionally substituted on carbon with the side chain of alanine, valine, leucine, isoleucine, methionine, phenylalanine, tryptophan, serine, threonine, cysteine, asparagine, glutamine, lysine, arginine or histidine;
$R^1$ is uracil or cytosine;
$R^2$ and $R^3$ independently represent H or $C_{1-4}$alkyl;
$R^5$ and $R^6$ independently represent Cl, mesyl or tosyl; and
$R^7$, $R^8$, $R^9$ and $R^{10}$ independently represent H, $C_{1-4}$alkyl, $C_{1-4}$alkoxy, F or Cl; or a salt thereof.

21. The mustard ribonucleotide according to claim 20 in which:
Q is NH;
X is —$(CH_2)_n$— where n is 1–4;
Y is —C(O)—;
$R^1$ is uracil or cytosine;
$R^2$ and $R^3$ are H;
$R^5$ and $R^6$ are Cl; and
$R^7$, $R^8$, $R^9$ and $R^{10}$ are H; or a salt thereof.

22. The mustard ribonucleotide according to claim 20 which is O—[(2R,3S,4R,5R)-2-(aminoacetamidomethyl)-5-(2,4-dioxo-1,2,3,4-tetrahydropyrimidin-1-yl)-4-hydroxy-2,3,4,5-tetrahydrofuran-3-yl]O-[4-(bis[2-chloroethyl]amino)phenoxy]hydrogen phosphate or a salt thereof.

23. A pharmaceutical composition comprising a pharmaceutically effective amount of the mustard ribonucleotide according to any one of claims 19–22 in combination with a pharmaceutically acceptable diluent.

24. A pharmaceutical composition according to claim 23 which is sterile.

25. A method of controlling the growth of neoplastic cells in a host by sequential administration to said host an effective amount of each component of the two component system of claim 1, which method comprises
administering to said host an effective amount of said first component whereby at least a portion of said targeting moiety binds to said tumour associated antigen;
allowing unbound first component to clear substantially from general circulation in the host; and
thereafter administering to said host an effective amount of said second component, whereby at least a portion of said prodrug is converted to said antineoplastic drug under the influence of mutated enzyme linked to said bound targeting moiety.

26. The method according to claim 25 wherein said first component comprises a mutated enzyme based on a natural enzyme from the same species as the host to which said first component is administered.

27. The method according to claim 25 wherein the targeting moiety is an antibody fragment.

28. The method according to claim 27 wherein the targeting moiety is an F(ab')$_2$ fragment.

29. The method according to claim 25 wherein the mutated enzyme is mutated ribonuclease.

30. The method according to claim 29 wherein the mutated enzyme is human ribonuclease comprising a negatively charged amino acid at position 66.

31. The method according to claim 30 wherein the negatively charged amino acid at position 66 is Glu.

32. The method according to claim 25 wherein the mutated enzyme is mutated glucuronidase.

33. The method according to claim 25 wherein the second component comprises a mustard-ribonucleotide of Formula 1

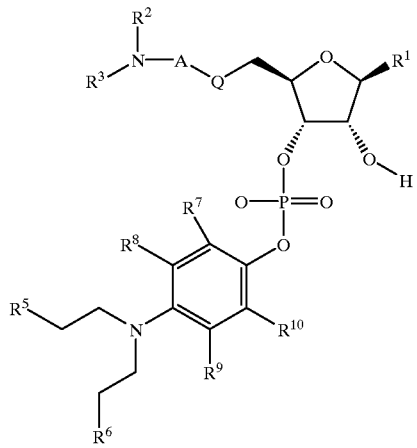

1 wherein:

Q is O or NH;

A is a group of formula —X—Y—, with Y next to Q, wherein
Y is SO$_2$, CO or a single bond with the proviso that when Q is oxygen then Y is not SO$_2$; and
X is —(CH$_2$)$_n$—, where n=1–4, which is optionally substituted by C$_{1-4}$alkykl on any carbon atom or when Y is CO and n=1 then X is optionally substituted on carbon with the side chain of alanine, valine, leucine, isoleucine, methionine, phenylalanine, tryptophan, serine, threonine, cysteine, asparagine, glutamine, lysine, arginine or histidine;

r$^1$ is uracil or cytosine;

R$^2$ and R$^3$ independently represent H or C$_{1-4}$alkyl;

R$^5$ and R$^6$ independently represent Cl, mesyl or tosyl; and

R$^7$, R$^8$, R$^9$ and R$^{10}$ independently represent H, C$_{1-4}$alkyl, C$_{1-4}$alkoxy, F or Cl; or a salt thereof.

34. The method according to claim 33 wherein the second component comprises a mustard-ribonucleotide in which:

Q is NH;

X is —(CH$_2$)$_n$— where n is 1–4;

Y is —C(O)—;

R$^1$ is uracil or cytosine;

R$^2$ and R$^3$ are H;

R$^5$ and R$^6$ are Cl; and

R$^7$, R$^8$, R$^9$ and R$^{10}$ are H; or a salt thereof.

35. The method according to claim 25 wherein the second component comprises the compound O—[(2R,3S,4R,5R)-2-(aminoacetamidomethyl)-5-(2,4-dioxo-1,2,3,4-tetrahydropyrimidin-1-yl)-4-hydroxy-2,3,4,5-tetrahydrofuran-3-yl]O-[4-(bis[2-chloroethyl]amino)phenoxy]hydrogen phosphate or a salt thereof.

36. Plasmid pQR162 deposited as deposit reference NCIMB 40678.

37. A polynucleotide sequence from:
a polynucleotide sequence encoding a first component as defined in claim 1; or
a polynucleotide sequence encoding a mutated enzyme as defined in claim 1.

38. A vector comprising a polynucleotide as defined in claim 37.

39. A cell comprising a polynucleotide as defined in claim 37.

* * * * *